United States Patent
Iyer et al.

(10) Patent No.: US 11,033,569 B2
(45) Date of Patent: Jun. 15, 2021

(54) COMPOUNDS, COMPOSITIONS, AND METHODS FOR THE TREATMENT OF DISEASE

(71) Applicant: Sperovie Biosciences, Inc., Hopkinton, MA (US)

(72) Inventors: Radhakrishnan P. Iyer, Shrewsbury, MA (US); Anjaneyulu Sheri, Shrewsbury, MA (US); Seetharamaiyer Padmanabhan, Lexington, MA (US); Geeta Meher, Milford, MA (US); Shenghua Zhou, Shrewsbury, MA (US); Sreerupa Challa, Shrewsbury, MA (US); Rayomand H. Gimi, Chelmsford, MA (US); Dillon Cleary, Middleborough, MA (US)

(73) Assignee: Sperovie Biosciences, Inc., Hopkinton, MA (US)

(*) Notice: Subject to any disclaimer, the term of this patent is extended or adjusted under 35 U.S.C. 154(b) by 0 days.

(21) Appl. No.: 16/315,472

(22) PCT Filed: Jul. 6, 2017

(86) PCT No.: PCT/US2017/040882
§ 371 (c)(1),
(2) Date: Jan. 4, 2019

(87) PCT Pub. No.: WO2018/009648
PCT Pub. Date: Jan. 11, 2018

(65) Prior Publication Data
US 2019/0262372 A1  Aug. 29, 2019

Related U.S. Application Data

(60) Provisional application No. 62/508,846, filed on May 19, 2017, provisional application No. 62/470,746, filed on Mar. 13, 2017, provisional application No. 62/462,679, filed on Feb. 23, 2017, provisional application No. 62/444,141, filed on Jan. 9, 2017, provisional application No. 62/411,424, filed on Oct. 21, 2016, provisional application No. 62/403,530, filed on Oct. 3, 2016, provisional application No. 62/363,118, filed on Jul. 15, 2016, provisional application No. 62/359,039, filed on Jul. 6, 2016.

(51) Int. Cl.
| A61K 31/7052 | (2006.01) |
| A61K 31/7084 | (2006.01) |
| A61P 35/00 | (2006.01) |
| A61K 9/00 | (2006.01) |
| A61K 39/39 | (2006.01) |
| A61K 45/06 | (2006.01) |
| C07H 21/00 | (2006.01) |
| A61K 39/12 | (2006.01) |
| A61K 39/00 | (2006.01) |

(52) U.S. Cl.
CPC ........ *A61K 31/7084* (2013.01); *A61K 9/0019* (2013.01); *A61K 9/0029* (2013.01); *A61K 39/12* (2013.01); *A61K 39/39* (2013.01); *A61K 45/06* (2013.01); *A61P 35/00* (2018.01); *C07H 21/00* (2013.01); *A61K 2039/55511* (2013.01)

(58) Field of Classification Search
CPC . A61K 31/7052; A61K 31/7084; A61K 39/12
See application file for complete search history.

(56) References Cited

U.S. PATENT DOCUMENTS

| 2014/0220056 A1 | 8/2014 | Shishido et al. |
| 2014/0329889 A1 | 11/2014 | Vance et al. |

FOREIGN PATENT DOCUMENTS

| CN | 102199183 B | 12/2013 |
| WO | WO-2011/003025 A1 | 1/2011 |
| WO | WO-2013/185052 A1 | 12/2013 |
| WO | WO-2014/093936 A1 | 6/2014 |
| WO | WO-2014/189805 A1 | 11/2014 |
| WO | WO-2015/185565 A1 | 12/2015 |
| WO | WO 2016/096174 * | 6/2016 |
| WO | WO-2016.096577 A1 | 6/2016 |
| WO | WO-2016/120305 A1 | 8/2016 |
| WO | WO-2016/145102 A1 | 9/2016 |
| WO | WO-2017/009829 A1 | 1/2017 |
| WO | WO-2017/027645 A1 | 2/2017 |
| WO | WO-2017/027646 A1 | 2/2017 |
| WO | WO-2017/075477 A1 | 5/2017 |
| WO | WO-2017/093933 A1 | 6/2017 |
| WO | WO-2017/096963 A1 | 6/2017 |
| WO | WO 2017/106740 * | 6/2017 |
| WO | WO-2017/106740 A1 | 6/2017 |
| WO | WO-2017/123657 A1 | 7/2017 |
| WO | WO-2017/123669 A1 | 7/2017 |
| WO | WO-2017/151922 A1 | 9/2017 |

(Continued)

OTHER PUBLICATIONS

Pearce et al., Failure modes in anticancer drug discovery and development, Cancer Drug Design and Discovery Edited by Stephen Neidle, Chapter 18, pp. 424-435 (2008).*

(Continued)

*Primary Examiner* — Deepak R Rao
(74) *Attorney, Agent, or Firm* — Foley Hoag LLP; Dana M. Gordon; Alexander J. Chatterley

(57) ABSTRACT

Disclosed are compounds and compositions for the activation or induction of expression of a pattern recognition receptor (e.g., STING, RIG-I, MDA5), and methods of use thereof.

32 Claims, 87 Drawing Sheets

(56) References Cited

FOREIGN PATENT DOCUMENTS

| WO | WO-2018/009466 A1 | 1/2018 |
|---|---|---|
| WO | WO-2018/045204 A1 | 3/2018 |
| WO | WO-2018/067423 A1 | 4/2018 |
| WO | WO-2018/100558 A2 | 6/2018 |
| WO | WO-2018/118664 A1 | 6/2018 |
| WO | WO-2018/118665 A1 | 6/2018 |
| WO | WO-2018/156625 A1 | 8/2018 |
| WO | WO-2018/198076 A1 | 11/2018 |
| WO | WO-2018/208667 A1 | 11/2018 |
| WO | WO-2018/234805 A1 | 12/2018 |
| WO | WO-2018/234807 A1 | 12/2018 |
| WO | WO-2018/234808 A1 | 12/2018 |

OTHER PUBLICATIONS

Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Acute Leukemia, Merck Manual (Online Edition) 6 pages, pp. 1-6 (2013).*
Du et al., "Structure-efficacy Relationships of Immunostimulatory Activity of CpG-containing Oligodeoxynucleotides on Mouse Spleen Cells," Acta Pharm Sinic, 28(10): 1637-1644 (2007).
International Search Report and Written Opinion for International Application No. PCT/US17/40882 dated Sep. 22, 2017.
Libanova et al., "Cyclic di-nucleotides: New Era for Small Molecules as Adjuvants," Microb Biotechnol, 5(2): 168-176 (2012).
Shanahan et al., "Identification of c-di-GMP Derivatives Resistant to an EAL Domain Phosphodiesterase," Biochemistry, 52(2): 365-377 (2013).
Chi et al., "Design and synthesis of specific inhibitors of the 3'-processing step of HIV-1 integrase," Nucleosides, Nucleotides and Nucleic Acids, 24(5-7):481-484 (2005).
Extended European Search Report for EP Application No. 17824876.1 dated Jan. 3, 2020.
Gaffney et al., "One-flask syntheses of c-di-GMP and the [ R p, R p] and [ R p, S p] Thiophosphate analogues," Organic Letters, 12(14):3269-3271 (2010).
Hyodo et al., "Synthesis of cyclic bis(3'-5')diguanylic acid (c-di-GMP) analogs," Tetrahedron, 62(13):3089-3094 (2006).
Shanahan et al., "Differential analogue binding by two classes of c-di-GMP riboswitches," Journal of the American Chemical Society, 133(39): 15578-15592 (2011).
Smietana et al., "Efficient and simple solid-phase synthesis of short cyclic oligodeoxynucleotides bearing a phosphorothioate linkage," Angewandte Chemie, 41(19):3704-3707 (2002).
Smietana et al., "Solid-phase synthesis and screening of macrocyclic nucleotide-hybrid compounds targeted to hepatitis?c?NS5B," Chemistry—A European Journal, 10(1):173-181 (2004).
Tezuka et al., "Synthesis of 2'-modified cyclic bis(3'-5') diadenylic acids (c-di-AMPs) and their promotion of cell division in a freshwater green alga," Chemistry Letters, 41(12):1723-1725 (2012).
Zhao et al., "Thiophosphate analogs of c-Di-GMP: Impact on polymorphism," Nucleosides, Nucleotides and Nucleic Acids, 28(5):352-378 (2009).
Zhou et al., "Potent suppression of c-di-GMP synthesis via I-site allosteric inhibition of diguanylate cyclases with 2'F-c-di-GMP," Bioorganic & Medicinal Chemistry, 21(14):4396-4404 (2013).

* cited by examiner

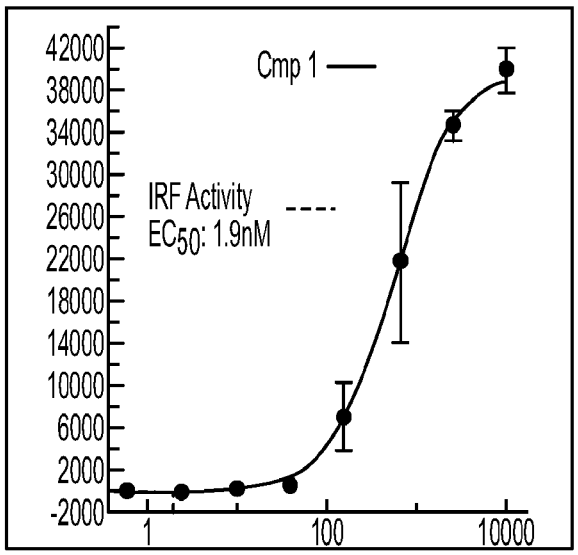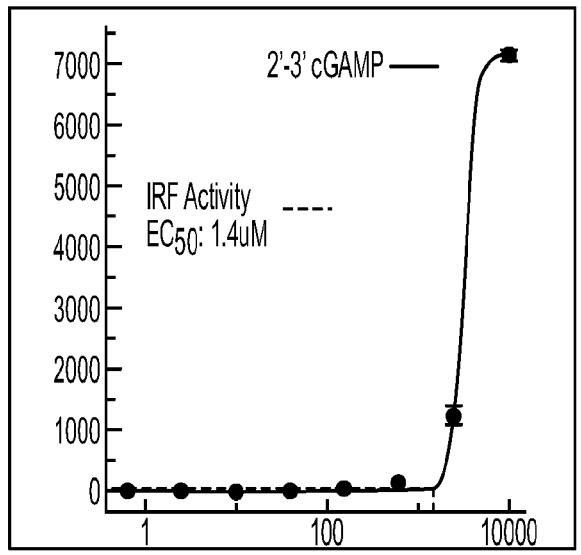
FIG. 2A  FIG. 2B
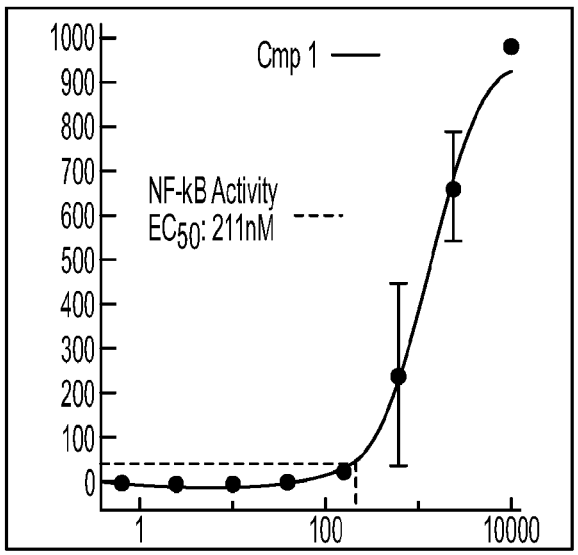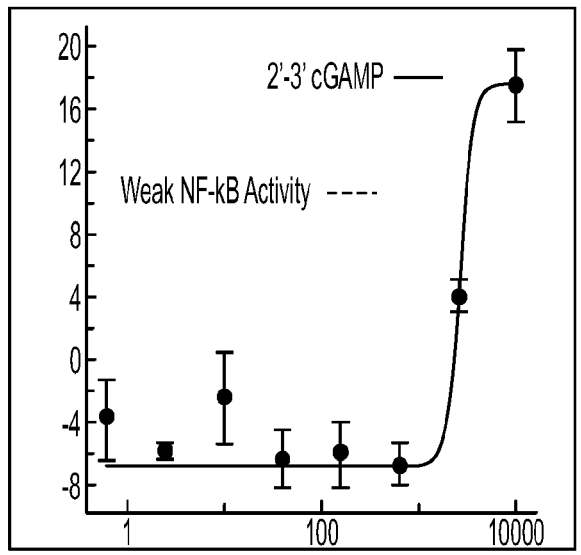
FIG. 2C  FIG. 2D

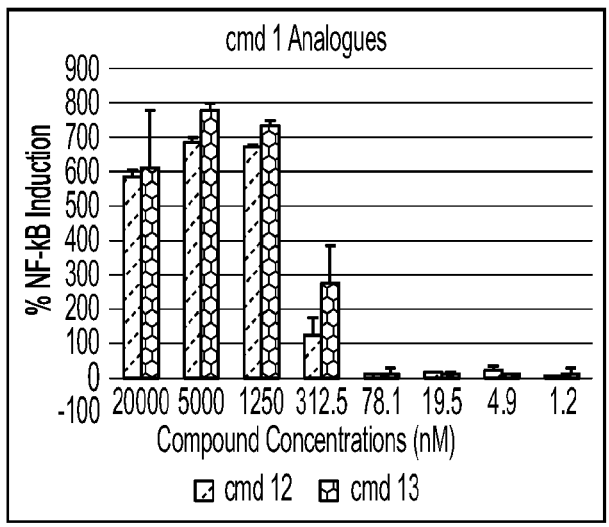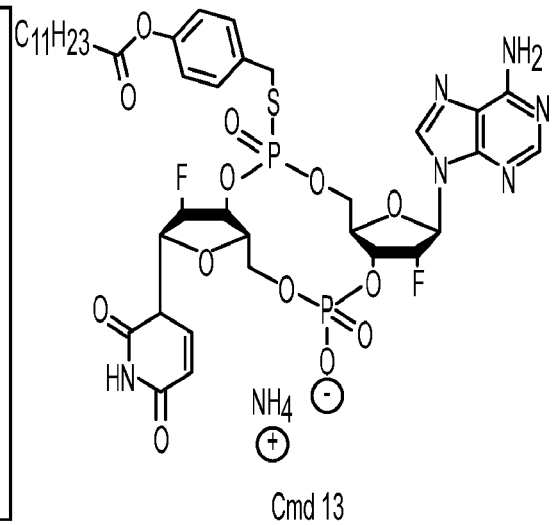
FIG. 21A
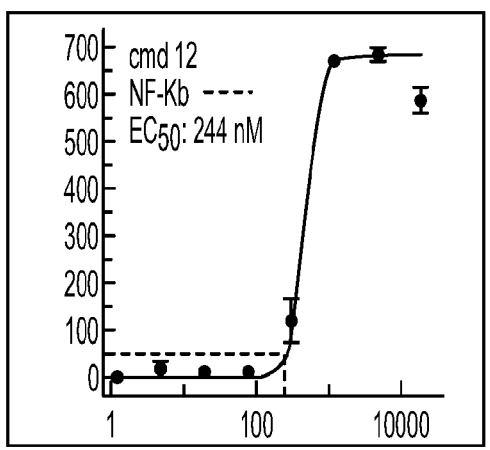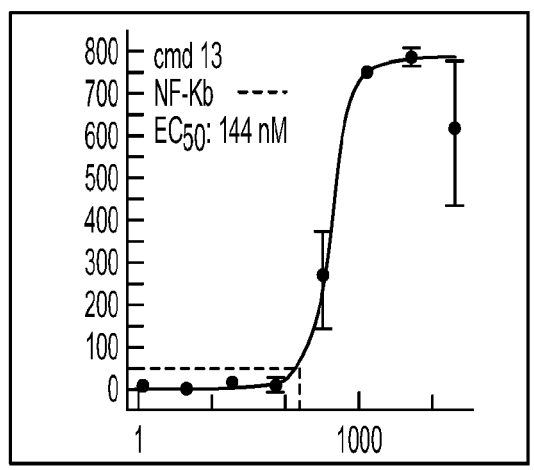
FIG. 21B
FIG. 21C

| Polymorphisms | Human Population Percentage |
|---|---|
| WT STING | 57.9% |
| R71H-G230A-R293Q (HAQ) | 20.4% |
| R232H | 13.7% |
| G230A-R293Q (AQ) | 5.2% |
| R293Q | 1.5% |

| Group | Number | Agent | Dosing | Route |
|---|---|---|---|---|
| Vehicle | 10 | Saline | 1,2,4,6 & 8 | Intra tumoral (i.t) |
| Cmd 1 | 10 | 100 μg | 1,2,4,6 & 8 | Intra tumoral (i.t) |

- Group 1: vehicle (itu, days 3,4,6,8,10)
- Group 2: VS1 (100 µg/animal,itu, days 3,4,6,8,10)
- Group 3: cyclophosphamide (100 mg/kg,ip, days 1,2)
- Group 4: cyclophosphamide (100 mg/kg,ip, days 1,2), VS1 (100 µg/animal,itu, days 3,4,6,8,10)

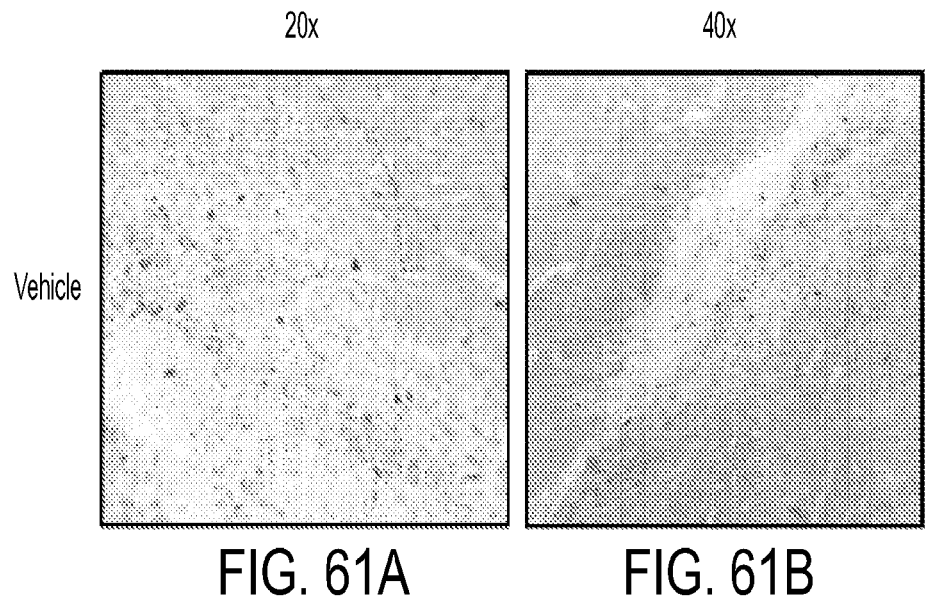
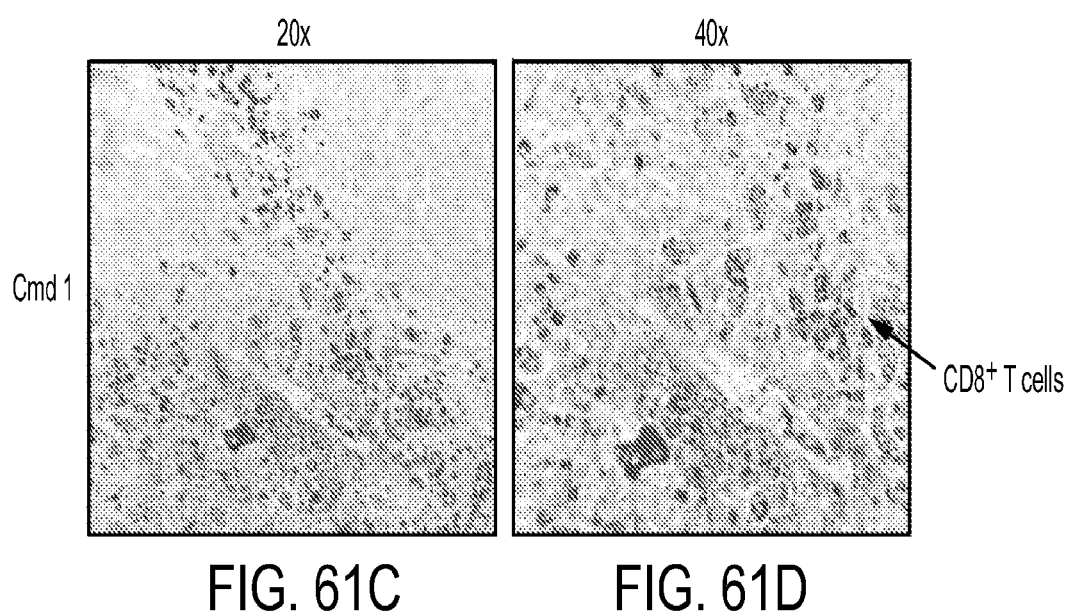

| Group | Number | Agent | Dosing | Route | Mean Tumor Vol (day 12) mm³ |
|---|---|---|---|---|---|
| Vehicle | 10 | Saline | 1,4,7,10 & 17 | i.t | 1196 |
| Cmd 1 | 10 | 50 μg | 1,4,7,10 & 17 | i.t | 222 |
| Anti-CTLA4 Ab | 10 | 5 mg/kg (followed by 2.5 mg/kg) | 1, (4 & 7) | i.p | 906 |
| Anti-CTLA4 Ab + Cmd 1 | 10 | 5 mg/kg (followed by 2.5 mg/kg) + (50ug) | 1, (4 & 7) + (1,4,7,10 & 17) | i.p + (i.t) | 173 |

Tumor tissue from Vehicle

Tumor tissue from Cmd 1 (i.t) on days 3,4,6,8 &10

Tumor tissue from vehicle group

Tumor tissue from Cmd 1 group (i.t) on days 3,4,6,8 &10

Tumor tissue from vehicle group

Tumor tissue from Cmd 1 group (i.t) on days 3,4,6,8 &10

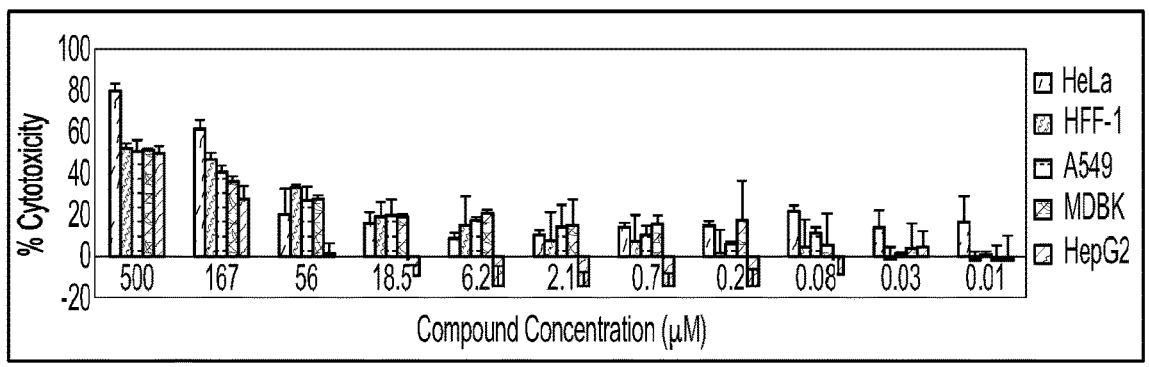
FIG. 68A
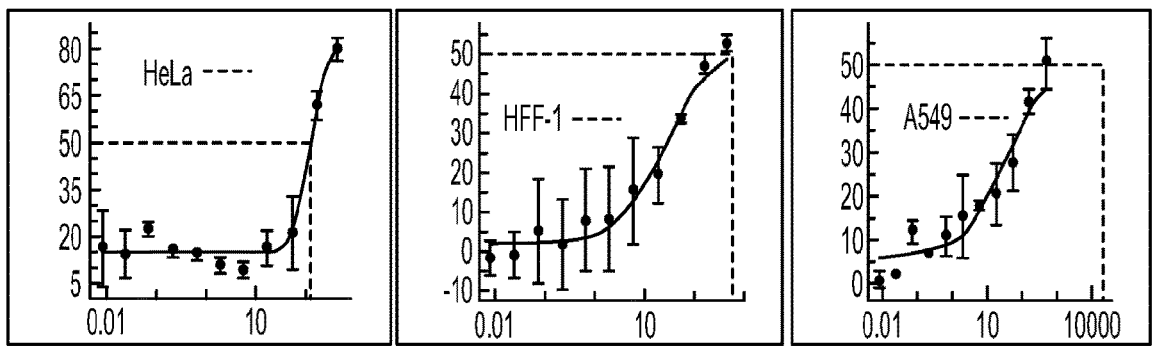
FIG. 68B  FIG. 68C  FIG. 68D
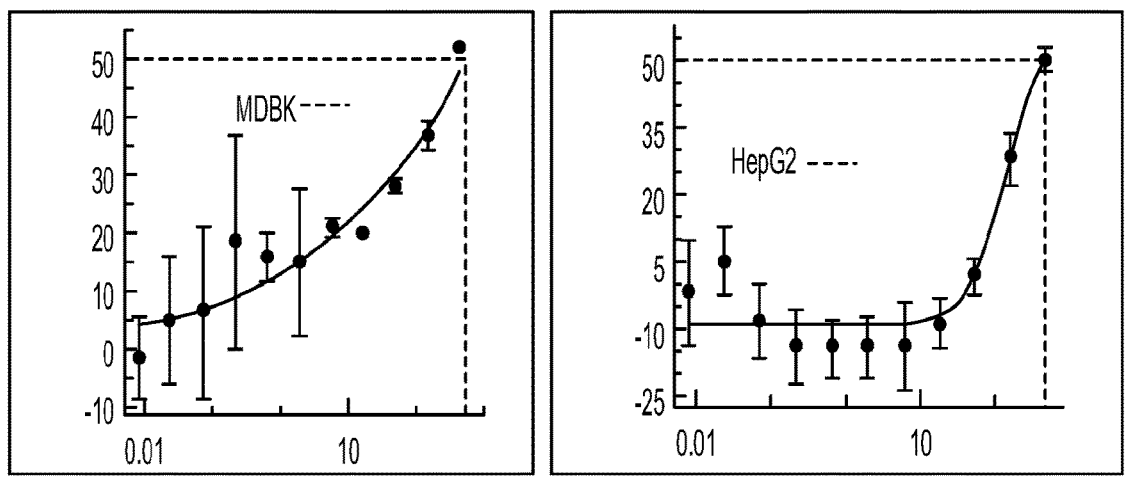
FIG. 68E  FIG. 68F
| Name | HeLa | HFF-1 | A549 | MDBK | HepG2 |
|---|---|---|---|---|---|
| $CC_{50}(\mu M)$ | 128 | > 500 | > 500 | > 500 | 481 |
FIG. 68G

COMPOUNDS, COMPOSITIONS, AND METHODS FOR THE TREATMENT OF DISEASE

RELATED APPLICATIONS

This application is a U.S. § 371 national stage application based on Patent Cooperation Treaty Application No. PCT/US2017/040882, filed Jul. 6, 2017; which claims the benefit of priority to U.S. provisional patent application Nos. 62/359,039, filed Jul. 6, 2016; 62/363,118, filed Jul. 15, 2016; 62/403,530, filed Oct. 3, 2016; 62/411,424, filed Oct. 21, 2016; 62/444,141, filed Jan. 9, 2017; 62/462,679, filed Feb. 23, 2017; 62/470,746, filed Mar. 13, 2017; and 62/508,846, May 19, 2017.

FIELD OF DISCLOSURE

This disclosure relates to compounds and compositions that activate the innate immune defense system and induce expression of pattern recognition receptors in a host, as well as methods of use for the treatment of a proliferative disease (e.g., cancer).

BACKGROUND OF DISCLOSURE

A key feature of the innate immune system is the recognition and elimination of foreign substances. Identification of these pathogenic invaders occurs through host recognition of evolutionarily conserved microbial structures known as pathogen-associated molecular patterns (PAMPs) (Jensen, S. and Thomsen, A. R. *J Virol* (2012) 86:2900-2910). These PAMPs include a wide array of molecular structures, such as nucleic acids, lipopolysaccharides, and glycoproteins that may be broadly shared by multiple microbial species and are critical to their survival and/or pathogenicity. Host recognition may occur by multiple pathways, such as activation of pattern recognition receptors (PRRs), which ultimately lead to downstream signaling events and culminate in the mounting of an immune response.

To date, several PRRs have been identified that serve as sensors of pathogenic infection. For example, the retinoic acid-inducible gene-I (RIG-I) protein is a RNA helicase that also functions as a sensor of microbial-derived RNA. RIG-I is important factor in host recognition of RNA viruses from a variety of different viral families, including Flaviviridae (e.g., West Nile virus, Hepatitis C virus, Japanese encephalitis virus, Dengue virus), Paramyxoviridae (e.g., Sendai virus, Newcastle disease virus, Respiratory syncytial virus, Measles virus), Rhabdoviridae (e.g., Rabies virus), Orthomyxoviridae (e.g., influenza A virus, influenza B virus), and Arenaviridae (e.g., Lassa virus), as well as a biomarker for the prediction of prognosis for certain types of cancer, such as hepatocellular carcinoma (Hou, J. et al, *Cancer Cell* (2014) 25:49-63). The stimulator of interferon genes (STING) is a cytoplasmic adaptor protein that activates the TBK1-IRF3 signaling complex, resulting in induction of type I interferons (IFN-β and IFN-α) and other immune pathway proteins. Other PRRs also play a role in sensing microbial-derived nucleic acids, including NOD2, LGP2, MDA5, and a number of Toll-like receptors (TLRs) that are expressed on the cell surface and within endosomal compartments.

Recent publications have highlighted the importance of RIG-I and STING as mediators of innate and adaptive immunity, and RIG-I and STING agonists have been recognized as immuno-oncology agents in cancer therapy (Li, X. Y. et al, *Mol Cell Oncol* (2014) 1:e968016; Woo, S. R. *Trends in Immunol* (2015) 36:250-256). In particular, RIG-I is involved in the regulation of basic cellular processes such as hematopoietic proliferation and differentiation, maintenance of leukemic sternness, and tumorigenesis of hepatocellular carcinoma, indicating that RIG-I performs an essential function as a tumor suppressor. Importantly, the STING pathway of cytosolic DNA sensing has been shown to play an important mechanistic role in innate immune sensing, driving type I IFN production in cancer and in the context of immune-oncology applications including therapeutics and diagnostics.

SUMMARY OF DISCLOSURE

Cyclic dinucleotide compounds, compositions comprising cyclic dinucleotide compounds, and related methods of use are described herein.

In one aspect, the disclosure features a compound of Formula (I):

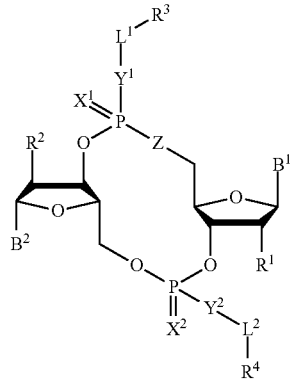

Formula (I)

or a pharmaceutically acceptable salt or stereoisomer thereof, wherein: Z is either S or O; each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), OC(O) $OC_1$-$C_{20}$ alkyl (e.g., $C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl (e.g., $C_1$-$C_6$ alkyl), C(O)O—$C_1$-$C_{20}$ alkyl (e.g., $C_1$-$C_6$ alkyl), OC(O)O—$C_1$-$C_{20}$ alkyl (e.g., $C_1$-$C_6$ alkyl), C(O)N($R^5$)—$C_1$-$C_{20}$ alkyl (e.g., $C_1$-$C_6$ alkyl), N($R^5$)C(O)—$C_1$-$C_{20}$ alkyl (e.g., $C_1$-$C_6$ alkyl), OC(O)N($R^5$)—$C_1$-$C_{20}$ alkyl (e.g., $C_1$-$C_6$ alkyl), O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N($R^5$)-aryl, C(O)N($R^5$)-heteroaryl, N($R^5$)C(O)-aryl, N($R^5$)$_2$C(O)-aryl, or N($R^5$)C(O)-heteroaryl, S(O)$_2$N($R^5$)-aryl, wherein each alkyl, heteroalkyl, aryl, and heteroaryl is optionally substituted by one or more $R^9$; and each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

In some embodiments, the compound is a compound of Formula (I-a):

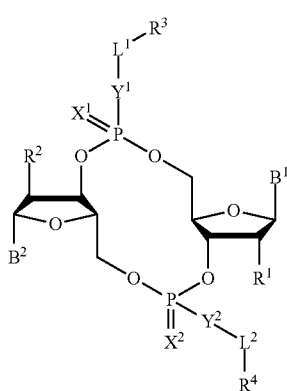

Formula (I-a)

or a pharmaceutically acceptable salt or stereoisomer thereof, wherein each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl, C(O)O—$C_1$-$C_{20}$ alkyl, OC(O)O—$C_1$-$C_{20}$ alkyl, C(O)N($R^5$)—$C_1$-$C_{20}$ alkyl, N($R^5$)C(O)—$C_1$-$C_{20}$ alkyl, OC(O)N($R^5$)—$C_1$-$C_{20}$ alkyl, O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N($R^5$)-aryl, C(O)N($R^5$)-heteroaryl, N($R^5$)C(O)-aryl, or N($R^5$)C(O)-heteroaryl, wherein each alkyl, heteroalkyl, aryl, and heteroaryl is optionally substituted by one or more $R^9$; and each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

In some embodiments, each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), cycloalkyl, heterocyclyl, aryl, or heteroaryl, wherein each alkyl, heteroalkyl, cycloalkyl, heterocyclyl, aryl, and heteroaryl is optionally substituted with 1-5 $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with 1-5 $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with 1-5 $R^9$; each $R^8$ is independently $C_1$-$C_{20}$ alkyl (e.g., $C_1$-$C_6$ alkyl), C(O)-aryl, C(O)-heteroaryl, OC(O)-aryl, C(O)O-aryl, OC(O)-heteroaryl, or C(O)O-heteroaryl, wherein each alkyl, aryl, and heteroaryl is optionally substituted by 1-5 $R^9$; and each $R^9$ is independently $C_1$-$C_{20}$ alkyl, O—$C_1$-$C_{20}$ alkyl, halo, —CN, OH, O—$C_1$-$C_{20}$ alkyl, O—$C_1$-$C_{20}$ heteroalkyl, O-aryl, or O-heteroaryl.

In some embodiments, the compound is a compound of Formulas (I-b), (I-c), (I-d), or (I-e):

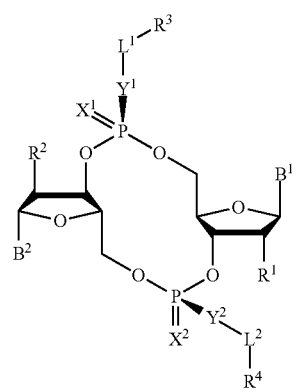

Formula (I-b)

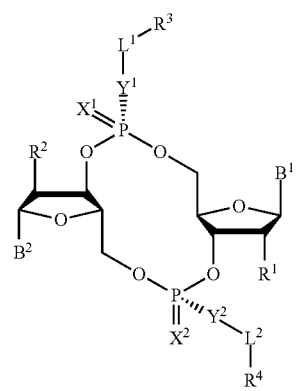

Formula (I-c)

-continued

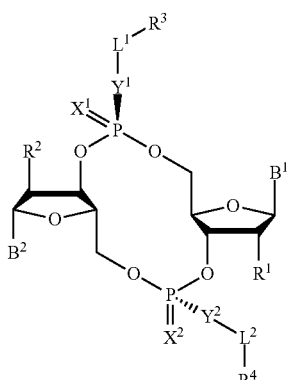

Formula (I-d)

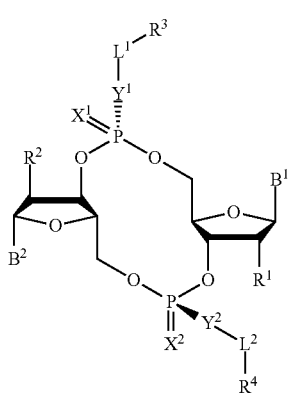

Formula (I-e)

or a pharmaceutically acceptable salt thereof, wherein each of $B^1$, $B^2$, $X^1$, $X^2$, $Y^1$, $Y^2$, $L^1$, $L^2$, $R^1$, $R^2$, $R^3$, $R^4$, and subvariables thereof are defined as above.

In some embodiments, at least one of $B^1$ or $B^2$ is a purinyl nucleobase. In some embodiments, each of $B^1$ or $B^2$ is independently a purinyl nucleobase. In some embodiments, $B^1$ is a purinyl nucleobase. In some embodiments, $B^2$ is a pyrimidinyl nucleobase. In some embodiments, $B^1$ is a purinyl nucleobase and $B^2$ is a pyrimidinyl nucleobase. In some embodiments, $B^1$ is adenosinyl or guanosinyl. In some embodiments, $B^2$ is cytosinyl, thyminyl, or uracilyl. In some embodiments, $B^1$ is adenosinyl or guanosinyl and $B^2$ is cytosinyl, thyminyl, or uracilyl. In some embodiments, each of $B^1$ is and $B^2$ is independently uracilyl. In some embodiments, each of $B^1$ is and $B^2$ is independently adenosinyl.

In some embodiments, each of $R^1$ and $R^2$ is independently hydrogen, halo, or $OR^7$. In some embodiments, each of $R^1$ and $R^2$ is independently halo (e.g., fluoro). In some embodiments, each of $R^1$ and $R^2$ is not hydrogen or $OR^7$.

In some embodiments, $X^1$ is O. In some embodiments, $X^2$ is O. In some embodiments, each of $X^1$ and $X^2$ is independently O.

In some embodiments, $Y^1$ is O or S. In some embodiments, $Y^2$ is O or S. In some embodiments, each of $Y^1$ and $Y^2$ is independently O or S. In some embodiments, one of $Y^1$ or $Y^2$ is O and the other of $Y^1$ or $Y^2$ is S. In some embodiments, each of $Y^1$ or $Y^2$ is independently S. In some embodiments, each of $Y^1$ or $Y^2$ is independently O.

In some embodiments, $L^1$ is $C_1$-$C_6$ alkyl (e.g., $CH_2$). In some embodiments, $L^2$ is $C_1$-$C_6$ alkyl (e.g., $CH_2$). In some embodiments, each of $L^1$ and $L^2$ is independently $C_1$-$C_6$ alkyl (e.g., $CH_2$).

In some embodiments, $R^3$ is hydrogen, aryl, or heteroaryl, wherein aryl and heteroaryl is optionally substituted with 1-5 $R^8$. In some embodiments, $R^3$ is aryl or heteroaryl, each of which is optionally substituted with 1-5 $R^8$. In some embodiments, $R^3$ is phenyl substituted with 1 $R^8$.

In some embodiments, $R^4$ is independently hydrogen, aryl, or heteroaryl, wherein aryl and heteroaryl is optionally substituted with 1-5 $R^8$. In some embodiments, $R^4$ is aryl or heteroaryl, each of which is optionally substituted with 1-5 $R^8$. In some embodiments, $R^4$ is phenyl substituted with 1 $R^8$.

In some embodiments, each of $R^3$ and $R^4$ is independently hydrogen, aryl, or heteroaryl, wherein aryl and heteroaryl is optionally substituted with 1-5 $R^8$. In some embodiments, $R^3$ is aryl or heteroaryl, each of which is optionally substituted with 1-5 $R^8$, and $R^4$ is hydrogen. In some embodiments, $R^3$ is phenyl substituted with 1 $R^8$ and $R^4$ is hydrogen. In some embodiments, each of $R^3$ and $R^4$ is independently phenyl substituted with 1 $R^8$.

In some embodiments, each of $Y^1$ and $Y^2$ is O and each of $R^3$ and $R^4$ is independently hydrogen. In some embodiments, $Y^2$ is O and $R^4$ is hydrogen. In some embodiments, each of $Y^1$ and $Y^2$ is independently S and each of $R^3$ and $R^4$ is independently substituted with 1 $R^8$. In some embodiments, $Y^1$ is S and $R^3$ is substituted with 1 $R^8$.

In some embodiments, each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl, OC(O)O—$C_1$-$C_{20}$ alkyl, OC(O)N($R^5$)—$C_1$-$C_{20}$ alkyl, O-aryl, C(O)-aryl, OC(O)-aryl, or C(O)N($R^5$)-aryl, wherein each alkyl, heteroalkyl, aryl, and heteroaryl is optionally substituted by one or more $R^9$.

In some embodiments, $R^8$ is OC(O)-aryl optionally substituted by 1-5 $R^9$ (e.g., 1 $R^9$).

In some embodiments, $R^9$ is O—$C_1$-$C_{12}$ alkyl (e.g., O—$CH_2(CH_2)CH_3$). In some embodiments, $R^9$ is O—$C_1$-$C_{10}$ alkyl (e.g., O—$CH_2(CH_2)CH_3$). In some embodiments, $R^9$ is O—$C_1$-$C_8$ alkyl (e.g., O—$CH_2(CH_2)_6CH_3$). In some embodiments, $R^9$ is O—$C_1$-$C_6$ alkyl (e.g., O—$CH_2(CH_2)_4CH_3$).

In some embodiments, the compound is a compound of Formula (I-f):

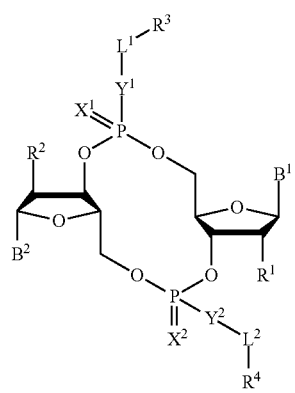

Formula (I-f)

or a pharmaceutically acceptable salt or stereoisomer thereof, wherein each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_{20}$ alkyl (e.g., $C_1$-$C_6$ alkyl) or $C_1$-$C_{20}$ heteroalkyl (e.g., $C_1$-$C_6$ heteroalkyl), wherein each $C_1$-$C_{20}$ alkyl and $C_1$-$C_{20}$ heteroalkyl is optionally substituted with $R^6$;

each of $R^1$ and $R^2$ is independently halo; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), cycloalkyl, heterocyclyl, aryl, or heteroaryl, wherein each $C_1$-$C_{20}$ alkyl, $C_1$-$C_{20}$ heteroalkyl, cycloalkyl, heterocyclyl, aryl, and heteroaryl is optionally substituted with 1-5 $R^8$; $R^5$ is hydrogen or $C_1$-$C_6$ alkyl; $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each $C_1$-$C_{20}$ alkyl, cycloalkyl, heterocyclyl, aryl, or heteroaryl is optionally substituted with 1-5 $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each $C_1$-$C_{20}$ alkyl, cycloalkyl, heterocyclyl, aryl, or heteroaryl is optionally substituted with 1-5 $R^9$; each $R^8$ is independently $C_1$-$C_{20}$ alkyl (e.g., $C_1$-$C_6$ alkyl), C(O)-aryl, C(O)-heteroaryl, OC(O)-aryl, or OC(O)-heteroaryl, wherein each $C_1$-$C_{20}$ alkyl, C(O)-aryl, C(O)-heteroaryl, OC(O)-aryl, or OC(O)-heteroaryl is optionally substituted by 1-5 $R^9$; and each $R^9$ is independently $C_1$-$C_{20}$ alkyl, halo, —CN, OH, O—$C_1$-$C_{20}$ alkyl, O—$C_1$-$C_{20}$heteroalkyl, O-aryl, or O-heteroaryl.

In some embodiments, the compound is a compound of Formula (I-g):

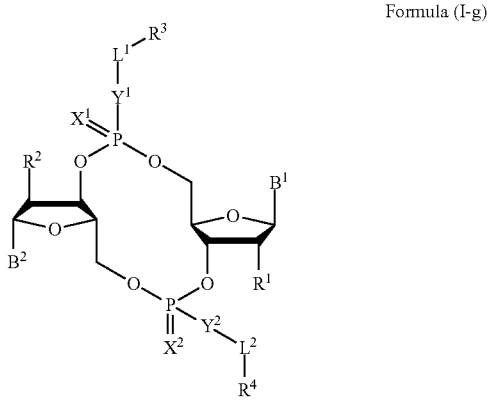

Formula (I-g)

or a pharmaceutically acceptable salt or stereoisomer thereof, wherein each of $B^1$ and $B^2$ is independently a purinyl nucleobase or pyrimidinyl nucleobase; each of $X^1$ and $X^2$ is independently O; each of $Y^1$ and $Y^2$ is independently O or S; each of $L^1$ and $L^2$ is independently absent or $C_1$-$C_6$ alkyl; each of $R^1$ and $R^2$ is independently halo or OH; each of $R^3$ and $R^4$ is independently hydrogen or aryl optionally substituted with 1-5 $R^8$; each $R^8$ is independently OC(O)-aryl optionally substituted by 1-5 $R^9$; and each $R^9$ is independently O—$C_1$-$C_{12}$ alkyl.

In some embodiments, the compound of Formula (I) is selected from a compound of Table 1, Table 2, or a pharmaceutically acceptable salt thereof.

In some embodiments, the compound of Formula (I-a) is selected from a compound of Table 1, Table 2, or a pharmaceutically acceptable salt thereof.

In another aspect, the disclosure features a method of treating cancer in a subject, the method comprising administering to the subject a compound of Formula (I),

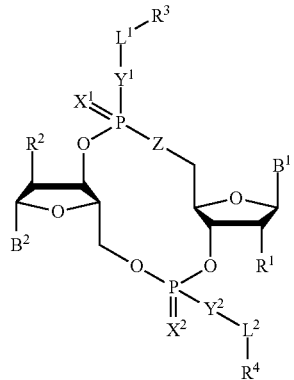

Formula (I)

or a pharmaceutically acceptable salt or stereoisomer thereof, wherein: Z is either S or O; each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), OC(O) O$C_1$-$C_{20}$ alkyl (e.g., $C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl (e.g., $C_1$-$C_6$ alkyl), C(O)O—$C_1$-$C_{20}$ alkyl (e.g., $C_1$-$C_6$ alkyl), OC(O)O—$C_1$-$C_{20}$ alkyl (e.g., $C_1$-$C_6$ alkyl), C(O)N($R^5$)—$C_1$-$C_{20}$ alkyl (e.g., $C_1$-$C_6$ alkyl), N($R^5$)C(O)—$C_1$-$C_{20}$ alkyl (e.g., $C_1$-$C_6$ alkyl), OC(O)N($R^5$)—$C_1$-$C_{20}$ alkyl (e.g., $C_1$-$C_6$ alkyl), O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N($R^5$)-aryl, C(O)N($R^5$)-heteroaryl, N($R^5$)C(O)-aryl, N($R^5$)$_2$C(O)-aryl, or N($R^5$)C(O)-heteroaryl, S(O)$_2$N($R^5$)-aryl, wherein each alkyl, heteroalkyl, aryl, and heteroaryl is optionally substituted by one or more $R^9$; and each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

In some embodiments, the disclosure features a method of treating cancer in a subject, the method comprising administering to the subject a compound of Formula (I-a),

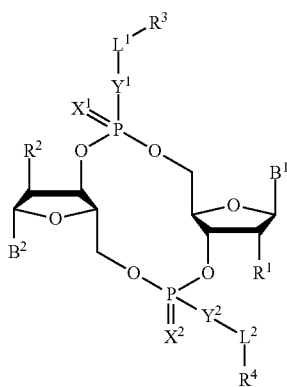

Formula (I-a)

or a pharmaceutically acceptable salt or stereoisomer thereof, wherein each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl, C(O)O—$C_1$-$C_{20}$ alkyl, OC(O)O—$C_1$-$C_{20}$ alkyl, C(O)N($R^5$)—$C_1$-$C_{20}$ alkyl, N($R^5$)C(O)—$C_1$-$C_{20}$ alkyl, OC(O)N($R^5$)—$C_1$-$C_{20}$ alkyl, O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N($R^5$)-aryl, C(O)N($R^5$)-heteroaryl, N($R^5$)C(O)-aryl, or N($R^5$)C(O)-heteroaryl, wherein each alkyl, heteroalkyl, aryl, and heteroaryl is optionally substituted by one or more $R^9$; and each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

In some embodiments, the cancer is a cancer of the breast, bone, brain, cervix, colon, gastrointestinal tract, eye, gall bladder, lymph nodes, blood, lung, liver, skin, mouth, prostate, ovary, penis, pancreas, uterus, testicles, stomach, thymus, thyroid, or other part of the body (e.g., a cancer of the liver). In some embodiments, the cancer has differential expression of STING relative to the noncancerous tissue, e.g., liver cancer, melanoma, skin cancer, or thyrod cancer.

In some embodiments, the cancer comprises a PD-1 resistant tumor.

In some embodiments, the method comprises oral administration of the compound of Formula (I) or a pharmaceutically acceptable salt thereof, or a pharmaceutical composition thereof. In some embodiments, the method comprises oral administration of the compound of Formula (I-a) or a pharmaceutically acceptable salt thereof, or a pharmaceutical composition thereof. In some embodiments, the method comprises parenteral administration (e.g., subcutaneous, intramuscular, intraperitoneal, or intravenous administration) of the compound of Formula (I) or a pharmaceutically acceptable salt thereof, or a pharmaceutical composition thereof. In some embodiments, the method comprises parenteral administration (e.g., subcutaneous, intramuscular, intraperitoneal, or intravenous administration) of the compound of Formula (I-a) or a pharmaceutically acceptable salt thereof, or a pharmaceutical composition thereof. In some embodiments, the method comprises intraperitoneal administration of the compound of Formula (I) or a pharmaceutically acceptable salt thereof, or a pharmaceutical composition thereof. In some embodiments, the method comprises intraperitoneal administration of the compound of Formula (I-a) or a pharmaceutically acceptable salt thereof, or a pharmaceutical composition thereof. In some embodiments, the method comprises intratumoral administration of the compound of Formula (I) or a pharmaceutically acceptable salt thereof, or a pharmaceutical composition thereof. In some embodiments, the method comprises intratumoral administration of the compound of Formula (I-a) or a pharmaceutically acceptable salt thereof, or a pharmaceutical composition thereof.

In some embodiments, the method further comprises administration of an additional agent (e.g., an anticancer agent or an immunooncology agent). In some embodiments, the additional agent comprises methotrexate, 5-fluorouracil, doxorubicin, vincristine, bleomycin, vinblastine, dacarbazine, toposide, cisplatin, epirubicin, or sorafenib tosylate.

In another aspect, the disclosure features a composition comprising a vaccine, and a vaccine adjuvant comprising a compound of Formula (I),

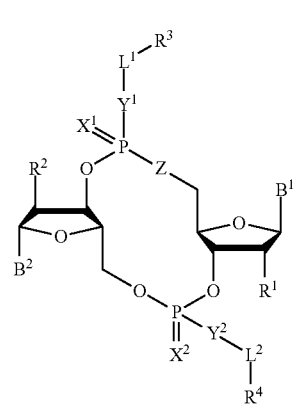

Formula (I)

or a pharmaceutically acceptable salt or stereoisomer thereof, wherein: Z is either S or O; each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), OC(O) O$C_1$-$C_{20}$ alkyl (e.g., $C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl (e.g., $C_1$-$C_6$ alkyl), C(O)O—$C_1$-$C_{20}$ alkyl (e.g., $C_1$-$C_6$ alkyl), OC(O)O—$C_1$-$C_{20}$ alkyl (e.g., $C_1$-$C_6$ alkyl), C(O)N($R^5$)—$C_1$-$C_{20}$ alkyl (e.g., $C_1$-$C_6$ alkyl), N($R^5$)C(O)—$C_1$-$C_{20}$ alkyl (e.g., $C_1$-$C_6$ alkyl), OC(O)N($R^5$)—$C_1$-$C_{20}$ alkyl (e.g., $C_1$-$C_6$ alkyl), O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N($R^5$)-aryl, C(O)N($R^5$)-heteroaryl, N($R^5$)C(O)-aryl, N($R^5$)$_2$C(O)-aryl, or N($R^5$)C(O)-heteroaryl, S(O)$_2$N($R^5$)-aryl, wherein each alkyl, heteroalkyl, aryl, and heteroaryl is optionally substituted by one or more $R^9$; and each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

In some embodiments, the disclosure features a composition comprising a vaccine, and a vaccine adjuvant comprising a compound of Formula (I-a),

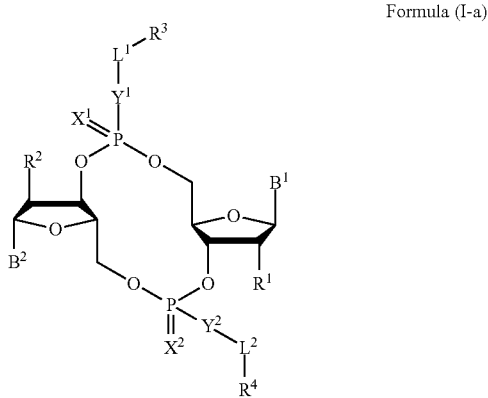

Formula (I-a)

or a pharmaceutically acceptable salt or stereoisomer thereof, wherein each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl, C(O)O—$C_1$-$C_{20}$ alkyl, OC(O)O—$C_1$-$C_{20}$ alkyl, C(O)N($R^5$)—$C_1$-$C_{20}$ alkyl, N($R^5$)C(O)—$C_1$-$C_{20}$ alkyl, OC(O)N($R^5$)—$C_1$-$C_{20}$ alkyl, O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N($R^5$)-aryl, C(O)N($R^5$)-heteroaryl, N($R^5$)C(O)-aryl, or N($R^5$)C(O)-heteroaryl, wherein each alkyl, heteroalkyl, aryl, and heteroaryl is optionally substituted by one or more $R^9$; each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl, wherein each alkyl, heteroalkyl, aryl, or heteroaryl is optionally substituted with one or more $R^{10}$; each $R^{10}$ is independently $C_1$-$C_{20}$ alkyl, $C_1$-$C_{20}$ alkenyl, $C_1$-$C_{20}$ alkynyl, $C_1$-$C_{20}$ heteroalkyl, halo, —CN, or OH, oxo; and each $R^5$ is independently hydrogen or $C_1$-$C_{20}$ alkyl.

In another aspect, the disclosure features a method of inducing the expression of a pattern recognition receptors (PRR) for immune-modulation in a subject, the method comprising administering to the subject a compound of Formula (I),

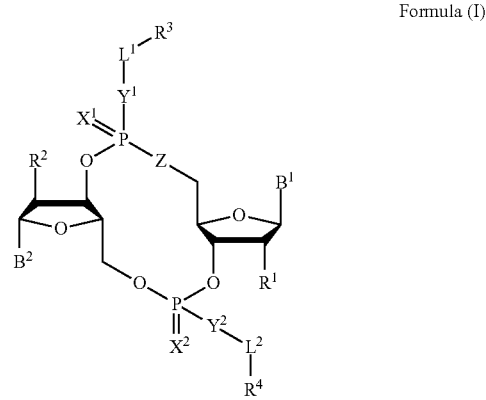

Formula (I)

or a pharmaceutically acceptable salt or stereoisomer thereof, wherein: Z is either S or O; each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), OC(O) OC$_1$-$C_{20}$ alkyl (e.g., $C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl (e.g., $C_1$-$C_6$ alkyl), C(O)O—$C_1$-$C_{20}$ alkyl (e.g., $C_1$-$C_6$ alkyl), OC(O)O—$C_1$-$C_{20}$ alkyl (e.g., $C_1$-$C_6$ alkyl), C(O)N($R^5$)—$C_1$-$C_{20}$ alkyl (e.g., $C_1$-$C_6$ alkyl), N($R^5$)C(O)—$C_1$-$C_{20}$ alkyl (e.g., $C_1$-$C_6$ alkyl), OC(O)N($R^5$)—$C_1$-$C_{20}$ alkyl (e.g., $C_1$-$C_6$ alkyl), O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N($R^5$)-aryl, C(O)N($R^5$)-heteroaryl, N($R^5$)C(O)-aryl, N($R^5$)$_2$C(O)-aryl, or N($R^5$)C(O)-heteroaryl, S(O)$_2$N($R^5$)-aryl, wherein each alkyl, heteroalkyl, aryl, and heteroaryl is optionally substituted by one or more $R^9$; and each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

In some embodiments, the disclosure features a method of inducing the expression of a pattern recognition receptors (PRR) for immune-modulation in a subject, the method comprising administering to the subject a compound of Formula (I-a),

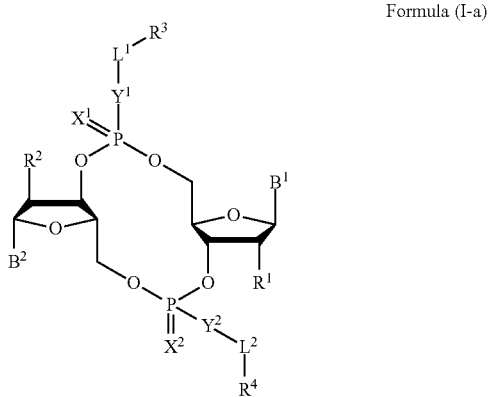

Formula (I-a)

or a pharmaceutically acceptable salt or stereoisomer thereof, wherein each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl, C(O)O—$C_1$-$C_{20}$ alkyl, OC(O)O—$C_1$-$C_{20}$ alkyl, C(O)N($R^5$)—$C_1$-$C_{20}$ alkyl, N($R^5$)C(O)—$C_1$-$C_{20}$ alkyl, OC(O)N($R^5$)—$C_1$-$C_{20}$ alkyl, O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N($R^5$)-aryl, C(O)N($R^5$)-heteroaryl, N($R^5$)C(O)-aryl, or N($R^5$)C(O)-heteroaryl, wherein each alkyl, heteroalkyl, aryl, and heteroaryl is optionally substituted by one or more $R^9$; each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

In another aspect, the disclosure features a method of inducing the expression of a pattern recognition receptor (PRR) for immunomodulation and inducing a therapeutic response in a subject having cancer, the method comprising administering to the subject a compound of Formula (I),

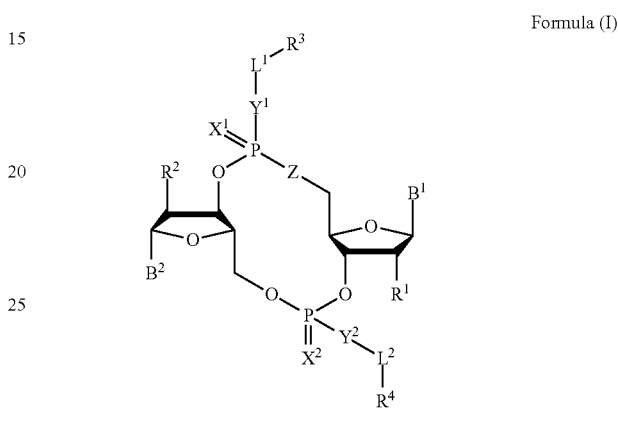

Formula (I)

or a pharmaceutically acceptable salt or stereoisomer thereof, wherein: Z is either S or O; each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), OC(O) O$C_1$-$C_{20}$ alkyl (e.g., $C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl (e.g., $C_1$-$C_6$ alkyl), C(O)O—$C_1$-$C_{20}$ alkyl (e.g., $C_1$-$C_6$ alkyl), OC(O)O—$C_1$-$C_{20}$ alkyl (e.g., $C_1$-$C_6$ alkyl), C(O)N($R^5$)—$C_1$-$C_{20}$ alkyl (e.g., $C_1$-$C_6$ alkyl), N($R^5$)C(O)—$C_1$-$C_{20}$ alkyl (e.g., $C_1$-$C_6$ alkyl), OC(O)N($R^5$)—$C_1$-$C_{20}$ alkyl (e.g., $C_1$-$C_6$ alkyl), O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N($R^5$)-aryl, C(O)N($R^5$)-heteroaryl, N($R^5$)C(O)-aryl, N($R^5$)$_2$C(O)-aryl, or N($R^5$)C(O)-heteroaryl, S(O)$_2$N($R^5$)-aryl, wherein each alkyl, heteroalkyl, aryl, and heteroaryl is optionally substituted by one or more $R^9$; and each $R^9$ is independently $C_1$-$C_{20}$ alkyl, O—$C_1$-$C_{20}$ alkyl, $C_1$-$C_{20}$ heteroalkyl, O—$C_1$-$C_{20}$—$NR^{10}R^{10}$, halo, —CN, OH, oxo, aryl, heteroaryl, O-aryl, or O-heteroaryl.

In some embodiments, the disclosure features a method of inducing the expression of a pattern recognition receptor (PRR) for immunomodulation and inducing a therapeutic response in a subject having cancer, the method comprising administering to the subject a compound of Formula (I-a),

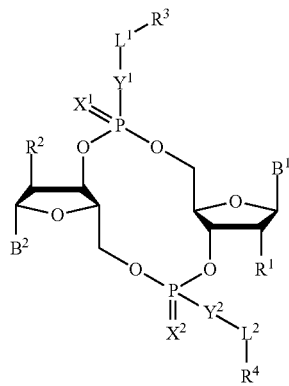

Formula (I-a)

or a pharmaceutically acceptable salt or stereoisomer thereof, wherein each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl, C(O)O—$C_1$-$C_{20}$ alkyl, OC(O)O—$C_1$-$C_{20}$ alkyl, C(O)N($R^5$)—$C_1$-$C_{20}$ alkyl, N($R^5$)C(O)—$C_1$-$C_{20}$ alkyl, OC(O)N($R^5$)—$C_1$-$C_{20}$ alkyl, O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N($R^5$)-aryl, C(O)N($R^5$)-heteroaryl, N($R^5$)C(O)-aryl, or N($R^5$)C(O)-heteroaryl, wherein each alkyl, heteroalkyl, aryl, and heteroaryl is optionally substituted by one or more $R^9$; each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

In another aspect, the present disclosure features a method of inducing an immune response in a subject, the method comprising administering to the subject a compound of Formula (I),

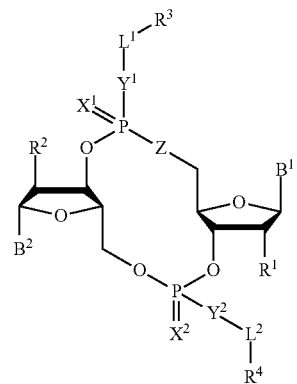

Formula (I)

or a pharmaceutically acceptable salt or stereoisomer thereof, wherein: Z is either S or O; each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), OC(O) OC$_1$-$C_{20}$ alkyl (e.g., $C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl (e.g., $C_1$-$C_6$ alkyl), C(O)O—$C_1$-$C_{20}$ alkyl (e.g., $C_1$-$C_6$ alkyl), OC(O)O—$C_1$-$C_{20}$ alkyl (e.g., $C_1$-$C_6$ alkyl), C(O)N($R^5$)—$C_1$-$C_{20}$ alkyl (e.g., $C_1$-$C_6$ alkyl), N($R^5$)C(O)—$C_1$-$C_{20}$ alkyl (e.g., $C_1$-$C_6$ alkyl), OC(O)N($R^5$)—$C_1$-$C_{20}$ alkyl (e.g., $C_1$-$C_6$ alkyl), O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N($R^5$)-aryl, C(O)N($R^5$)-heteroaryl, N($R^5$)C(O)-aryl, N($R^5$)$_2$C(O)-aryl, or N($R^5$)C(O)-heteroaryl, S(O)$_2$N($R^5$)-aryl, wherein each alkyl, heteroalkyl, aryl, and heteroaryl is optionally substituted by one or more $R^9$; and each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

In some embodiments aspect, the present disclosure features a method of inducing an immune response in a subject, the method comprising administering to the subject a compound of Formula (I-a),

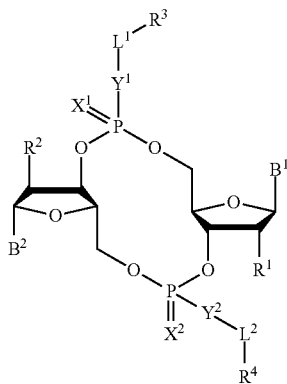

Formula (I-a)

or a pharmaceutically acceptable salt or stereoisomer thereof, wherein each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl, C(O)O—$C_1$-$C_{20}$ alkyl, OC(O)O—$C_1$-$C_{20}$ alkyl, C(O)N($R^5$)—$C_1$-$C_{20}$ alkyl, N($R^5$)C(O)—$C_1$-$C_{20}$ alkyl, OC(O)N($R^5$)—$C_1$-$C_{20}$ alkyl, O-aryl, O-heteroaryl, C(O)-aryl, C(O)-heteroaryl, OC(O)-aryl, OC(O)-heteroaryl, C(O)O-aryl, C(O)O-heteroaryl, C(O)N($R^5$)-aryl, C(O)N($R^5$)-heteroaryl, N($R^5$)C(O)-aryl, or N($R^5$)C(O)-heteroaryl, wherein each alkyl, heteroalkyl, aryl, and heteroaryl is optionally substituted by one or more $R^9$; each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

In some embodiments, the immune response comprises antitumoral immunity. In some embodiments, the immune response comprises induction of a PRR (e.g., STING, RIG-I, MDA5).

BRIEF DESCRIPTION OF THE DRAWINGS

FIG. 1A describes the results of a primary screen for STING agonists, in which HEK293 cells stably expressing ISG54 (ISRE)-promoter driven firefly luciferase gene were used to screen a compound library. Cells transfected with human STING and internal control Renilla-luciferase were treated with 25 uM exemplary compounds, and IRF activity was assessed by measuring luciferase levels.

FIGS. 2A-2F show the potency comparison of an exemplary compound (Cmd 1) vs. a natural STING ligand, 2'-3' cGAMP.

FIGS. 21A-21C show IRF induction by an exemplary compound.

In FIG. 30B, Peak 1 and Peak 2 represent Cmds 1-A and 1-B, respectively.

In FIG. 31B, Peak 1 and Peak 2 represent Cmds 15-A and 15-B, respectively.

FIG. 51A shows 250 μM of Cmd 1 analog with 20 μM to 0 μM of STING. FIG. 51B shows 10 μM of STING with 1 mM to 0 mM of Cmd 1 analog. FIG. 51C shows an immunoblot to detect STING.

FIGS. 52A-52P show immunoblots in which THP-1 cells were treated with 5 μM Cmd 1 or 2'-3' cGAMP.

FIG. 54A is a graph showing the fold induction of gene expression in THP-1 cells treated with 5 uM of either Cmd 1 or 2'3-cGAMP. Gene expression was evaluated by Taqman Assays. Fold Induction was calculated by ΔΔct method. In FIG. 54B, THP-1 cells were treated with luM of Cmd 1 and secretion of certain cytokines was evaluated by on Quansys Biosciences' (Logan, Utah) Q-Plex™ Human Custom, IFN, and IL-1 Family multiplexed ELISA arrays.

In FIG. 54D, a higher BAX/BCL2 ratio in cells administered Cmd 1 promotes apoptosis via upregulation of caspase 3.

FIGS. 61A-61D are images showing immunohistochemistry data on tissues taken from mice treated with Cmd 1. The images show that the anti-tumor activity of Cmd 1 correlates with the induction of the innate and adaptive immune response.

FIGS. 68A-68G show administration of Cmd 1 to a panel of normal cell lines, indicating that Cmd 1 is non-cytotoxic.

FIG. 73A shows tumor volume of tumor in left flank and FIG. 73B shows tumor volume of tumor on right flank over 13 days post initiation treatment. Cmd 1 showed considerable tumor growth inhibition compared with the vehicle.

DETAILED DESCRIPTION OF THE DISCLOSURE

Figure 1A:
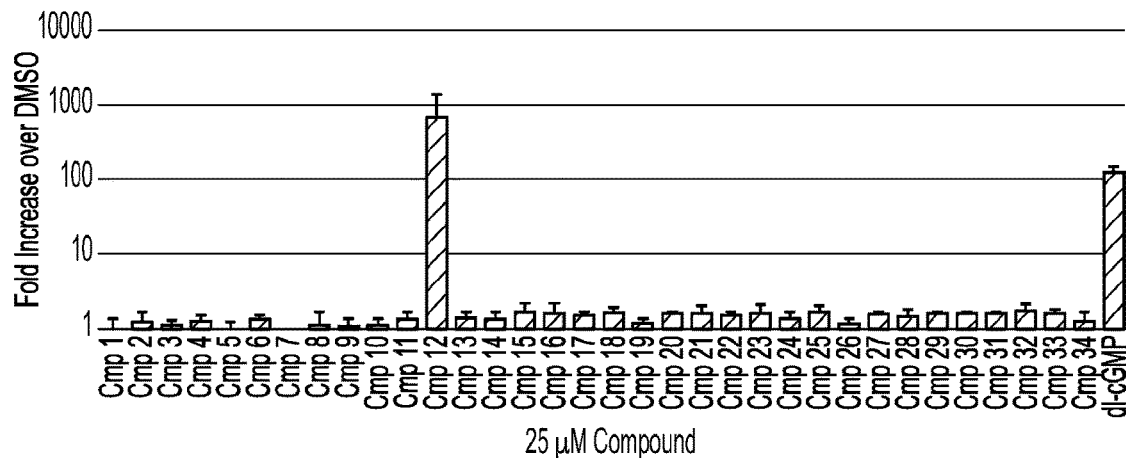
FIGS. 1A-1C show that an exemplary compound engages/bind STING to activate type I IFN signaling.
Figure 1B:
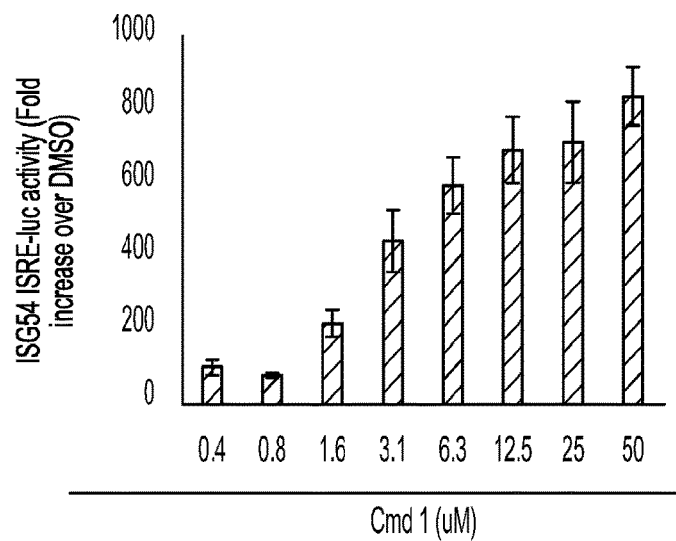
Figure 1C:
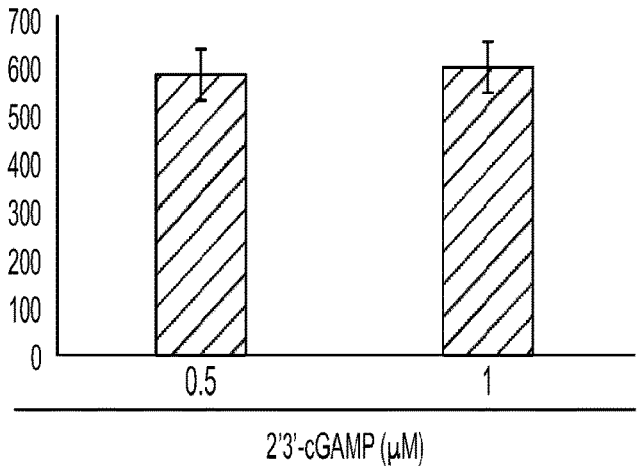
Figure 2E:
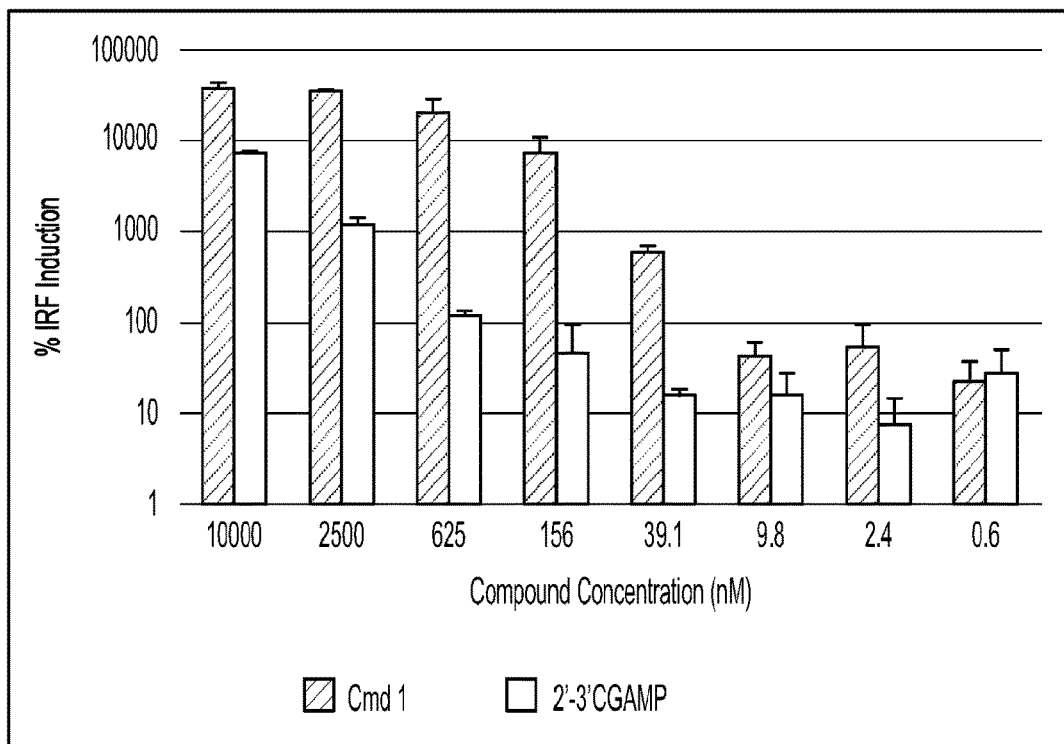
Figure 2F:
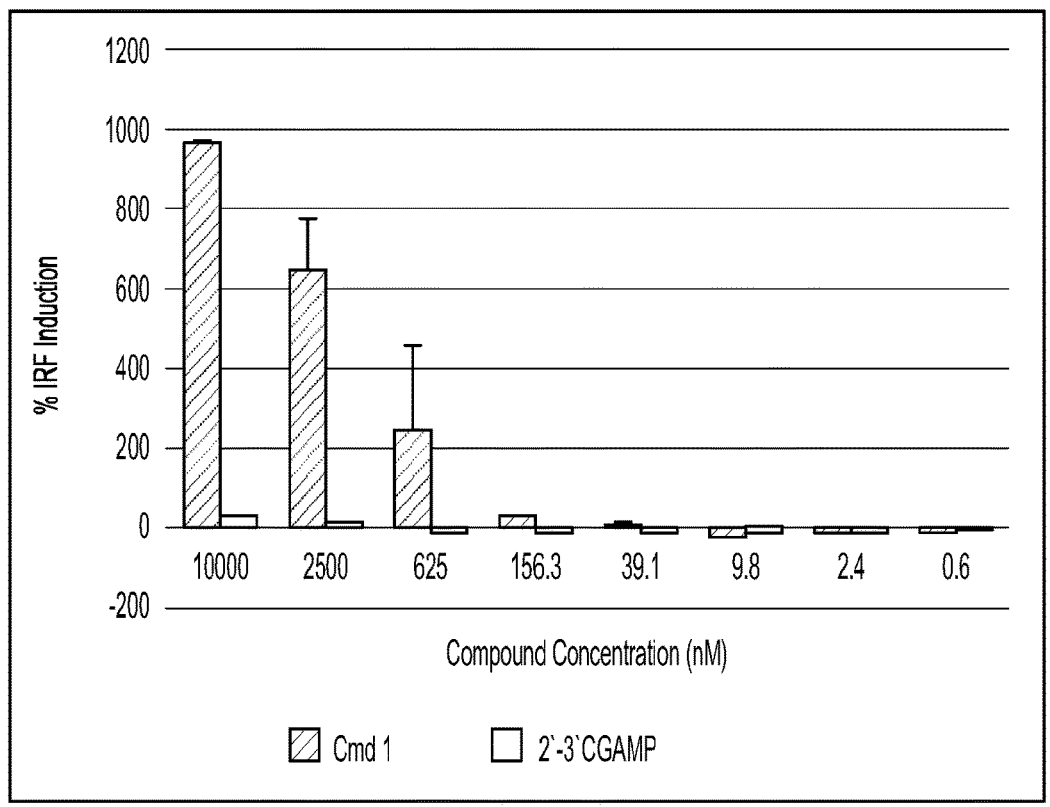
Figure 3A:
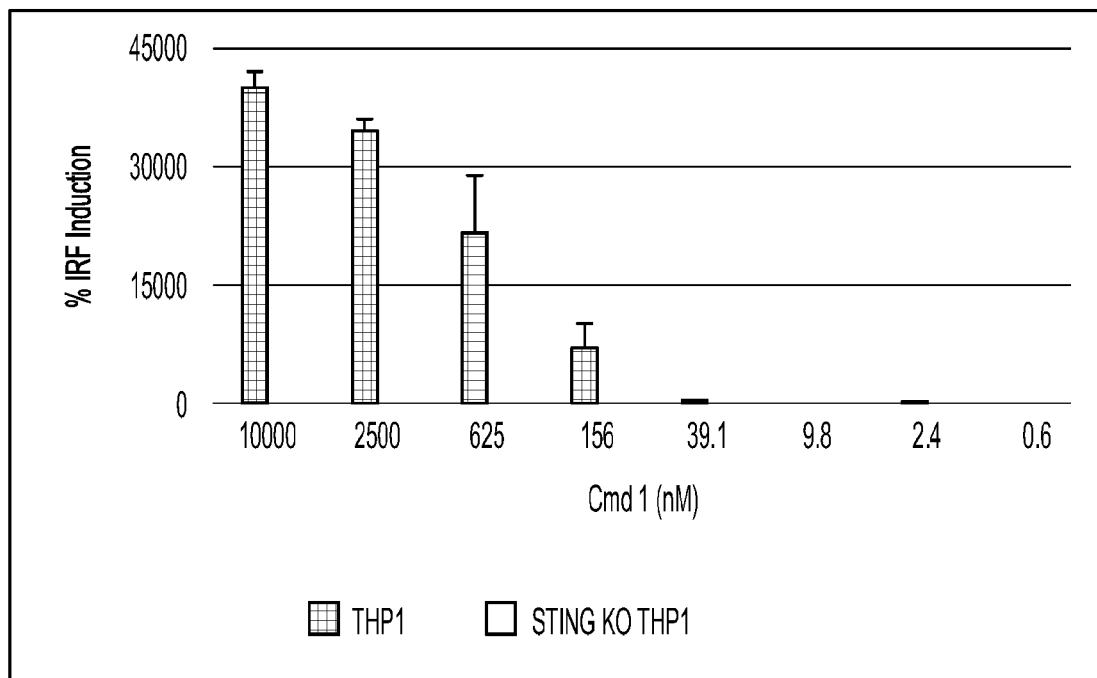
FIGS. 3A-3B show that an exemplary compound has STING-dependent activity.
Figure 3B:
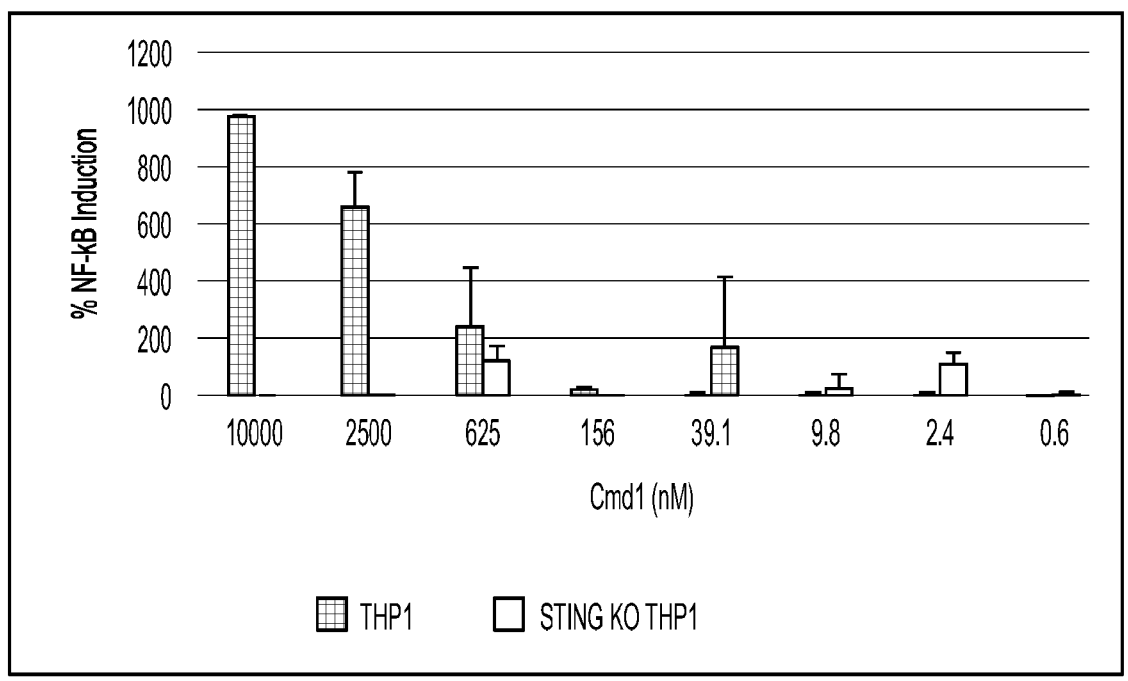
Figure 4:
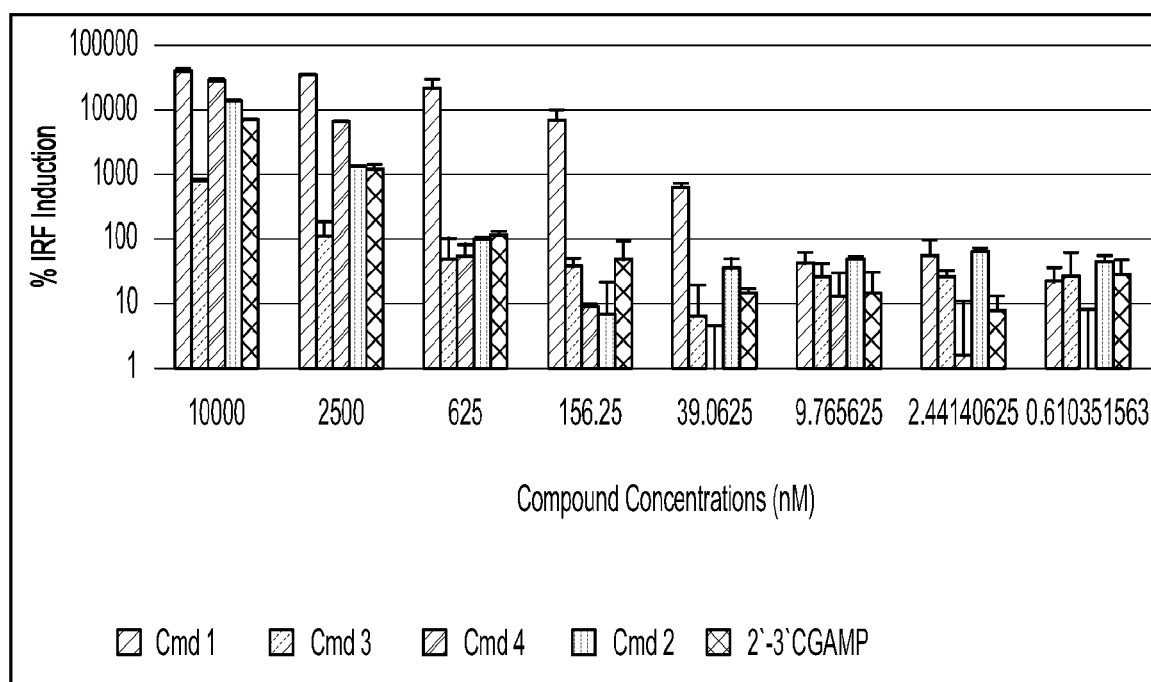
FIG. 4 shows IRF induction by exemplary compounds.
Figure 5A:
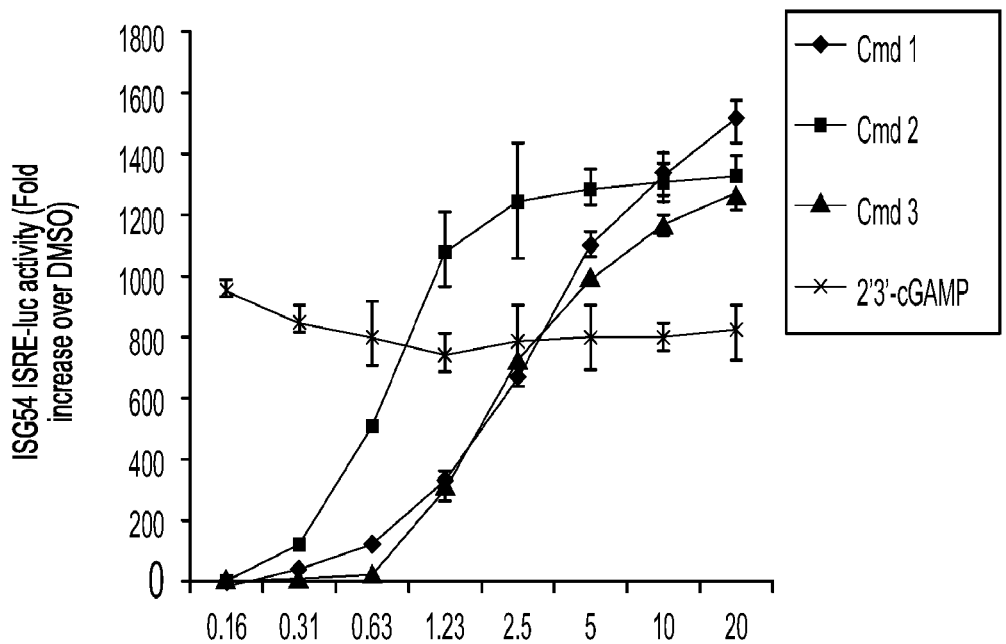
FIGS. 5A-5B show that exemplary compounds engage with STING and activate STING-dependent type I IFN and NF-κB signaling in HEK293 cells.
Figure 5B:
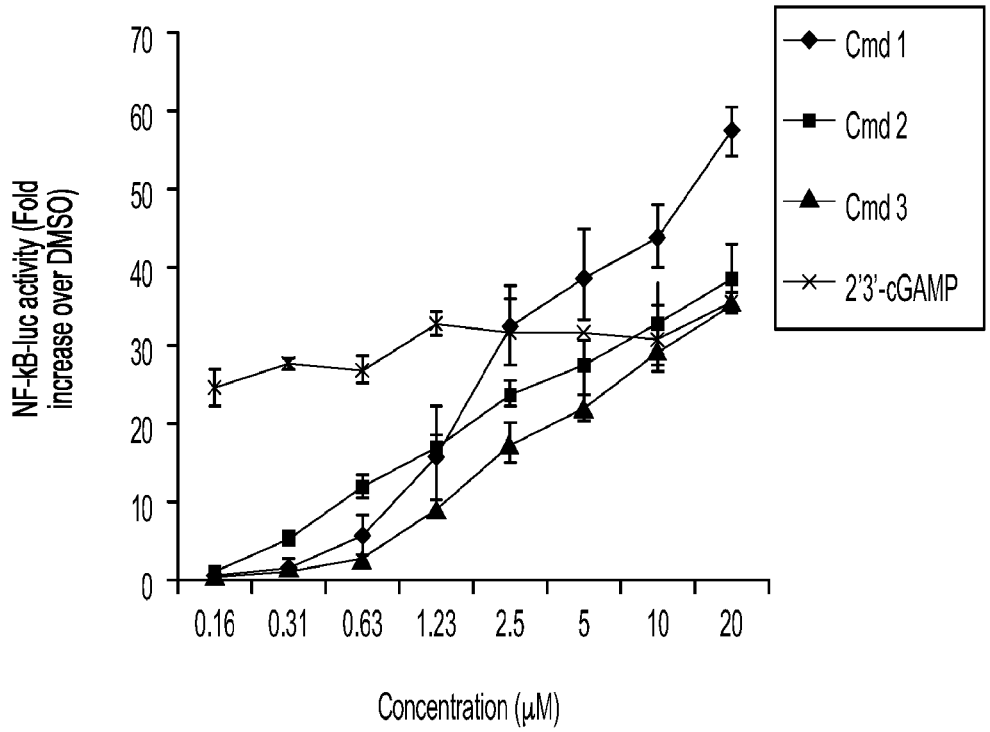
Figure 6:
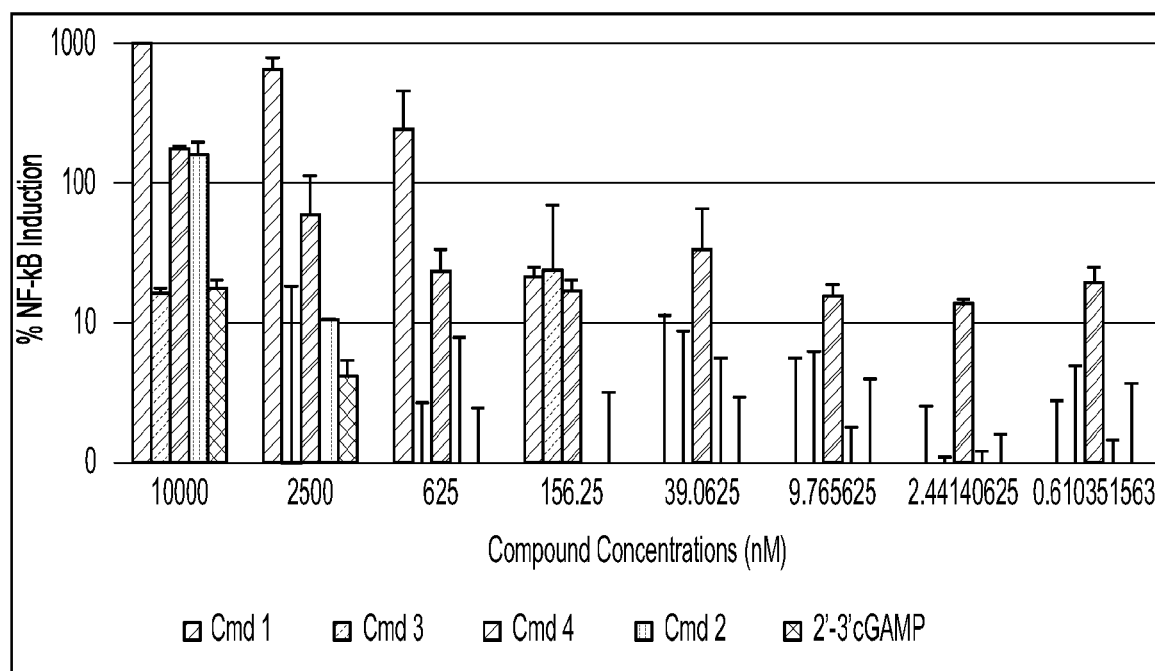
FIG. 6 shows NF-KB induction by exemplary compounds.
Figure 7A:
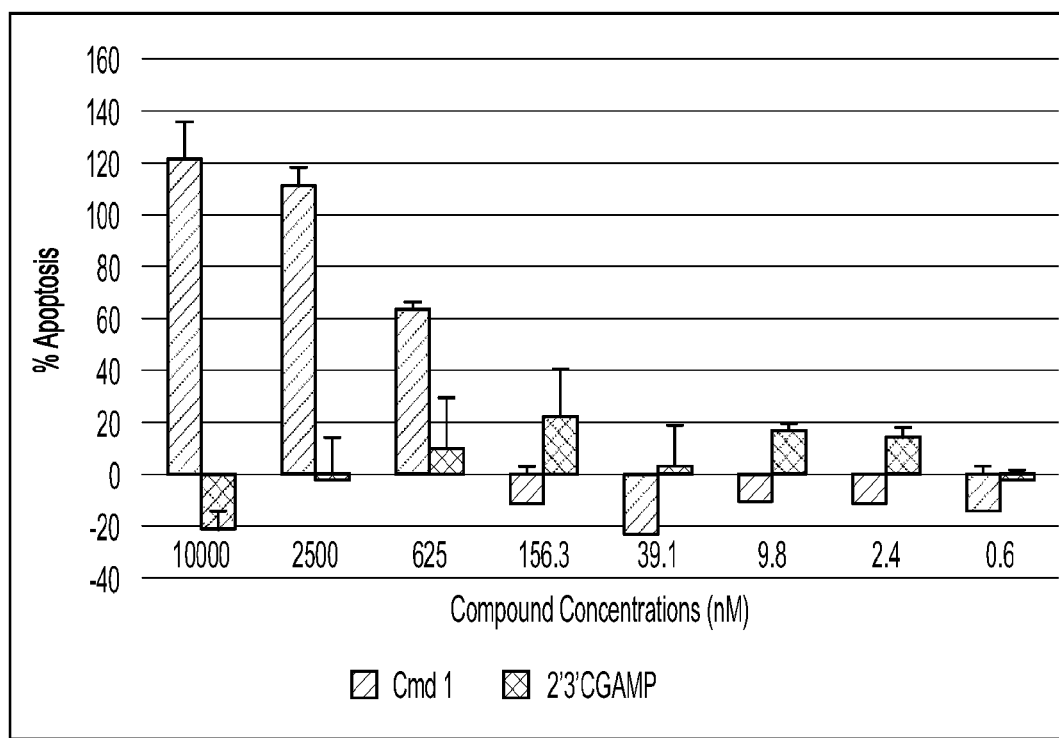
FIGS. 7A-7E show that an exemplary compound causes cell death by apoptosis through the modulation of BAX and BCL-2 levels.
Figure 7B:
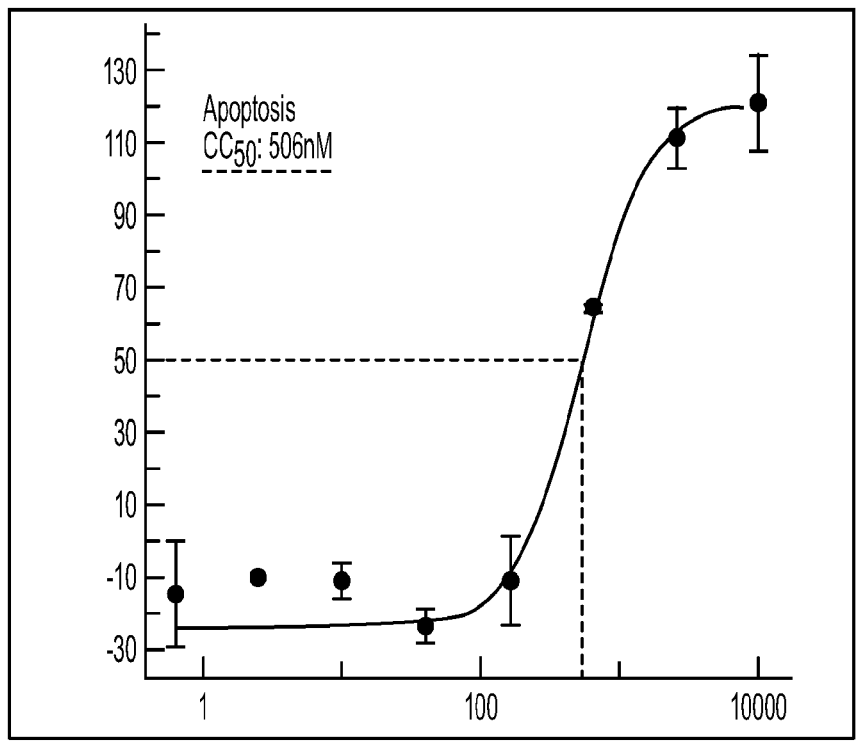
Figure 7C:
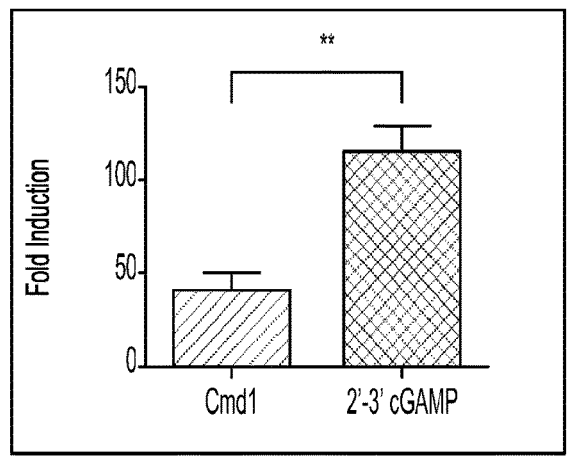
Figure 7D:
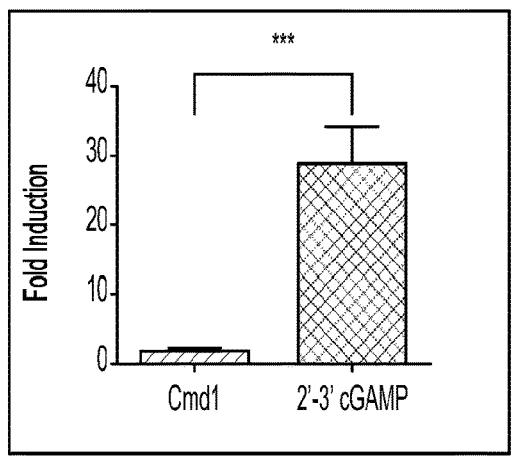
Figure 7E:
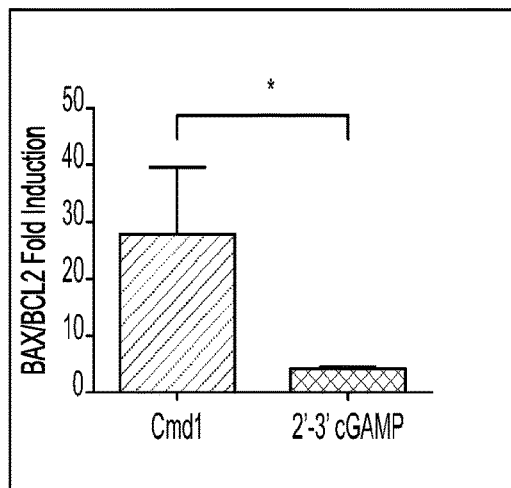
Figure 8A:
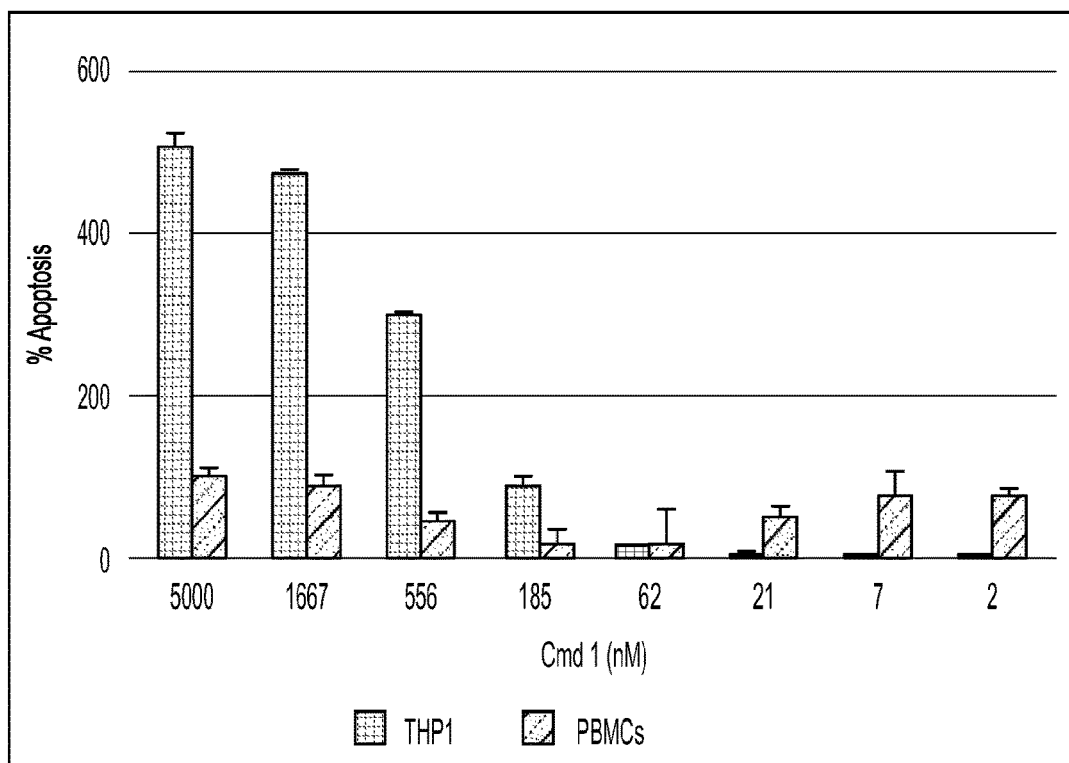
FIGS. 8A-8B show the selective induction of apoptosis by Cmd 1 in acute monocytic leukemia cell line (THP1) vs. PBMCs.
Figure 8B:
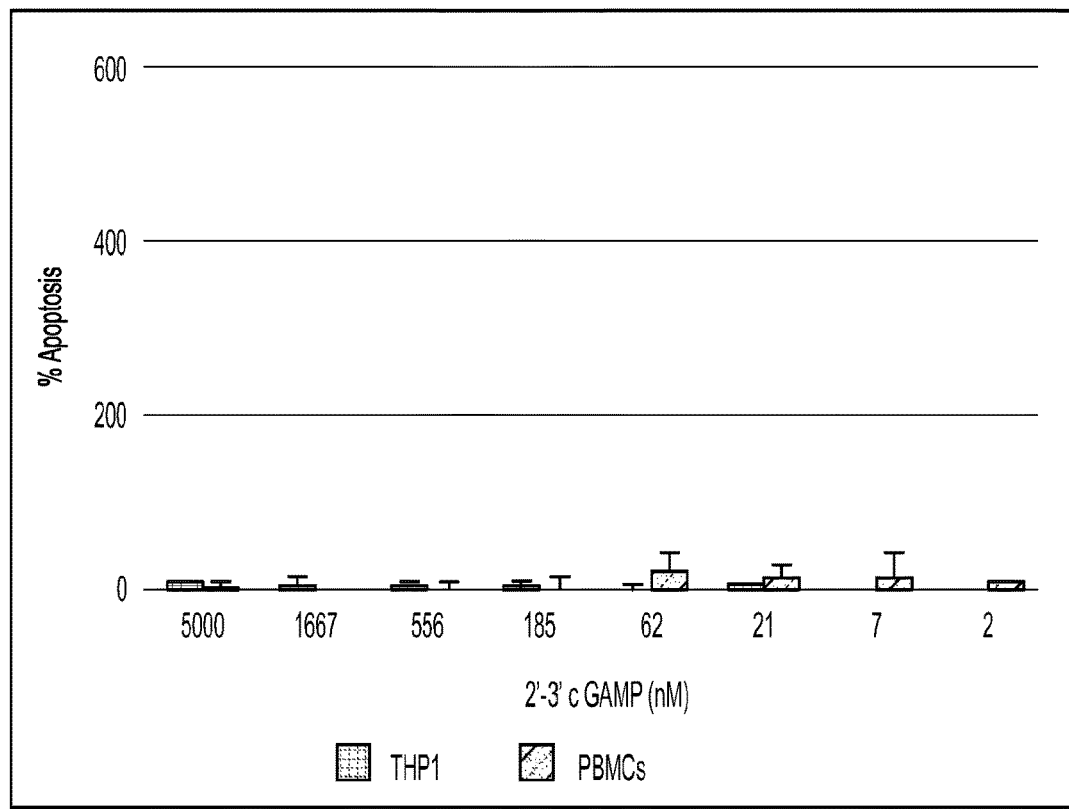

The present disclosure relates to methods of activating and/or inducing the expression of PRRs (e.g., STING) in a subject, in particular for the treatment of a proliferative disease (e.g., cancer). In some embodiments, the method comprises administration of a compound of Formula (I) or pharmaceutically acceptable salt thereof. It is to be noted that induction of any PRR with these compounds can stimulate interferon and/or NF-κB production which can induce the expression of a variety of PRRs which are inducible genes by feedback mechanism.

Definitions

As used herein, the articles "a" and "an" refer to one or to more than one (e.g., to at least one) of the grammatical object of the article.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

As used herein, the term "acquire" or "acquiring" as the terms are used herein, refer to obtaining possession of a physical entity (e.g., a sample, e.g., blood sample or liver biopsy specimen), or a value, e.g., a numerical value, by "directly acquiring" or "indirectly acquiring" the physical entity or value. "Directly acquiring" means performing a process (e.g., an analytical method) to obtain the physical entity or value. "Indirectly acquiring" refers to receiving the physical entity or value from another party or source (e.g., a third party laboratory that directly acquired the physical entity or value). Directly acquiring a value includes performing a process that includes a physical change in a sample or another substance, e.g., performing an analytical process which includes a physical change in a substance, e.g., a sample, performing an analytical method, e.g., a method as described herein, e.g., by sample analysis of bodily fluid, such as blood by, e.g., mass spectroscopy, e.g., LC-MS.

As used herein, the terms "induce" or "induction of" refer to the increase or enhancement of a function, e.g., the increase or enhancement of the expression of a pattern recognition receptor (e.g, STING). In some embodiments, "induction of PRR expression" refers to induction of transcription of PRR RNA, e.g., STING RNA (e.g., mRNA, e.g., an increase or enhancement of), or the translation of a PRR protein, e.g., the STING protein (e.g., an increase or enhancement of). In some embodiments, induction of PRR expression (e.g., STING expression) refers to the increase or enhancement of the concentration of a PRR RNA, e.g., or STING RNA (e.g., mRNA) or the STING protein, e.g., in a cell. In some embodiments, induction of PRR expression (e.g., STING expression) refers to the increase of the number of copies of PRR RNA, e.g., STING RNA (e.g., mRNA) or PRR protein, e.g., the STING protein, e.g., in a cell. In some embodiments, to induce expression of a PRR (e.g., STING) may refer to the initiation of PRR RNA (e.g., STING RNA (e.g., mRNA)) or transcription or PRR protein (e.g., STING protein) translation. In some embodiments, to induce expression of a PRR (e.g., STING) may refer to an increase in the rate of PRR RNA (e.g., STING RNA (e.g., mRNA)) transcription or an increase in the rate of PRR protein (e.g., STING protein) expression.

As used herein, the terms "activate" or "activation" refer to the stimulation or triggering of a function, e.g., of a downstream pathway, e.g., a downstream signaling pathway. In some embodiments, activation of a pattern recognition receptor (PRR) (e.g., STING) refers to the stimulation of a specific protein or pathway, e.g., through interaction with a downstream signaling partner (e.g., IFN-β promoter stimulator 1 (IPS-1), IRF3, IRF7, NF-κB, interferons (e.g., IFN-α or IFN-β 3) and/or cytokines). In some embodiments, activation is distinct from the induction of expression of a PRR. In some embodiments, a PRR may be activated without resulting in an induction of PRR expression (e.g., expression of STING). In some embodiments, activation may include induction of expression of a PRR (e.g., STING). In some embodiments, activation of a PRR may trigger the induction of expression of a PRR (e.g., STING) by about 0.1%, about 0.5%, about 1%, about 5%, about 10%, about 15%, about 20%, about 25%, about 30%, about 40%, about 50%, about 60%, about 70%, about 80%, about 90%, about 95%, or more compared to a reference standard (e.g., basal expression levels of a PRR (e.g., STING)).

As used herein, an amount of a compound, conjugate, or substance effective to treat a disorder (e.g., a disorder described herein), "therapeutically effective amount," "effective amount" or "effective course" refers to an amount of the compound, substance, or composition which is effective, upon single or multiple dose administration(s) to a subject, in treating a subject, or in curing, alleviating, relieving or improving a subject with a disorder (e.g., a microbial infection) beyond that expected in the absence of such treatment.

As used herein, the terms "prevent" or "preventing" as used in the context of a disorder or disease, refer to administration of an agent to a subject, e.g., the administration of a compound of the present disclosure (e.g., compound of Formula (I)) to a subject, such that the onset of at least one symptom of the disorder or disease is delayed as compared to what would be seen in the absence of administration of said agent.

As used herein, the terms "reference treatment" or "reference standard" refer to a standardized level or standardized treatment that is used as basis for comparison. In some embodiments, the reference standard or reference treatment is an accepted, well known, or well characterized standard or treatment in the art. In some embodiments, the reference standard describes an outcome of a method described herein. In some embodiments, the reference standard describes a level of a marker (e.g., a level of induction of a PRR, e.g., STING) in a subject or a sample, e.g., prior to initiation of treatment, e.g., with a compound or composition described herein. In some embodiments, the reference standard describes a measure of the presence of, progression of, or severity of a disease or the symptoms thereof, e.g., prior to initiation of treatment, e.g., with a compound or composition described herein.

As used herein, the term "subject" is intended to include human and non-human animals. Exemplary human subjects include a human patient having a disorder, e.g., a disorder described herein, or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dogs, cats, cows, pigs, etc. In exemplary embodiments of the disclosure, the subject is a woodchuck (e.g., an Eastern woodchuck (*Marmota monax*)).

As used herein, the terms "treat" or "treating" a subject having a disorder or disease refer to subjecting the subject to a regimen, e.g., the administration of a compound of Formula (I) or pharmaceutically acceptable salt thereof, or a composition comprising Formula (I) or pharmaceutically acceptable salt thereof, such that at least one symptom of the disorder or disease is cured, healed, alleviated, relieved, altered, remedied, ameliorated, or improved. Treating includes administering an amount effective to alleviate, relieve, alter, remedy, ameliorate, improve or affect the disorder or disease, or the symptoms of the disorder or disease. The treatment may inhibit deterioration or worsening of a symptom of a disorder or disease.

As used herein, the term "Cmd" refers to the word "compound" or "Compound", and all of the terms are used interchangeably.

Numerous ranges, e.g., ranges for the amount of a drug administered per day, are provided herein. In some embodiments, the range includes both endpoints. In other embodiments, the range excludes one or both endpoints. By way of example, the range can exclude the lower endpoint. Thus, in such an embodiment, a range of 250 to 400 mg/day, excluding the lower endpoint, would cover an amount greater than 250 that is less than or equal to 400 mg/day.

Definitions

The term "alkyl," as used herein, refers to a monovalent saturated, straight- or branched-chain hydrocarbon such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Examples of alkyl groups include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like.

The terms "alkenyl" and "alkynyl" are art-recognized and refer to unsaturated aliphatic groups analogous in length and possible substitution to the alkyls described above, but that contain at least one double or triple bond, respectively. Exemplary alkenyl groups include, but are not limited to, —CH=CH$_2$ and —CH$_2$CH=CH$_2$.

The term "alkylene" refers to the diradical of an alkyl group.

The terms "alkenylene" and "alkynylene" refer to the diradicals of an alkenyl and an alkynyl group, respectively.

The term "methylene unit" refers to a divalent —CH$_2$— group present in an alkyl, alkenyl, alkynyl, alkylene, alkenylene, or alkynylene moiety.

The term "carbocyclic ring system", as used herein, means a monocyclic, or fused, spiro-fused, and/or bridged bicyclic or polycyclic hydrocarbon ring system, wherein each ring is either completely saturated or contains one or more units of unsaturation, but where no ring is aromatic.

The term "carbocyclyl" refers to a radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

The term "aromatic ring system" is art-recognized and refers to a monocyclic, bicyclic or polycyclic hydrocarbon ring system, wherein at least one ring is aromatic.

The term "aryl" refers to a radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

The term "heteroalkyl" refers to an "alkyl" moiety wherein at least one of the carbone molecules has been replaced with a heteroatom such as O, S, or N.

The term "heteroaromatic ring system" is art-recognized and refers to monocyclic, bicyclic or polycyclic ring system wherein at least one ring is both aromatic and comprises a heteroatom; and wherein no other rings are heterocyclyl (as defined below). In certain instances, a ring which is aromatic and comprises a heteroatom contains 1, 2, 3, or 4 independently selected ring heteroatoms in such ring.

The term "heteroaryl" refers to a radical of a heteroaromatic ring system. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl. In certain embodiments, the heteroaryl is a monocyclic or bicyclic ring, wherein each of said rings contains 5 or 6 ring atoms where 1, 2, 3, or 4 of said ring atoms are a heteroatom independently selected from N, O, and S.

The term "heterocyclic ring system" refers to monocyclic, or fused, spiro-fused, and/or bridged bicyclic and polycyclic ring systems where at least one ring is saturated or partially unsaturated (but not aromatic) and comprises a heteroatom. A heterocyclic ring system can be attached to its pendant group at any heteroatom or carbon atom that results in a stable structure and any of the ring atoms can be optionally substituted.

The term "heterocyclyl" refers to a radical of a heterocyclic ring system. Representative heterocyclyls include ring systems in which (i) every ring is non-aromatic and at least one ring comprises a heteroatom, e.g., tetrahydrofuranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine. In certain embodiments, the heterocyclyl is a monocyclic or bicyclic ring, wherein each of said rings contains 3-7 ring atoms where 1, 2, 3, or 4 of said ring atoms are a heteroatom independently selected from N, O, and S.

The term "saturated heterocyclyl" refers to a radical of heterocyclic ring system wherein every ring is saturated, e.g., tetrahydrofuran, tetrahydro-2H-pyran, pyrrolidine, piperidine and piperazine.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

The term "nucleobase" as used herein, is a nitrogen-containing biological compound found linked to a sugar within a nucleoside—the basic building blocks of deoxyribonucleic acid (DNA) and ribonucleic acid (RNA). The primary, or naturally occurring, nucleobases are cytosine (DNA and RNA), guanine (DNA and RNA), adenine (DNA and RNA), thymine (DNA) and uracil (RNA), abbreviated as C, G, A, T, and U, respectively. Because A, G, C, and T appear in the DNA, these molecules are called DNA-bases; A, G, C, and U are called RNA-bases. Adenine and guanine belong to the double-ringed class of molecules called purines (abbreviated as R). Cytosine, thymine, and uracil are all pyrimidines. Other nucleobases that do not function as normal parts of the genetic code are termed non-naturally occurring.

As described herein, compounds of the disclosure may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

As used herein, the definition of each expression, e.g., alkyl, m, n, etc., when it occurs more than once in any structure, is intended to be independent of its definition elsewhere in the same structure.

As described herein, compounds of the disclosure may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Pattern Recognition Receptors

The disclosure presented herein features methods for the activation and induction of PRR expression (e.g., STING expression) in a subject, e.g., a subject with a proliferative disease (e.g., cancer). Pattern recognition receptors (PRRs) are a broad class of proteins which recognize pathogen-associated molecular patterns (PAMPs) conserved within pathogenic invaders. PAMPs are typically products of biosynthetic pathways that are essential to the survival and/or infectivity of the pathogen, e.g., lipopolysaccharides, glycoproteins, and nucleic acids. Recognition of PAMPs by their cognate PRRs activates signaling pathways that result in the production of immune defense factors such as pro-inflammatory and anti-inflammatory cytokines, type I interferons (IFN-α, IFN-β), and/or interferon stimulated genes (ISGs). It is well known that induction of innate immune signaling also results in the activation of T cell responses as well as the induction of adaptive immunity. These downstream immune effects are essential for clearance of the virus through apoptosis and killing of infected cells through cytotoxic T lymphocytes and other defense mechanisms. It is also well known that interferons act on ISRE (interferon response elements) that can trigger the production of ISGs, which play an important role in antiviral cellular defense.

The stimulator of interferon genes (STING) is a cytosolic microbial-derived DNA sensor that has been shown to be particularly sensitive to double-stranded DNA and cyclic dinucleotides (e.g., cyclic di-GMP) (Burdette, D. L. and Vance, R. E. (2013) *Nat Immunol* 14:19-26). Two molecules of STING form a homodimer mediated by an α-helix present in the C-terminal dimerization domain, and molecular binding studies have revealed that each STING dimer binds one molecule of microbial nucleic acids, e.g., DNA or a cyclic dinucleotide. Upon ligand binding, STING activates the innate immune response through interaction with RIG-I and IPS-1, resulting in interferon production (e.g., IFN-α and IFN-β 3) and other downstream signaling events. Since its discovery, STING has been shown to function as a critical sensor of viruses (e.g., adenovirus, herpes simplex virus, hepatitis B virus, vesicular stomatitis virus, hepatitis C virus), bacteria (e.g., *Listeria monocytogenes, Legionella pneumopholia, Mycobacterium tuberculosis*) and protozoa (*Plasmodium falciparum, Plasmodium berghei*). In addition, STING has been shown to play a major role in the innate immune response against tumor antigens, driving dendritic cell activation and subsequent T cell priming in several cancers (Woo, S. R. et al. *Trends in Immunol* (2015) 36:250-256).

Another class of PRRs includes RIG-I, which is the founding member of a family of PRRs termed RIG-I-like receptors (RLRs) that primarily detect RNA derived from foreign sources. It is a critical sensor of microbial infection (e.g., viral infection) in most cells and is constitutively expressed at low levels in the cytosol. After ligand binding, the expression of RIG-I is rapidly enhanced, leading to increased RIG-I concentrations in the cell (Jensen, S. and Thomsen, A. R. *J Virol* (2012) 86:2900-2910; Yoneyama M. et al. *Nat Immunol* (2004) 5:730-737). RIG-I is an ATP-dependent helicase containing a central DExD/H box ATPase domain and tandem N-terminal caspase-recruiting domains (CARDs) that mediate downstream signaling. The C-terminus of RIG-I comprises an ssRNA/dsRNA-binding domain that when unbound acts to silence CARD function at the N-terminus. Without wishing to be bound by theory, it is believed that upon recognition of target RNA structures, two N-terminal CARDs are exposed, allowing for interaction with the CARD of a downstream binding partner, IFN-β promoter stimulator 1 (IPS-1), also known as mitochondrial antiviral signaling molecule (MAVS) and CARDIF. This interaction in turn triggers further downstream signaling, such as induction of IRF3, IRF7, NF-κB, IFNs, and cytokine production that results in the initiation of the host immune response.

Other RLRs are homologous to RIG-I and function in a similar manner, including MDA5, LGP2, and RNase L. MDA5 is highly homologous to RIG-I, and has been shown to be crucial for triggering a cytokine response upon infection with picornaviruses (e.g., encephalomyocarditis virus (EMCV), Theiler's virus, and Mengo virus), Sendai virus, rabies virus, West Nile virus, rabies virus, rotavirus, murine hepatitis virus, and murine norovirus. LPG2 lacks a CARD domain found in RIG-I and MDA5, which is responsible for direct interaction with IPS-1 to initiate downstream signaling. As such, LPG2 is believed to behave as a modulator of the innate immune response in conjunction with other CARD-bearing RLRs such as RIG-I and MDA5.

Another class of PRRs encompasses the nucleotide-binding and oligomerization domain (NOD)-like receptors, or NLR family (Caruso, R. et al, *Immunity* (2014) 41:898-908), which includes the microbial sensor NOD2. NOD2 is composed of an N-terminal CARD, a centrally-located nucleotide-binding oligomerization domain, and a C-terminal leucine rich repeat domain that is responsible for binding microbial PAMPs, such as bacterial peptidoglycan fragments and microbial nucleic acids. Ligand binding activates NOD2 and is believed to drive interaction with the CARD-containing kinase RIPK2, which in turn activates a number of downstream proteins including NF-κB, MAPK, IRF7, and IRF3, the latter of which results in the induction of type 1 interferons. NOD2 is expressed in a diverse set of cell types, including macrophages, dendritic cells, paneth cells, epithelial cells (e.g., lung epithelial cells, intestinal epithelia), and osteoblasts. NOD2 has been established as a sensor of infection by variety of pathogenic invaders, such as protozoa (e.g., *Toxoplasma gondii* and *Plasmodium berghei*), bacteria (e.g., *Bacillus anthracis, Borrelia burgdorferi, Burkholderia pseudomallei, Helicobacter hepaticus, Legionella pneumophilia, Mycobacterium tuberculosis, Propionibacterium acne, Porphyromonas gingivalis, Salmonella enterica,* and *Streptococcus pneumonia*), and viruses (e.g., respiratory syncytial virus and murine norovirus-1) (Moreira, L. O. and Zamboni, D. S. *Front Immunol* (2012) 3:1-12). Recent work has shown that mutation of NOD2 may contribute to inflammatory diseases such as Crohn's disease, resulting in an aberrant inflammatory response upon stimulation.

Compounds

The present disclosure features compounds and methods for the induction of PRR expression (e.g., STING expression) in a subject (e.g., a subject with a proliferative disease, e.g., a cancer), comprising administration of a compound of Formula (I) or a prodrug or pharmaceutically acceptable salt thereof.

In some embodiments, the present disclosure features a compound of Formula (I) in which the 3'-OH end of one nucleoside is joined to the 5'-OH of the second nucleoside through a linkage as shown. In some other embodiments, the 2'-OH end of one nucleoside may be joined to the 5'-OH of the second nucleoside through a linkage.

In some embodiments, the compound is a compound of Formula (I):

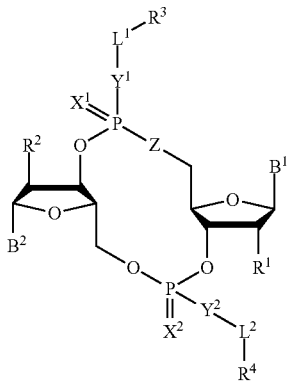

Formula (I)

or a pharmaceutically acceptable salt or stereoisomer thereof, wherein: Z is either S or O; each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), OC(O)O$C_1$-$C_{20}$ alkyl (e.g., $C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl (e.g., $C_1$-$C_6$ alkyl), C(O)O—$C_1$-$C_{20}$ alkyl (e.g., $C_1$-$C_6$ alkyl), OC(O)O—$C_1$-$C_{20}$ alkyl (e.g., $C_1$-$C_6$ alkyl), C(O)N($R^5$)—$C_1$-$C_{20}$ alkyl (e.g., $C_1$-$C_6$ alkyl), N($R^5$)C(O)—$C_1$-$C_{20}$ alkyl (e.g., $C_1$-$C_6$ alkyl), OC(O)N($R^5$)—$C_1$-$C_{20}$ alkyl (e.g., $C_1$-$C_6$ alkyl), O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N($R^5$)-aryl, C(O)N($R^5$)-heteroaryl, N($R^5$)C(O)-aryl, N($R^5$)$_2$C(O)-aryl, or N($R^5$)C(O)-heteroaryl, S(O)$_2$N($R^5$)-aryl, wherein each alkyl, heteroalkyl, aryl, and heteroaryl is optionally substituted by one or more $R^9$; and each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

In some embodiments, the compound is a compound of Formula (I-a):

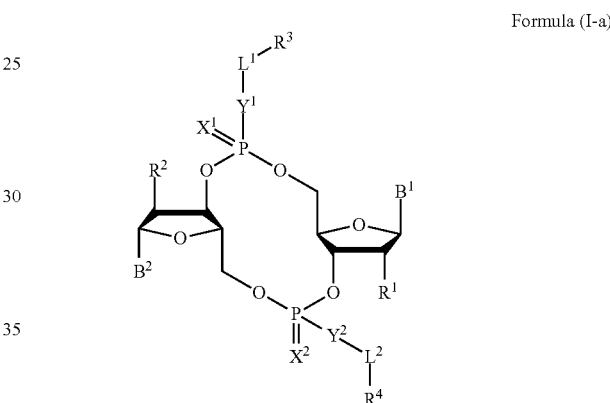

Formula (I-a)

or a pharmaceutically acceptable salt or stereoisomer thereof, wherein each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_{20}$ alkyl or $C_1$-$C_{20}$ heteroalkyl, wherein each alkyl and heteroalkyl is optionally substituted with $R^6$; each of $R^1$ and $R^2$ is independently hydrogen, halo, —CN, $C_1$-$C_{20}$ alkyl, or $OR^7$; each of $R^3$ and $R^4$ is independently hydrogen, $C_1$-$C_{20}$ alkyl, $C_1$-$C_{20}$ heteroalkyl, cycloalkyl, heterocyclyl, aryl, or heteroaryl, wherein each alkyl, heteroalkyl, cycloalkyl, heterocyclyl, aryl, and heteroaryl is optionally substituted with 1-5 $R^8$; $R^5$ is hydrogen or $C_1$-$C_{20}$ alkyl; $R^6$ is halo, —CN, $C_1$-$C_{20}$ alkyl, $OR^7$, oxo, cycloalkyl, heterocyclyl, aryl, or heteroaryl, wherein each alkyl, cycloalkyl, heterocyclyl, aryl, or heteroaryl is optionally substituted with 1-5 $R^9$; $R^7$ is hydrogen, $C_1$-$C_{20}$ alkyl, cycloalkyl, heterocyclyl, aryl, or heteroaryl, wherein each alkyl, cycloalkyl, heterocyclyl, aryl, or heteroaryl is optionally substituted with 1-5 $R^9$; each $R^8$ is independently $C_1$-$C_{20}$ alkyl, $C_1$-$C_{20}$ heteroalkyl, C(O)—$C_1$-$C_{20}$ alkyl, OC(O)—$C_1$-$C_{20}$ alkyl, C(O)O—$C_1$-$C_{20}$ alkyl, OC(O)O—$C_1$-$C_{20}$ alkyl, C(O)N($R^5$)—$C_1$-$C_{20}$ alkyl, N($R^5$)C(O)—$C_1$-$C_{20}$ alkyl, OC(O)N($R^5$)—$C_1$-$C_{20}$ alkyl, O-aryl, O-heteroaryl, C(O)-aryl, C(O)-heteroaryl, OC(O)-aryl, OC(O)-heteroaryl, C(O)O-aryl, C(O)O— heteroaryl, C(O)N($R^5$)-aryl, C(O)N($R^5$)-heteroaryl, N($R^5$)C(O)-aryl, N($R^5$)C(O)-heteroaryl, wherein each alkyl, heteroalkyl, aryl, or heteroaryl is optionally substituted by 1-5 R$^9$; each R$^9$ is independently C$_1$-C$_{20}$ alkyl, O—C$_1$-C$_{20}$ alkyl, C$_1$-C$_{20}$ heteroalkyl, halo, —CN, OH, oxo, aryl, heteroaryl, O-aryl, or O-heteroaryl, wherein each alkyl, heteroalkyl, aryl.

In some embodiments, the compound is a compound of Formulas (I-b), (I-c), (I-d), or (I-e):

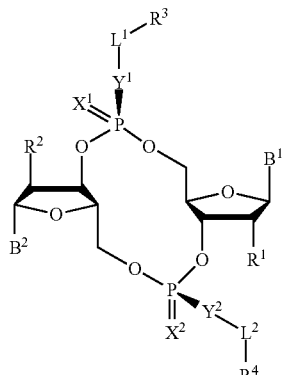

Formula (I-b)

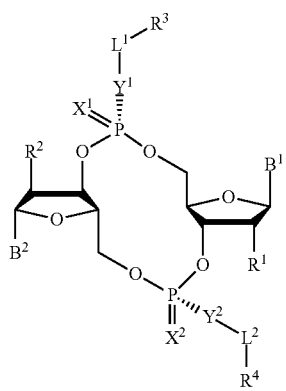

Formula (I-c)

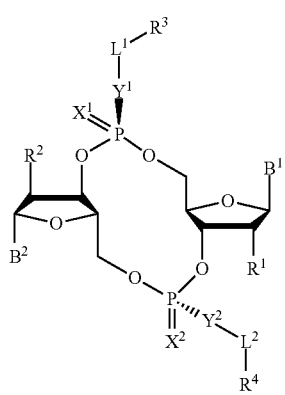

Formula (I-d)

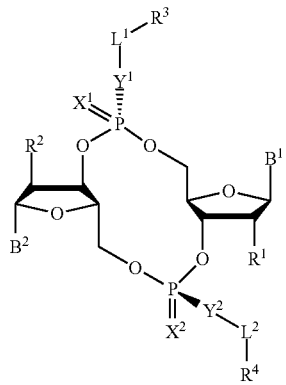

Formula (I-e)

or a pharmaceutically acceptable salt thereof, wherein each of B$^1$, B$^2$, X$^1$, X$^2$, Y$^1$, Y$^2$, L$^1$, L$^2$, R$^1$, R$^2$, R$^3$, R$^4$, and subvariables thereof as previously described.

In some embodiments, at least one of B$^1$ or B$^2$ is a purinyl nucleobase. In some embodiments, each of B$^1$ or B$^2$ is independently a purinyl nucleobase. In some embodiments, B$^1$ is a purinyl nucleobase. In some embodiments, B$^2$ is a pyrimidinyl nucleobase. In some embodiments, B$^1$ is a purinyl nucleobase and B$^2$ is a pyrimidinyl nucleobase.

In some embodiments, each of B$^1$ or B$^2$ is selected from a naturally occurring nucleobase or a modified nucleobase. In some embodiments, each of B$^1$ or B$^2$ is selected from adenosinyl, guanosinyl, cytosinyl, thyminyl, uracilyl, 5'-methylcytosinyl, 5'-fluorouracilyl, 5'-propynyluracilyl, and 7-deazaadenosinyl. In some embodiments, each of B$^1$ or B$^2$ is selected from:

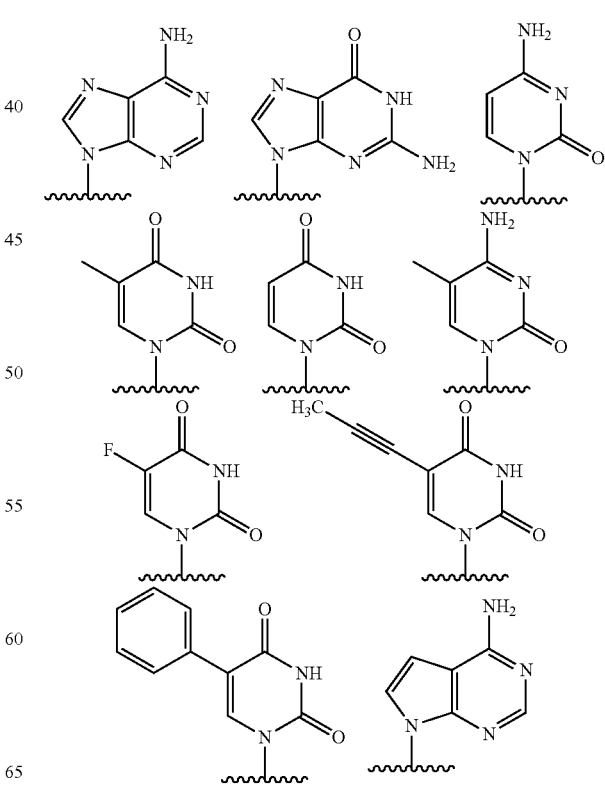

wherein "~~~" indicates the linkage of the nucleobase to the ribose ring.

In some embodiments, one of $B^1$ or $B^2$ is selected from a naturally occurring nucleobase and the other of $B^1$ or $B^2$ is a modified nucleobase. In some embodiments, one of $B^1$ or $B^2$ is adenosinyl, guanosinyl, thyminyl, cytosinyl, or uracilyl, and the other of $B^1$ or $B^2$ is 5'-methylcytosinyl, 5'-fluorouracilyl, 5'-propynyluracilyl, or 7-deazaadenosinyl.

In some embodiments, $B^1$ is adenosinyl or guanosinyl. In some embodiments, $B^2$ is cytosinyl, thyminyl, or uracilyl. In some embodiments, $B^1$ is adenosinyl or guanosinyl and $B^2$ is cytosinyl, thyminyl, or uracilyl. In some embodiments, each of $B^1$ and $B^2$ is independently uracilyl. In some embodiments, each of $B^1$ and $B^2$ is independently adenosinyl.

In some embodiments, each of $R^1$ and $R^2$ is independently hydrogen, halo, or $OR^7$. In some embodiments, each of $R^1$ and $R^2$ is independently halo (e.g., fluoro). In some embodiments, each of $R^1$ and $R^2$ is not hydrogen or $OR^7$.

In some embodiments, $X^1$ is O. In some embodiments, $X^2$ is O. In some embodiments, each of $X^1$ and $X^2$ is independently O.

In some embodiments, $Y^1$ is O or S. In some embodiments, $Y^2$ is O or S. In some embodiments, each of $Y^1$ and $Y^2$ is independently O or S. In some embodiments, one of $Y^1$ or $Y^2$ is O and the other of $Y^1$ or $Y^2$ is S. In some embodiments, each of $Y^1$ or $Y^2$ is independently S. In some embodiments, each of $Y^1$ or $Y^2$ is independently O.

In some embodiments, $L^1$ is $C_1$-$C_6$ alkyl (e.g., $CH_2$). In some embodiments, $L^2$ is $C_1$-$C_6$ alkyl (e.g., $CH_2$). In some embodiments, each of $L^1$ and $L^2$ is independently $C_1$-$C_6$ alkyl (e.g., $CH_2$).

In some embodiments, $R^3$ is hydrogen, aryl, or heteroaryl, wherein aryl and heteroaryl is optionally substituted with 1-5 $R^8$. In some embodiments, $R^3$ is aryl or heteroaryl, each of which is optionally substituted with 1-5 $R^8$. In some embodiments, $R^3$ is phenyl substituted with 1 $R^8$.

In some embodiments, $R^4$ is independently hydrogen, aryl, or heteroaryl, wherein aryl and heteroaryl is optionally substituted with 1-5 $R^8$. In some embodiments, $R^4$ is aryl or heteroaryl, each of which is optionally substituted with 1-5 $R^8$. In some embodiments, $R^4$ is phenyl substituted with 1 $R^8$.

In some embodiments, each of $R^3$ and $R^4$ is independently hydrogen, aryl, or heteroaryl, wherein aryl and heteroaryl is optionally substituted with 1-5 $R^8$. In some embodiments, $R^3$ is aryl or heteroaryl, each of which is optionally substituted with 1-5 $R^8$, and $R^4$ is hydrogen. In some embodiments, $R^3$ is phenyl substituted with 1 $R^8$ and $R^4$ is hydrogen. In some embodiments, each of $R^3$ and $R^4$ is independently phenyl substituted with 1 $R^8$.

In some embodiments, each of $Y^1$ and $Y^2$ is O and each of $R^3$ and $R^4$ is independently hydrogen. In some embodiments, $Y^2$ is O and $R^4$ is hydrogen. In some embodiments, each of $Y^1$ and $Y^2$ is independently S and each of $R^3$ and $R^4$ is independently substituted with 1 $R^8$.

In some embodiments, $Y^1$ is S and $R^3$ is substituted with 1 $R^8$.

In some embodiments, each $R^8$ is independently $C_1$-$C_{20}$ alkyl (e.g., $C_1$-$C_6$ alkyl), $C_1$-$C_{20}$ heteroalkyl, $C(O)$—$C_1$-$C_{20}$ alkyl, $OC(O)$—$C_1$-$C_{20}$ alkyl, $OC(O)O$—$C_1$-$C_{20}$ alkyl, $OC(O)N(R^5)$—$C_1$-$C_{20}$ alkyl, O-aryl, $C(O)$-aryl, $OC(O)$-aryl, or $C(O)N(R^5)$-aryl, wherein each alkyl, heteroalkyl, aryl, and heteroaryl is optionally substituted by one or more $R^9$.

In some embodiments, $R^8$ is $OC(O)$-aryl optionally substituted by 1-5 $R^9$ (e.g., 1 $R^9$).

In some embodiments, $R^9$ is O—$C_1$-$C_{12}$ alkyl (e.g., O—$CH_2(CH_2)CH_3$). In some embodiments, $R^9$ is O—$C_1$-$C_{10}$ alkyl (e.g., O—$CH_2(CH_2)CH_3$). In some embodiments, $R^9$ is O—$C_1$-$C_8$ alkyl (e.g., O—$CH_2(CH_2)_6CH_3$). In some embodiments, $R^9$ is O—$C_1$-$C_6$ alkyl (e.g., O—$CH_2(CH_2)_4CH_3$).

In some embodiments, the compound is a compound of Formula (I-f):

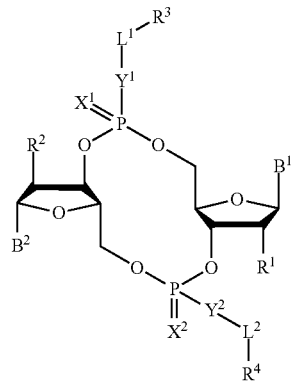

Formula (I-f)

or a pharmaceutically acceptable salt or stereoisomer thereof, wherein each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each $C_1$-$C_6$ alkyl and $C_1$-$C_6$ heteroalkyl is optionally substituted with $R^6$; each of $R^1$ and $R^2$ is independently halo; each of $R^3$ and $R^4$ is independently hydrogen, $C_1$-$C_{20}$ alkyl, $C_1$-$C_6$ heteroalkyl, cycloalkyl, heterocyclyl, aryl, or heteroaryl, wherein each $C_1$-$C_{20}$ alkyl, $C_1$-$C_6$ heteroalkyl, cycloalkyl, heterocyclyl, aryl, and heteroaryl is optionally substituted with 1-5 $R^8$; $R^5$ is hydrogen or $C_1$-$C_{20}$ alkyl; $R^6$ is halo, —CN, $C_1$-$C_{20}$ alkyl, $OR^7$, oxo, cycloalkyl, heterocyclyl, aryl, or heteroaryl, wherein each $C_1$-$C_{20}$ alkyl, cycloalkyl, heterocyclyl, aryl, or heteroaryl is optionally substituted with 1-5 $R^9$; $R^7$ is hydrogen, $C_1$-$C_{20}$ alkyl, cycloalkyl, heterocyclyl, aryl, or heteroaryl, wherein each $C_1$-$C_{20}$ alkyl, cycloalkyl, heterocyclyl, aryl, or heteroaryl is optionally substituted with 1-5 $R^9$; each $R^8$ is independently $C_1$-$C_{20}$ alkyl, $C(O)$-aryl, $C(O)$-heteroaryl, $OC(O)$-aryl, or $OC(O)$-heteroaryl, wherein each $C_1$-$C_{20}$ alkyl, $C(O)$-aryl, $C(O)$-heteroaryl, $OC(O)$-aryl, or $OC(O)$-heteroaryl is optionally substituted by 1-5 $R^9$; and each $R^9$ is independently $C_1$-$C_{20}$ alkyl, halo, —CN, OH, O—$C_1$-$C_{20}$ alkyl, O—$C_1$-$C_{20}$ heteroalkyl, O-aryl, or O-heteroaryl.

In some embodiments, the compound is a compound of Formula (I-g):

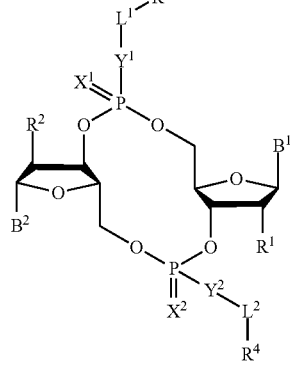

Formula (I-g)

or a pharmaceutically acceptable salt or stereoisomer thereof, wherein each of $B^1$ and $B^2$ is independently a purinyl nucleobase or pyrimidinyl nucleobase; each of $X^1$ and $X^2$ is independently O; each of $Y^1$ and $Y^2$ is independently O or S; each of $L^1$ and $L^2$ is independently absent or $C_1$-$C_6$ alkyl; each of $R^1$ and $R^2$ is independently halo or OH; each of $R^3$ and $R^4$ is independently hydrogen or aryl optionally substituted with 1-5 $R^8$; each $R^8$ is independently OC(O)-aryl optionally substituted by 1-5 $R^9$; and each $R^9$ is independently O—$C_1$-$C_{20}$ alkyl.

In some embodiments, the compound is selected from a compound depicted in Table 1:

TABLE 1

Structure

TABLE 1-continued
Structure
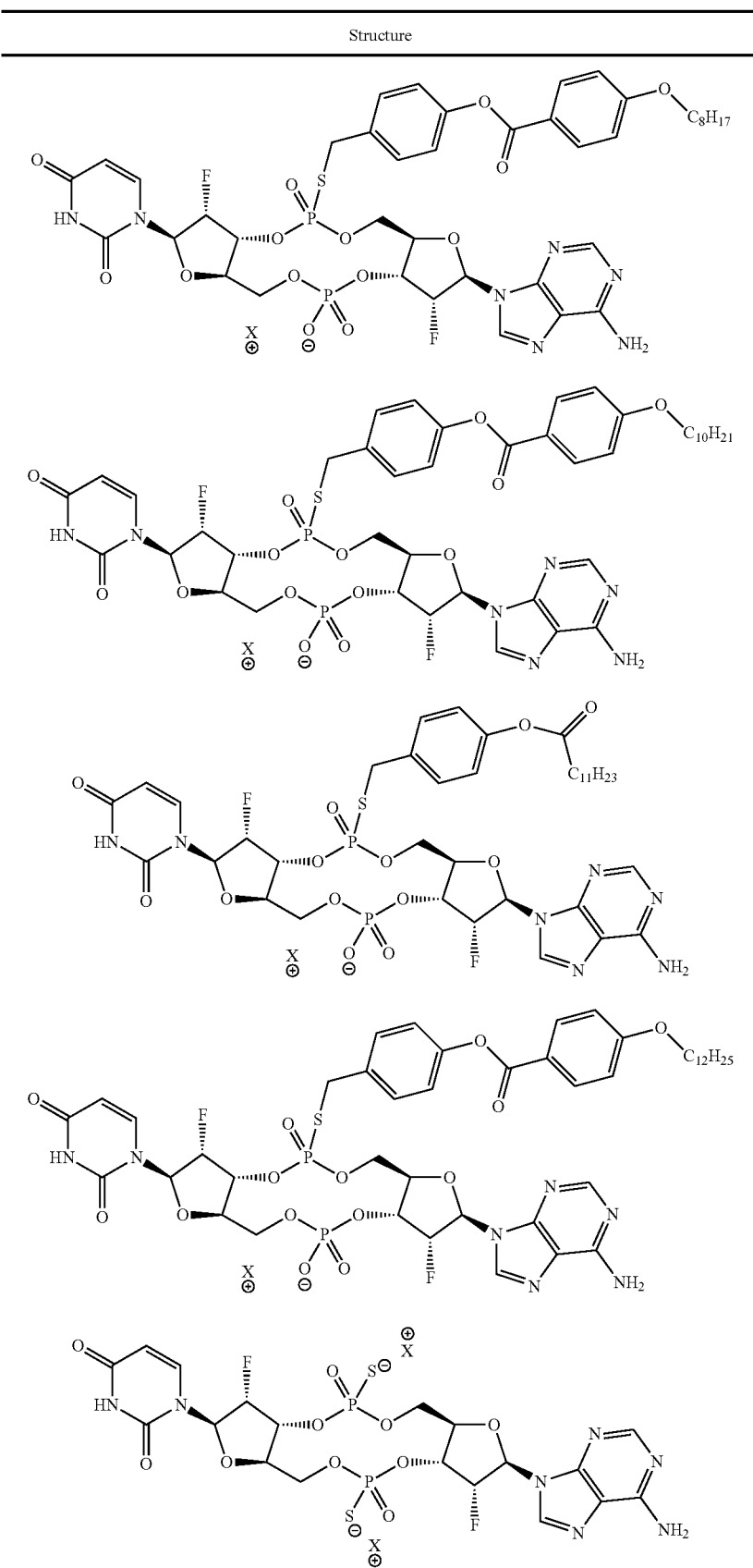

TABLE 1-continued
Structure
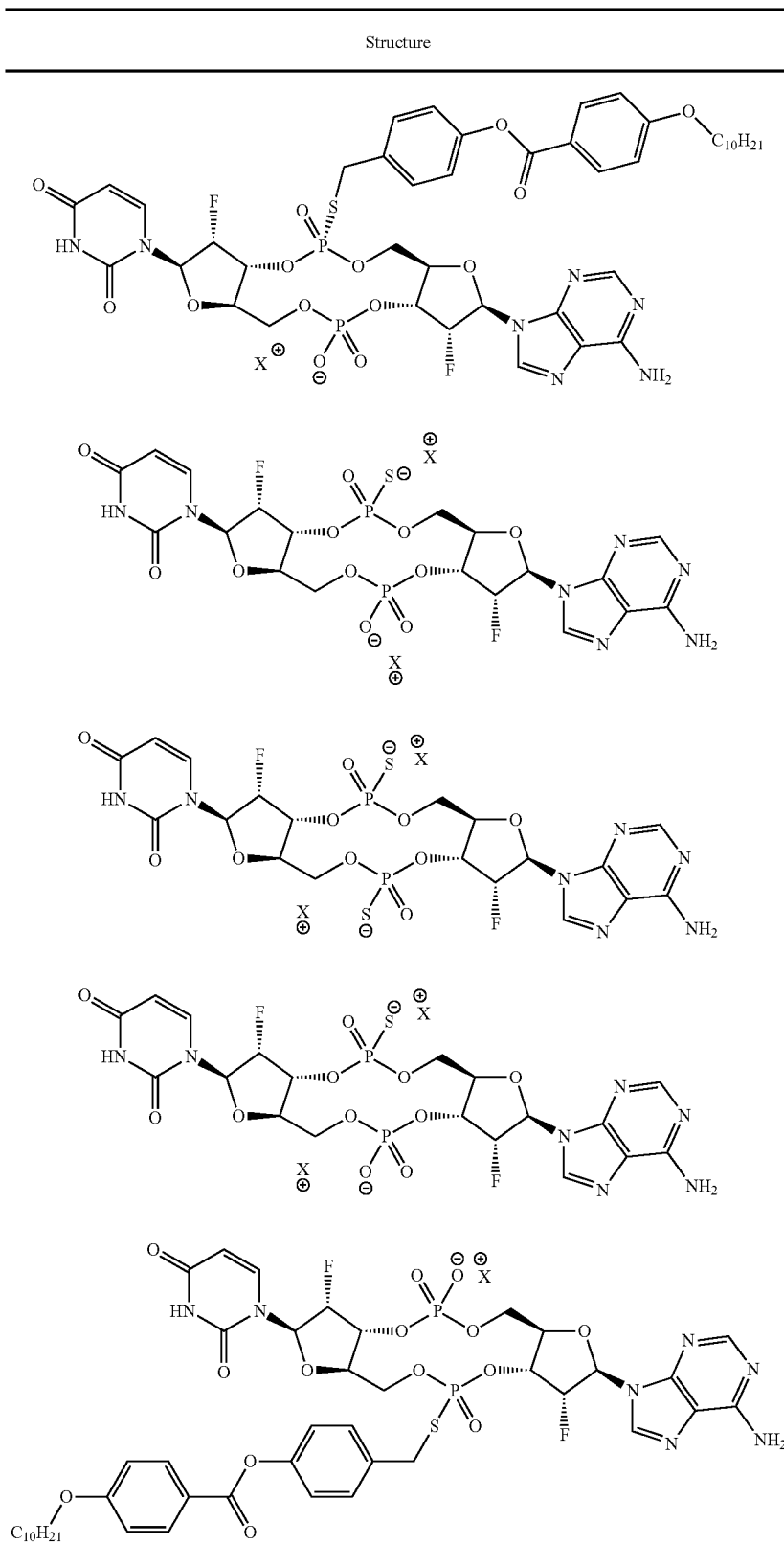

TABLE 1-continued

Structure

TABLE 1-continued

Structure

TABLE 1-continued
Structure
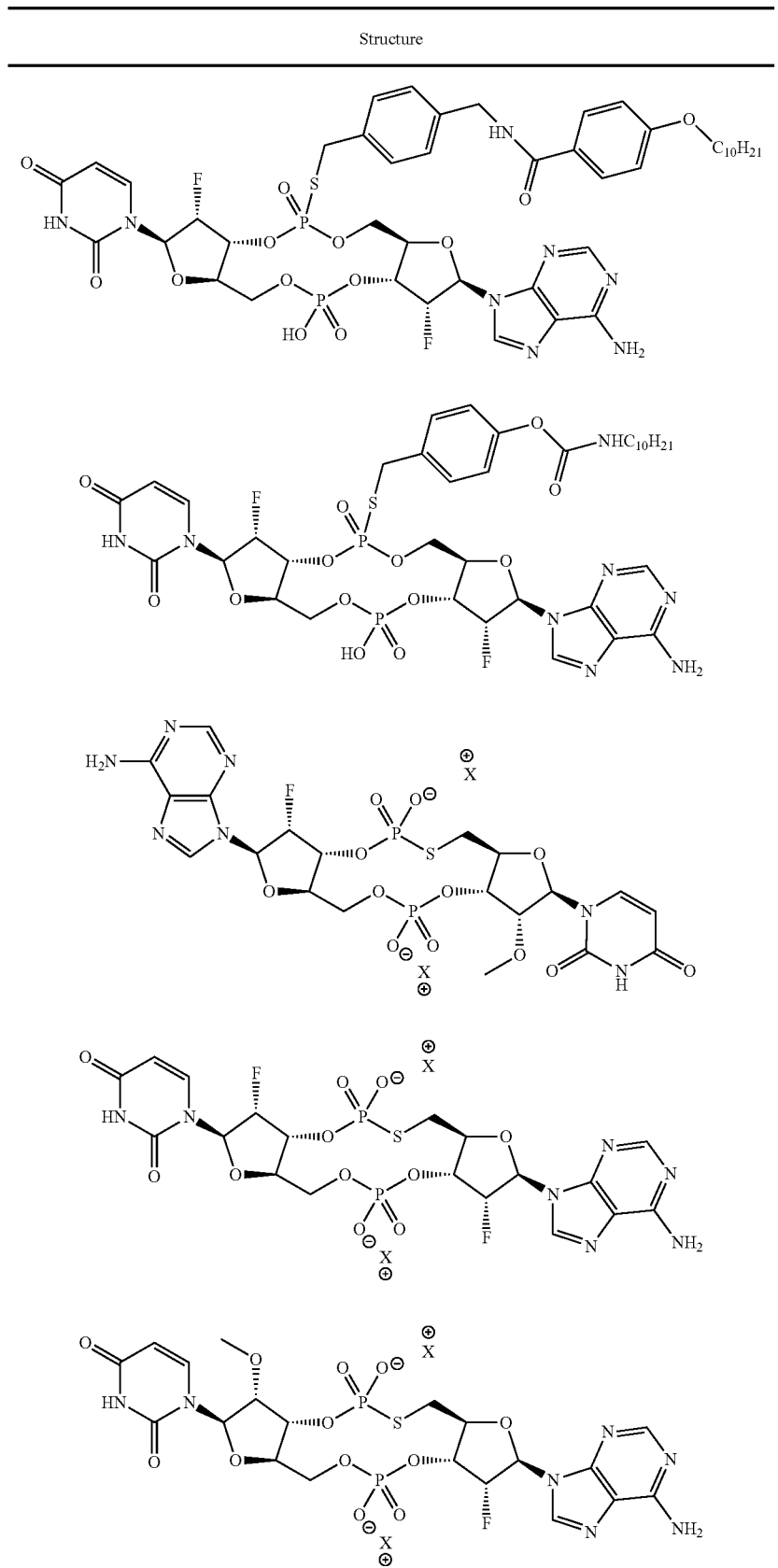

TABLE 1-continued

Structure

[Chemical structure: dinucleotide with 5-phenyluracil and adenine bases, containing phosphorothioate and phosphate linkages with fluorine substituents, shown with two X counterions]

wherein X is any pharmaceutically acceptable counterion, e.g., lithium, sodium, potassium, calcium, magnesium, aluminum, ammonium, ethylamine, diethylamine, ethylenediamine, ethanolamine, diethanolamine, piperazine and the like (see, for example, Berge et al., supra). In some embodiments, the compound of Table 1 is not a salt (e.g., is a free acid or free base).

In some embodiments, the compound is selected from a compound depicted in Table 2:

TABLE 2

| Compound No. | Structure |
| --- | --- |
| Cmd 5 | [Chemical structure: dinucleotide with uracil and adenine bases, fluorine substituents, phosphorothioate with isopropyl carbonate methyl group, and phosphate linkage with $NH_4^+$ counterion] |
| Cmd 16 | [Chemical structure: dinucleotide with uracil and adenine bases, 2'-OMe substituent, two phosphorothioate linkages each bearing an isopropyl carbonate methyl group] |

TABLE 2-continued
| Compound No. | Structure |
| --- | --- |
| Cmd 17 | 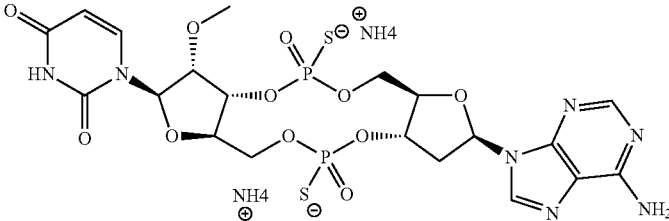 [SMILES: CO[C@@H]1[C@@H]2OP(=O)([S-])OC[C@H]3O[C@@H](n4cnc5c(N)ncnc54)C[C@@H]3OP(=O)([S-])OC[C@H]2O[C@H]1n1ccc(=O)[nH]c1=O ; [NH4+] ; [NH4+]] |
| Cmd 18 | 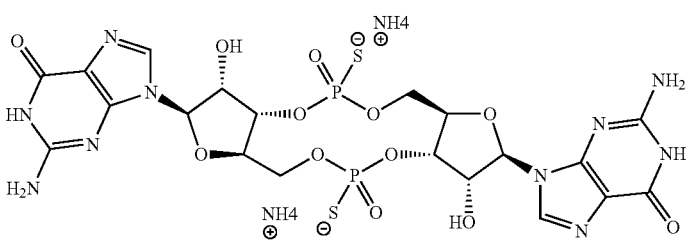 [SMILES: [NH4+] ; Nc1nc2c(ncn2[C@@H]2O[C@@H]3COP(=O)([S-])O[C@H]4[C@@H](O)[C@H](n5cnc6c(=O)[nH]c(N)nc65)O[C@@H]4COP(=O)([S-])O[C@H]3[C@H]2O)c(=O)[nH]1 ; [NH4+]] |
| Cmd 14 | 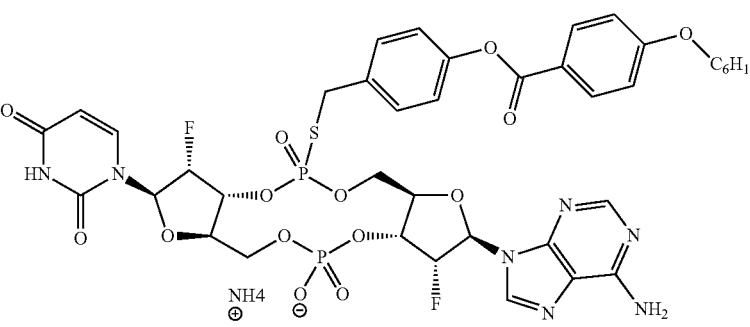 |
| Cmd 12 | 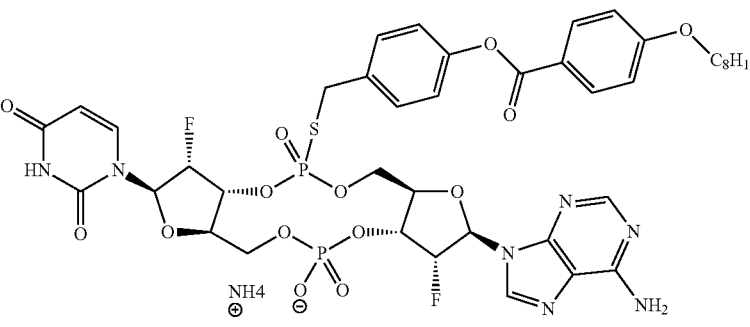 |
| Cmd 1 | 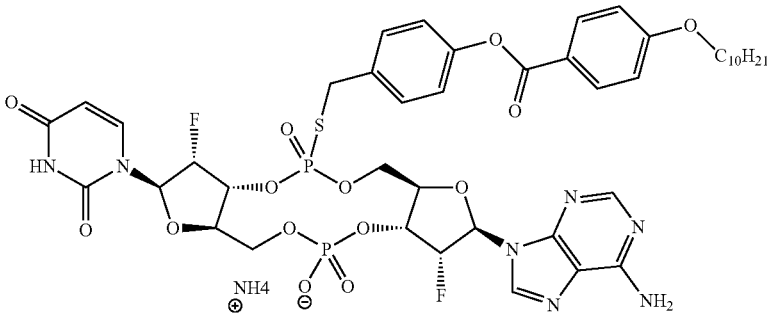 |

TABLE 2-continued

| Compound No. | Structure |
|---|---|
| Cmd 13 | 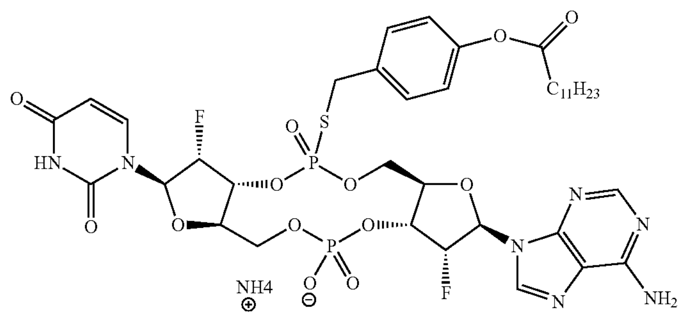 |
| Cmd 15 | 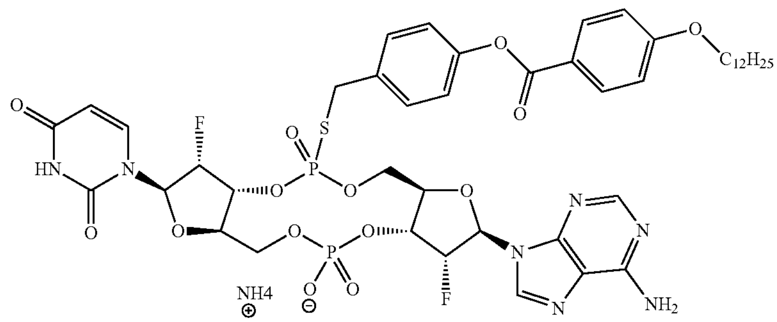 |
| Cmd 4 | 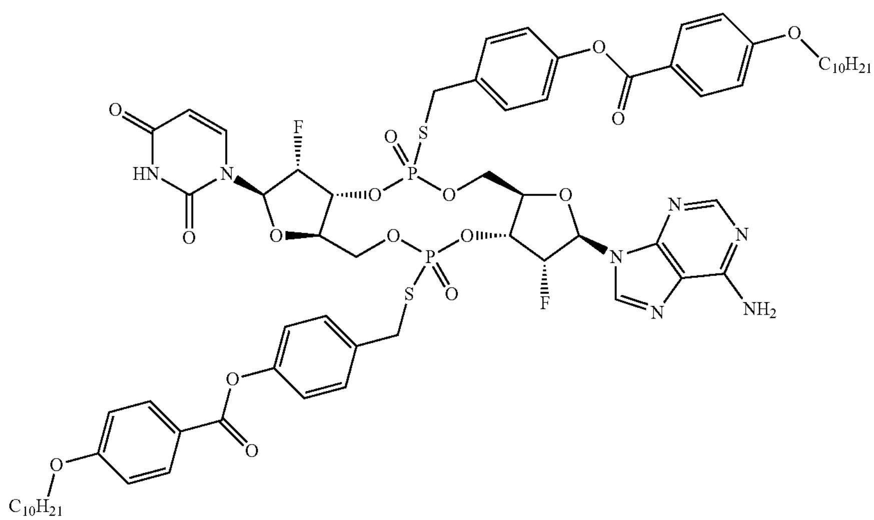 |
| Cmd 2 | 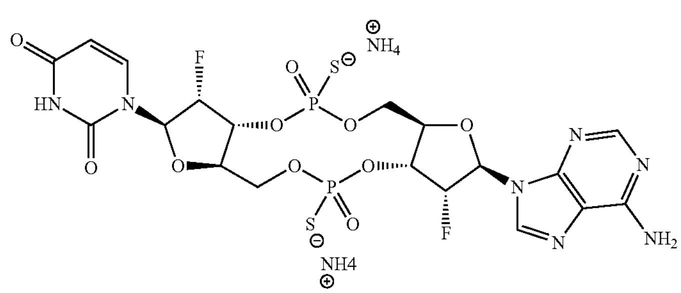 [SMILES: Nc1ncnc2c1ncn2[C@@H]1O[C@@H]2COP(=O)([S-])O[C@H]3[C@@H](F)[C@H](n4ccc(=O)[nH]c4=O)O[C@@H]3COP(=O)([S-])O[C@H]2[C@H]1F ; [NH4+] ; [NH4+]] |

TABLE 2-continued
| Compound No. | Structure |
|---|---|
| Cmd 1B | 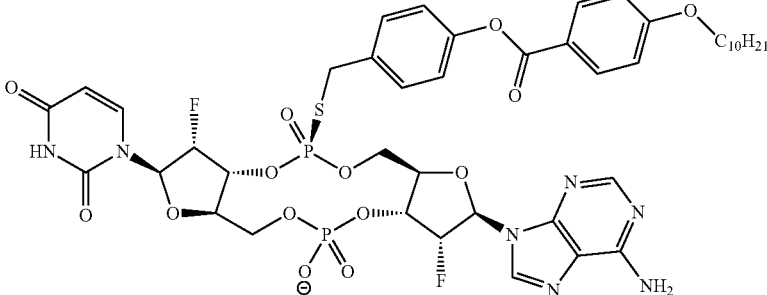 |
| Cmd 1A | 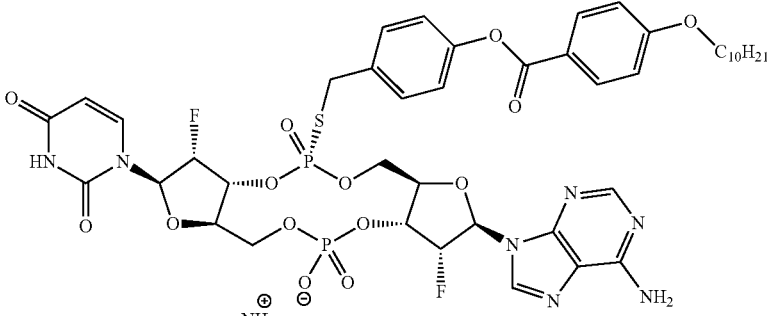 |
| Cmd 19 | 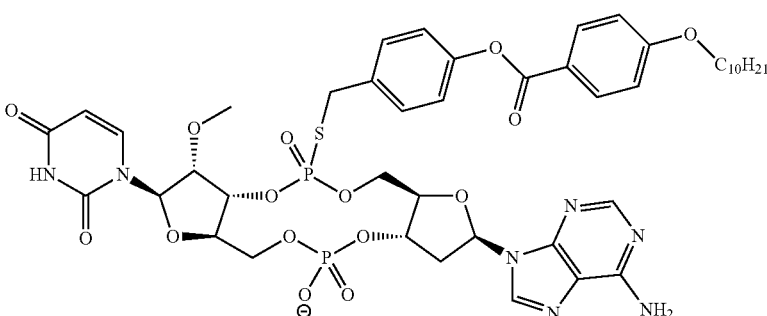 |
| Cmd 20 | 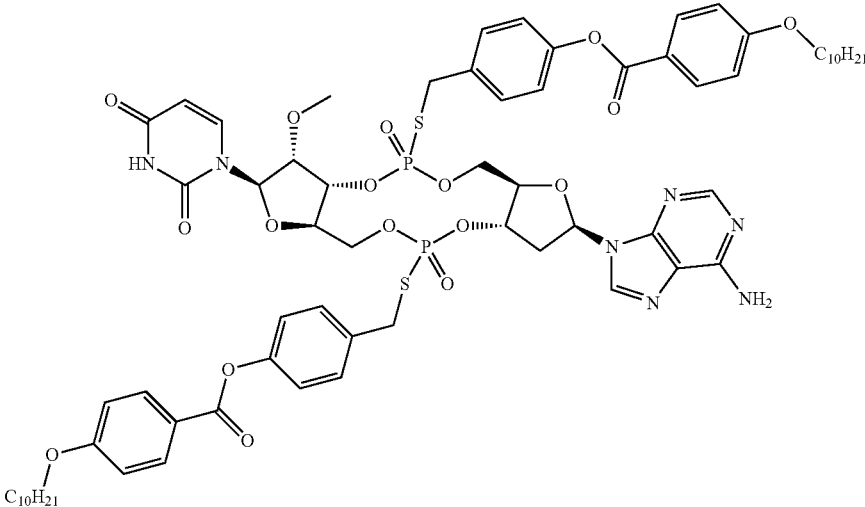 |

TABLE 2-continued

| Compound No. | Structure |
|---|---|
| Cmd 21 | *(chemical structure)* |
| Cmd 22 | *(chemical structure)* |
| Cmd 23 | *(chemical structure)* |
| Cmd 8 | *(chemical structure)* |
| Cmd 3 | *(chemical structure)* |

TABLE 2-continued
| Compound No. | Structure |
|---|---|
| Cmd 9 | 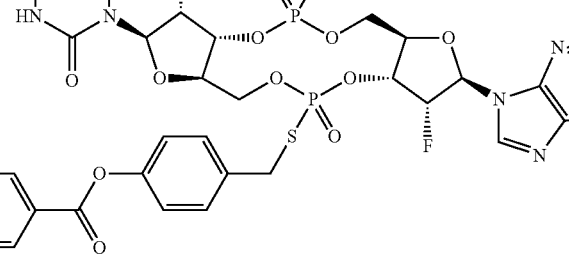 |
| Cmd 10 | 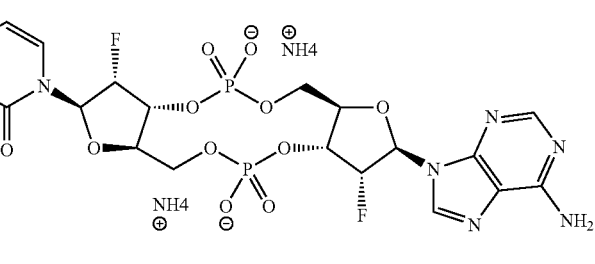 |
| Cmd 11 | 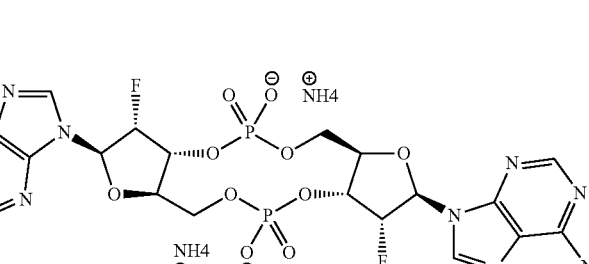 |
| Cmd 24 | 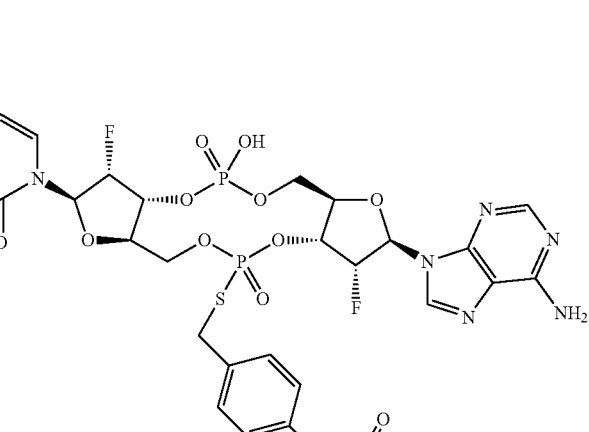 |

TABLE 2-continued

| Compound No. | Structure |
| --- | --- |
| Cmd 25 | 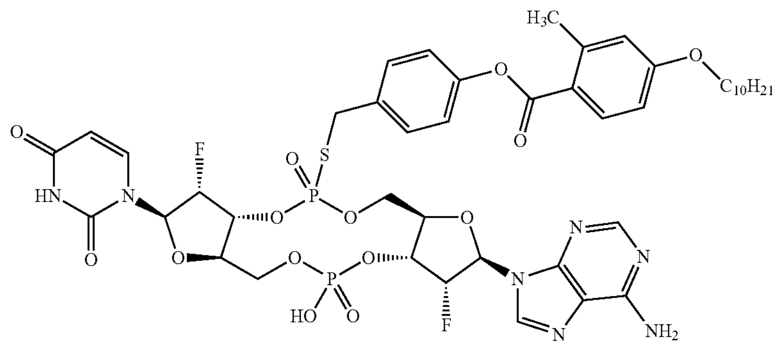 |
| Cmd 26 | 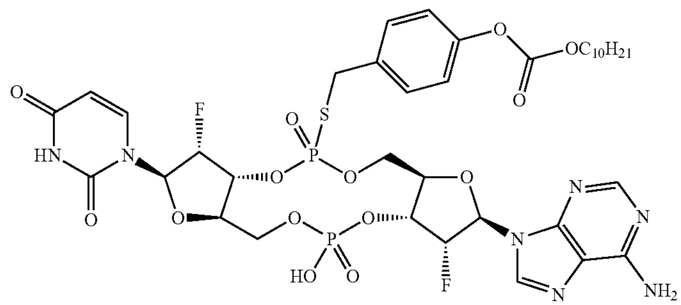 |
| Cmd 27 | 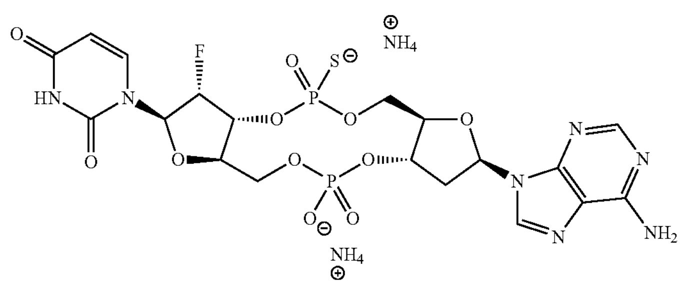 [SMILES: Nc1ncnc2c1ncn2[C@H]1C[C@@H]2OP(=O)([O-])OC[C@H]3O[C@@H](n4ccc(=O)[nH]c4=O)[C@H](F)[C@@H]3OP(=O)([S-])OC[C@H]2O1 ; [NH4+] ; [NH4+]] |
| Cmd 28 | 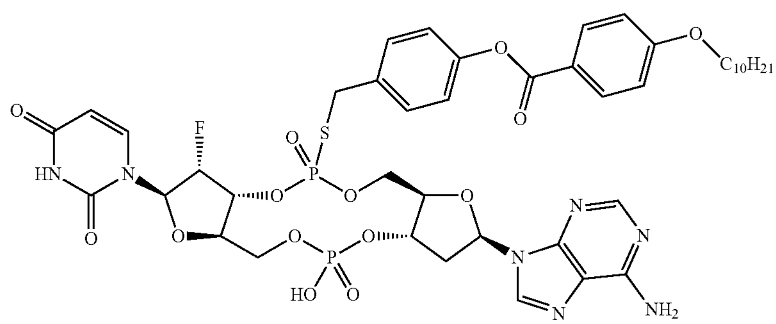 |

TABLE 2-continued
| Compound No. | Structure |
|---|---|
| Cmd 29 | 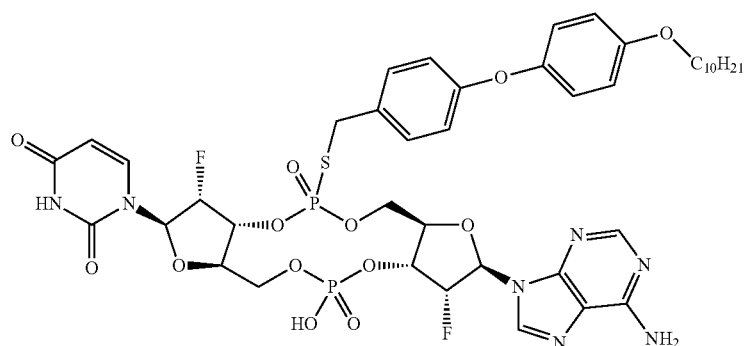 |
| Cmd 30 | 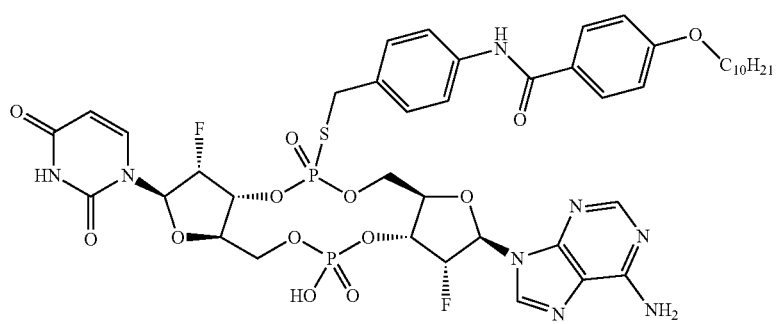 |
| Cmd 31 | 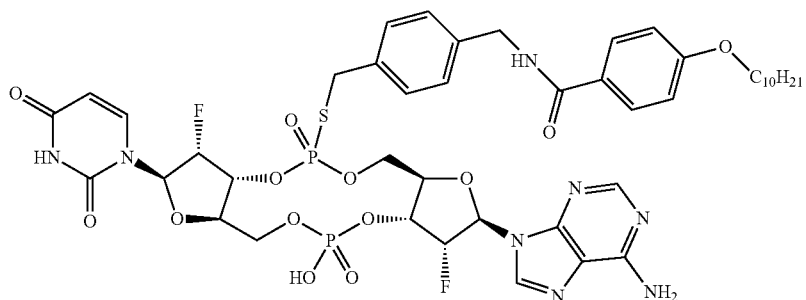 |
| Cmd 32 | 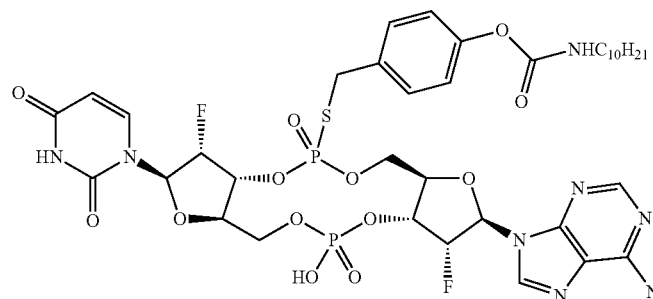 |
| Cmd 33 | 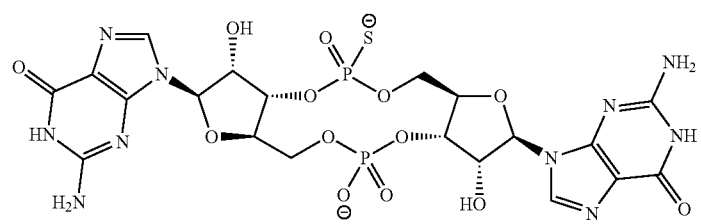 [SMILES: Nc1nc2c(ncn2[C@@H]2O[C@@H]3COP(=O)([S-])O[C@H]4[C@@H](O)[C@H](n5cnc6c(=O)[nH]c(N)nc65)O[C@@H]4COP(=O)([O-])O[C@H]3[C@H]2O)c(=O)[nH]1] |

TABLE 2-continued

| Compound No. | Structure |
|---|---|
| Cmd 34 | 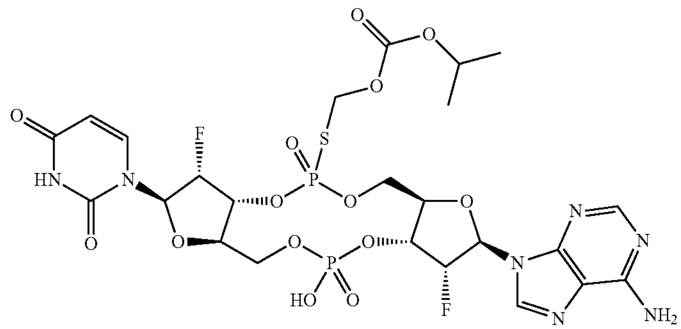 [SMILES: CC(C)OC(=O)OCSP1(=O)OC[C@H]2O[C@@H](n3cnc4c(N)ncnc43)[C@H](F)[C@@H]2OP(=O)(O)OC[C@H]2O[C@@H](n3ccc(=O)[nH]c3=O)[C@H](F)[C@@H]2O1] |
| Cmd 35 | 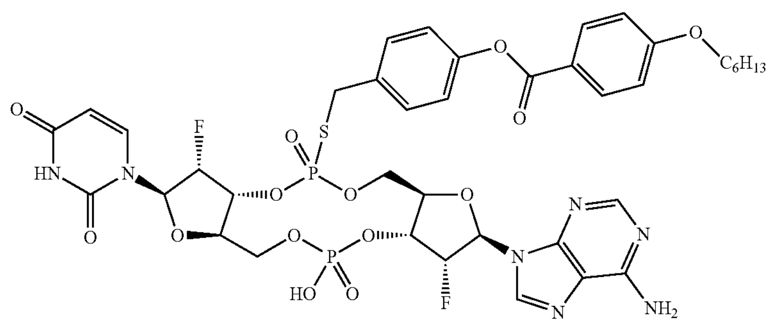 |
| Cmd 36 | 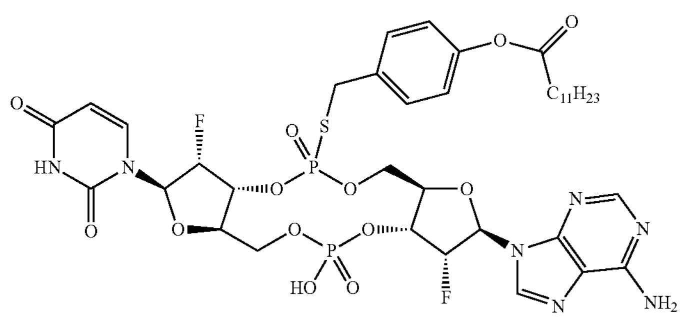 |
| Cmd 37 | 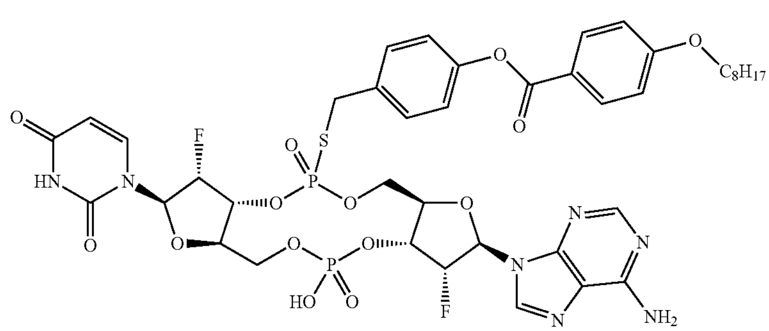 |

TABLE 2-continued

| Compound No. | Structure |
|---|---|
| Cmd 38 | (structure) |
| Cmd 39 | (structure) |
| Cmd 40 | (structure) |
| Cmd 41 | (structure) |

TABLE 2-continued
| Compound No. | Structure |
|---|---|
| Cmd 42 | 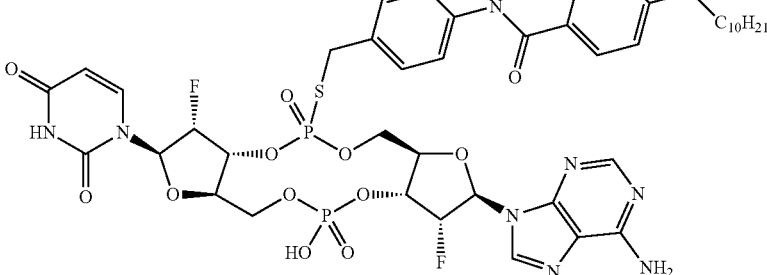 |
| Cmd 43 | 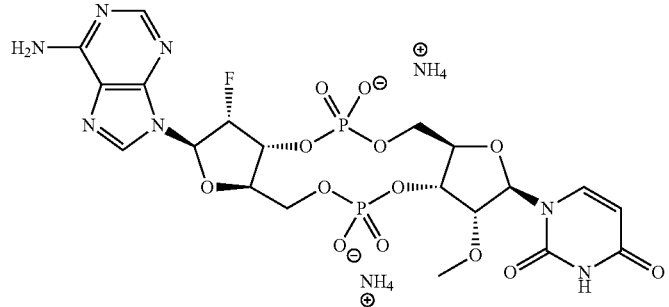 [SMILES: CO[C@@H]1[C@@H]2OP(=O)([O-])OC[C@H]3O[C@@H](n4cnc5c(N)ncnc54)[C@H](F)[C@@H]3OP(=O)([O-])OC[C@H]2O[C@H]1n1ccc(=O)[nH]c1=O ; [NH4+] ; [NH4+]] |
| Cmd 44 | 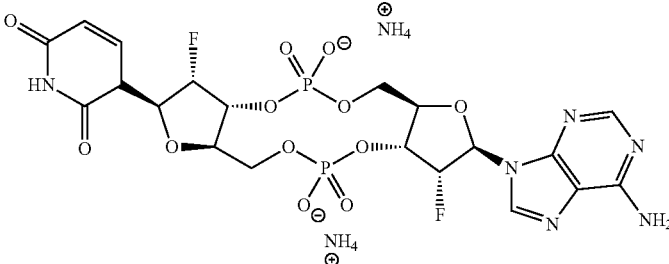 |
| Cmd 45 | 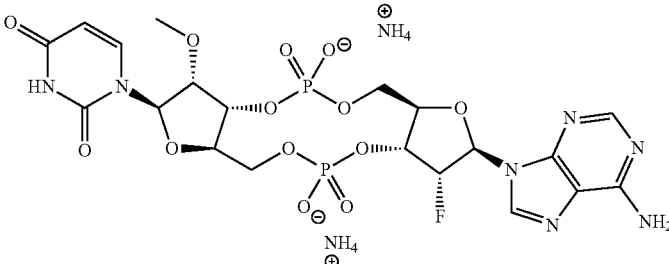 |
| Cmd 46 | 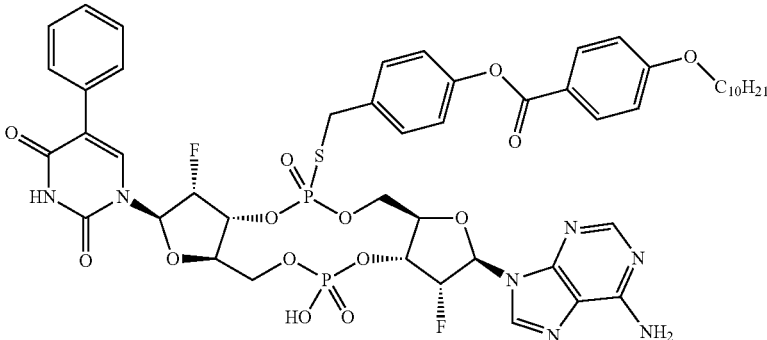 |

TABLE 2-continued

| Compound No. | Structure |
|---|---|
| Cmd 47 | 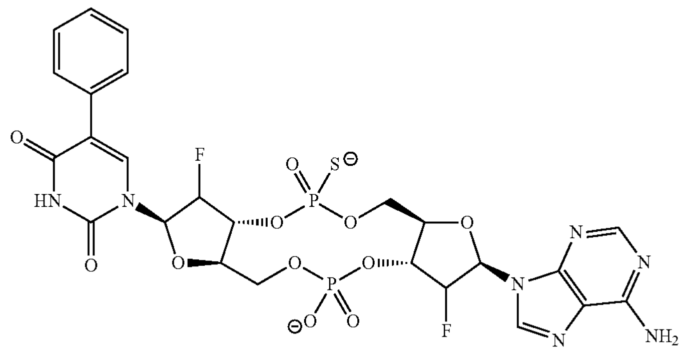 |
| Cmd 48 | 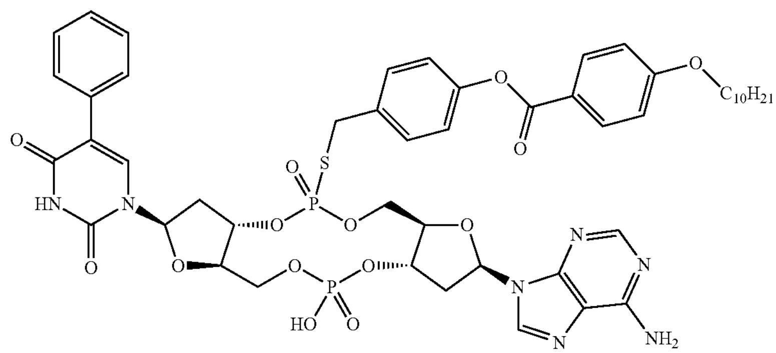 |
| Cmd 49 | 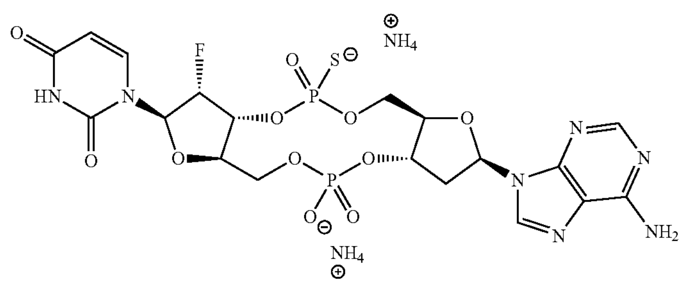 [SMILES: Nc1ncnc2c1ncn2[C@H]1C[C@@H]2OP(=O)([O-])OC[C@H]3O[C@@H](n4ccc(=O)[nH]c4=O)[C@H](F)[C@@H]3OP(=O)([S-])OC[C@H]2O1 ; [NH4+] ; [NH4+]] |
| Cmd 50 | 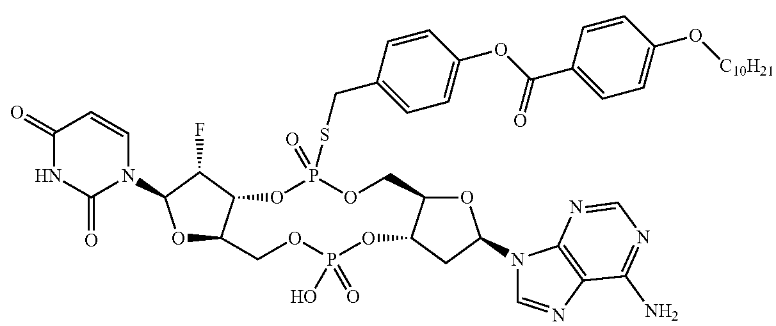 |
| Cmd 51 | 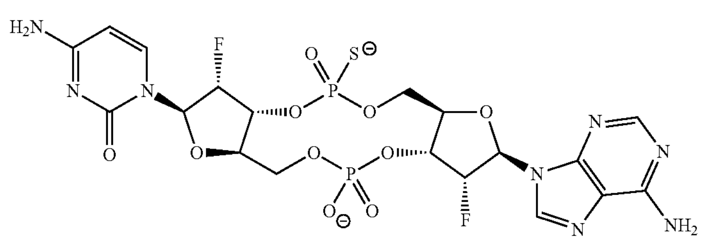 [SMILES: Nc1ccn([C@@H]2O[C@@H]3COP(=O)([O-])O[C@H]4[C@@H](F)[C@H](n5cnc6c(N)ncnc65)O[C@@H]4COP(=O)([S-])O[C@H]3[C@H]2F)c(=O)n1] |

TABLE 2-continued

| Compound No. | Structure |
|---|---|
| Cmd 52 | (structure image) | or a pharmaceutically acceptable salt thereof.

In an embodiment, a compound described herein is in the form of a pharmaceutically acceptable salt. Exemplary salts are described herein, such as ammonium salts. In some embodiments, the compound is a mono-salt. In some embodiments, the compound is a di-salt. In some embodiments, a compound described herein (e.g., a compound in Table 1 or Table 2) is not a salt (e.g., is a free acid or free base).

A compound of Formula (I) or Formula (I-a) is a small molecule nucleic acid hybrid (cyclic dinucleotide) compound that combines both antiviral and immune modulating activities. The latter activity mediates, for example, controlled apoptosis of virus-infected hepatocytes via stimulation of the innate immune response, similar to what is also achieved by IFN-α therapy in patients suffering from a viral infection.

Without wishing to be bound by theory, the mechanism of action of a compound of Formula (I) or Formula (I-a) entails its host immune stimulating activity, which may induce endogenous IFNs via the activation of a PRR, e.g., RIG-I, NOD2, and STING. Activation may occur by binding of a compound of Formula (I) to the nucleotide binding domain of a PRR (e.g., STING), as described previously, and may further result in the induction of PRR expression (e.g., STING expression).

The compounds provided herein may contain one or more asymmetric centers and thus occur as racemates and racemic mixtures, single enantiomers, individual diastereomers, and diastereomeric mixtures. All such isomeric forms of these compounds are expressly included within the scope. Unless otherwise indicated when a compound is named or depicted by a structure without specifying the stereochemistry and has one or more chiral centers, it is understood to represent all possible stereoisomers of the compound. The compounds provided herewith may also contain linkages (e.g., carbon-carbon bonds, phosphorus-oxygen bonds, or phosphorus-sulfur bonds) or substituents that can restrict bond rotation, e.g. restriction resulting from the presence of a ring or double bond.

In some embodiments, the method described herein comprises administration of a compound of Formula (I) or a pharmaceutically acceptable salt thereof. In some embodiments, the method described herein comprises administration of a compound of Formula (I-a) or a pharmaceutically acceptable salt thereof. In some embodiments, the compound of Formula (I) comprises an isomer (e.g., an Rp-isomer or Sp isomer) or a mixture of isomers (e.g., Rp-isomers or Sp isomers) of a compound of Formula (I). In some embodiments, the compound of Formula (I) comprises an isomer (e.g., an Rp-isomer or Sp isomer) or a mixture of isomers (e.g., Rp-isomers or Sp isomers) of a compound of Formula (I-a).

Methods of Use

The present disclosure relates to methods for inducing the expression of a PRR (e.g., STING) in a subject through administration of a compound of Formula (I) or a pharmaceutically acceptable salt thereof. In some embodiments, the subject may be suffering from a condition described below, e.g., a proliferative disease, e.g., a cancer.

It has been reported that many patients with advanced solid tumors show a spontaneous T cell-inflamed tumor microenvironment, which is predictive of prognosis and clinical response to immunotherapies. Recent findings suggest the STING pathway of cytosolic DNA sensing is an important innate immune sensing mechanism driving type I IFN production in the tumor context. Knowledge of this pathway is guiding the further development of novel immunotherapeutic strategies.

It has been reported that in early-stage colorectal cancer, the presence of activated CD8+ T cells within the tumor microenvironment significant positive prognostic outcome. Patients with other solid tumor histology also appear to have a spontaneous T cell infiltrate that may have similar positive prognostic value. These include breast cancer, renal cell carcinoma, melanoma, ovarian cancer, and gastrointestinal tumors. It is believed that T cell infiltrate includes tumor antigen-specific T cells that have been activated spontaneously in response to the growing tumor, perhaps through immune surveillance mechanisms. This attempted host immune response, even if it does not eliminate the tumor completely, is thought to delay tumor progression and thus yield improved clinical outcome. Furthermore, the innate immune mechanisms can lead to adaptive T cell response against tumor antigens even in the absence of exogenous infection. In this regard, human cancer gene expression profiling studies reveal an association between a type I IFN signature, T cell infiltration, and clinical outcome. Thus, innate immune sensing pathways that trigger type I IFN production might represent crucial intermediate mechanistic step. In gene expression profiling of melanoma, two major subsets of tumor microenvironment has been found that represent either the presence or absence of a transcriptional profile indicative of T cell infiltrate. In fact, CD8+ T cells, macrophages, as well as of some B cells and plasma cells in these lesions in melanoma metastases is similar to the phenotype described in early-stage colon cancer and other tumors in which activated T cells have been associated with favorable prognosis. CD8+ T cells were required for the up-regulation of all immune factors within the tumor microenvironment. Studies indicate that IFN production is necessary for optimal T cell priming against tumor antigens. There are many PRRs that trigger IFN-β production by host DCs in response to a growing tumor in vivo including STING. STING is an adapter protein that is activated by cyclic dinucleotides generated by cyclic GMP-AMP synthase (cGAS), which in turn is directly activated by cytosolic DNA. In the presence of these cyclic dinucleotides and/or DNA, STING is translocated from the endoplasmic reticulum to various perinuclear components; for example, palmitoylation of STING at the Golgi has been shown to be essential for STING activation (Mukai, K. et al (2016) Nat Commun doi: 10.1038/ncomms 11932).

Activated STING forms aggregates, activates TBK1, which in turn phosphorylates interferon regulatory factor 3 (IRF3) that directly contributes to type I IFN gene transcription.

This pathway has been implicated in the sensing of DNA viruses, and also in selected autoimmune models. Moreover, activating mutations of STING have recently been identified in human patients with a vasculitis/pulmonary inflammation syndrome that is characterized by increased type I IFN production. Mechanistic studies using mouse transplantable tumor models revealed that STING-knockout mice, and IRF3-knockout mice showed defective spontaneous T cell priming against tumor antigens in vivo, and rejection of immunogenic tumors was ablated. Similarly, tumor-derived DNA was found within the cytosol of a major population of tumor-infiltrating DCs, and this was associated with STING pathway activation and IFN-β production. Therefore, the host STING pathway appears to be an important innate immune sensing pathway that detects the presence of a tumor and to drive DC activation and subsequent T cell priming against tumor-associated antigens in vivo. A functional role for the STING pathway in vivo has also been reported in other mouse-tumor systems. An inducible glioma model was shown to result in induction of a type I IFN gene signature as part of the host response. This induction was substantially reduced in STING-knockout mice, and tumors grew more aggressively, leading to shorter mouse survival. Exogenous delivery of cyclic dinucleotides as STING agonists exerted a therapeutic effect in vivo. A crucial role for host type I IFNs and the host STING pathway was also confirmed in the B16.OVA and EL4.OVA models in response to cryo-ablation. Interestingly, the mechanisms involved paralleled what was observed in the Bm12 mouse model of lupus because host STING was also required for maximal production of anti-DNA antibodies. Thus, the antitumor immune response triggered in part by tumor DNA has overlap with the mechanisms involved in autoimmunity driven by extracellular DNA. A role for STING also has been explored in an inducible colon cancer model. It seems likely that the ability of a cancer in an individual patient to support STING pathway activation is linked to the spontaneous generation of a T cell-inflamed tumor microenvironment. Because this phenotype is associated with improved prognosis of early-stage cancer patients, and also with clinical response to immunotherapies in the metastatic setting, failed STING activation may therefore represent an early functional block, and thus itself may have prognostic/predictive value as a biomarker. Second, strategies that activate or mimic the output of the host STING pathway should have immunotherapeutic potential in the clinic. In as much as non-T cell-inflamed tumors appear to lack evidence of a type I IFN transcriptional signature, strategies to promote robust innate signaling via APCs in the tumor microenvironment might facilitate improved cross-priming of tumor antigen-specific CD8+ T cells, and also augment chemokine production for subsequent oncolytic activity.

Treatment of Cancer

Recognition of nucleic acid ligands by a PRRs such as cGAS, RIG-I and/STING stimulates the production of type I interferons (e.g., IFN-α or IFN-β 3), thus triggering a series of downstream signaling events that may lead to apoptosis in susceptible cells. In recent years, a connection between the induction of PRR expression and a number of cancers has been discovered. For example, RIG-I expression has been shown to be significantly downregulated in hepatocellular carcinoma, and patients exhibiting low RIG-I expression in tumors had shorter survival and poorer responses to IFN-α therapy (Hou, J. et al, Cancer Cell (2014) 25:49-63). As such, it has been suggested that the level of RIG-I expression may be useful as a biomarker for prediction of prognosis and response to immunotherapy. In other cases, induction of RIG-I expression has been shown to induce immunogenic cell death of pancreatic cancer cells, prostate cancer cells, breast cancer cells, skin cancer cells, and lung cancer cells (Duewell, P. et al, Cell Death Differ (2014) 21:1825-1837; Besch, R. et al, J Clin Invest (2009) 119: 2399-2411; Kaneda, Y. Oncoimmunology (2013) 2:e23566; Li, X. Y. et al, Mol Cell Oncol (2014) 1:e968016), highlighting a new approach in immune-mediated cancer treatment.

STING is recognized as the key adapter protein in the cGAS-STING-IFN cascade, although it is also reported to be a sensor for DNA. A role for STING in the stimulation of innate immunity in response to cancer has also been identified. Recent studies have revealed the presence of tumor-derived DNA in the cytosol of certain antigen-presenting cells, such as tumor-infiltrating dendritic cells, likely generated through tumor cell stress or cell death. This tumor-derived DNA is known to activate cGAS which causes the production of cyclic nucleotides that have been shown to activate STING, resulting in production of associated type 1 interferons (Woo, S. R. et al, Immunity (2014) 41:830-842).

Stimulation of STING and resulting downstream signaling pathways also likely contributes to effector T cell recruitment into the inflamed tumor microenvironment (Woo, S. R. Trends in Immunol (2015) 36:250-256). STING activation in the tumor microenvironment can induce adaptive immune response leading to anti-tumor activity. Hence, in those tumors that are STING-deficient, the described herein can still have anti-tumor activity through activation of antigen-presenting cells and dendritic cells, (APCs and DCs) and induction of adaptive immune response.

In some embodiments, the methods of inducing expression of a PRR (e.g., a PRR described herein) comprise administration of a compound of Formula (I) or a pharmaceutically acceptable salt thereof to a subject suffering from cancer. In some embodiments, the methods of inducing expression of a PRR (e.g., a PRR described herein) comprise administration of a compound of Formula (I-a) or a pharmaceutically acceptable salt thereof to a subject suffering from cancer. In some embodiments, the methods of inducing expression of STING disclosed herein comprise administration of a compound of Formula (I) or a pharmaceutically acceptable salt thereof to a subject suffering from cancer. In some embodiments, the methods of inducing expression of STING disclosed herein comprise administration of a compound of Formula (I-a) or a pharmaceutically acceptable salt thereof to a subject suffering from cancer. In some embodiments, the methods of inducing expression of RIG-I disclosed herein comprise administration of a compound of Formula (I) or a pharmaceutically acceptable salt thereof to a subject suffering from cancer. In some embodiments, the methods of inducing expression of RIG-I disclosed herein comprise administration of a compound of Formula (I-a) or a pharmaceutically acceptable salt thereof to a subject suffering from cancer. In some embodiments, the methods of inducing expression of NOD2 disclosed herein comprise administration of a compound of Formula (I) or a pharmaceutically acceptable salt thereof to a subject suffering from cancer. In some embodiments, the methods of inducing expression of NOD2 disclosed herein comprise administration of a compound of Formula (I-a) or a pharmaceutically acceptable salt thereof to a subject suffering from cancer. In some embodiments, the cancer is selected from a cancer of the breast, bone, brain, cervix, colon, gastrointestinal tract, eye, gall bladder, lymph nodes, blood, lung, liver, skin, mouth, prostate, ovary, penis, pancreas, uterus, testicles, stomach, thymus, thyroid, or other part of the body. In some embodiments, the cancer comprises a solid tumor (e.g., a carcinoma, a sarcoma, or a lymphoma). In some embodiments, the cancer is a hepatocellular carcinoma or other cancer of the liver. In some embodiments, the cancer is a leukemia or other cancer of the blood. In some embodiments, the cancer comprises breast cancer, renal cell carcinoma, colon cancer, melanoma, ovarian cancer, head and neck squamous cell carcinoma, pancreatic cancer, prostate cancer, lung cancer, brain cancer, thyroid cancer, renal cancer, testis cancer, stomach cancer, urothelial cancer, skin cancer, cervical cancer, endometrial cancer, liver cancer, lung cancer, lymphoma or gastrointestinal stromal cancer and solid tumors. In some embodiments, the cancer cells (e.g., tumor cells) comprise specific cancer-associated antigens that induce a T-cell-mediated anti-tumor response.

In some embodiments, the methods of inducing expression of a PRR (e.g., STING, RIG-I, MDA5, LGP2) in a subject suffering from a cancer disclosed herein result in an increase in PRR expression (e.g., STING expression). In some embodiments, expression of a PRR (e.g., STING) is induced by a factor of about 1.1, about 1.2, about 1.3, about 1.4, about 1.5, about 1.6, about 1.7, about 1.8, about 1.9, about 2, about 2.5, about 3, about 4, about 5, about 7.5, about 10, about 15, about 20, about 25, about 30, about 40, about 50, about 75, about 100, about 150, about 200, about 250, about 500, about 1000, about 1500, about 2500, about 5000, about 10,000, or more. In some embodiments, induction of expression of a PRRs e.g., STING) occurs within about 5 minutes of administration of a compound of Formula (I) or a pharmaceutically acceptable salt thereof. In some embodiments, induction of expression of a PRRs e.g., STING) occurs within about 5 minutes of administration of a compound of Formula (I-a) or a pharmaceutically acceptable salt thereof. In some embodiments, induction of expression of a PRRs (e.g., STING) occurs within about 5 minutes of administration of a compound of Formula (I) or a pharmaceutically acceptable salt thereof. In some embodiments, induction of expression of a PRR (e.g., STING) occurs within about 10 minutes, about 15 minutes, about 20 minutes, about 25 minutes, about 30 minutes, about 45 minutes, about 1 hour, about 1.5 hours, about 2 hours, about 3 hours, about 4 hours, about 5 hours, about 6 hours, about 7 hours, about 8 hours, about 10 hours, about 12 hours or more following administration of a compound of Formula (I) or a pharmaceutically acceptable salt thereof. In some embodiments, induction of expression of a PRR (e.g., STING) occurs within about 10 minutes, about 15 minutes, about 20 minutes, about 25 minutes, about 30 minutes, about 45 minutes, about 1 hour, about 1.5 hours, about 2 hours, about 3 hours, about 4 hours, about 5 hours, about 6 hours, about 7 hours, about 8 hours, about 10 hours, about 12 hours or more following administration of a compound of Formula (I-a) or a pharmaceutically acceptable salt thereof. It is recognized that activation of STING by compounds may lead to induction of expression of other PRRs such as RIG-I, MDA5, NOD2 etc. which may further amplify IFN production in the tumor microenvironment and prime T-cells for enhanced anti-tumor activity.

In some embodiments, the methods of inducing expression of a PRR (e.g., STING) in a subject suffering from a cancer disclosed herein result in an increase in PRR expression (e.g., STING expression). In some embodiments, expression of a PRR (e.g., STING) is induced by a factor of about 1.1, about 1.2, about 1.3, about 1.4, about 1.5, about 1.6, about 1.7, about 1.8, about 1.9, about 2, about 2.5, about 3, about 4, about 5, about 7.5, about 10, about 15, about 20, about 25, about 30, about 40, about 50, about 75, about 100, about 150, about 200, about 250, about 500, about 1000, about 1500, about 2500, about 5000, about 10,000, or more. In some embodiments, induction of expression of a PRR (e.g., STING) occurs within about 5 minutes of administration of a compound of Formula (I) or a pharmaceutically acceptable salt or stereoisomer thereof. In some embodiments, induction of expression of a PRR (e.g., STING) occurs within about 5 minutes of administration of a compound of Formula (I-a) or a pharmaceutically acceptable salt or stereoisomer thereof. In some embodiments, induction of expression of a PRR (e.g., STING) occurs within about 10 minutes, about 15 minutes, about 20 minutes, about 25 minutes, about 30 minutes, about 45 minutes, about 1 hour, about 1.5 hours, about 2 hours, about 3 hours, about 4 hours, about 5 hours, about 6 hours, about 7 hours, about 8 hours, about 10 hours, about 12 hours or more following administration of a compound of Formula (I) or a pharmaceutically acceptable salt thereof. In some embodiments, induction of expression of a PRR (e.g., STING) occurs within about 10 minutes, about 15 minutes, about 20 minutes, about 25 minutes, about 30 minutes, about 45 minutes, about 1 hour, about 1.5 hours, about 2 hours, about 3 hours, about 4 hours, about 5 hours, about 6 hours, about 7 hours, about 8 hours, about 10 hours, about 12 hours or more following administration of a compound of Formula (I-a) or a pharmaceutically acceptable salt thereof.

Pharmaceutical Compositions

The present disclosure features methods for inducing the expression of a PRR (e.g., STING) in a subject, the methods comprising administering a compound of Formula (I), or Formula (1-a) or a pharmaceutically acceptable salt thereof.

While it is possible for the compound of the present disclosure (e.g., a compound of Formula (I)) to be administered alone, it is preferable to administer said compound as a pharmaceutical composition or formulation, where the compounds are combined with one or more pharmaceutically acceptable diluents, excipients or carriers. The compounds according to the disclosure may be formulated for administration in any convenient way for use in human or veterinary medicine. In certain embodiments, the compounds included in the pharmaceutical preparation may be active itself, or may be a prodrug, e.g., capable of being converted to an active compound in a physiological setting. Regardless of the route of administration selected, the compounds of the present disclosure, which may be used in a suitable hydrated form, and/or the pharmaceutical compositions of the present disclosure, are formulated into a pharmaceutically acceptable dosage form such as described below or by other conventional methods known to those of skill in the art.

The amount and concentration of compounds of the present disclosure (e.g., a compound of Formula (I)) in the pharmaceutical compositions, as well as the quantity of the pharmaceutical composition administered to a subject, can be selected based on clinically relevant factors, such as medically relevant characteristics of the subject (e.g., age, weight, gender, other medical conditions, and the like), the solubility of compounds in the pharmaceutical compositions, the potency and activity of the compounds, and the manner of administration of the pharmaceutical compositions. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

Thus, another aspect of the present disclosure provides pharmaceutically acceptable compositions comprising a therapeutically effective amount or prophylactically effective amount of a compound described herein (e.g., a compound of Formula (I)), formulated together with one or more pharmaceutically acceptable carriers (additives) and/or diluents. As described in detail below, the pharmaceutical compositions of the present disclosure may be specially formulated for administration in solid or liquid form, including those adapted for oral, intratumoral, parenteral administration, for example, by subcutaneous, intramuscular, intraperitoneal, or intravenous injection as, for example, a sterile solution or suspension. However, in certain embodiments the subject compounds may be simply dissolved or suspended in sterile water. In certain embodiments, the pharmaceutical preparation is non-pyrogenic, i.e., does not elevate the body temperature of a patient.

The phrases "systemic administration," "administered systemically," "peripheral administration" and "administered peripherally" as used herein mean the administration of the compound other than directly into the central nervous system, such that it enters the patient's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, stabilizing agent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include, but are not limited to: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) ascorbic acid; (17) pyrogen-free water; (18) isotonic saline; (19) Ringer's solution; (20) ethyl alcohol; (21) phosphate buffer solutions; (22) cyclodextrins such as Captisol®; and (23) other non-toxic compatible substances such as antioxidants and antimicrobial agents employed in pharmaceutical formulations.

As set out above, certain embodiments of the compounds described herein may contain a basic functional group, such as an amine, and are thus capable of forming pharmaceutically acceptable salts with pharmaceutically acceptable acids. The term "pharmaceutically acceptable salts" in this respect, refers to the relatively non-toxic, inorganic and organic acid addition salts of compounds of the present disclosure. These salts can be prepared in situ during the final isolation and purification of the compounds of the disclosure, or by separately reacting a purified compound of the disclosure in its free base form with a suitable organic or inorganic acid, and isolating the salt thus formed.

Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, for example, Berge et al. (1977) "Pharmaceutical Salts", *J. Pharm. Sci.* 66:1-19).

In other cases, the compounds of the present disclosure may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of the compound of the present disclosure (e.g., a compound of Formula (I). These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The pharmaceutically acceptable carriers, as well as wetting agents, emulsifiers, lubricants, coloring agents, release agents, coating agents, sweetening, flavoring agents, perfuming agents, preservatives, antioxidants, and other additional components may be present in an amount between about 0.001% and 99% of the composition described herein.

For example, said pharmaceutically acceptable carriers, as well as wetting agents, emulsifiers, lubricants, coloring agents, release agents, coating agents, sweetening, flavoring agents, perfuming agents, preservatives, antioxidants, and other additional components may be present from about 0.005%, about 0.01%, about 0.05%, about 0.1%, about 0.25%, about 0.5%, about 0.75%, about 1%, about 1.5%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 85%, about 90%, about 95%, or about 99% of the composition described herein.

Pharmaceutical compositions of the present disclosure may be in a form suitable for oral administration, e.g., a liquid or solid oral dosage form. In some embodiments, the liquid dosage form comprises a suspension, a solution, a linctus, an emulsion, a drink, an elixir, or a syrup. In some embodiments, the solid dosage form comprises a capsule, tablet, powder, dragée, or powder. The pharmaceutical composition may be in unit dosage forms suitable for single administration of precise dosages. Pharmaceutical compositions may comprise, in addition to the compound described herein (e.g., a compound of Formula (I)) or a pharmaceutically acceptable salt thereof, a pharmaceutically acceptable carrier, and may optionally further comprise one or more pharmaceutically acceptable excipients, such as, for example, stabilizers (e.g., a binder, e.g., polymer, e.g., a precipitation inhibitor, diluents, binders, and lubricants.

In some embodiments, the composition described herein comprises a liquid dosage form for oral administration, e.g., a solution or suspension. In other embodiments, the composition described herein comprises a solid dosage form for oral administration capable of being directly compressed into a tablet. In addition, said tablet may include other medicinal or pharmaceutical agents, carriers, and or adjuvants. Exemplary pharmaceutical compositions include compressed tablets (e.g., directly compressed tablets), e.g., comprising a compound of the present disclosure (e.g., a compound of Formula (I)) or a pharmaceutically acceptable salt thereof.

Formulations of the present disclosure include those suitable for parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about 99 percent of active ingredient, preferably from about 5 percent to about 70 percent, most preferably from about 10 percent to about 30 percent. Pharmaceutical compositions of this disclosure suitable for parenteral administration comprise compounds of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a compound of the present disclosure (e.g., a compound of Formula (I)), it may be desirable to slow the absorption of the drug from subcutaneous, intraperitoneal, or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered form of the compound of the present disclosure is accomplished by dissolving or suspending compound in an oil vehicle.

In some embodiments, it may be advantageous to administer the compound of the present disclosure (e.g., a compound of Formula (I)) in a sustained fashion. It will be appreciated that any formulation that provides a sustained absorption profile may be used. In certain embodiments, sustained absorption may be achieved by combining a compound of the present disclosure with other pharmaceutically acceptable ingredients, diluents, or carriers that slow its release properties into systemic circulation.

Routes of Administration

The compounds and compositions used in the methods described herein may be administered to a subject in a variety of forms depending on the selected route of administration, as will be understood by those skilled in the art. Exemplary routes of administration of the compositions used in the methods described herein include topical, enteral, or parenteral applications. Topical applications include but are not limited to epicutaneous, inhalation, enema, eye drops, ear drops, and applications through mucous membranes in the body. Enteral applications include oral administration, rectal administration, vaginal administration, and gastric feeding tubes. Parenteral administration includes intravenous, intraarterial, intracapsular, intraorbital, intracardiac, intradermal, transtracheal, subcuticular, intraarticular, subcapsular, subarachnoid, intraspinal, epidural, intrastemal, intraperitoneal, subcutaneous, intramuscular, transepithelial, nasal, intrapulmonary, intrathecal, rectal, and topical modes of administration. Parenteral administration may be by continuous infusion over a selected period of time. In certain embodiments of the disclosure, a composition described herein comprising a compound of Formula (I) is administered orally. In certain embodiments of the disclosure, a composition described herein comprising a compound of Formula (I-a) is administered orally. In other embodiments of the disclosure, a composition described herein comprising a compound of Formula (I) is administered parenterally (e.g., intraperitoneally). It is recognized that for treatment of solid tumors, direct injection of the compounds into the tumor may also be carried out (e.g., intratumoral administration). In other embodiments of the disclosure, a composition described herein comprising a compound of Formula (I-a) is administered parenterally (e.g., intraperitoneally). It is recognized that for treatment of solid tumors, direct injection of the compounds into the tumor may also be carried out (e.g., intratumoral administration).

For intravenous, intraperitoneal, or intrathecal delivery or direct injection (e.g., intratumoral), the composition must be sterile and fluid to the extent that the composition is deliverable by syringe. In addition to water, the carrier can be an isotonic buffered saline solution, ethanol, polyol (for example, glycerol, propylene glycol, and liquid polyethelyne glycol, and the like), and suitable mixtures thereof. Proper fluidity can be maintained, for example, by use of a coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

The choice of the route of administration will depend on whether a local or systemic effect is to be achieved. For example, for local effects, the composition can be formulated for topical administration and applied directly where its action is desired. For systemic, long term effects, the composition can be formulated for enteral administration and given via the digestive tract. For systemic, immediate and/or short term effects, the composition can be formulated for parenteral administration and given by routes other than through the digestive tract.

Dosages

The compositions of the present disclosure are formulated into acceptable dosage forms by conventional methods known to those of skill in the art. Actual dosage levels of the active ingredients in the compositions of the present disclosure (e.g., a compound of Formula (I)) may be varied so as to obtain an amount of the active ingredient which is effective to achieve the desired therapeutic response for a particular subject, composition, and mode of administration, without being toxic to the subject. The selected dosage level will depend upon a variety of pharmacokinetic factors including the activity of the particular compositions of the present disclosure employed, the route of administration, the time of administration, the rate of absorption of the particular agent being employed, the duration of the treatment, other drugs, substances, and/or materials used in combination with the particular compositions employed, the age, sex, weight, condition, general health and prior medical history of the subject being treated, and like factors well known in the medical arts. A physician or veterinarian having ordinary skill in the art can readily determine and prescribe the effective amount of the composition required. For example, the physician or veterinarian can start doses of the substances of the disclosure employed in the composition at levels lower than that required in order to achieve the desired therapeutic effect and gradually increase the dosage until the desired effect is achieved. In general, a suitable daily dose of a composition of the disclosure will be that amount of the substance which is the lowest dose effective to produce a therapeutic effect. Such an effective dose will generally depend upon the factors described above. Preferably, the effective daily dose of a therapeutic composition may be administered as two, three, four, five, six or more sub-doses administered separately at appropriate intervals throughout the day, optionally, in unit dosage forms.

Preferred therapeutic dosage levels are between about 0.1 mg/kg to about 1000 mg/kg (e.g., about 0.2 mg/kg, 0.5 mg/kg, 1.0 mg/kg, 1.5 mg/kg, 2 mg/kg, 3 mg/kg, 4 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 600 mg/kg, 700 mg/kg, 800 mg/kg, 900 mg/kg, or 1000 mg/kg) of the composition per day administered (e.g., orally or intraperitoneally) to a subject afflicted with the disorders described herein (e.g., HBV infection). Preferred prophylactic dosage levels are between about 0.1 mg/kg to about 1000 mg/kg (e.g., about 0.2 mg/kg, 0.5 mg/kg, 1.0 mg/kg, 1.5 mg/kg, 2 mg/kg, 3 mg/kg, 4 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 600 mg/kg, 700 mg/kg, 800 mg/kg, 900 mg/kg, or 1000 mg/kg) of the composition per day administered (e.g., orally or intraperitoneally) to a subject. The dose may also be titrated (e.g., the dose may be escalated gradually until signs of toxicity appear, such as headache, diarrhea, or nausea).

The frequency of treatment may also vary. The subject can be treated one or more times per day (e.g., once, twice, three, four or more times) or every so-many hours (e.g., about every 2, 4, 6, 8, 12, or 24 hours). The composition can be administered 1 or 2 times per 24 hours. The time course of treatment may be of varying duration, e.g., for two, three, four, five, six, seven, eight, nine, ten, or more days, two weeks, 1 month, 2 months, 4 months, 6 months, 8 months, 10 months, or more than one year. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Patient Selection and Monitoring

The methods of the present disclosure described herein entail administration of a compound of Formula (I) or a pharmaceutically acceptable salt thereof to a subject to activate the PRR for IFNs, ISGs and cytokines production or additionally induce the expression of PRRs (e.g., RIG-I, STING etc.). In some embodiments, the subject is suffering from or is diagnosed with a condition, e.g., a proliferative disease, e.g., cancer. Accordingly, a patient and/or subject can be selected for treatment using a compound of Formula (I) or a pharmaceutically acceptable salt thereof by first evaluating the patient and/or subject to determine whether the subject is infected with a proliferative disease, e.g., cancer. A subject can be evaluated as infected with a proliferative disease (e.g., cancer) using methods known in the art. The subject can also be monitored, for example, subsequent to administration of a compound described herein (e.g., a compound of Formula (I) or a pharmaceutically acceptable salt thereof.

In some embodiments, the subject is a mammal. In some embodiments, the subject is a human. In some embodiments, the subject is an adult. In some embodiments, the subject has a proliferative disease, e.g., cancer. In some embodiments, the subject has a cancer of the of the breast, bone, brain, cervix, colon, gastrointestinal tract, eye, gall bladder, lymph nodes, blood, lung, liver, skin, mouth, prostate, ovary, penis, pancreas, uterus, testicles, stomach, thymus, thyroid, or other part of the body. In some embodiments, the subject has a cancer comprising a solid tumor (e.g., a carcinoma, a sarcoma, or a lymphoma). In some embodiments, the subject has a hepatocellular carcinoma or other cancer of the liver. In some embodiments, the subject has a leukemia or other cancer of the blood. In some embodiments, the subject has a breast cancer, renal cell carcinoma, colon cancer, melanoma, ovarian cancer, head and neck squamous cell carcinoma, pancreatic cancer, prostate cancer, lung cancer, brain cancer, or gastrointestinal stromal cancer. In some embodiments, the subject has cancer cells (e.g., tumor cells) comprising specific cancer-associated antigens that induce a T-cell response.

In some embodiments, the subject is treatment naïve. In some embodiments, the subject has been previously treated for a proliferative disease (e.g., a cancer). In some embodiments, the subject has relapsed.

Combination Therapies

A compound described herein may be used in combination with other known therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A compound described herein and the at least one additional therapeutic agent can be administered simultaneously, in the same or in separate compositions, or sequentially. For sequential administration, the compound described herein can be administered first, and the additional agent can be administered second, or the order of administration can be reversed.

In some embodiments, the combination of a compound of Formula (I) or a pharmaceutically acceptable salt thereof and the additional agent has a synergistic or additive effect. In some embodiments, the term "additive" refers to an outcome wherein when two agents are used in combination, the combination of the agents acts in a manner equal to but not greater than the sum of the individual activity of each agent.

In some embodiments, the combination of a compound of Formula (I-a) or a pharmaceutically acceptable salt thereof and the additional agent has a synergistic or additive effect. In some embodiments, the term "additive" refers to an outcome wherein when two agents are used in combination, the combination of the agents acts in a manner equal to but not greater than the sum of the individual activity of each agent. In some embodiments, the terms "synergy" or "synergistic" refer to an outcome wherein when two agents are used in combination, the combination of the agents acts so as to require a lower concentration of each individual agent than the concentration required to be efficacious in the absence of the other agent. In some embodiments, a synergistic effect results in a reduced in a reduced minimum inhibitory concentration of one or both agents, such that the effect is greater than the sum of the effects. A synergistic effect is greater than an additive effect. In some embodiments, the agents in the composition herein may exhibit a synergistic effect, wherein the activity at a particular concentration is greater than at least about 1.25, 1.5, 1.75, 2, 2.5, 3, 4, 5, 10, 12, 15, 20, 25, 50, or 100 times the activity of either agent alone.

For example, any of the methods described herein may further comprise the administration of a therapeutically effective amount of an additional agent. Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In some embodiments, the additional agent is an anti-cancer agent, e.g., an alkylating agent (e.g., cyclophosphamide).

In an embodiment, the additional agent is an immunooncology agent, for example, an agent that activate the immune system, e.g., making it able to recognize cancer cells and destroy them. Exemplary immonooncology compounds are compounds that inhibit the immune checkpoint blockade pathway. In an embodiment, the compound is an antibody such as a PD-1 or PD-L1 antibody or a co-stimulatory antibody. In some embodiments, the compound is an anti-CTLA4 antibody. In another embodiment, the agent is a cell based agent such as CAR-t therapy.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Abbreviations used in the following examples and elsewhere herein are:

DCA dichloroacetic acid
DCC N,N'-dicyclohexylcarbodiimide
DCM dichloromethane
DMAP 4-dimethylaminopyridine
ETT 5-(ethylthio)-1H-tetrazole
h hours
IPA isopropyl alcohol
LCMS liquid chromatography-mass spectrometry
MeOH methanol
PTSA p-Toluenesulfonic acid
r.t. room temperature
THF tetrahydrofuran
TLC thin-layer chromatography Example 1. Synthesis of Exemplary Compounds of the Disclosure Procedure for Synthesis of Cyclic Dinucleotide Prodrug 9 and 4 and Cyclic Thio-Diphosphates Scheme
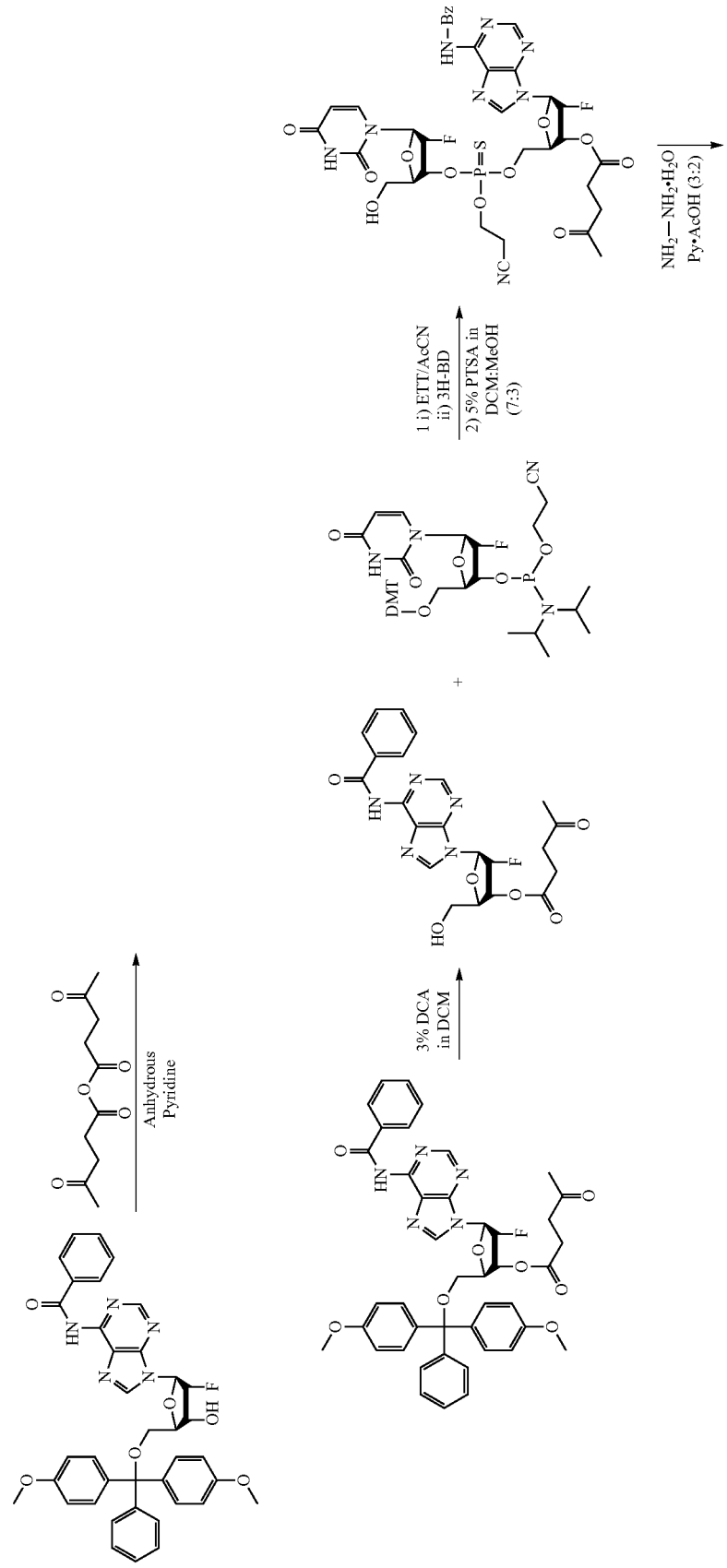

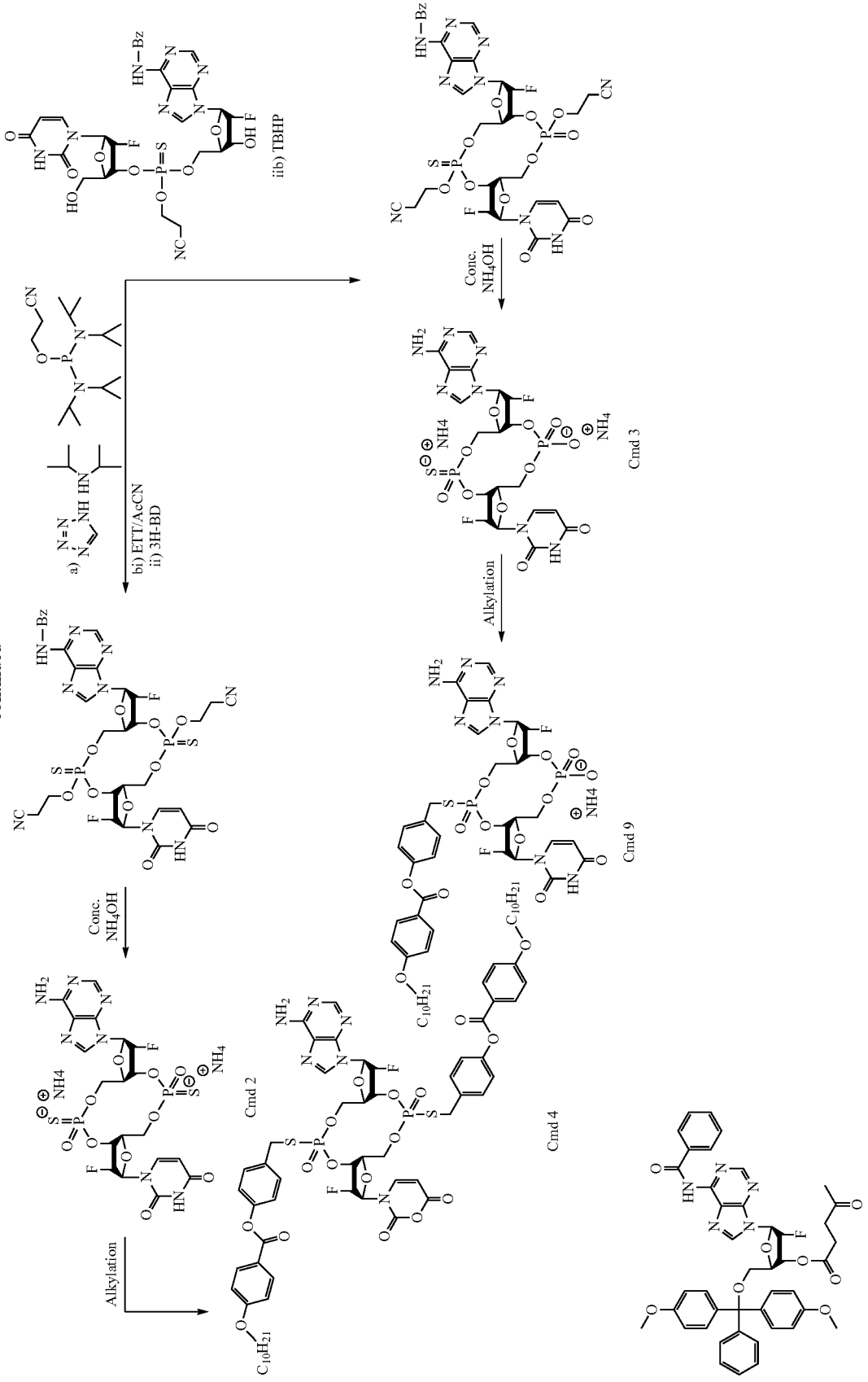

Synthesis of 5'-OH-3'-Levulinyl-2'F-dA

Levulinic acid (2.148 g, 18.5 mmol) was dissolved in dry-dioxane (50 mL) and the solution was cooled to 5-10° C. on an ice-water bath. DCC (1.939 g, 9.4 mmol) was added portion wise over 1 h. The ice-water bath was removed and the reaction was allowed to warm to room temperature over 2 hours. The resulting dicyclohexyl urea precipitate was filtered off, and washed with dry-dioxane (10 mL). The filtrate was added to a solution of 5'DMT-2'F-3'OH-dA (5.0 g, 7.4 mmol) in dry pyridine (50 mL) and a catalytic amount of DMAP then was added under atmosphere of argon. After stirring for 2 hours at room temperature, the mixture was evaporated to dryness. The residue was dissolved in DCM (150 mL) and the organic phase was washed with 5% $NaHCO_3$ (100 mL) and brine (100 mL), dried over $Na_2SO_4$ and concentrated under reduced pressure to provide the desired product as a white solid.

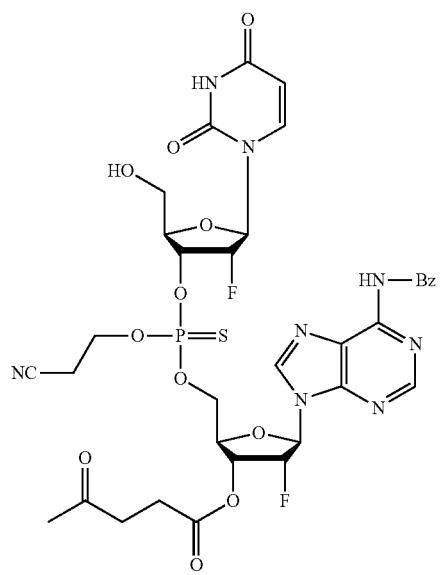

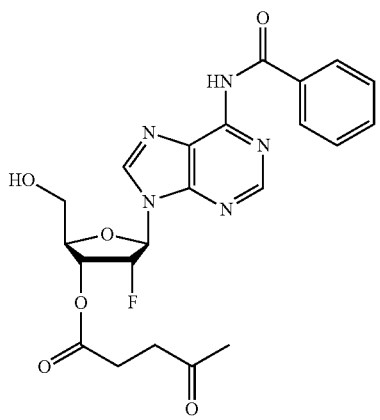

Detritylation:

Above solid was dissolved in DCM (100 mL), and water (1.33 mL, 74 mmol) was added to reaction mixture. 6% DCA in DCM (100 mL) was then added and the reaction mixture was stirred at room temperature for 10-15 min. The resulting mixture was quenched by the addition of methanol (25 mL) and then washed with 5% $NaHCO_3$ solution (150 mL) and brine (150 mL). The combined organic layers were dried over $Na_2SO_4$ and concentrated under reduced pressure. The crude residue was purified using combi-flash silicagel column chromatography eluting with 0-5% MeOH in DCM to give 3.45 g (62% yield) of pure desired product as a white solid.

Coupling:

5'OH-3'-Levulinylated-2'F-deoxy-Adinosine (700 mg, 1.48 mmol) and 5'DMT-2'F-3'CED-Phosphoamidite-deoxy-Uridine (1.66 g, 2.22 mmol) mixture was dried under high vacuum for 1-2 hours. Argon was flushed over the round bottom flask containing reaction mixture. Anhydrous acetonitrile (40 mL) was added to reaction mixture Followed by ETT (279 mg, 2.146 mmol) in acetonitrile (5.0 mL) under atmosphere of argon. The resulting mixture was stirred at room temperature under argon for 2 h. Once TLC analysis showed reaction completion, water was added (80 µL, 2 equivalents to amidite).

Sulfurization:

In a silanized flask, Beaucage reagent (3H-BD) (592 mg, 2.96 mmol) was dissolved in acetonitrile (5.0 mL). The above coupling reaction mixture was transferred to solution of sulfurizing reagent (3H-BD) in acetonitrile and under an atmosphere of argon. The resulting mixture was stirred at room temperature for 45 min. to complete the sulfurization reaction. Methanol (10 mL) was added and the reaction mixture was then stirred for 30 min. The resulting mixture was evaporated under reduced pressure to dryness. The crude residue was dissolved in DCM (100 mL) and washed with water (75 mL). DCM layer was separated, dried over $Na_2SO_4$ and used for in the detritylation step.

Detritylation:

The above obtained DCM layer containing the sulfurization product was cooled in an ice-water bath. 5% PTSA solution in DCM:MeOH (7:3, 100 mL) was added and the reaction mixture was stirred for 15 min. to complete the detritylation reaction. Water (50 mL) was then added and the resulting mixture was stirred for another 15 minutes. The reaction mixture was transferred to separator funnel and the water was layer was separated. The organic layer was washed 5% $NaHCO_3$ solution (100 mL), pH of the aqueous layer is above 7.0. The combined organic layers were dried over $Na_2SO_4$ and concentrated under reduced pressure to give the crude product. The crude product was purified using combiflash silicagel column chromatography eluting with 0-5% MeOH in DCM to give 960 mg of pure desired product as a white solid.

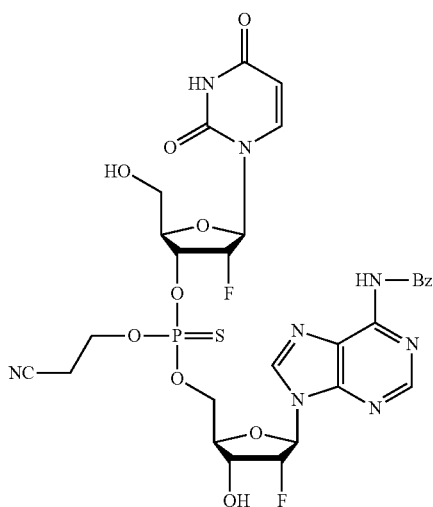

Levulinyl Group Deprotection:

3'-Levulinyl protected dinucleotide thiophosphate was treated with 0.5M hydrazine monohydrate in a mixture of pyridine:acetic acid (3:2 and the reaction mixture stirred at room temperature for 15 minutes. Once TLC analysis showed reaction completion. 2,4-pentanedione (2.0, mL) was then added to quench unreacted hydrazine hydrate. The volatiles were removed under reduced pressure and the reaction mixture was partitioned between 25% IPA in DCM (50 mL) and water (50 mL). The organic layers were collected and evaporated to dryness under reduced pressure to give thick liquid, which was co-evaporated with toluene (2×15 mL) to provide crude residue which was purified on Combiflash silicagel column chromatography using 0-10% MeOH in DCM to give 725 mg of pure desired product as a white solid.

Cyclization:

Dinucleotide phosphorothioate trimester (1 equivalent) and 2-cyanoethyl tetra isopropyl phosphorodiamidite (bisamidite) (1 equivalent) were dissolved in a mixture of dry acetonitrile and dry DCM (2:1, 30 mL). Disopropylaminotetrazolide (1 equivalent) was added to reaction mixture in 4 portions over a period of 1 hour under an inert atmosphere. The solution was stirred for an additional 2 h at r.t. and ETT (2.0 equivalent) was then added to the reaction mixture was stirred for overnight. Deoxygenated water (29 μL) was then added to reaction mixture.

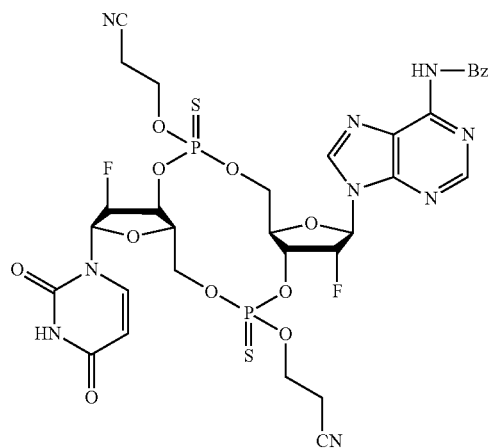

Sulfurization (Synthesis of Protected Cyclic Phosphorothiodiphosphate):

Beaucage reagent (3H-BD) (2.0 equivalent) was dissolved in acetonitrile in a silanized flask. One portion of above cyclization product (two thirds) was added to sulfurizing reagent under an atmosphere of argon. and the reaction mixture was stirred at room temperature for 45 minutes. Methanol (10 mL) was then added and the resulting mixture was stirred for 30 minutes. Solvents were evaporated under reduced pressure and the crude residue was dissolved in DCM (50 mL) and washed with water (50 mL). The DCM layers were separated, dried over Na$_2$SO$_4$ and concentrated under reduced pressure. The crude product was purified using Combiflash silica gel column chromatography eluting with 0-10% MeOH in DCM to give 150 mg of pure desired product.

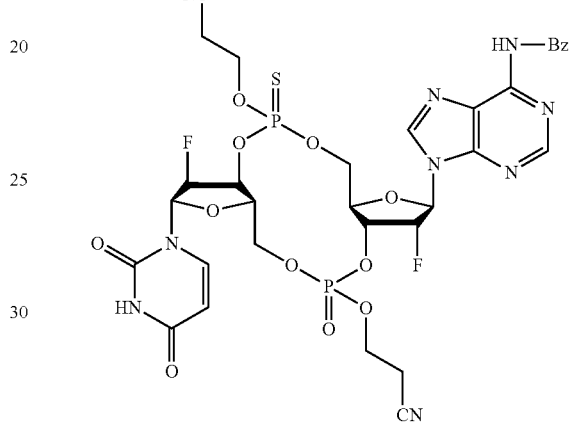

Oxidation (Synthesis of Protected Cyclic Phosphoromonothio Diphosphate):

TBHP (4.0 equivalent) was added to a stirred solution of a second portion of cyclization product (one third) at 0° C. and reaction mixture was warmed to r.t. over 15 minutes. Excess TBHP was quenched by addition of a saturated sodium bisulfite solution and the resulting mixture was evaporated under reduced pressure. The crude residue was dissolved in DCM (25 mL) and washed with water (20 mL). Organic layers were separated and dried over Na$_2$SO$_4$ and concentrated under reduced pressure. The resulting crude product was purified using Combiflash silicagel column chromatography eluting with 0-10% MeOH in DCM to give 60 mg of pure desired product.

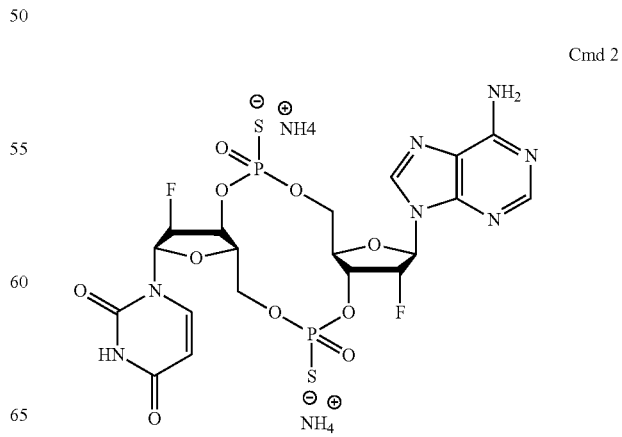

Cmd 2

Deprotection of Cyclic Phosphorothiodiphosphate [Synthesis of Cmd 2]:

Protected cyclic phosphorothiodiphosphate (60 mg) was dissolved in conc. NH$_4$OH (2.0 mL) and stirred at r.t. overnight. Once LCMS showed reaction completion, the mixture was evaporated under reduced pressure to remove ammonia. The water layer was washed with ethyl acetate (5×5 mL), separated and lyophilized to provide 100 mg of crude product as a white fluffy solid.

Deprotection of Cyclic Phosphoromonothio Diphosphate [Synthesis of Cmd 3]:

Protected cyclic phosphoro monothio diphosphate (60 mg) was dissolved in conc. NH$_4$OH (5.0 mL) and then stirred at r.t. for overnight. Once LCMS showed reaction, the mixture was evaporated under reduced pressure to remove ammonia. The water layer was washed with ethyl acetate (5×5 mL), separated and lyophilized to provide 50 mg of the crude desired product as a white fluffy solid.

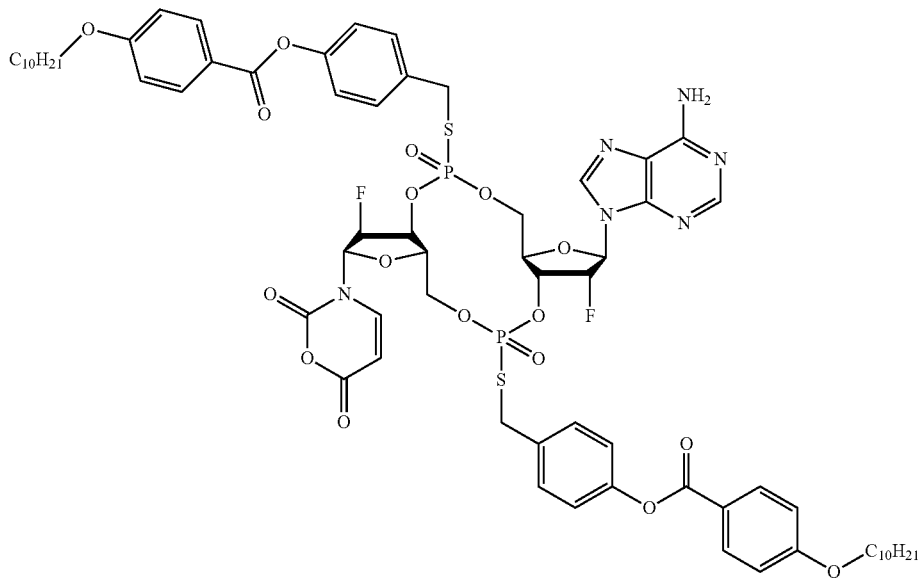

Cmd 4

Alkylation of Cyclic Phosphorothio Diphosphate [Synthesis of Cmd 4]:

Cyclic phosphorothio diphosphate (25 mg) was dissolved in water (250 µL). A solution of 4-(iodomethyl)phenyl 4-(decyloxy)benzoate (42 mg) in a mixture of THF:Acetone (1:1, 2.0 mL) was then added. Reaction mixture pH was approximately 3.5-4.0. The reaction mixture was stirred at r.t. for 40 hours. The crude product was purified using Combiflash silicagel column chromatography eluting 0-10% IPA in DCM to give 25 mg of the desired product as a yellowish brown solid.

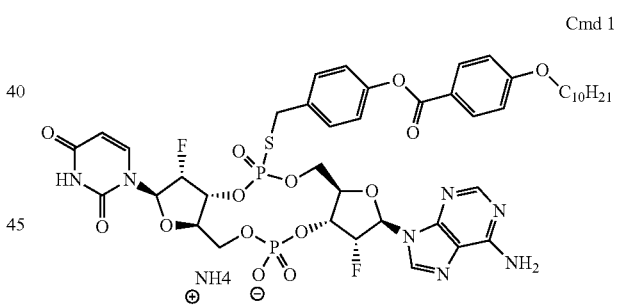

Cmd 1

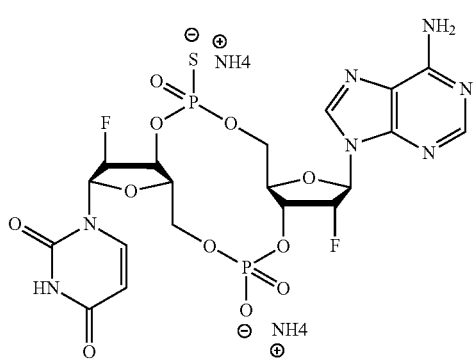

Cmd 3

Alkylation of Cyclic Phosphoromonothio Diphosphate [Synthesis of Cmd 1]:

Cyclic phosphoromonothio diphosphate (20 mg) was dissolved in water (200 µL). A solution of 4-(iodomethyl)phenyl 4-(decyloxy)benzoate (18 mg) in a mixture of THF:Acetone (1:1, 1.4 mL) was then added. The reaction mixture pH was approximately 4.0. The reaction mixture stirred at r.t. overnight and solvents were removed under reduced pressure. The resulting crude residue was redissolved in water:acetonitrile (1:1, 2.0 mL). A precipitate (unreacted alkylating reagent) formed and was removed by centrifugation. The mother liquor was lyophilized and the crude product was purified by using C$_{18}$ sep pack column (Waters, 4.0 g) with 0.2M ammonium acetate buffer. The compound was eluted with acetonitrile:water (1:1). The pure fractions were collected and lyophilized to provide 5-6 mg of pure desired product as a white fluffy solid.

Example 2. In Vitro Activation of ISG54 and NF-κβ in HEK293 Cells

In this experiment, HEK293 cells (SZ14) stably expressing either the ISG54 ISRE-luc reporter or the NF-κβ-luc reporter gene were treated in duplicate with an exemplary compound of the disclosure or 2',3'-cGAMP as a control, each in digitonin buffer for 5 hours, in order to screen for potential STING agonists. ISG54 or NF-κβ activity was determined using the Steady-glo buffer system (Promega), and are expressed as $EC_{50}$ values summarized in Table 3 below. In general, half maximal effective concentration ($EC_{50}$) refers to the concentration of a drug that induces a response halfway between the baseline and maximum after a specified exposure time. This calculation is applicable for compounds with enzyme inhibition activity, as the baseline for an untreated sample may be set at 100% enzymatic activity, and therefore % inhibition is evaluated based on this 100% maximal basis. For these studies, the $EC_{50}$ value relates to the concentration required to achieve a value 50% activity level above the untreated sample set at 0%.

In Table 3, "A" represents an $EC_{50}$ of less than 50 nM; "B" an $EC_{50}$ of between 50 nM and 500 nM; "C" an $EC_{50}$ of between 500 nM and 1 µM; "D" an $EC_{50}$ of between 1 µM and 2 µM; and "E" an $EC_{50}$ of greater than 2 µM. Data are shown as fold induction over cells that received DMSO (compound carrier) alone as the mean, +/−standard deviation of duplicate wells per stimulant.

TABLE 3

$EC_{50}$ values for exemplary compounds of the disclosure

| Compound No. | IRF $EC_{50}$ | NF-KB $EC_{50}$ |
|---|---|---|
| Cmd 5 | E | E |
| Cmd 17 | E | E |
| Cmd 18 | E | E |
| Cmd 14 | A | A |
| Cmd 12 | A | A |
| Cmd 1 | A | B |
| Cmd 13 | A | B |
| Cmd 15 | A | A |
| Cmd 4 | D | E |
| Cmd 2 | D | E |
| Cmd 1B | A | B |
| Cmd 1A | A | B |
| Cmd 20 | E | E |
| Cmd 21 | C | E |
| Cmd 22 | A | B |
| Cmd 23 | A | B |
| Cmd 25 | A | B |
| Cmd 26 | A | A |
| Cmd 29 | B | C |
| Cmd 30 | C | E |
| Cmd 31 | C | E |
| Cmd 32 | B | B |

Example 3. Evaluation of IRF-Type I IFN Activity in THP Cells

THP1-dual cells were treated in triplicate with exemplary compounds of the disclosure in lipofectamine (e.g., compound 2 or compound 3) or 2',3'-cGAMP in lipofectamine as a control at varying concentrations for 22 hours. Levels of IRF-inducible luciferase reporter activity in the cell culture supernatants were assayed using the Quanti-luc reagent, and are summarized in FIG. 9. Data are shown as fold induction over cells that received DMSO (compound carrier) alone as the mean, +/−standard deviation of duplicate wells per stimulant.

Example 4. Determination of Cytotoxicity of Exemplary Compounds

The cytotoxicity of exemplary compounds in THP1 cells was assessed using Cell titer Glo Assay (Promega). THP1 dual cells grown in complete media were treated with various concentrations of compounds or DMSO control. The CellTiter-Glo® Luminescent Cell Viability/cytotoxicity was a determined by assessing number of viable cells in culture based on quantitation of the ATP present through a "glow-type" luminescent signal, produced by the luciferase reaction. % apoptosis was calculated from fold change in luminescence compared to DMSO treated sample.

Example 5. Quantification of STING Binding

SZ14 HEK293 cells stably expressing the ISG54 ISRE-luc reporter gene were treated with compound exemplary compounds Cmd 1, 2' 3-cGAMP (natural STING ligand), or DMSO in the presence of digitonin for 5-6 hrs. ISRE-luciferase activity was determined and normalized to DMSO treated cells (mean±standard deviation of triplicate wells per stimulant).

Alternatively, raw-ISG-Dual cells in 96-well plates were stimulated in triplicate with compound/lipo, cGAMP/lipo complex or compound alone for 22-24 hrs at 37° C., 5% CO2. Activity of secreted luciferase in cell culture supernatant was measured using Invivogen Quanti-luc. Data are shown as fold induction over DMSO treated cells (mean±standard deviation of triplicate wells per stimulant).

Example 6. Induction of Type III IFN (IL-29) Production in THP Cells by Exemplary Compounds THP1-Dual (WT) cells were treated in triplicate with an exemplary compound alone or cGAMP/lipo for 21 hrs. Level of IL-29 in culture supernatant was determined using ELISA. Results shown are the average±standard deviation of duplicate wells.

Figure 9A:
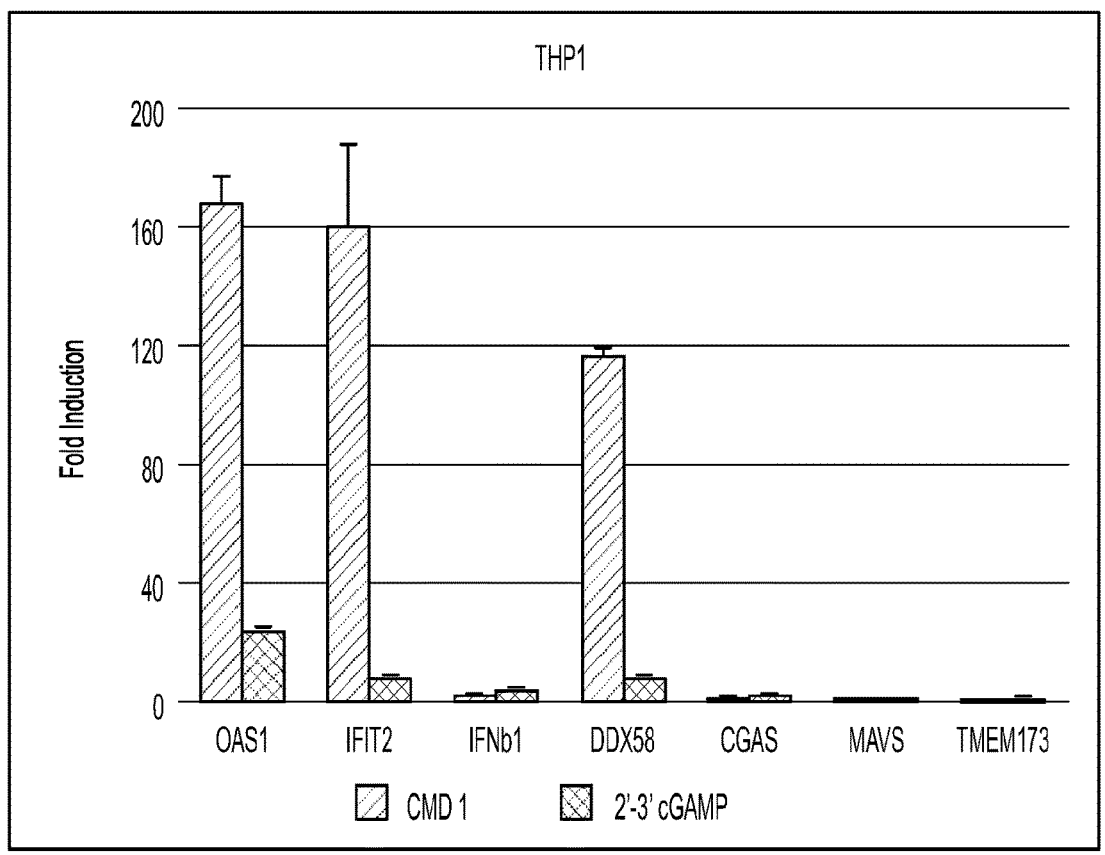
FIGS. 9A-9B show that an exemplary compound (Cmd 1) causes selective and enhanced induction of ISG and PRR-associated genes in acute monocytic leukemia cell line (THP1) compared to primary cells PBMCs. Gene expression analysis was conducted in THP1 and PBMCs.
Figure 9B:
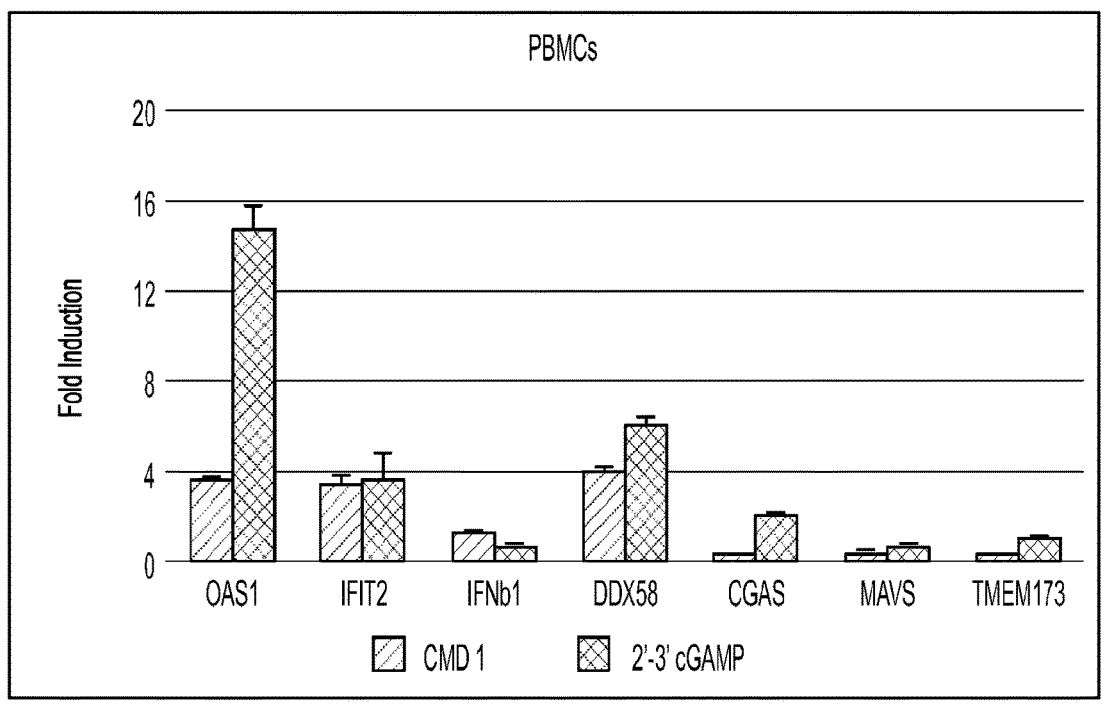

Example 7. FIG. 9 Shows that Cmd 1 Causes Cell Death by Apoptosis

The Apoptosis in THP1 cells was assessed using Caspase-Glo® 3/7 Assay (Promega). THP1 dual cells grown in complete media were treated with various concentrations of Cmd 1 or 2'3-cGAMP or DMSO control with Lipofectamine LTX. The caspase-3 and -7 activity was measured by using a pro-luminescent caspase-3/7 substrate that contains the tetrapeptide sequence DEVD which is cleaved to release amino-luciferin, a substrate of luciferase used in the production of light. After incubation for 20 h, Apoptotic activity was assessed by measuring levels of amino-luciferin. % Apoptosis was calculated from fold-change in luminescence compared to DMSO-treated sample. CC50 values are generated by curve fit in Xlfit.

Figure 10A:
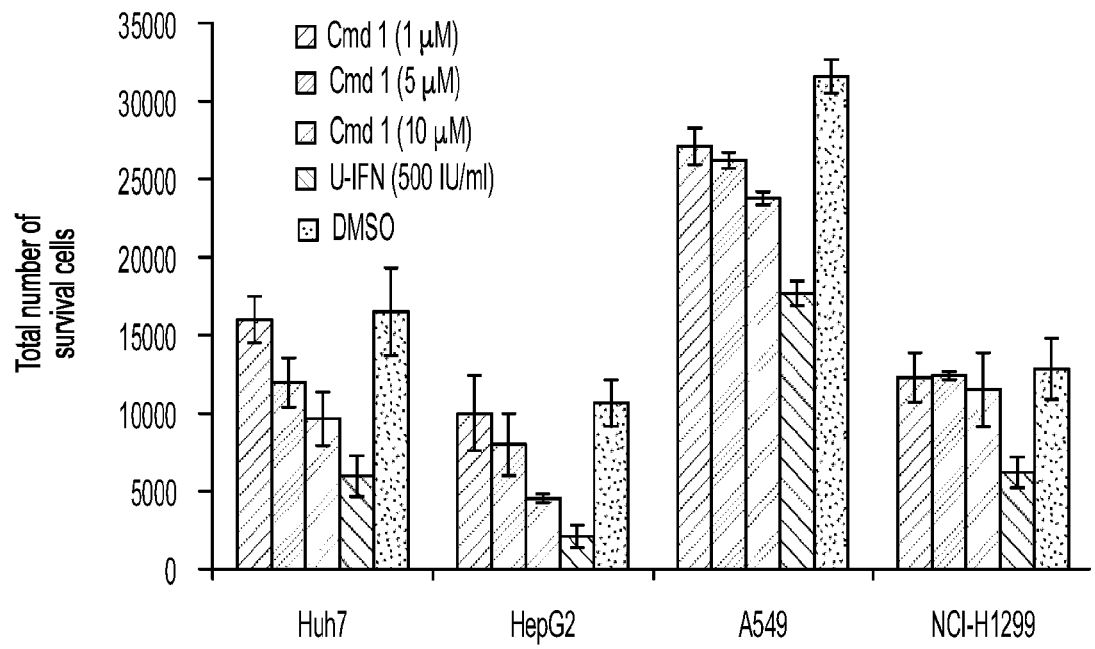
FIGS. 10A-10B show that an exemplary compound inhibits tumor cell growth.
Figure 10B:
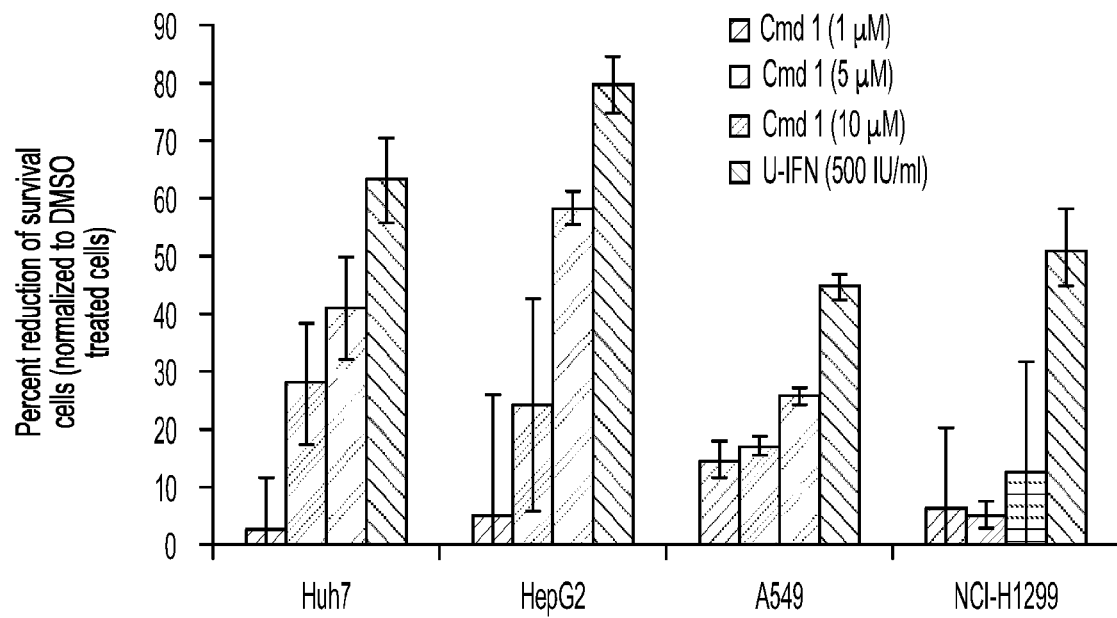

Example 8. FIG. 10 Shows the Selective Induction of Apoptosis by Cmd 1 in Acute Monocytic Leukemia Cell Line (THP1) Vs. PBMCs The Apoptosis in THP1 cells and PBMCs was assessed using Caspase-Glo® 3/7 Assay (Promega). THP1 cells and PBMCs grown in complete media were treated with various concentrations of Cmd 1 or 2'3-cGAMP or DMSO control with Lipofectamine LTX. The caspase-3 and -7 activity was measured by using a proluminescent caspase-3/7 substrate that contains the tetrapeptide sequence DEVD which will be cleaved to release aminoluciferin, a substrate of luciferase used in the production of light. After incubation for 20 h, Apoptotic activity was assessed by measure levels of aminoluciferin. % Apoptosis was calculated from fold change in luminescence compared to DMSO treated sample.

Figure 11A:
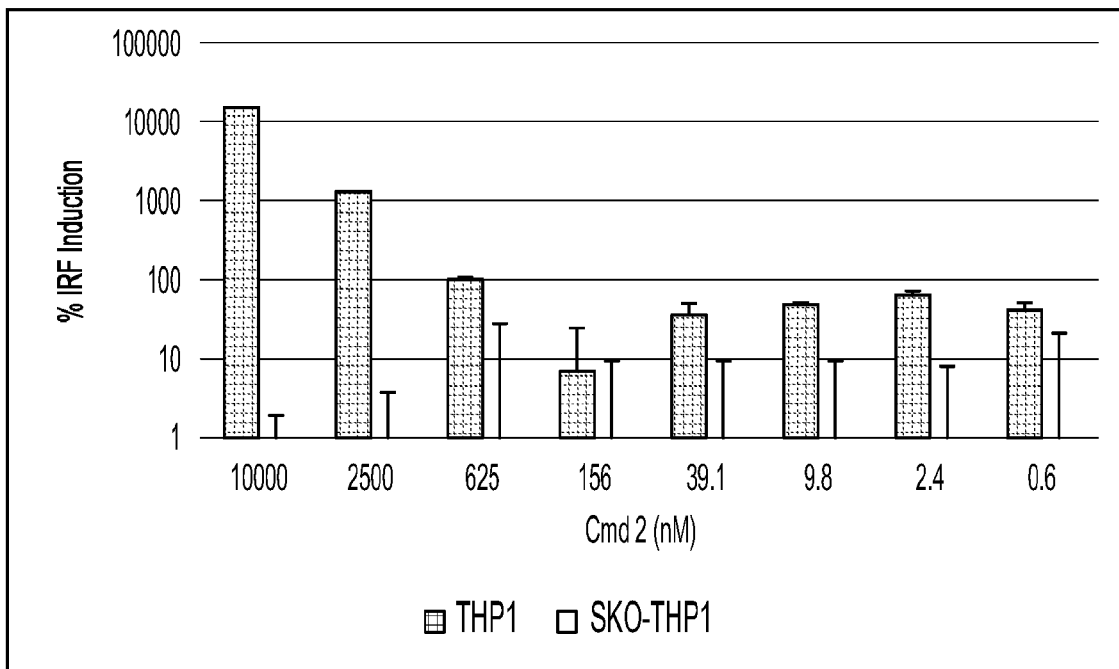
FIGS. 11A-11B show that an exemplary compound has STING-dependent IRF activity but does not cause NF-kB induction.
Figure 11B:
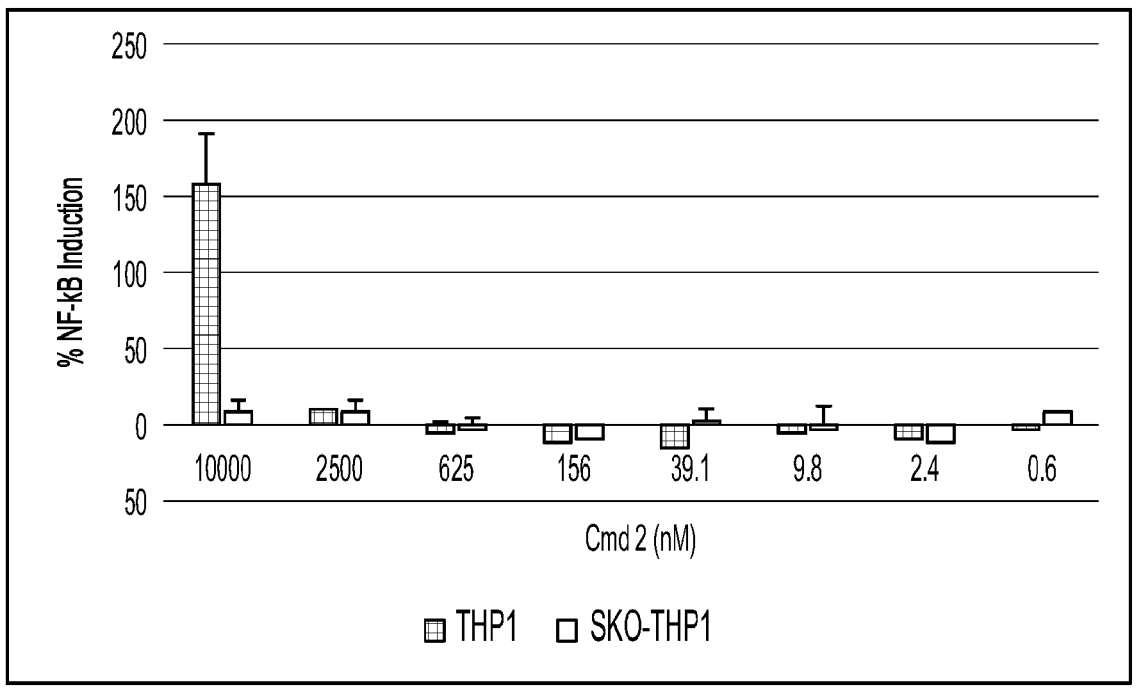

Example 9. FIG. 11 Shows that the Cmd 1 Causes Selective and Enhanced Induction of ISG and PRR-Associated Genes in Acute Monocytic Leukemia Cell Line (THP1) Compared to Primary Cells PBMCs. Gene Expression Analysis in THP1 and PBMCs THP1 cells and PBMCs grown in complete media were treated with 5 uM of either Cmd 1 or 2'3-cGAMP or DMSO control with Lipofectamine LTX. After incubation for 20 h, RNA was extracted and gene expression of different Interferon Stimulated Genes (ISGs) and various Pattern Recognition Receptors (PRRs) was evaluated by real time PCR. Fold Induction was calculated by ΔΔct method.

Figure 12:
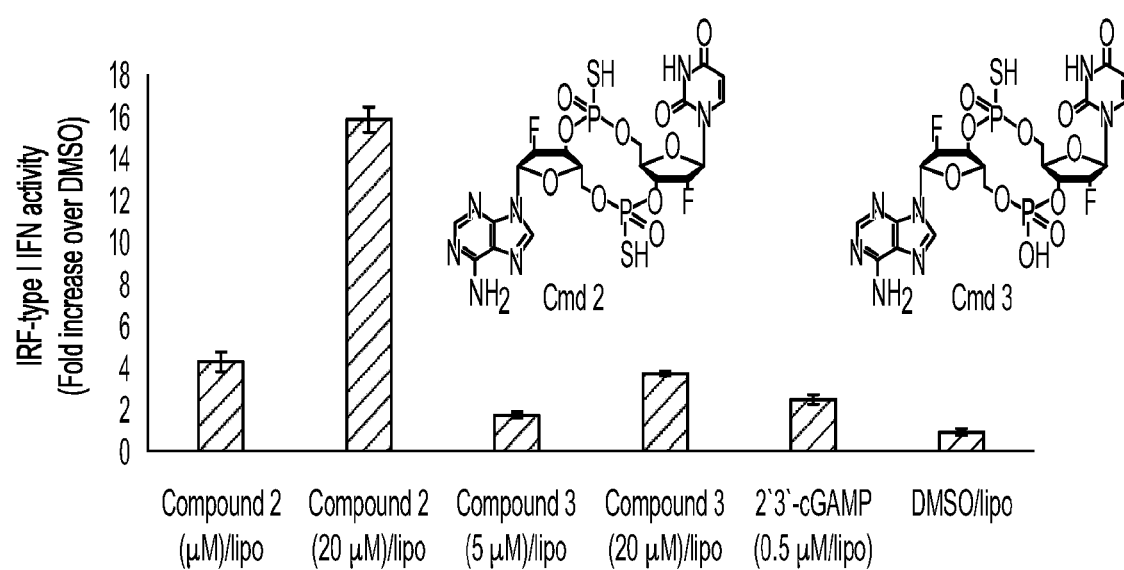
FIG. 12 shows that an exemplary compound activates IRF signaling in THP1 cells.
Figure 13A:
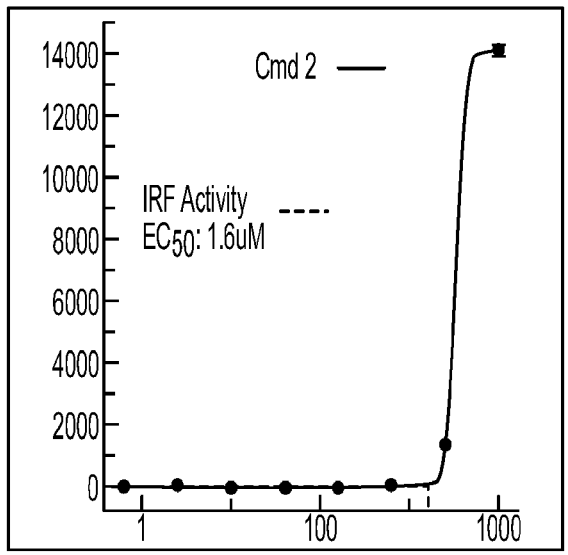
FIGS. 13A-13D show that an exemplary compound has similar activity as natural STING ligand 2'-3' cGAMP.
Figure 13B:
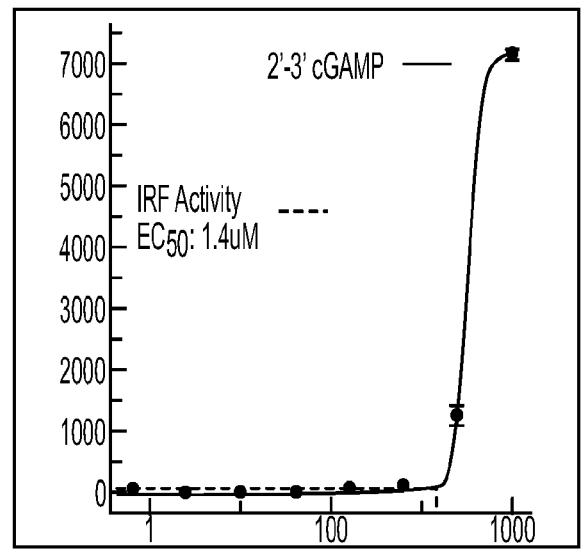
Figure 13C:
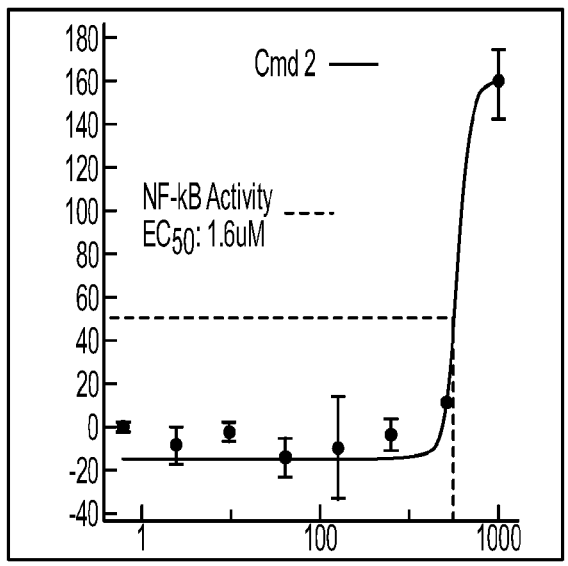
Figure 13D:
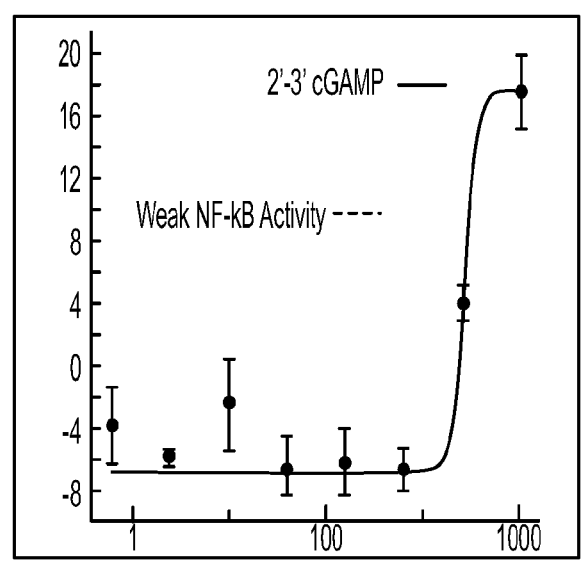
Figure 14:
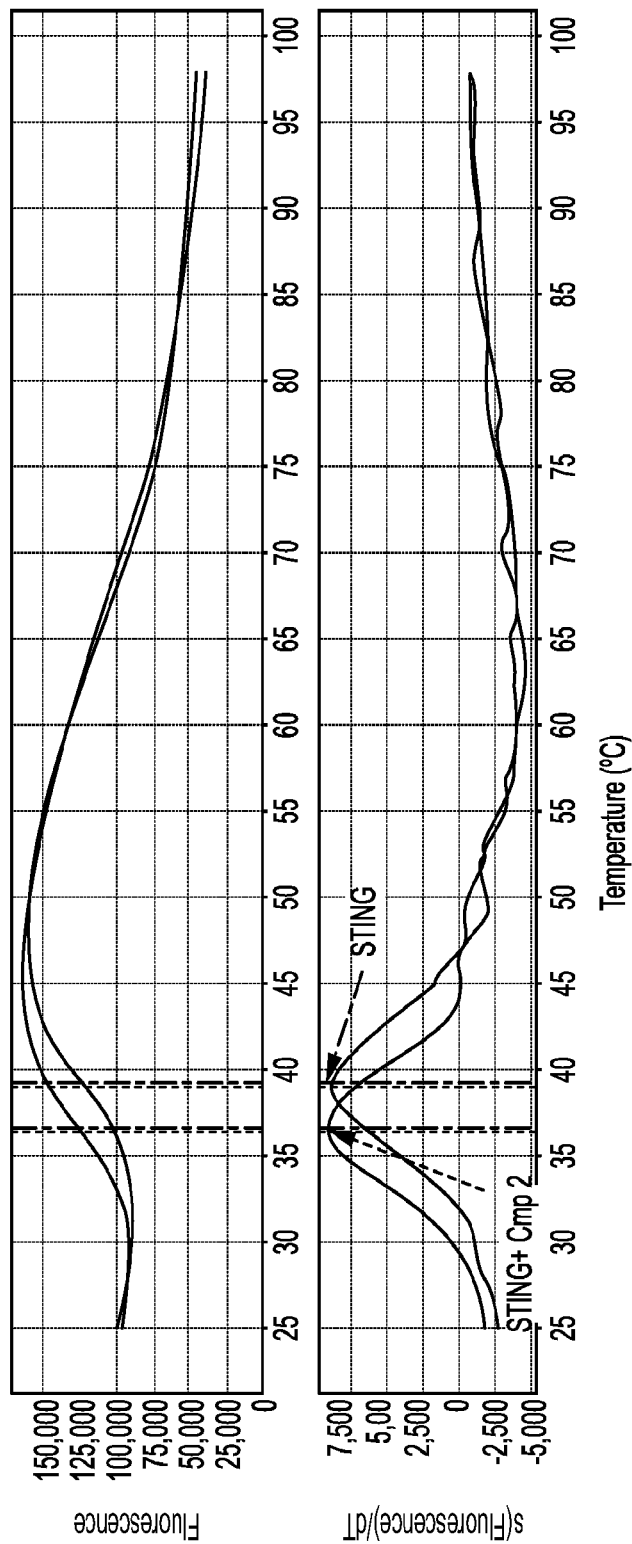
FIG. 14 shows that an exemplary compound directly binds to STING.
Figure 15A:
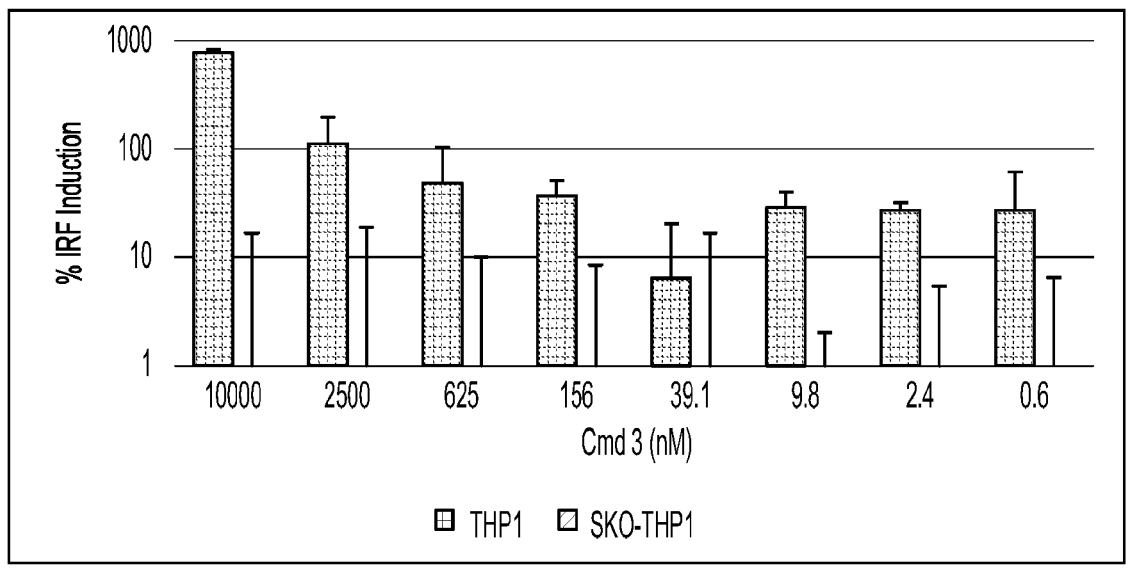
FIGS. 15A-15B show that an exemplary compound has STING dependent IRF activity but does not cause NF-kB induction.
Figure 15B:
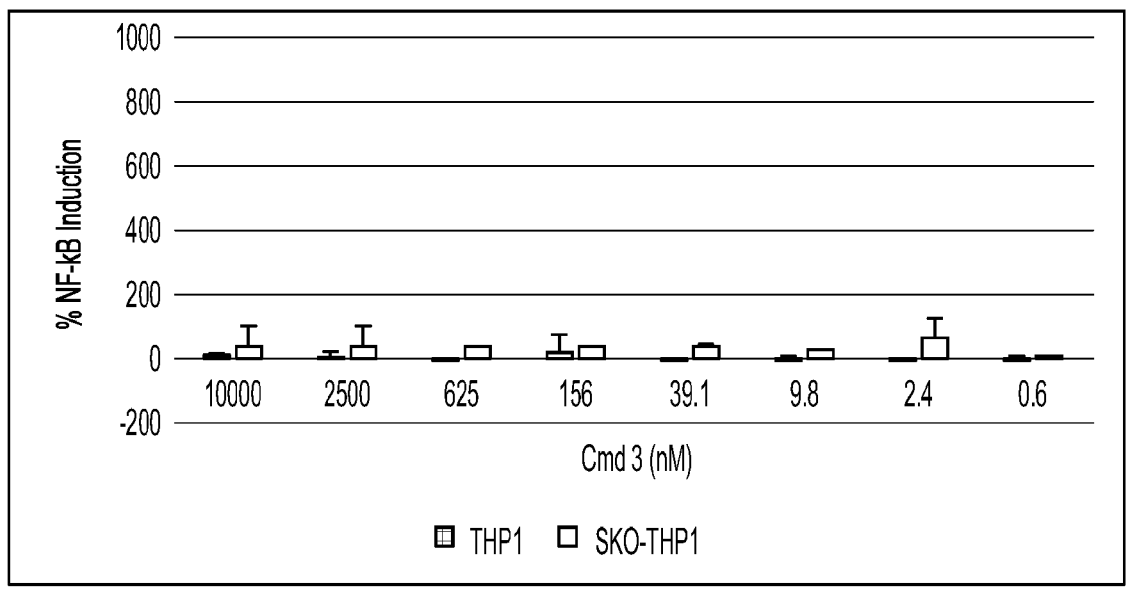
Figure 16:
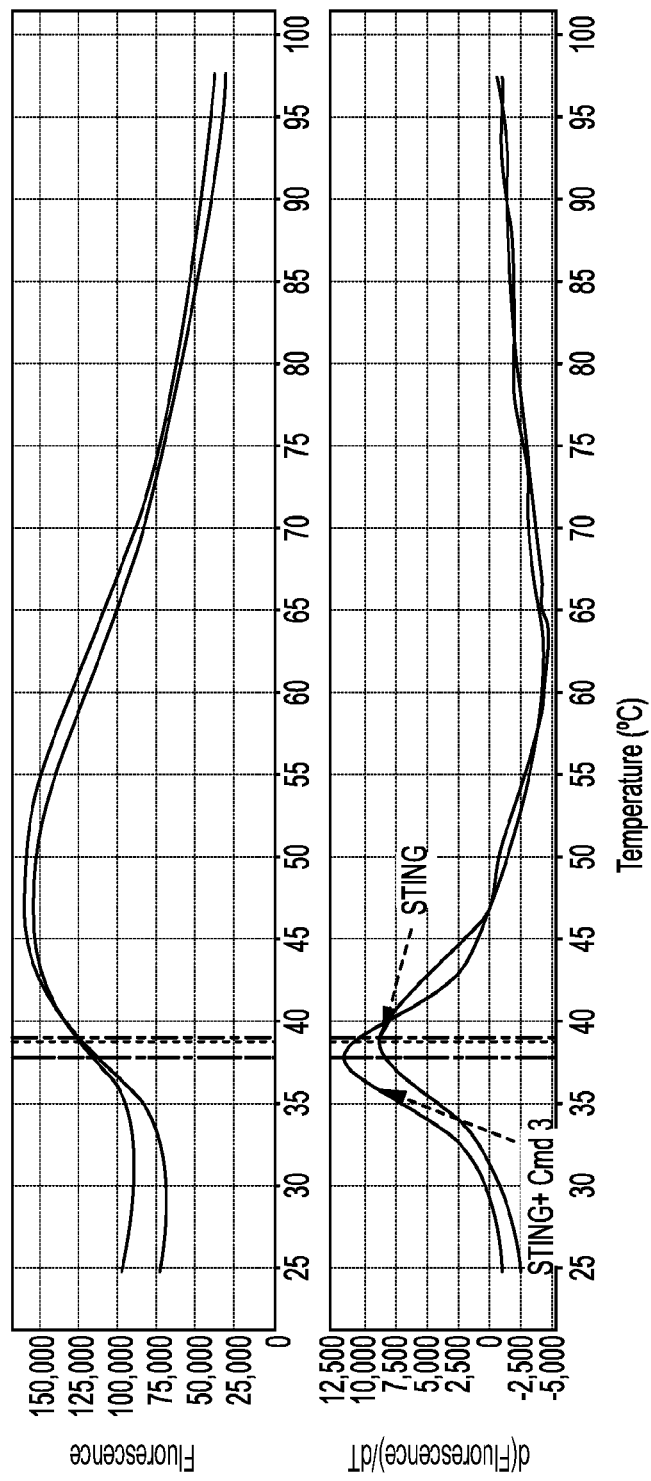
FIG. 16 shows that an exemplary compound directly binds to STING.
Figure 17A:
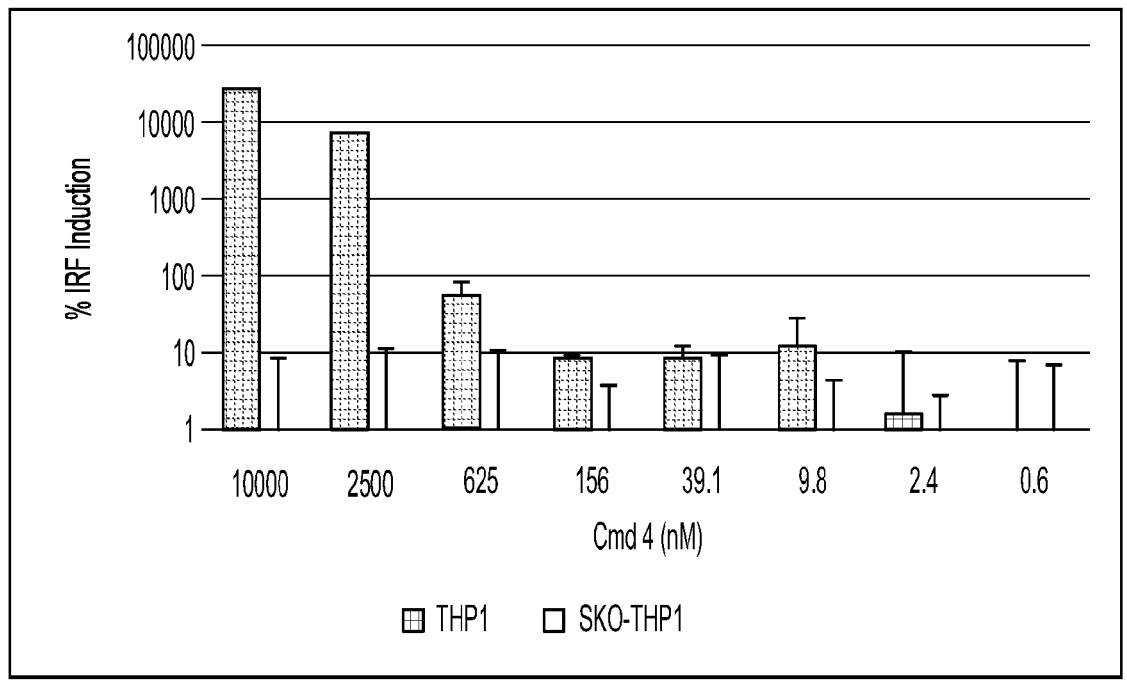
FIGS. 17A-17B show that an exemplary compound has STING dependent activity.
Figure 17B:
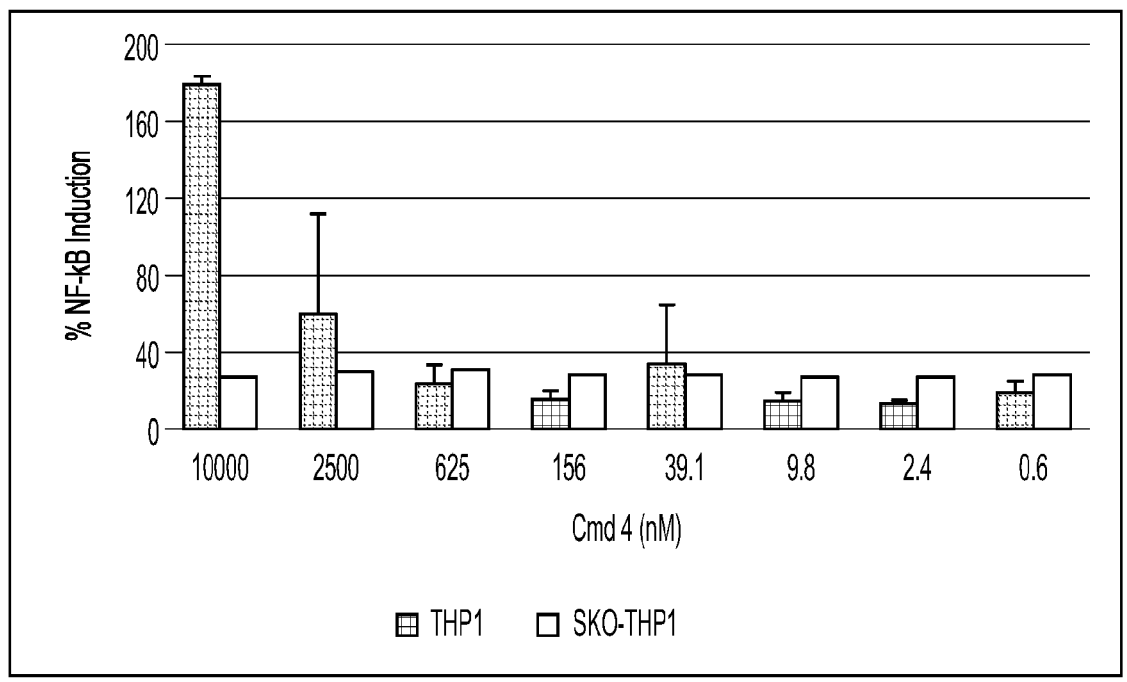
Figure 18A:
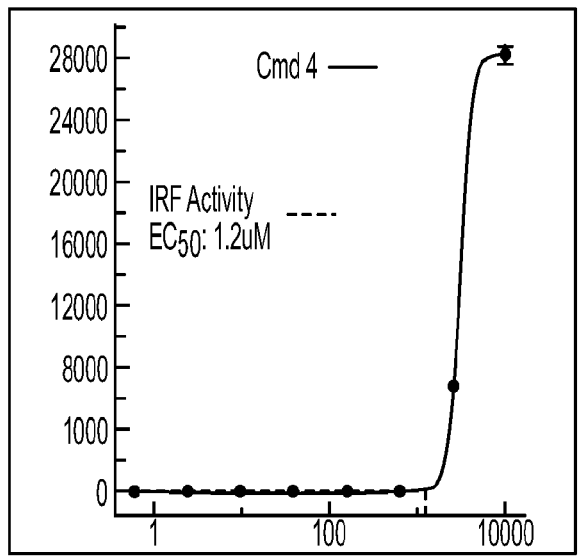
FIGS. 18A-18D show that an exemplary compound has similar potency as natural STING ligand 2'-3' cGAMP.
Figure 18B:
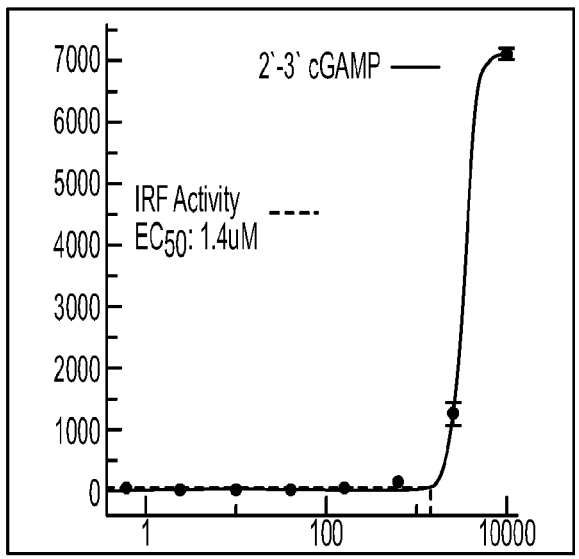
Figure 18C:
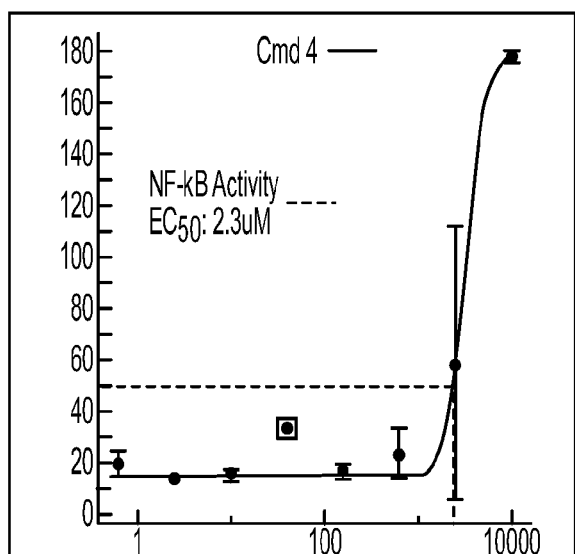
Figure 18D:
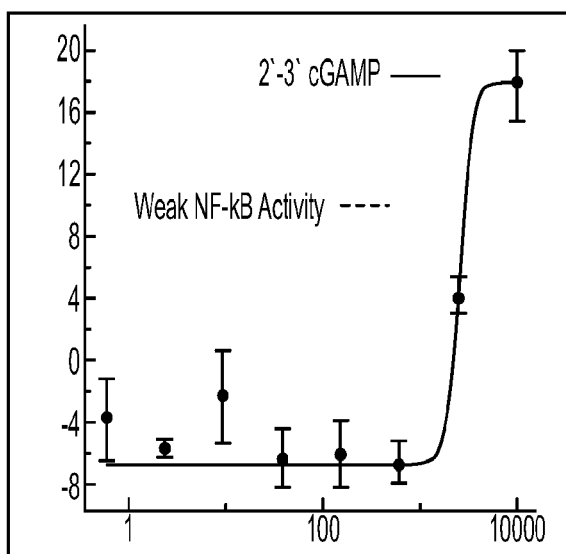
Figure 19A:
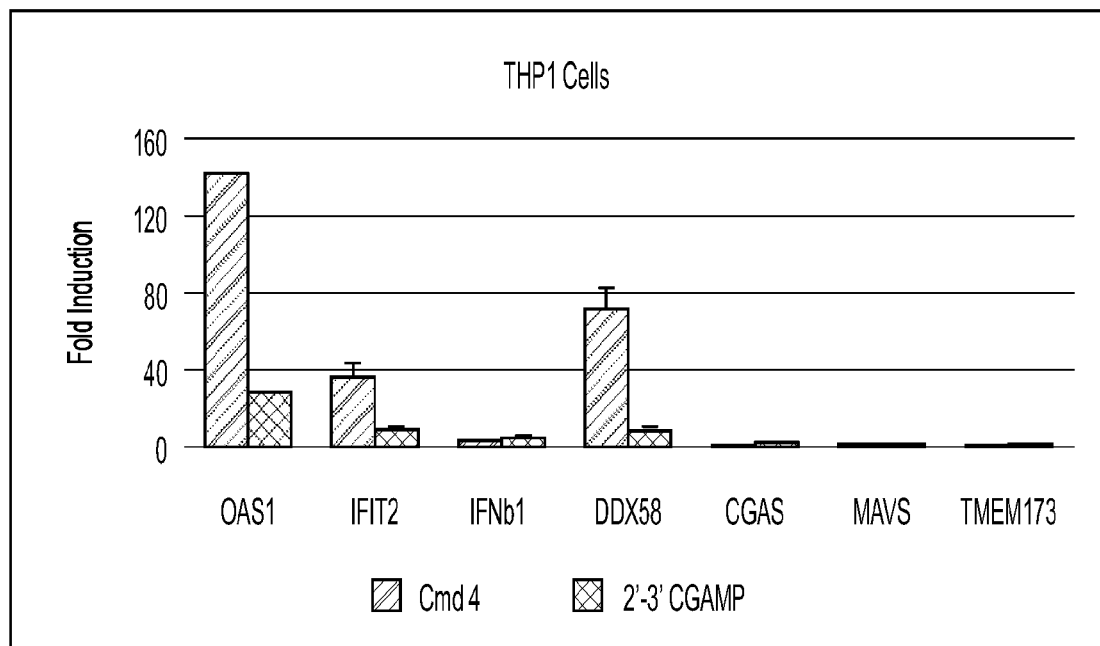
FIGS. 19A-19B shows that an exemplary compound has enhanced activity in acute monocytic leukemia cell line (THP1) compared to primary cells PBMCs.
Figure 19B:
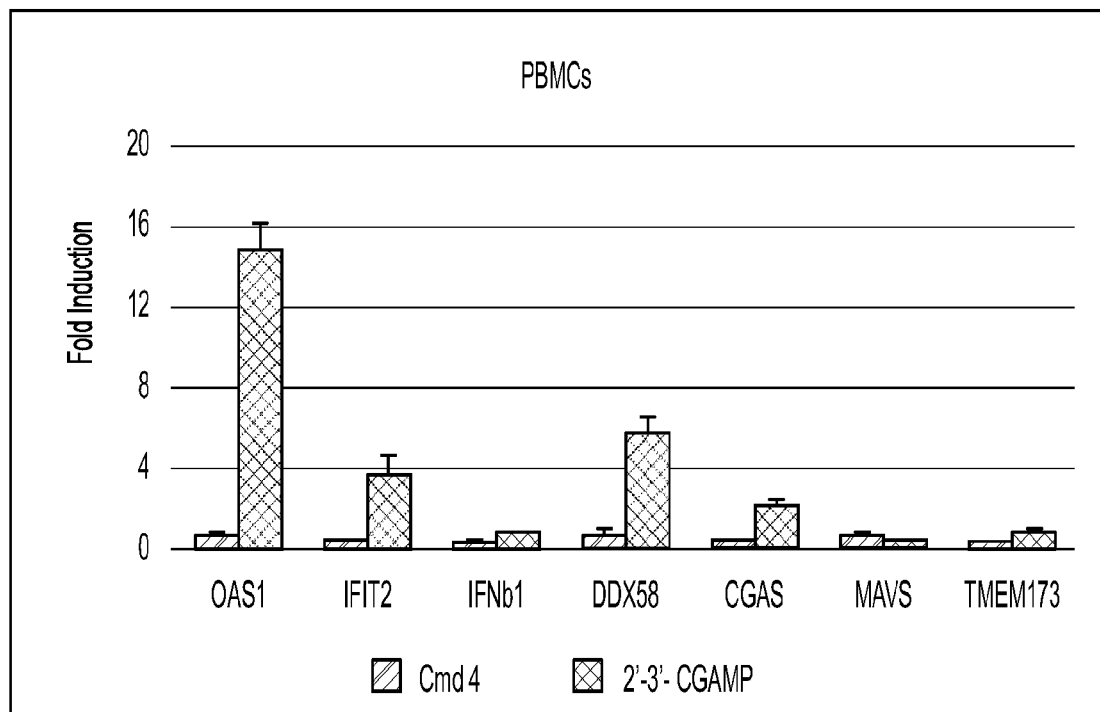
Figure 20A:
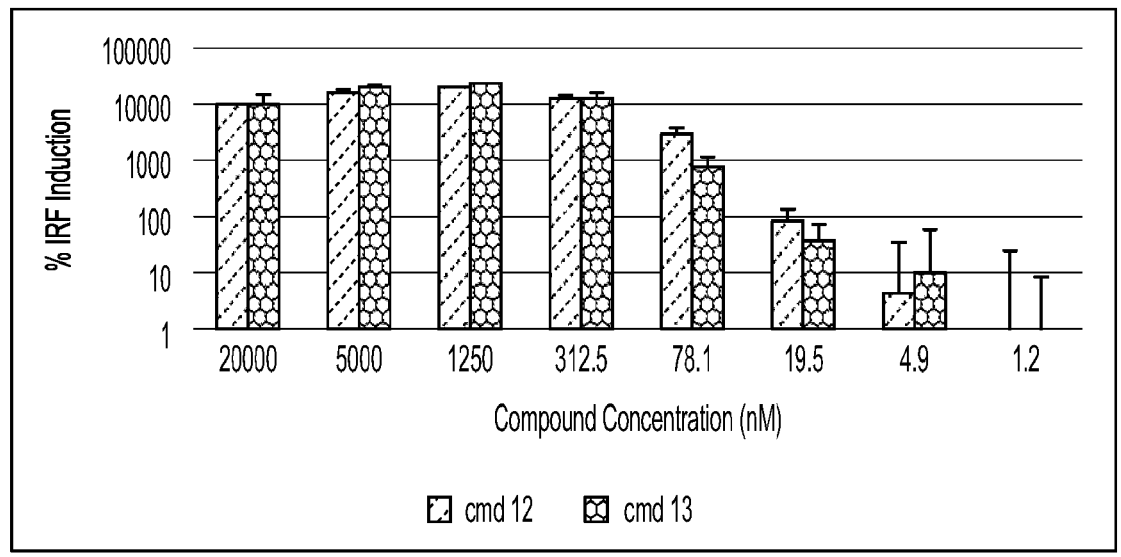
FIGS. 20A-20C show IRF induction by an exemplary compound.
Figures 20B, 20C:
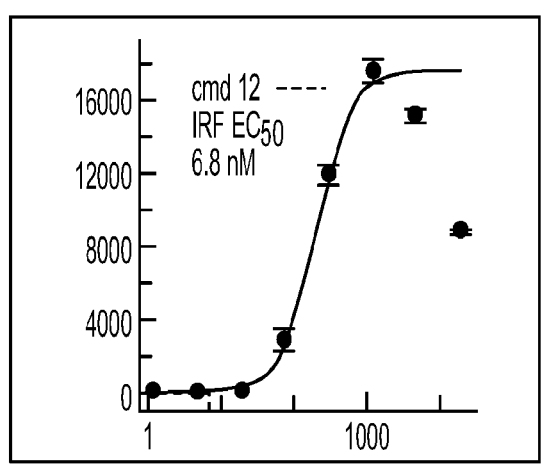
Figure 22A:
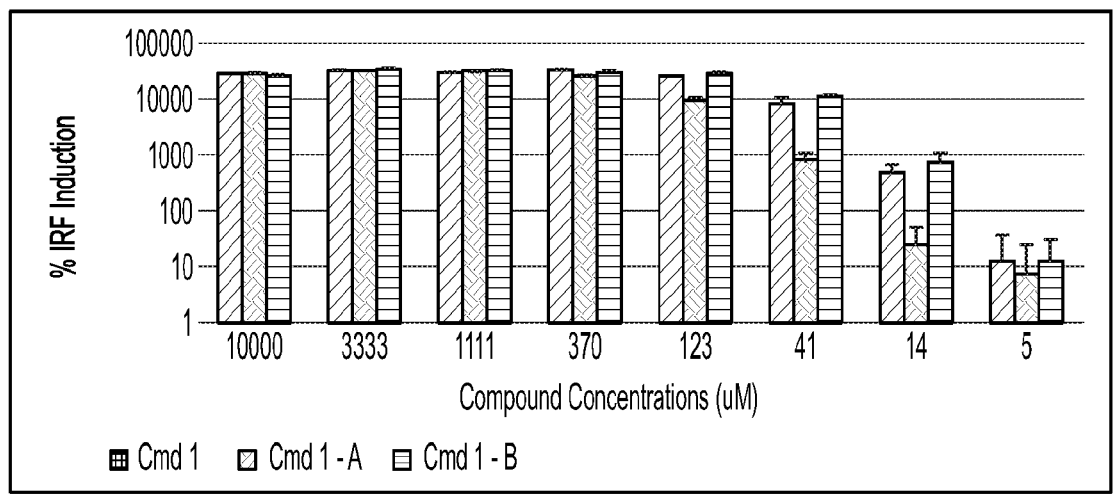
FIGS. 22A-22B are graphs showing the evaluation of percent (%) IRF induction (FIG. 22A) and percent (%) NF-κB (FIG. 22B) by Cmd 1, Cmd 1A, and Cmd 1B in THP1 dual cells that carry both the secreted embryonic alkaline phosphatase (SEAP) reporter gene under the control of an IFN-β minimal promoter fused to five copies of the NF-κB consensus transcription response element and Lucia reporter gene under the control of an ISG54 minimal promoter.
Figure 22B:
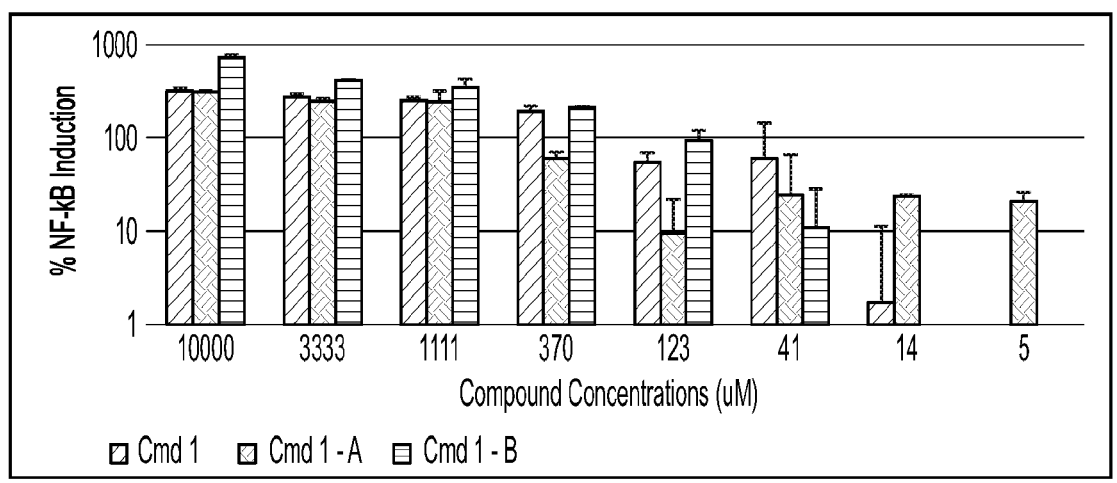
Figure 23A:
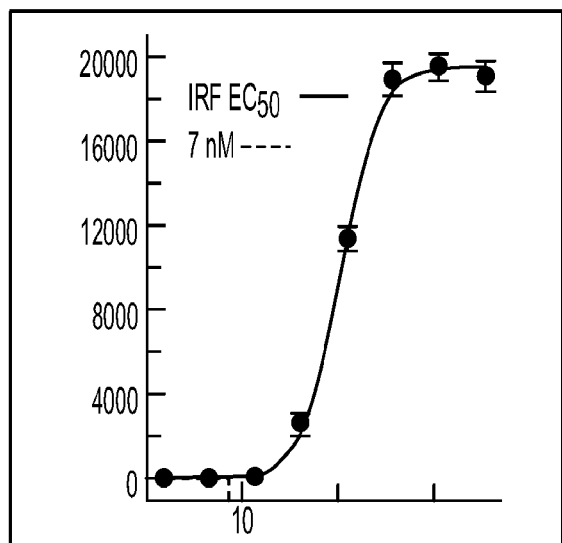
FIGS. 23A-23D are graphs showing the induction of IRF (FIGS. 23A-23B) and NF-κB (FIGS. 23C-23D) by Cmd 1, and indicate that Cmd1 is taken up by cells without the use of transfection agents.
Figure 23B:
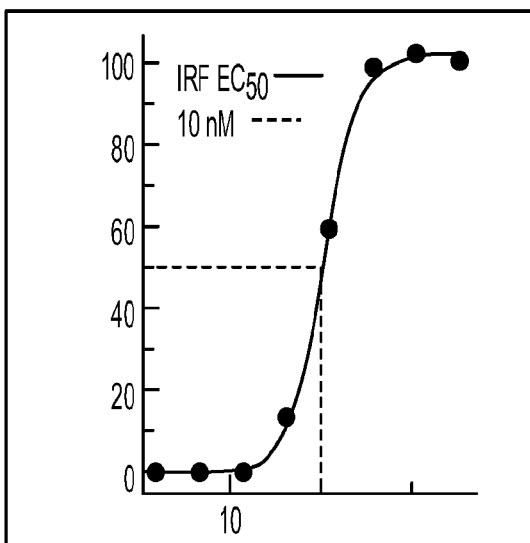
Figure 23C:
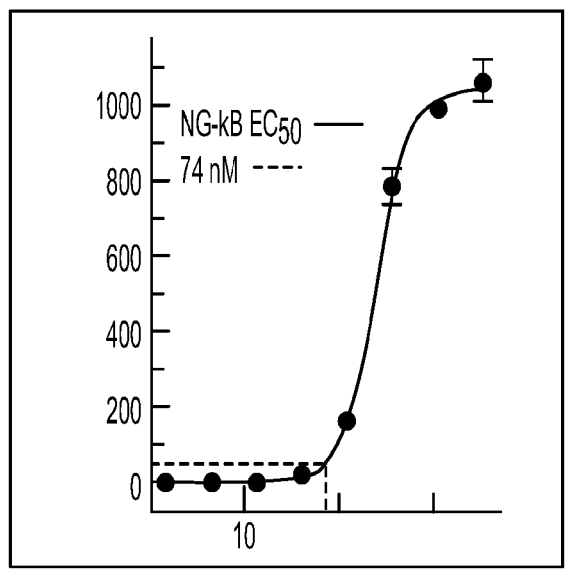
Figure 23D:
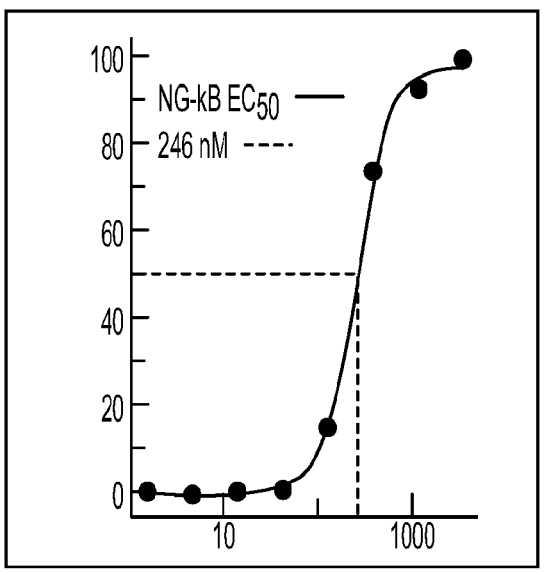
Figures 24A, 24B, 25A, 25B, 25C, 25D:
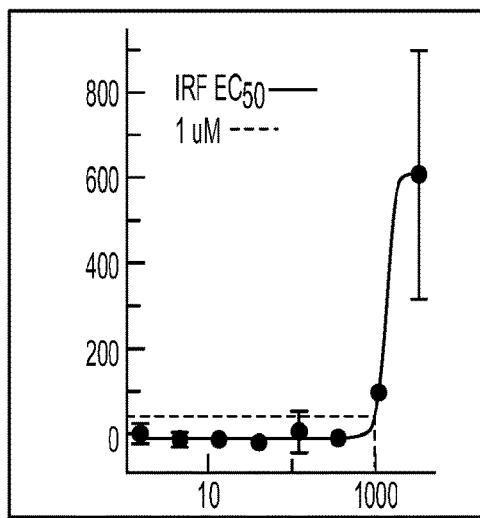
FIGS. 24A-24B are graphs showing the induction of IRF by Cmd 3, and indicate that Cmd 3 is taken up by cells without the use of transfection agents.
FIGS. 25A-25D are graphs showing the induction of IRF (FIGS. 25A-25B) and NF-κB (FIGS. 25C-25D) by Cmd 12, and indicate that Cmd12 is taken up by cells without the use of transfection agents.
Figures 26A, 26B:
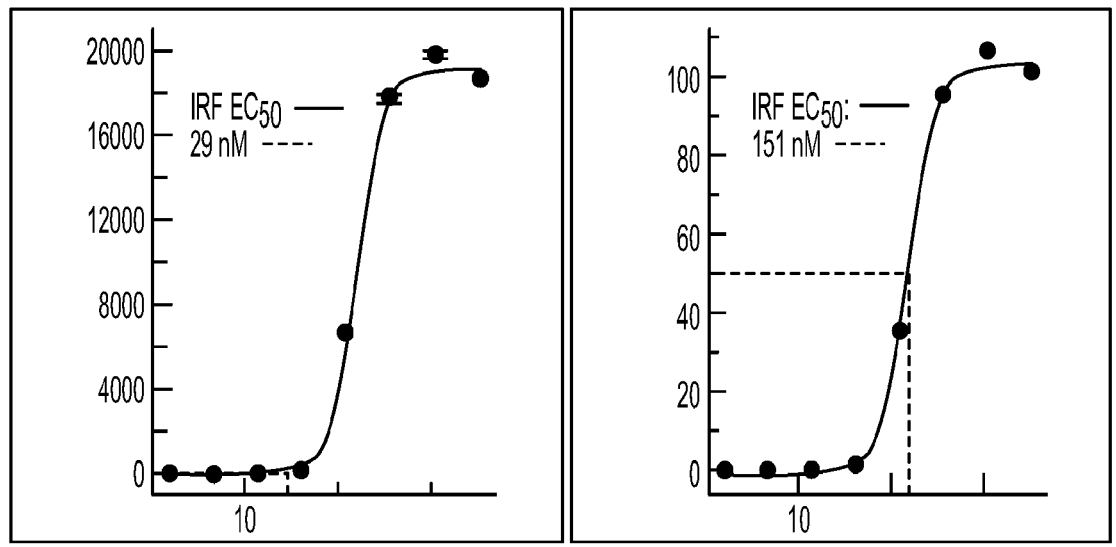
FIGS. 26A-26D are graphs showing the induction of IRF (FIGS. 26A-26B) and NF-κB (FIGS. 26C-26D) by Cmd 13, and indicate that Cmd13 is taken up by cells without the use of transfection agents.
Figures 26C, 26D:
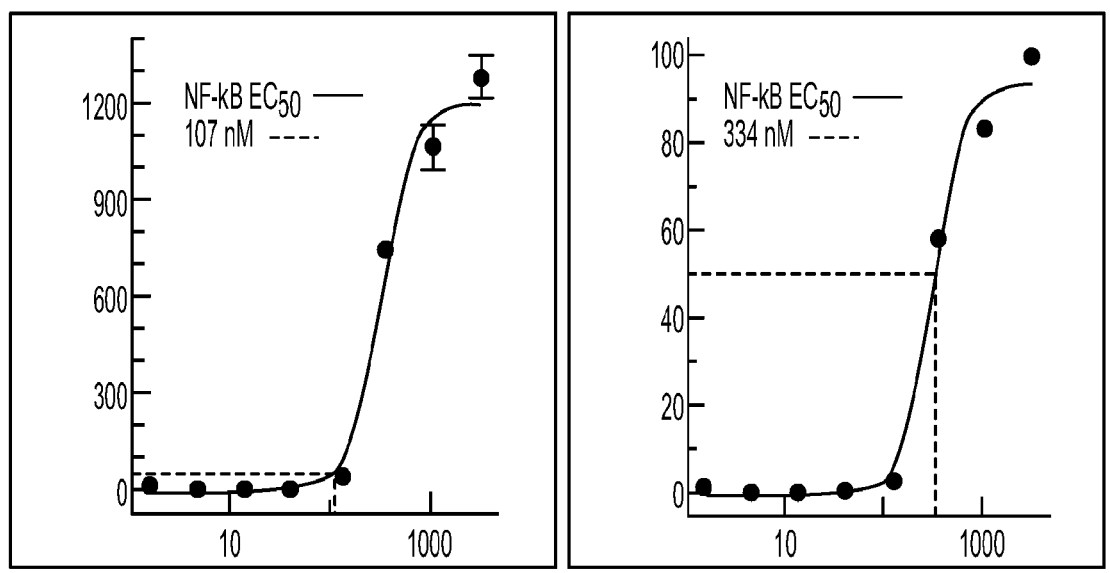
Figure 27A:
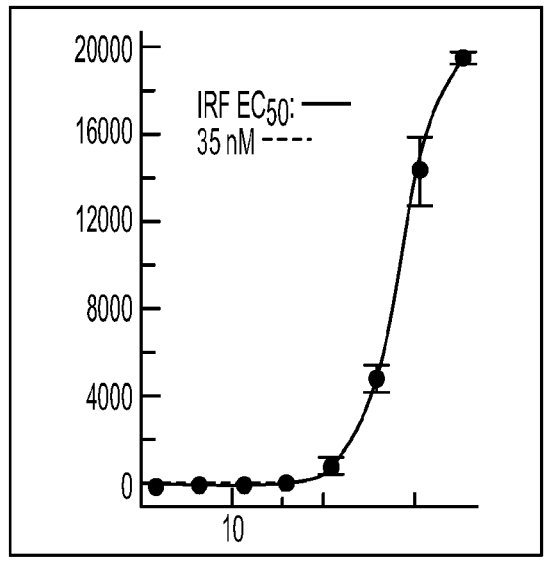
FIGS. 27A-27D are graphs showing the induction of IRF (FIGS. 27A-27B) and NF-κB (FIGS. 27C-27D) by Cmd 14, and indicate that Cmd14 is taken up by cells without the use of transfection agents.
Figure 27B:
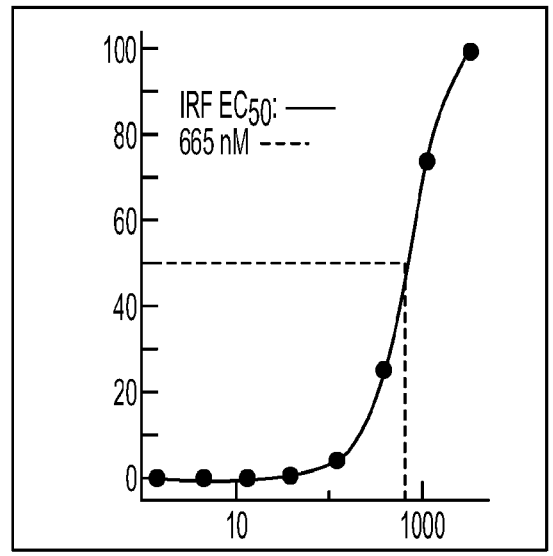
Figure 27C:
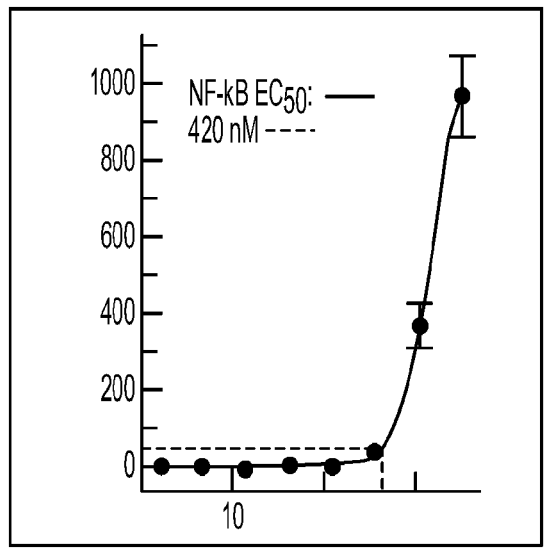
Figure 27D:
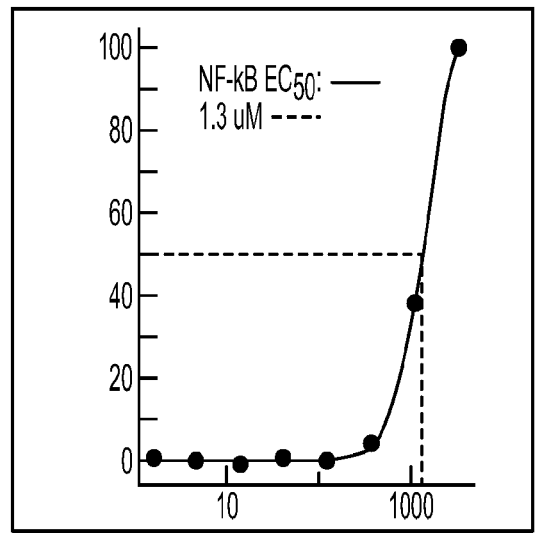
Figure 28A:
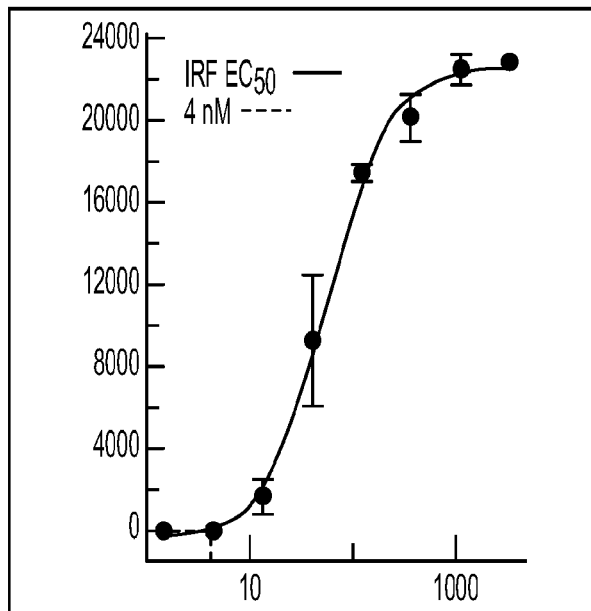
FIGS. 28A-28D are graphs showing the induction of IRF (FIGS. 28A-28B) and NF-κB (FIGS. 28C-28D) by Cmd 15, and indicate that Cmd15 is taken up by cells without the use of transfection agents.
Figure 28B:
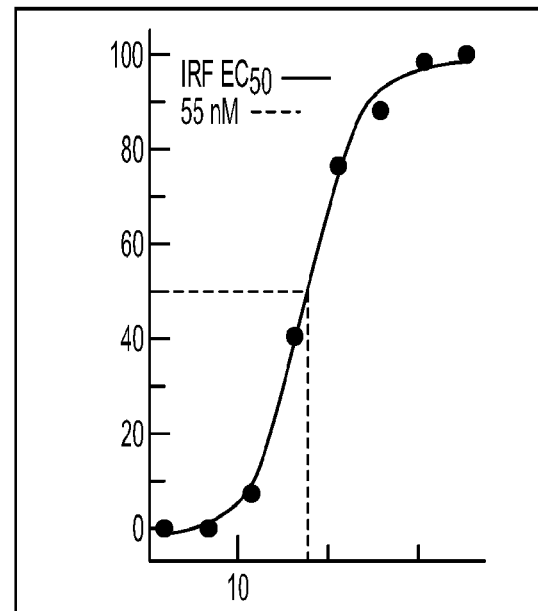
Figure 28C:
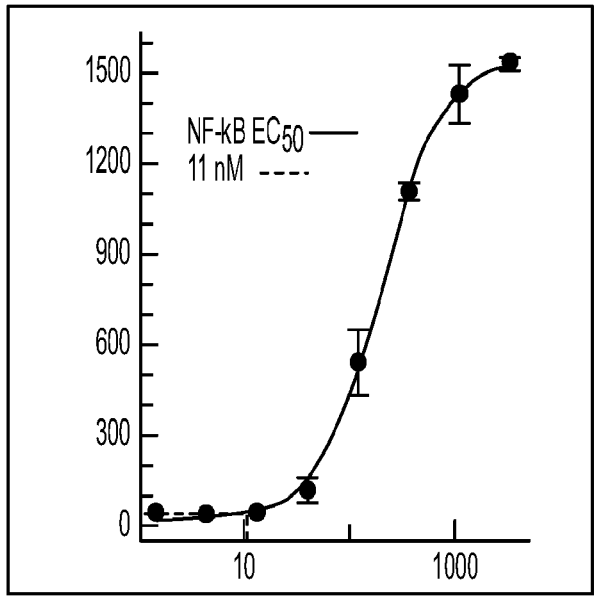
Figure 28D:
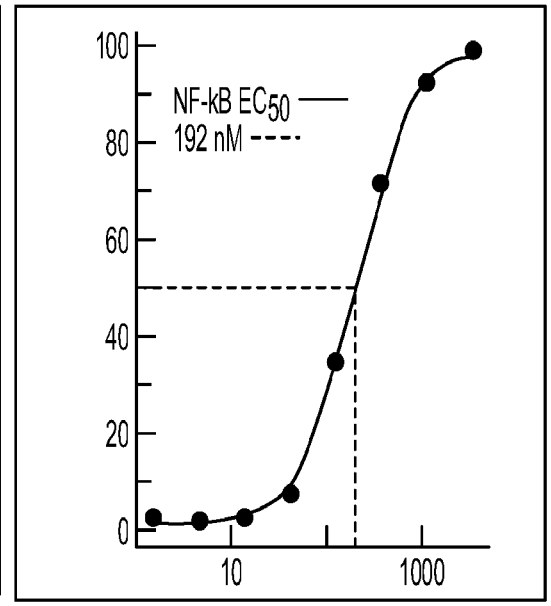
Figure 29A:
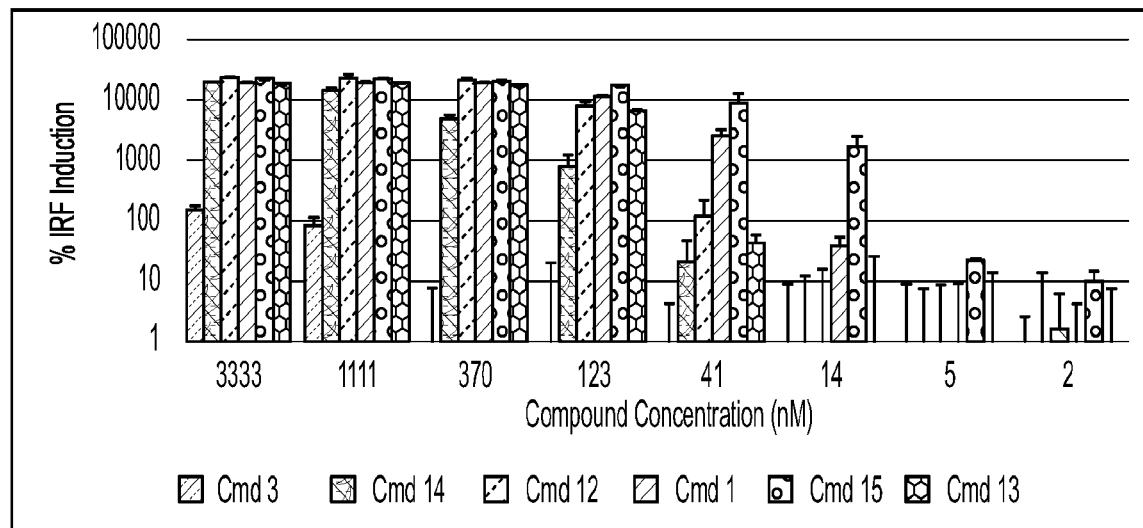
FIGS. 29A-29B are charts comparing the relative induction of IRF (FIG. 29A) and NF-κB (FIG. 291B) by Cmd 1, Cmd 3, Cmd 12, Cmd 13, Cmd 14, and Cmd 15.
Figure 29B:
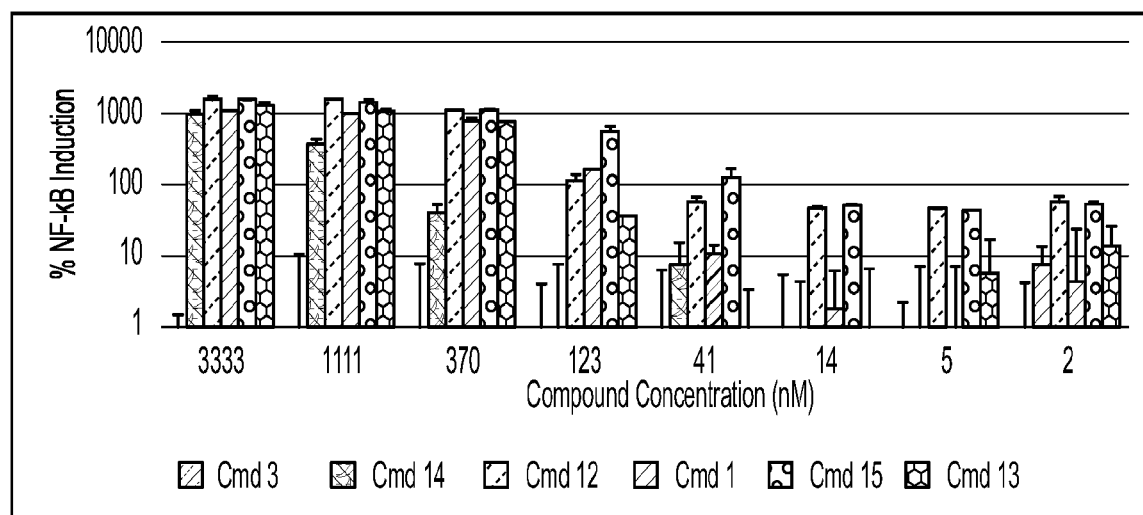
Figure 30A:
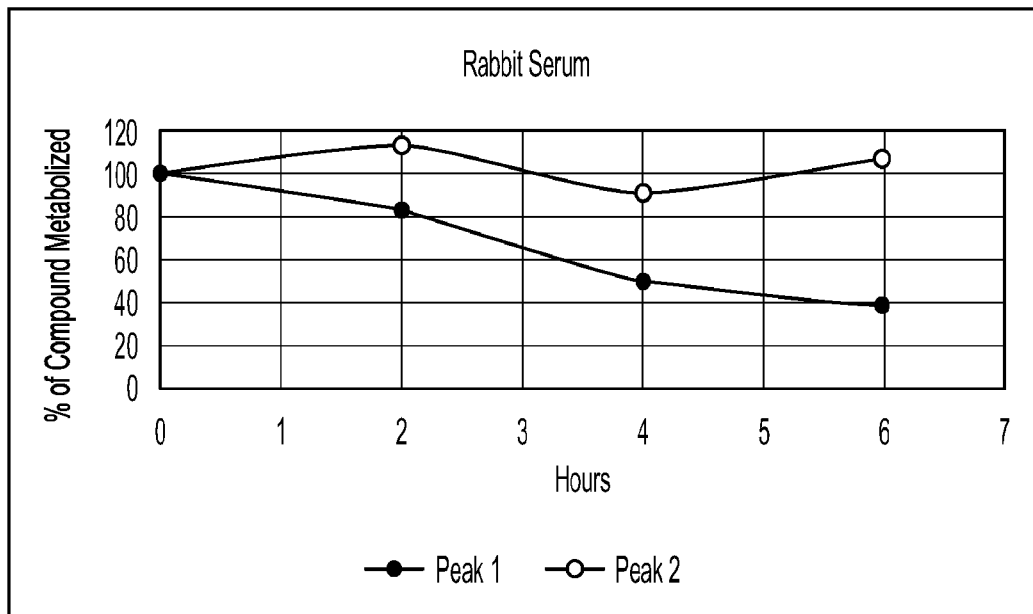
FIGS. 30A-30B are graphs showing the stability of Cmd 1 in serum (FIG. 30A) and in microsomes (FIG. 30B).
Figure 30B:
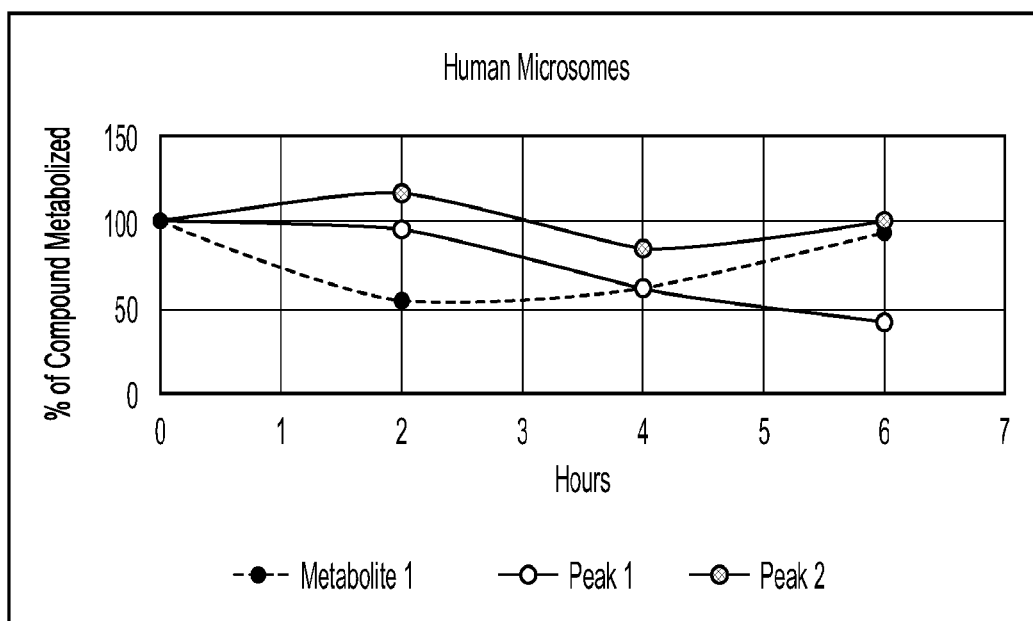
Figure 31A:
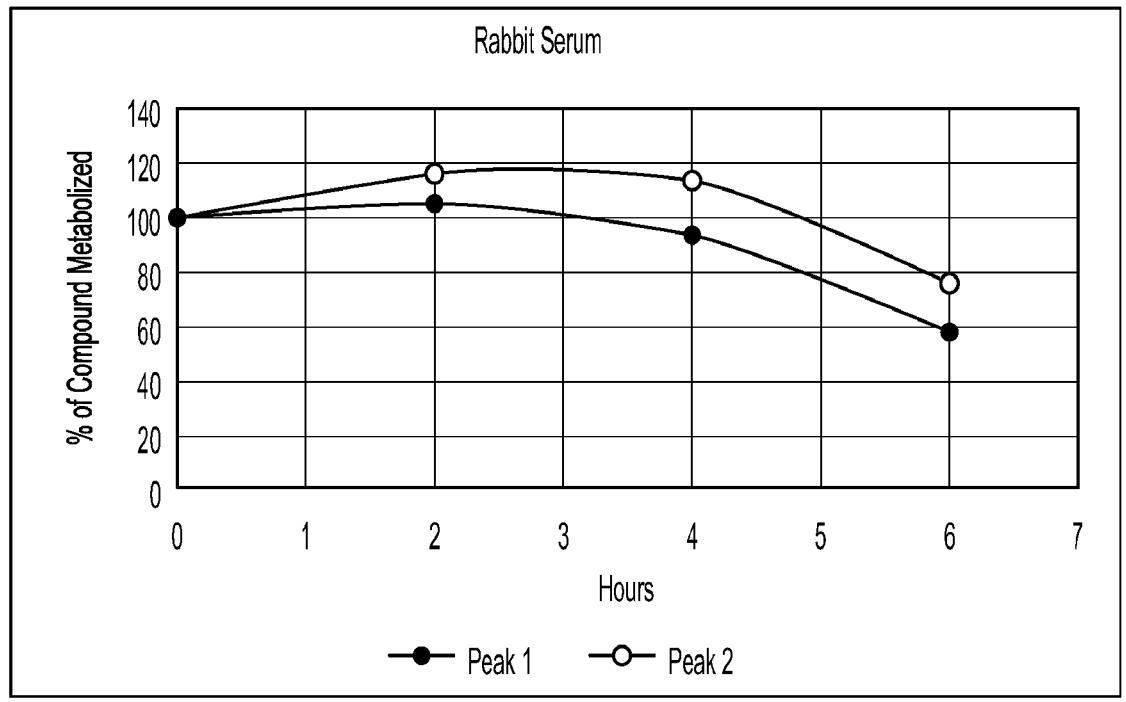
FIGS. 31A-31B are graphs showing the stability of Cmd 15 in serum (FIG. 31A) and in microsomes (FIG. 31B).
Figure 31B:
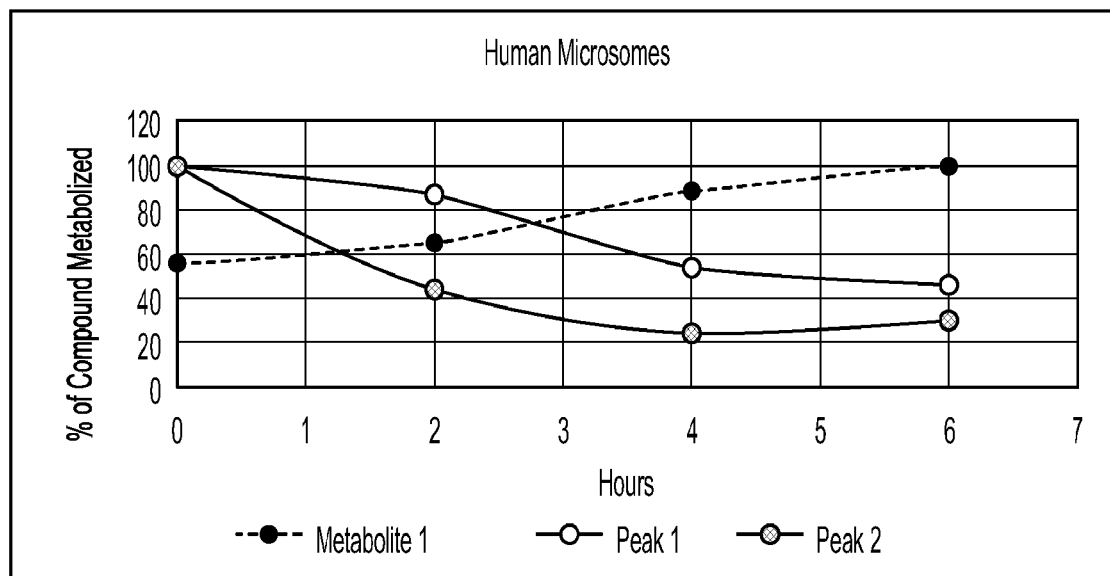
Figure 32A:
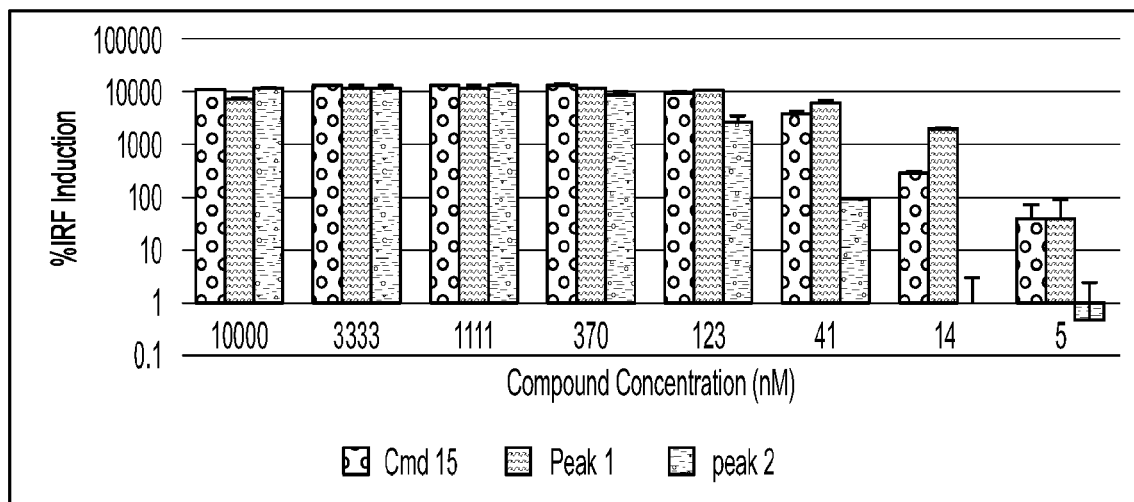
FIGS. 32A-32B are charts comparing the induction of IRF (FIG. 32A) and NF-κB (FIG. 32B) by Cmd 15 and its isomers, Cmd 15-A and Cmd 15-B.
Figure 32B:
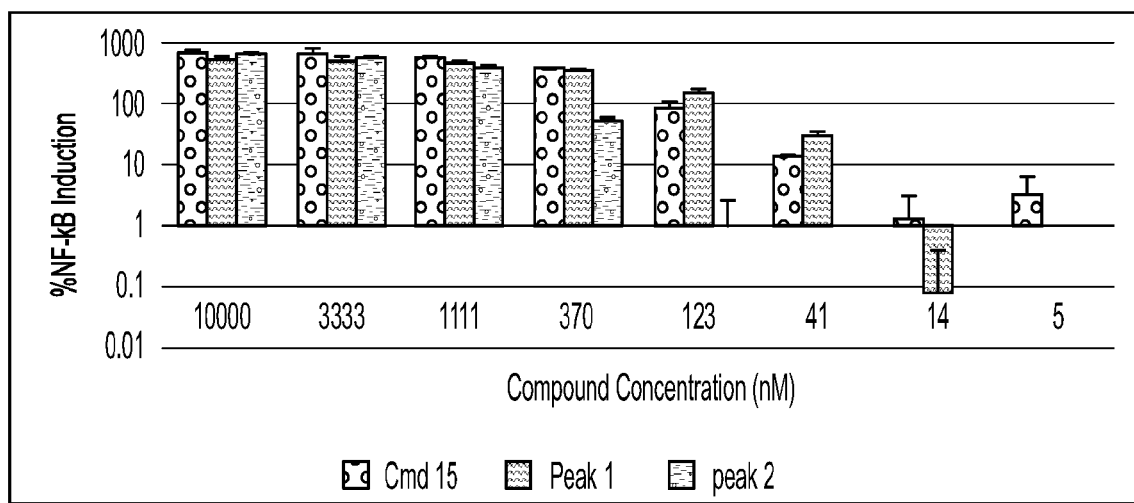
Figure 33:
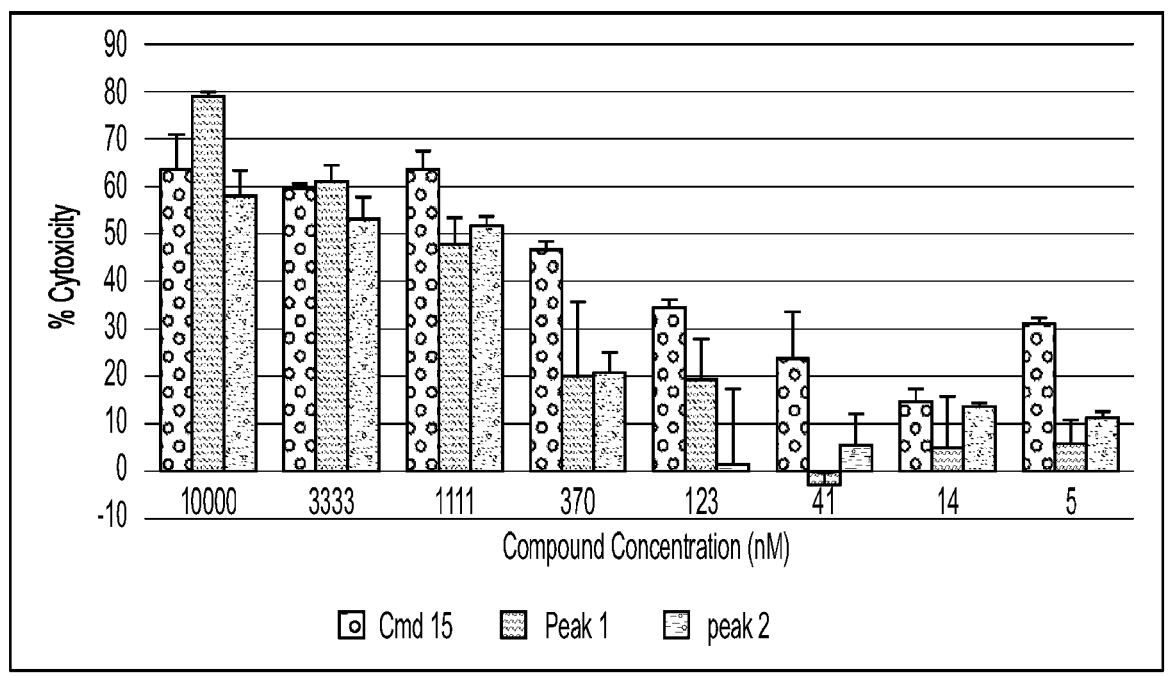
FIG. 33 is a chart showing the induction of apoptosis through % cytoxicity of THP1 cells by Cmd 15 and its isomers, Cmd 15-A and Cmd 15-B.
Figure 34A:
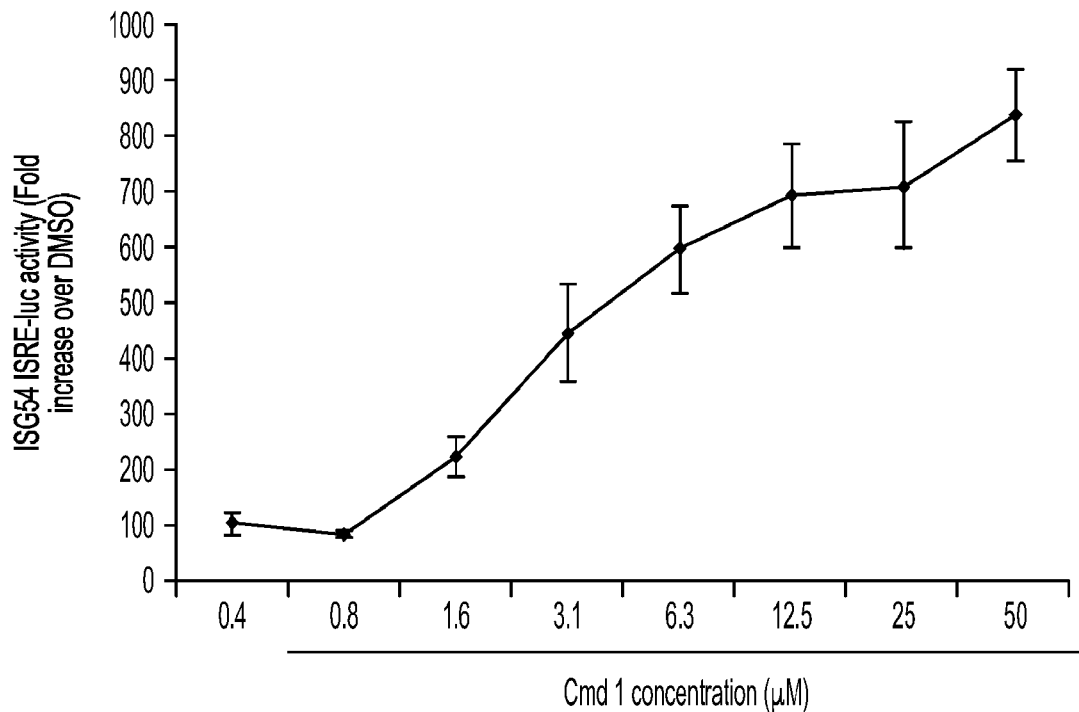
FIGS. 34A-34B show that Cmd 1 binds to STING to activate type 1 IFN signaling, similar to 2',3'-cGAMP.
Figure 34B:
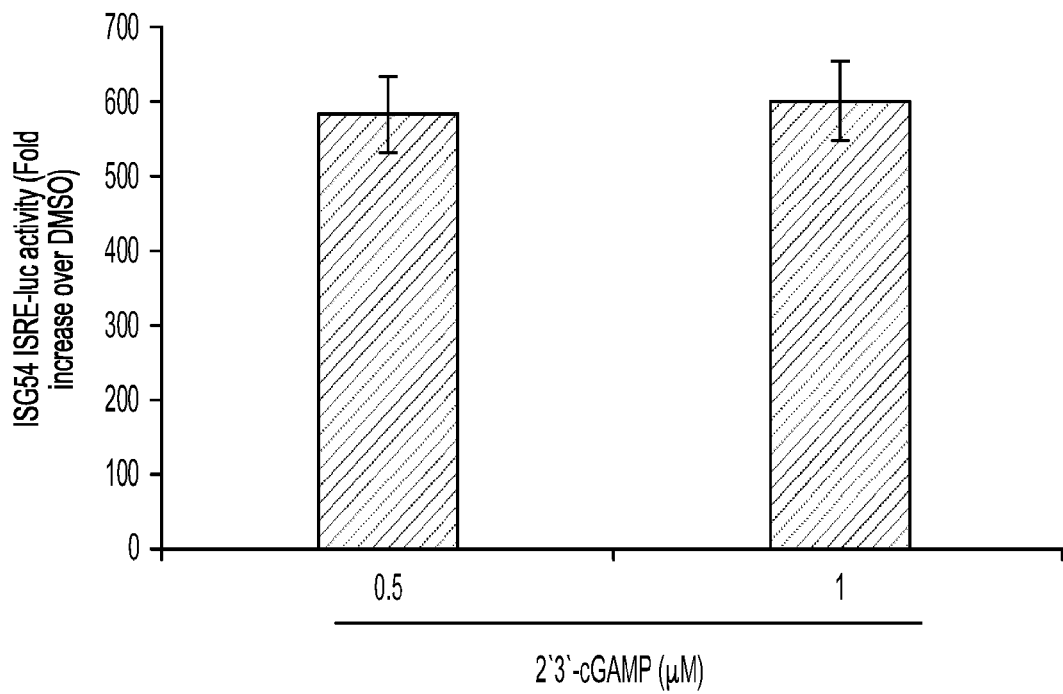
Figure 35:
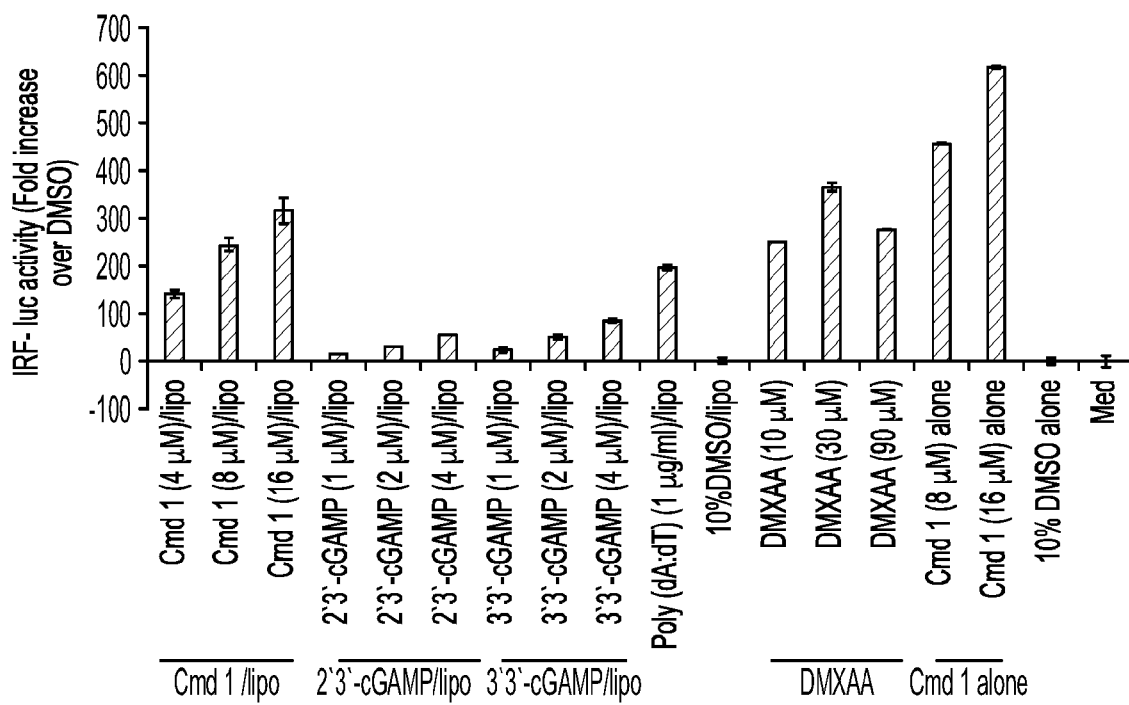
FIG. 35 is a chart showing that Cmd 1 is highly active in mouse macrophages in activating type 1 IFN signaling, similar to 2',3'-cGAMP.
Figure 36A:
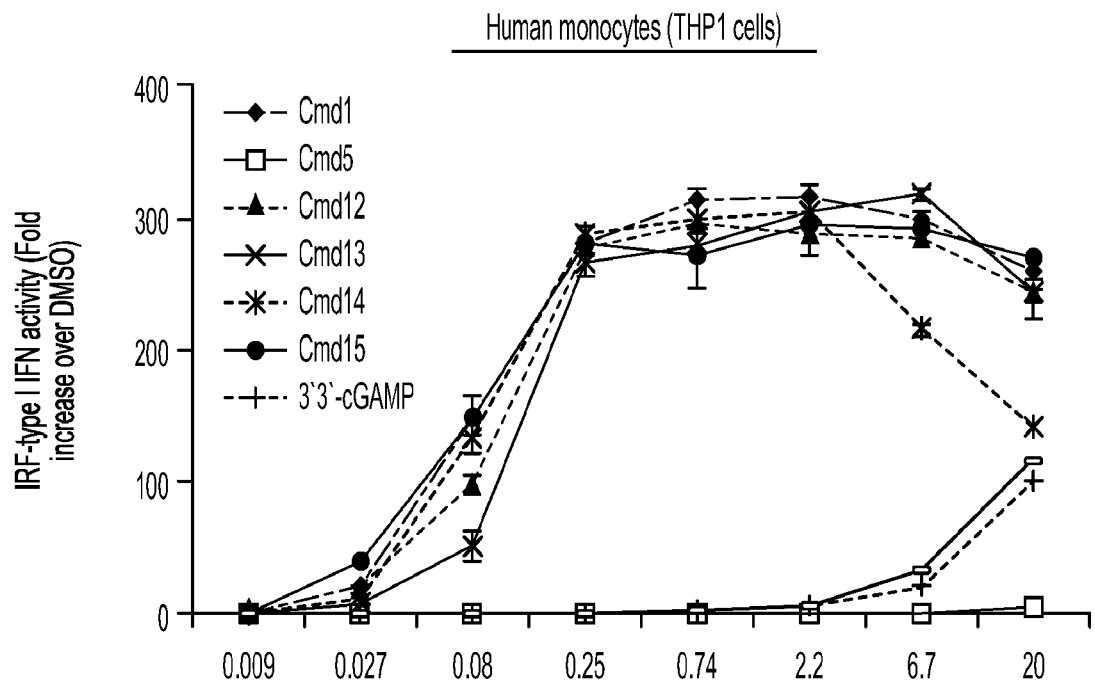
FIGS. 36A-36B are graphs that show that Cmd 1, Cmd 5, Cmd 12, Cmd 13, Cmd 14, and Cmd 15 are more active against the natural STING ligand 3',3'-cGAMP in human monocytes (FIG. 36A) and mouse macrophages (FIG. 36B).
Figure 36B:
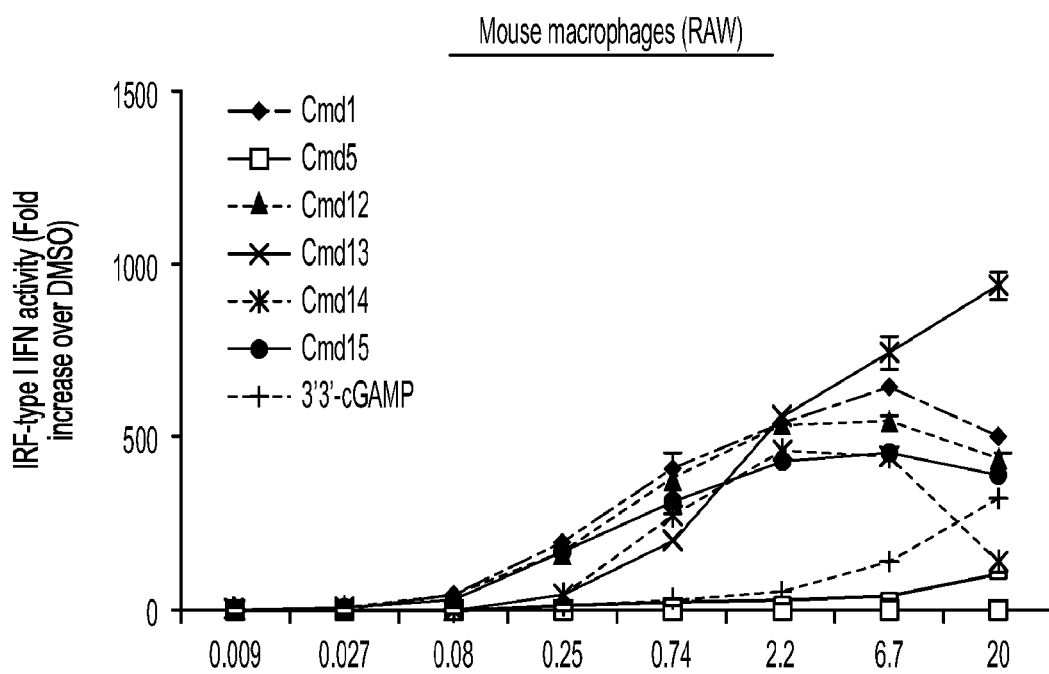
Figure 37A:
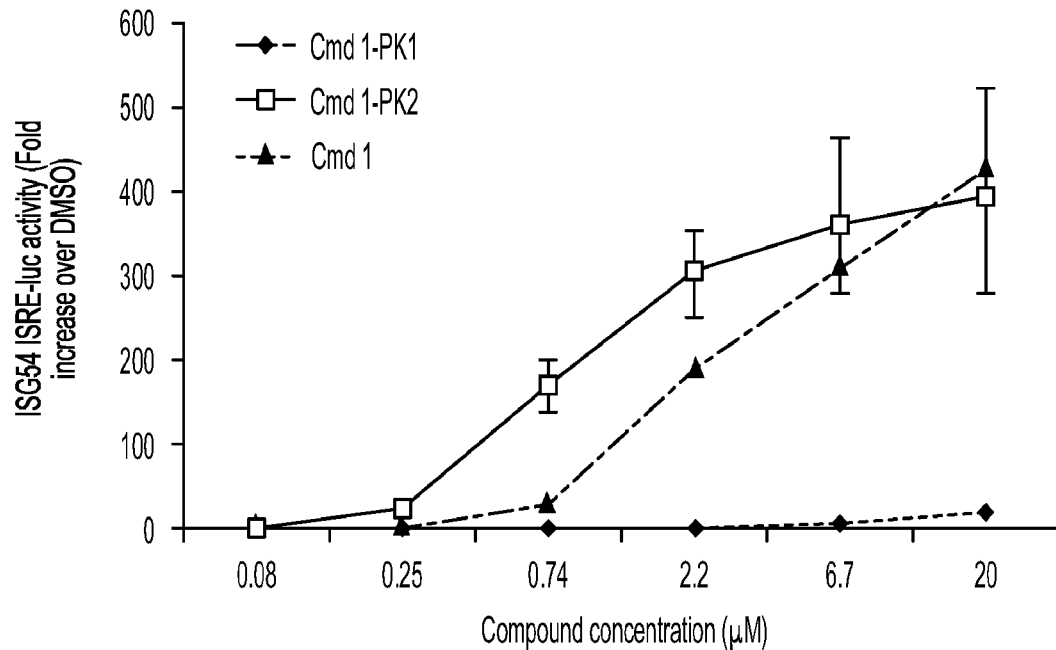
FIGS. 37A-37B are graphs that show the induction of type I IFN signaling in HEK293 (FIG. 37A) and THP1 (FIG. 37B) cells by Cmd 1 and its isomers Cmd 1A and Cmd 1B.
Figure 37B:
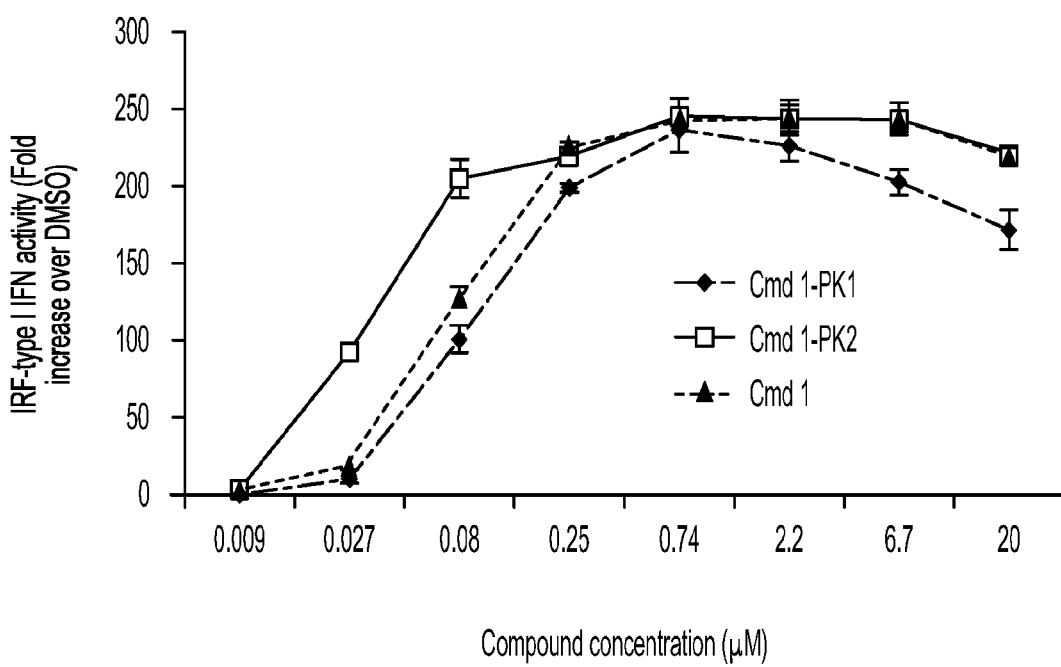
Figure 38A:
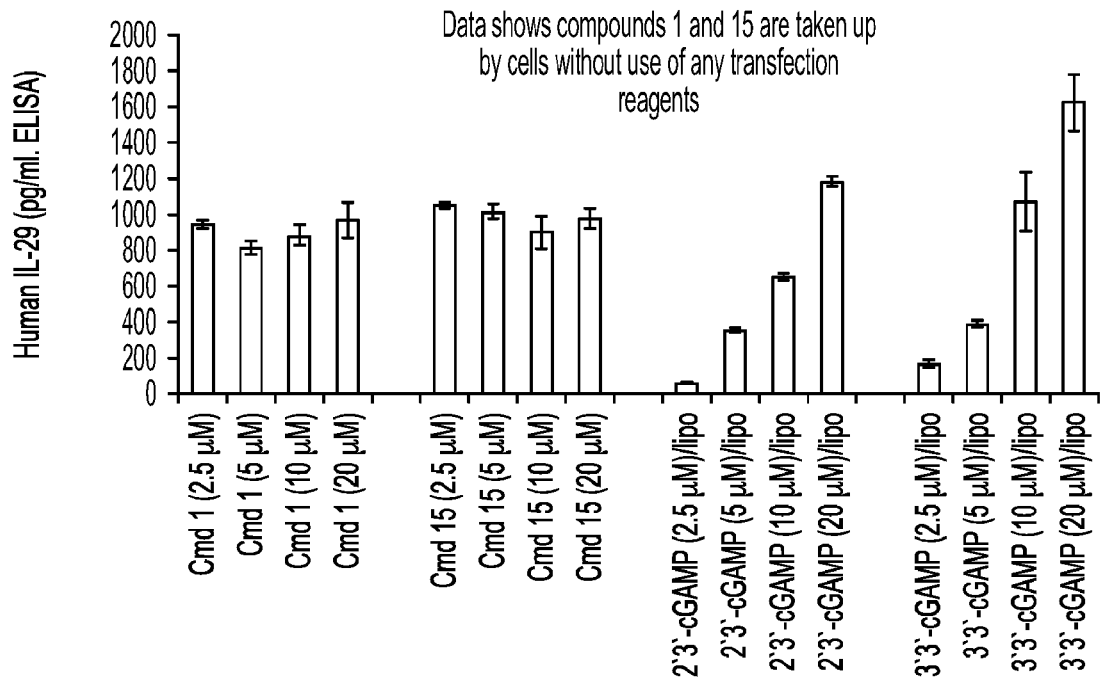
FIGS. 38A-38B are charts showing that Cmd 1 and Cmd 15 induce type III interferon (IL-29) production in THP1 cells (FIG. 38A), and that both Cmd 1 and Cmd 15 are taken up by cells without use of a transfection reagent (FIG. 38B).
Figure 38B:
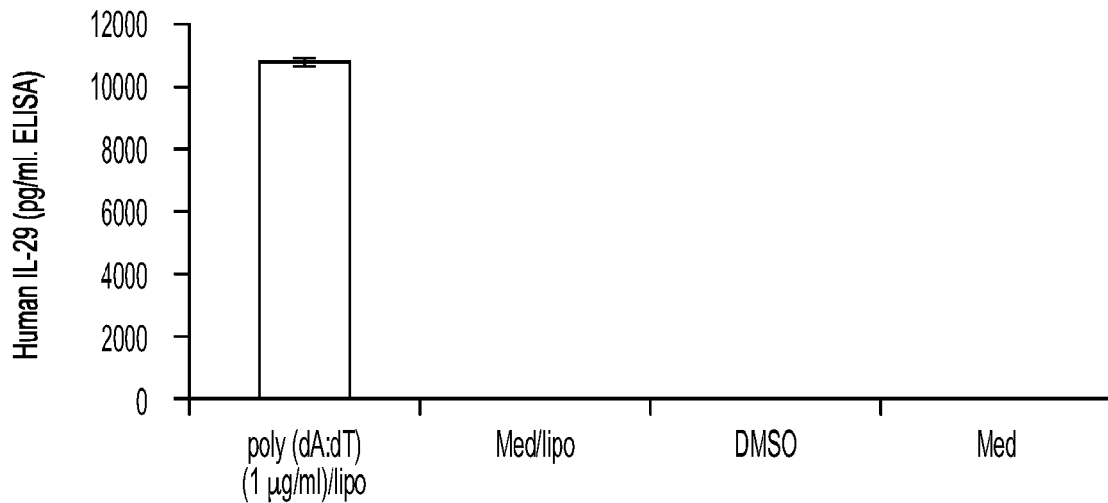
Figure 39A:
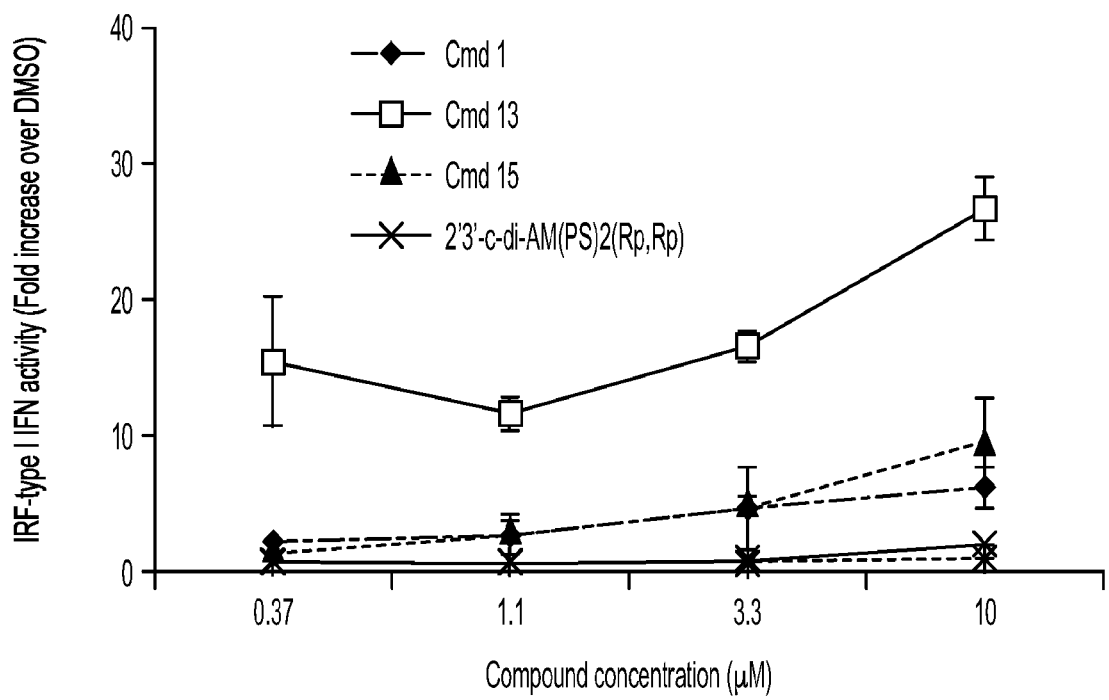
FIGS. 39A-39B are graphs comparing the induction of type I IFN signaling in THP1 cells by Cmd 1, Cmd 13, Cmd 15 as STING agonists.
Figure 39B:
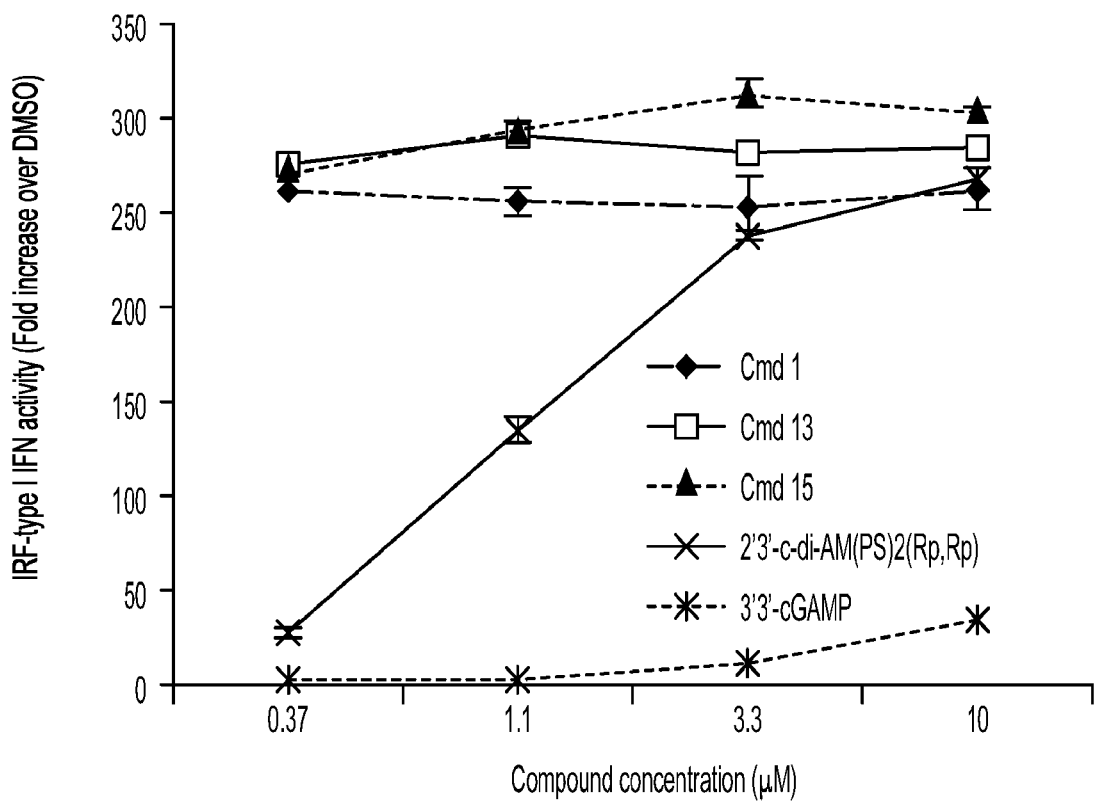
Figure 40A:
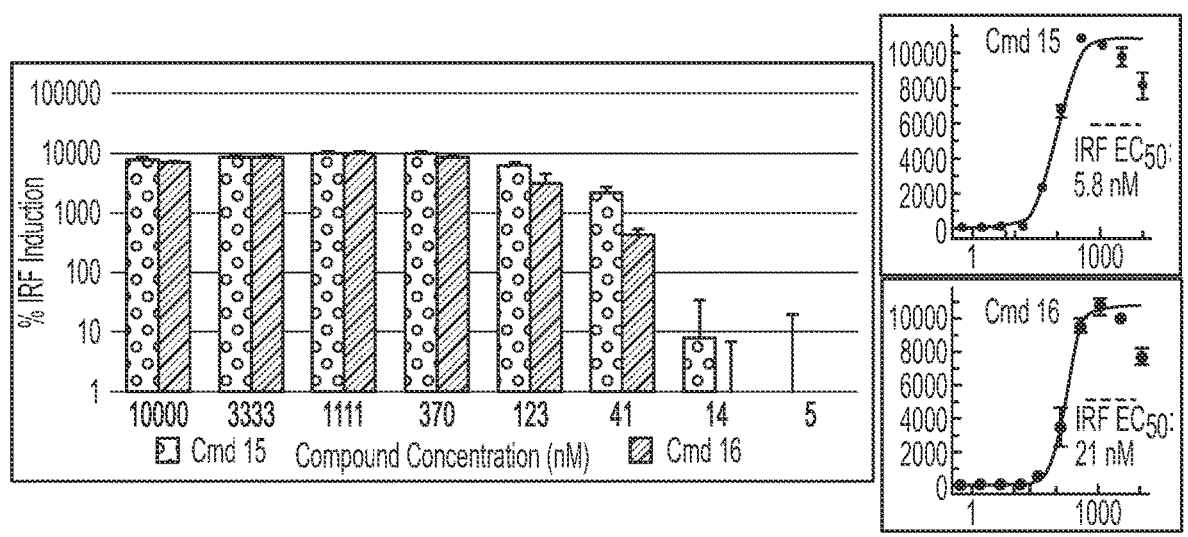
FIGS. 40A-40B are charts comparing the induction of IRF (FIG. 42A) and NF-κB (FIG. 42B) by Cmd 15 and Cmd 16.
Figure 40B:
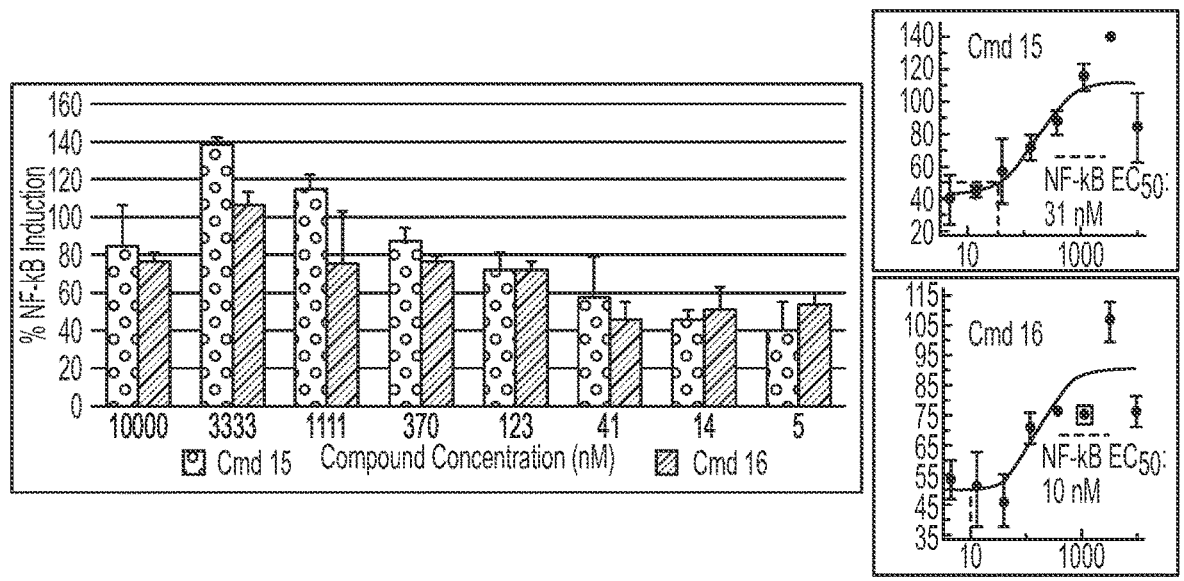
Figures 41A, 41B:
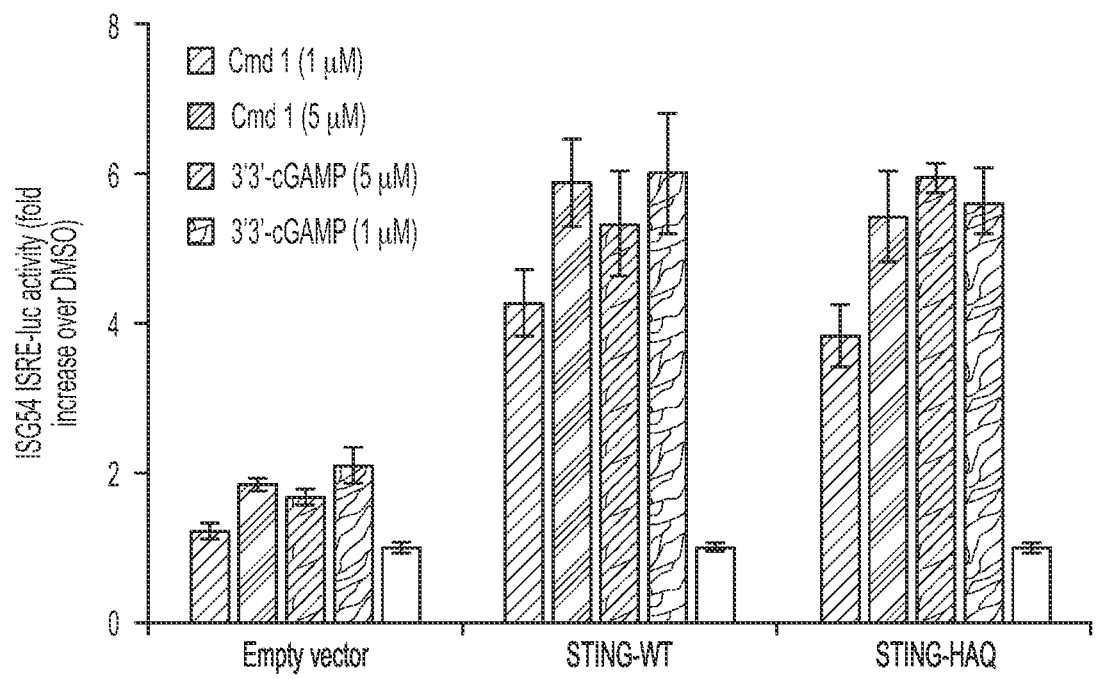
FIGS. 41A-41B show that Cmd1 is capable of activating the major STING-HAQ polymorphic variant in humans.
Figure 42:
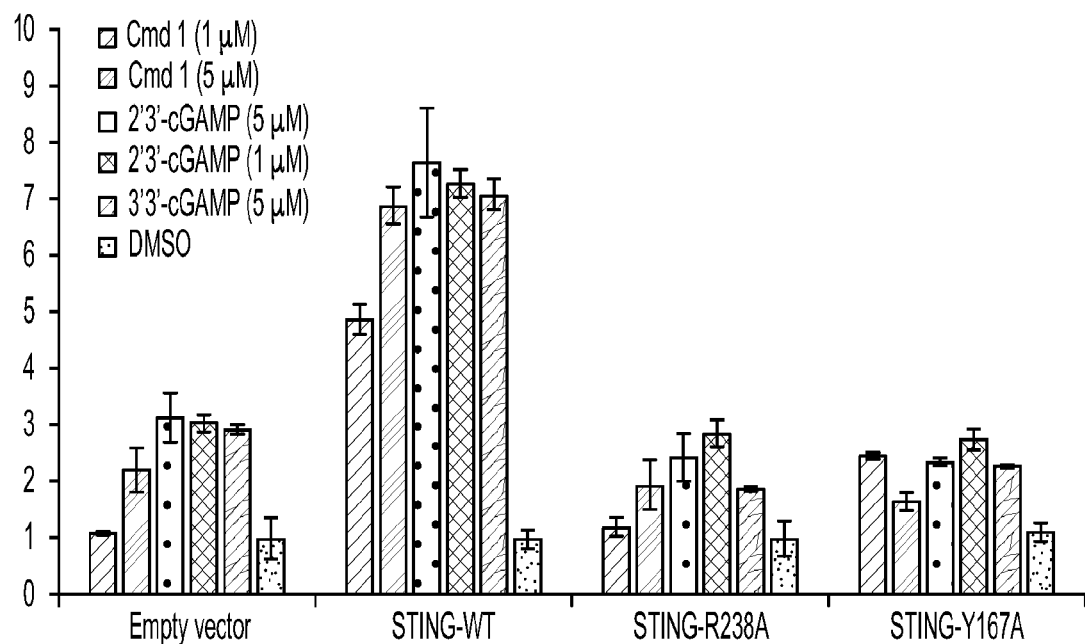
FIG. 42 shows that residues R238 and Y167 in STING Laboratory-generated loss-of-function STING mutants (STING-R238A and STING-Y167A) are critical for Cmd1 as well as cGAMP activation of STING-dependent IFN response.
Figure 43:
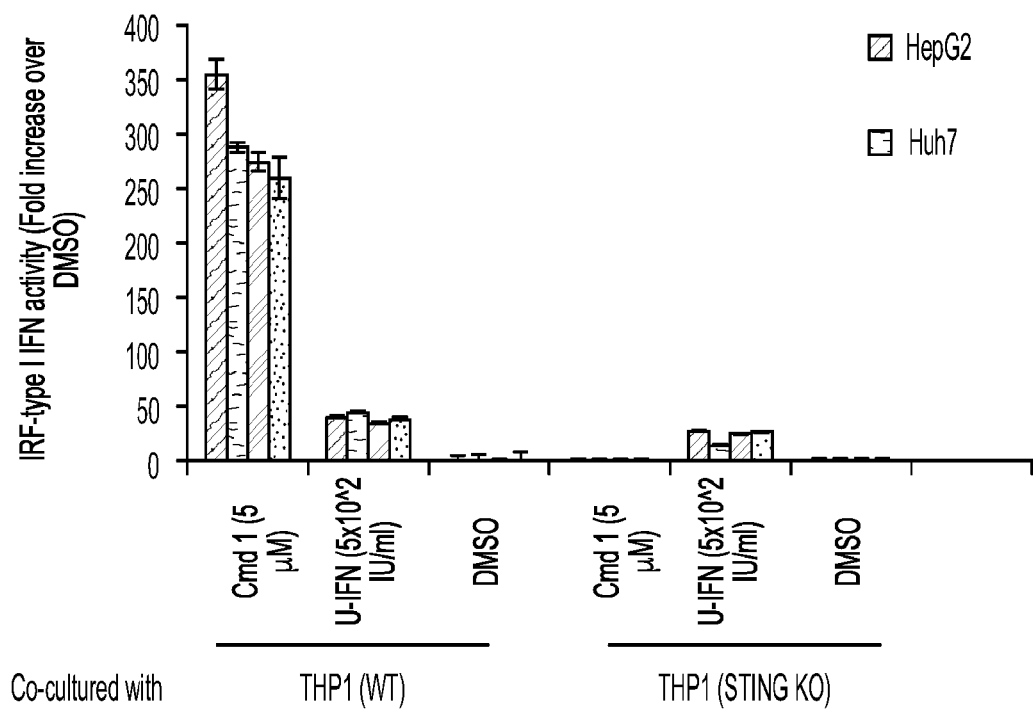
FIG. 43 shows IRF-type I IFN activity by Cmd1 in co-cultured tumor/THP1 cell system.
Figure 44A:
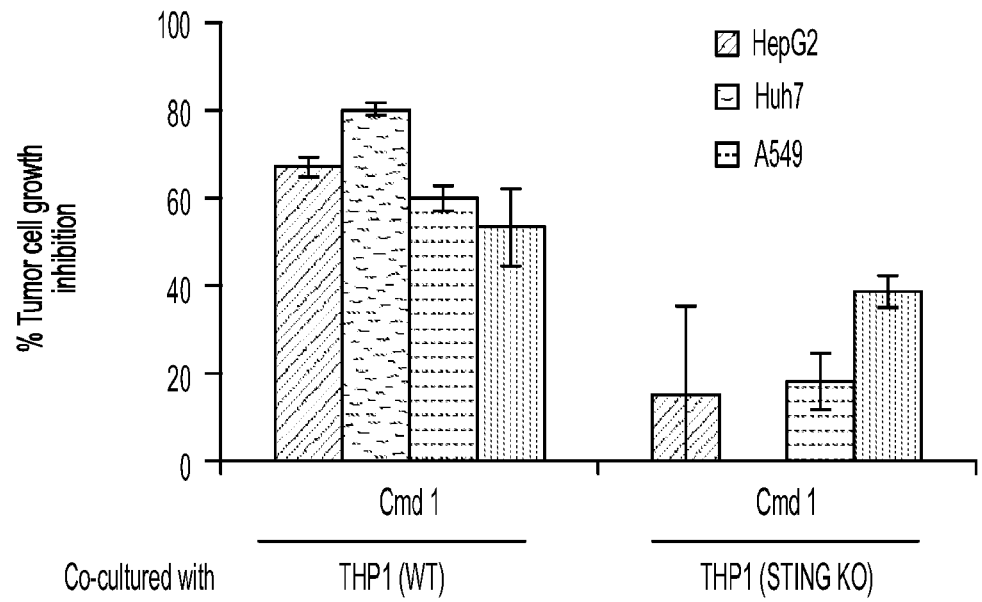
FIGS. 44A-44B show that Cmd1 inhibits tumor cell growth in tumor cells and THP1 cells using high-content image-based approach and is STING dependent.
Figure 44B:
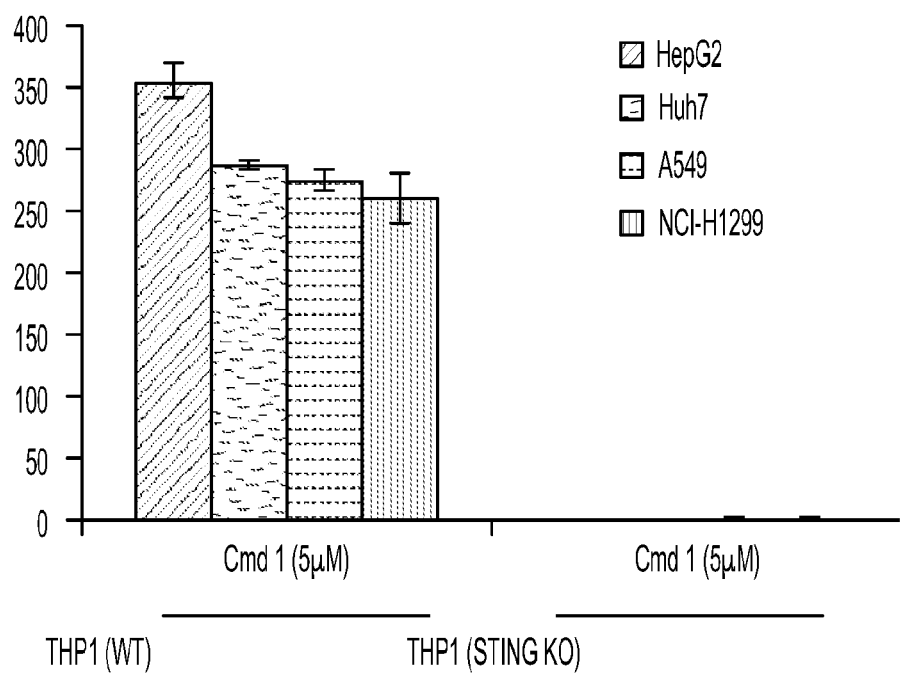
Figure 45A:
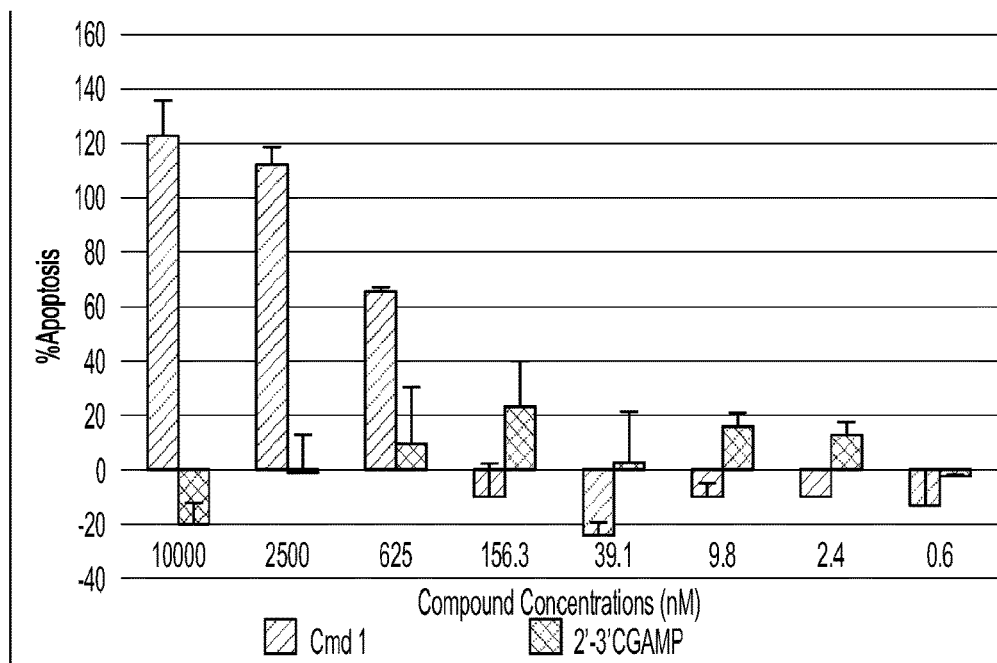
FIGS. 45A-45B show that Cmd 1 causes apoptosis acute monocytic leukemia cells.
Figure 45B:
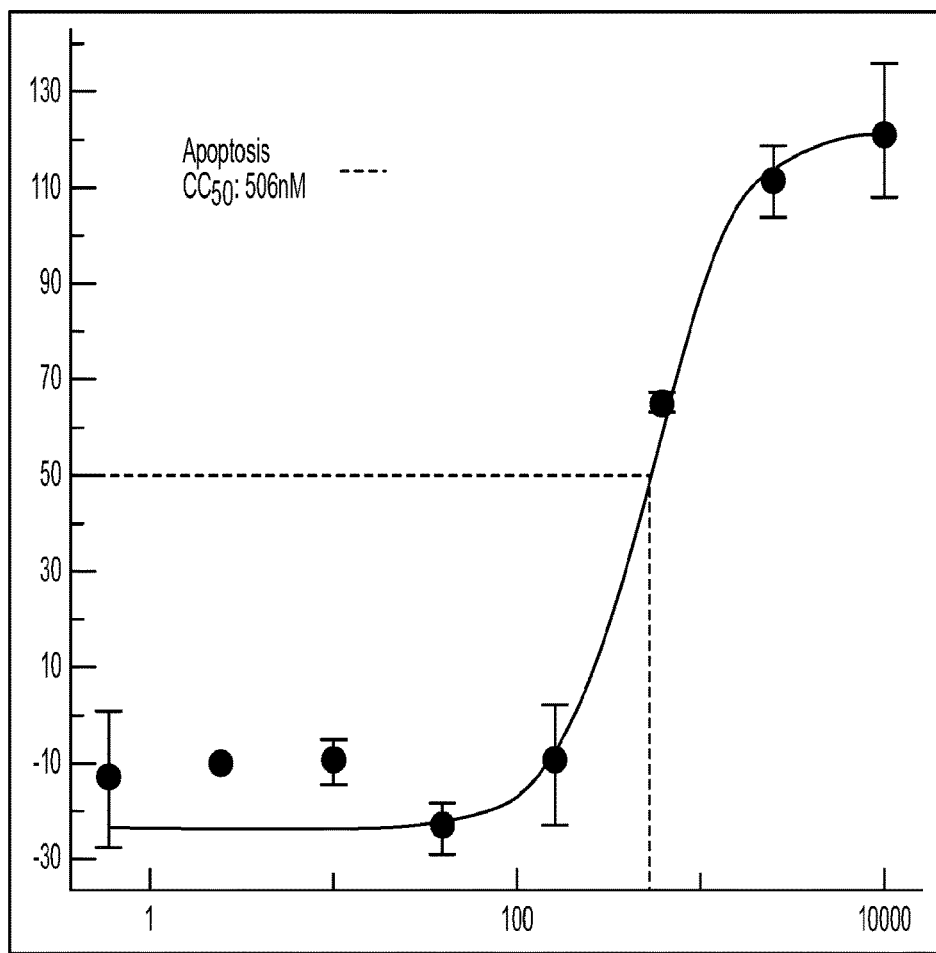
Figure 46A:
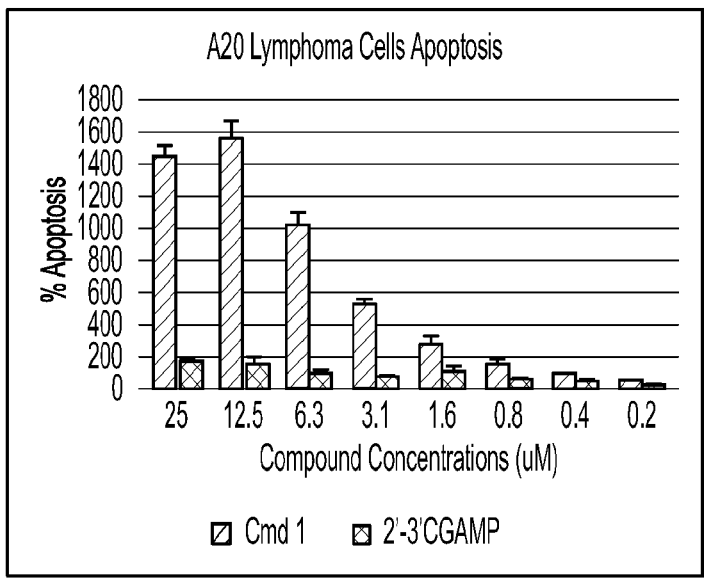
FIGS. 46A-46E show that Cmd 1 induces apoptosis in the mouse lymphoma cell line A20.
Figure 46B:
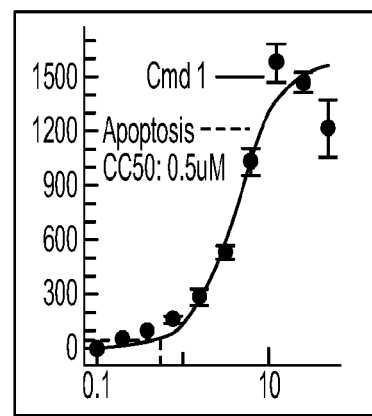
Figure 46C:
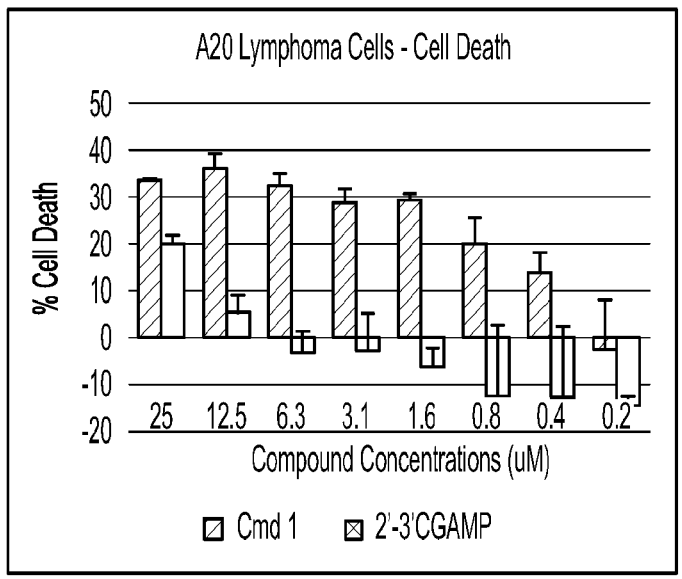
Figure 46D:
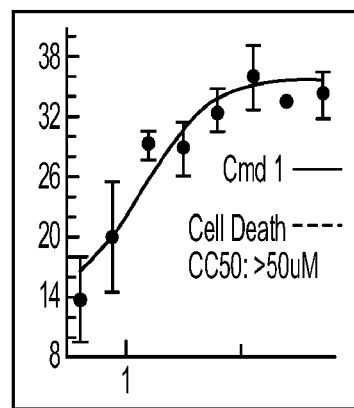
Figure 46E:
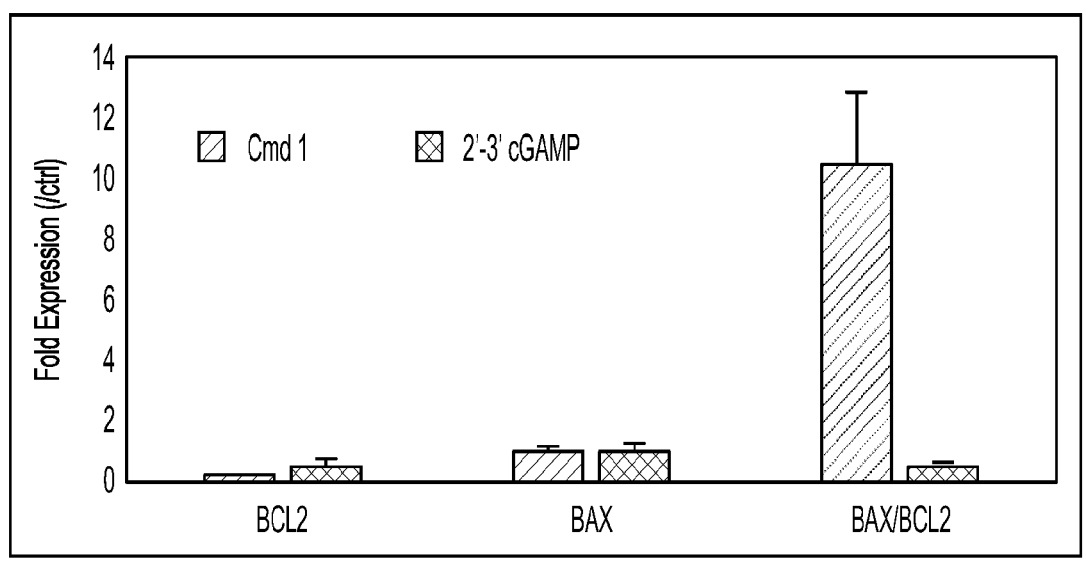
Figure 47A:
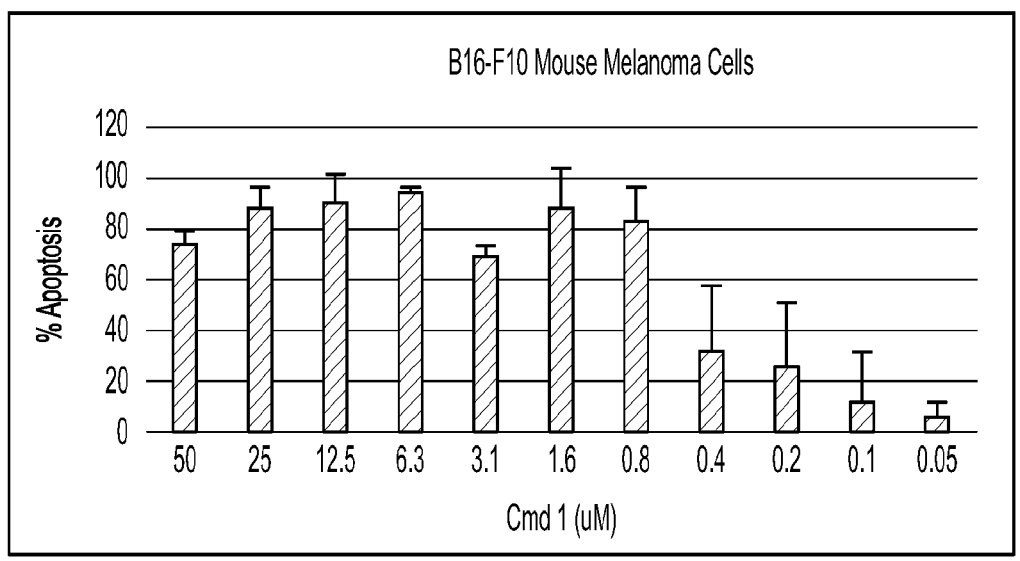
FIGS. 47A-47B show that Cmd1 causes apoptosis of mouse melanoma cells.
Figure 47B:
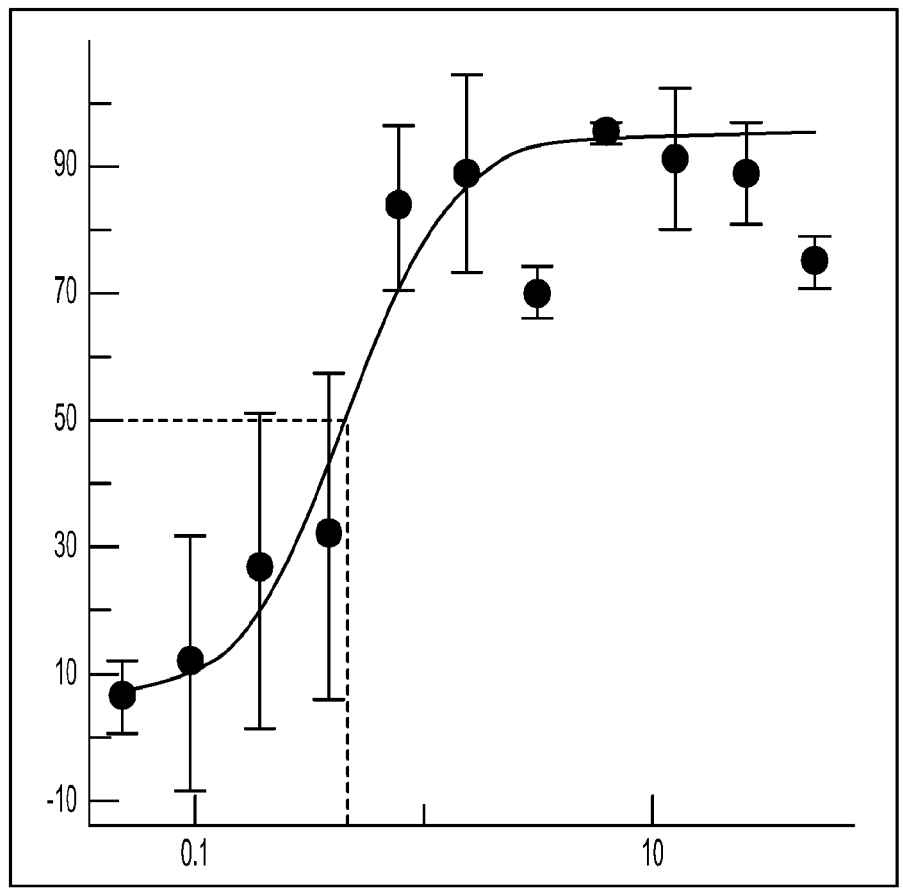
Figure 48A:
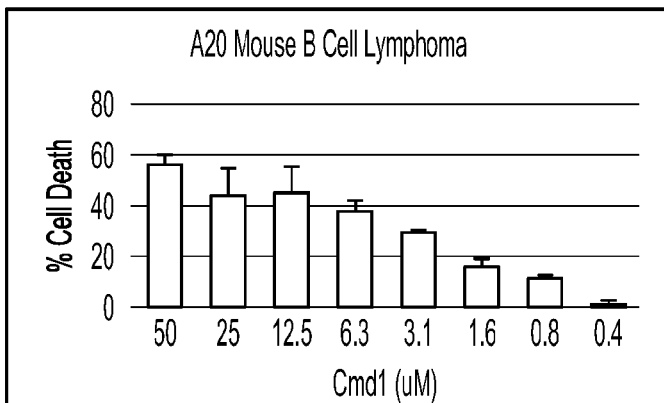
FIGS. 48A-48D show that Cmd1 inhibits mouse A20 B cell lymphoma tumor cells.
Figure 48B:
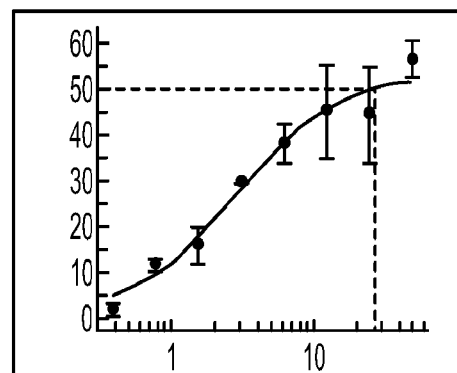
Figure 48C:
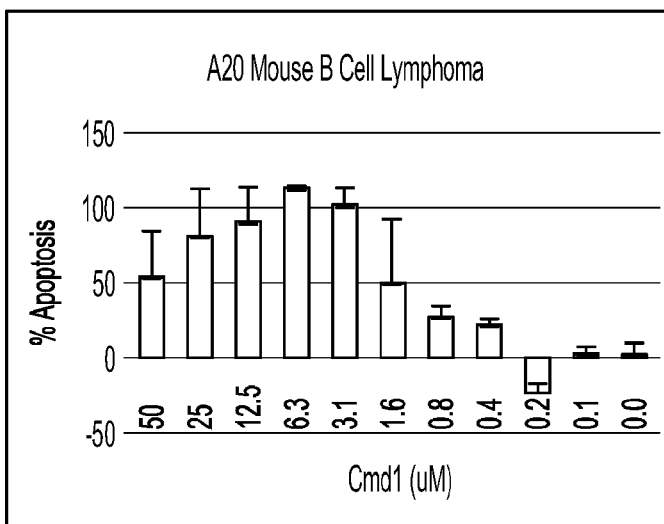
Figure 48D:
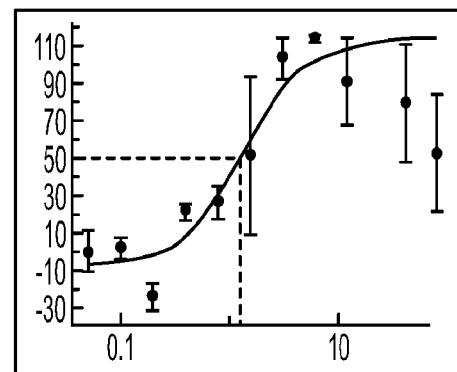
Figure 49:
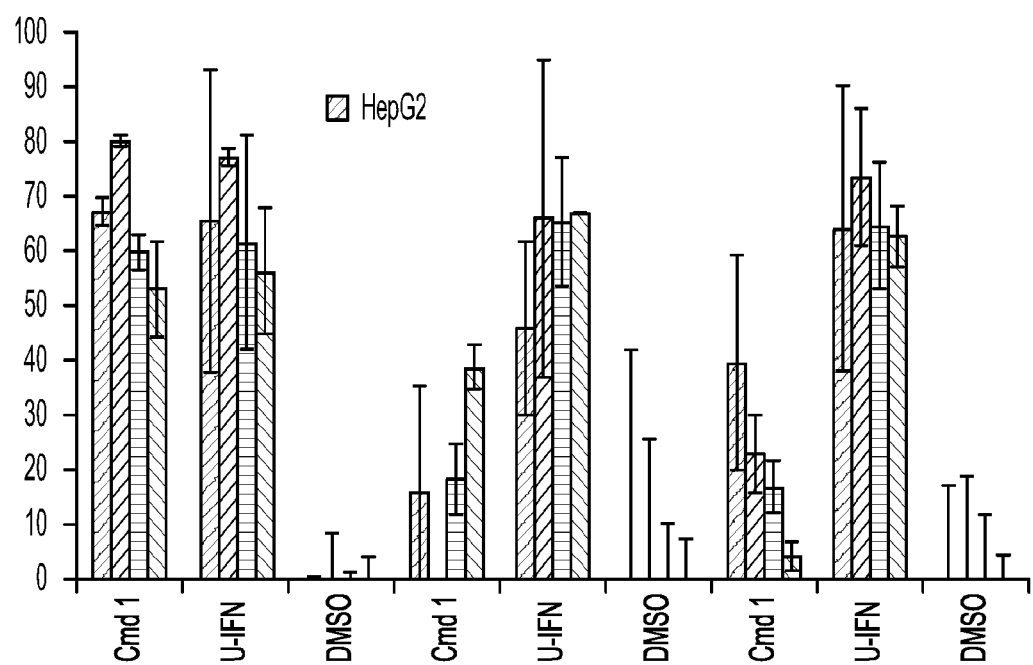
FIG. 49 shows anti-tumor activity of Cmd1 using high-content image-based approach.
Figure 50A:
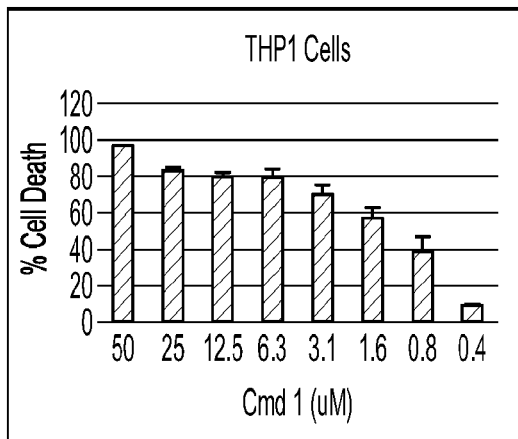
FIGS. 50A-50F show that the induction of cell death by Cmd1 is STING-mediated.
Figure 50B:
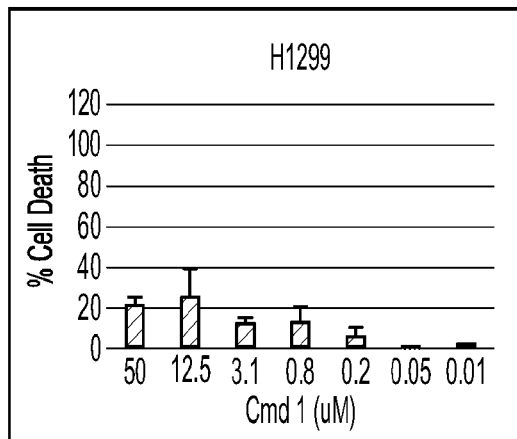
Figure 50C:
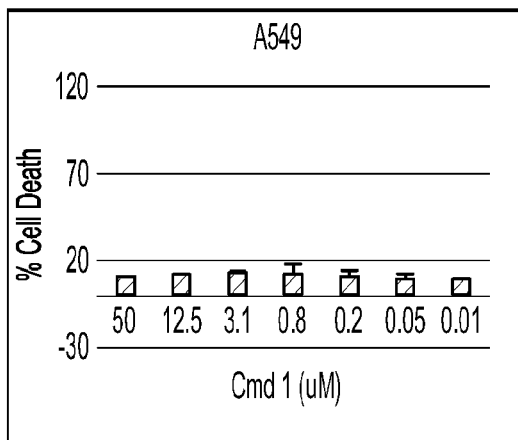
Figure 50D:
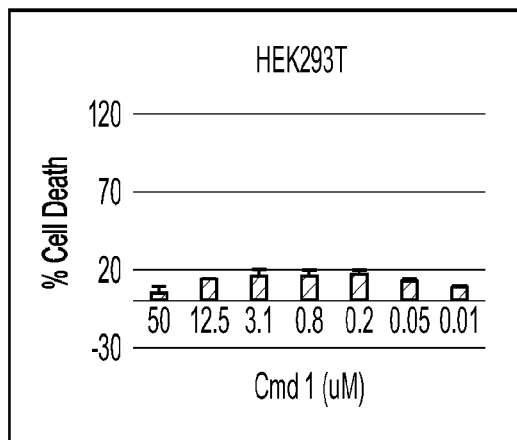
Figure 50E:
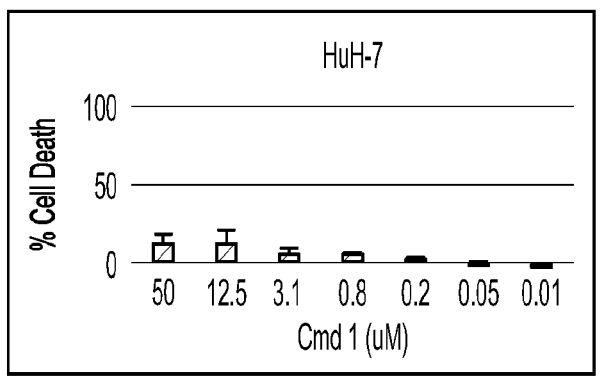
Figure 50F:
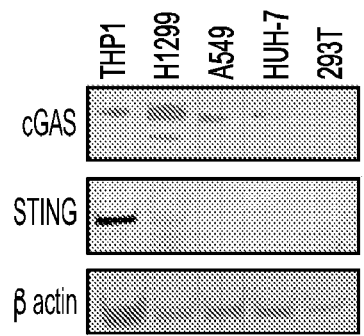
Figures 51A, 51B, 51C:
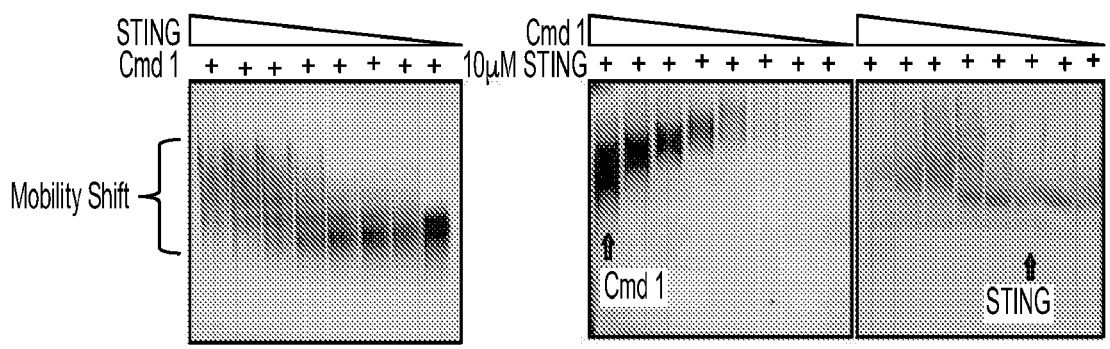
FIGS. 51A-51C show the results of a gel shift assay indicating that Cmd 1 binds to STING. A close structural analog of Cmd 1 carrying a fluorescent substituent was synthesized for Gel Shift Assay.
Figure 52A:
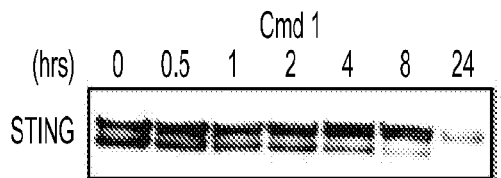
FIGS. 52A-52P show analysis of IRF3 & NF-κB pathways after Cmd 1 treatment.
Figure 52B:
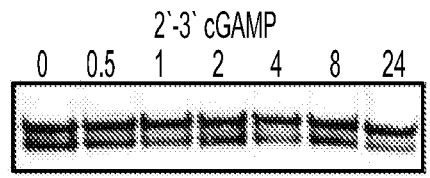
Figure 52C:
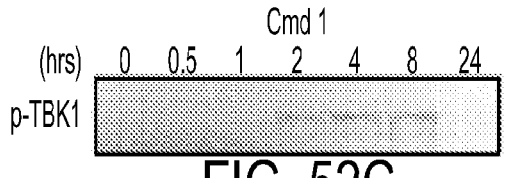
Figure 52D:
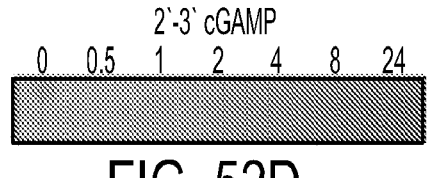
Figure 52E:
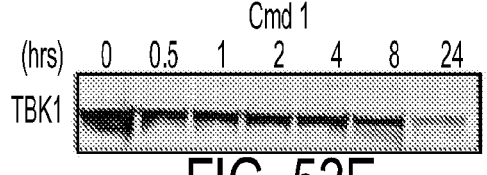
Figure 52F:
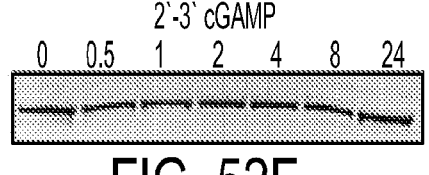
Figure 52G:
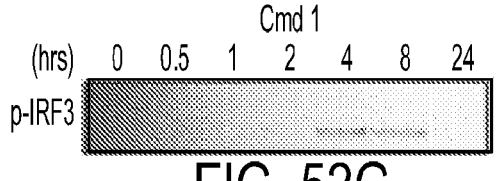
Figure 52H:
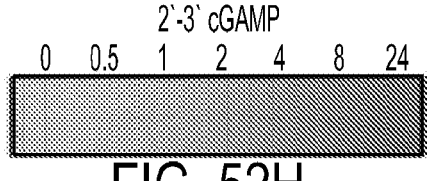
Figure 52I:
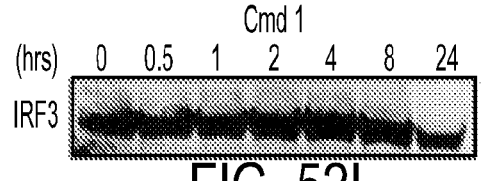
Figure 52J:
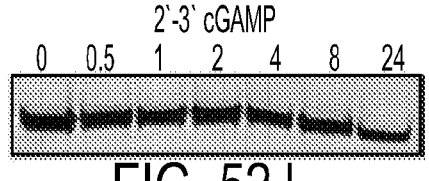
Figure 52K:
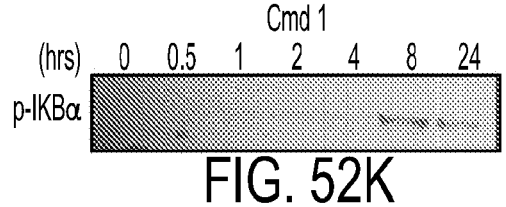
Figure 52L:
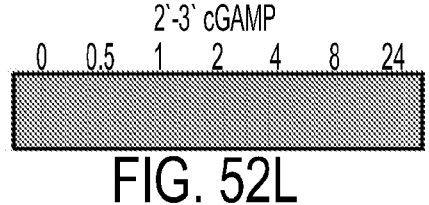
Figures 52M, 52N:
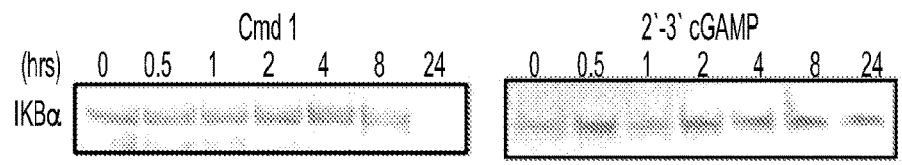
Figures 52O, 52P:
Figure 53A:
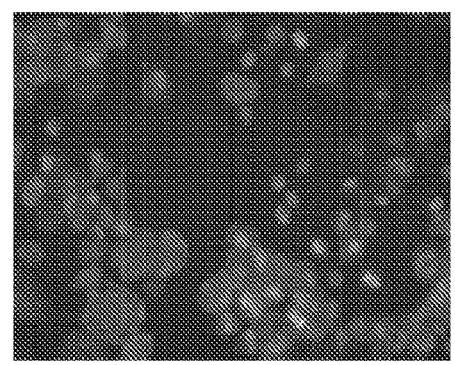
FIGS. 53A-53C show images in which THP-1 derived macrophages were treated with Cmd 1 or DMSO control for 2 hrs (FIG. 53A), 4 hrs (FIG. 53B), or 6 hrs (FIG. 53C) and analyzed for nuclear translocation. Cells were imaged on IXM (Molecular Devices) (40×) and were analyzed using ImageJ.
Figure 53B:
Figure 53C:
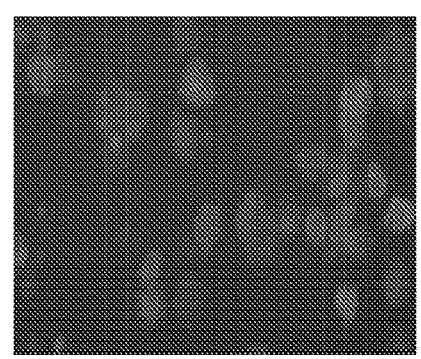
Figure 54A:
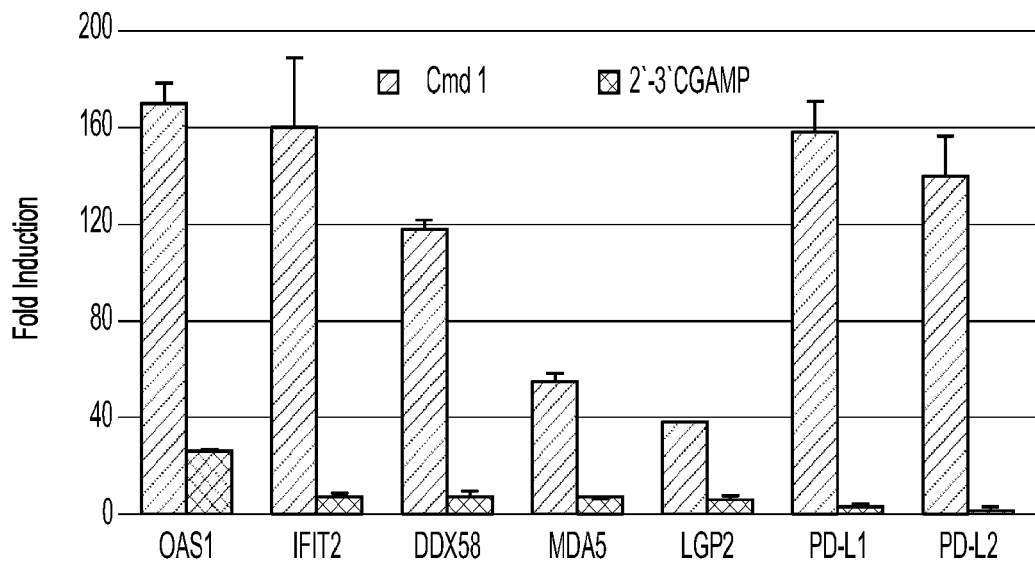
FIGS. 54A-54B show the evaluation of IFN secretion and gene expression after Cmd 1 treatment.
Figure 54B:
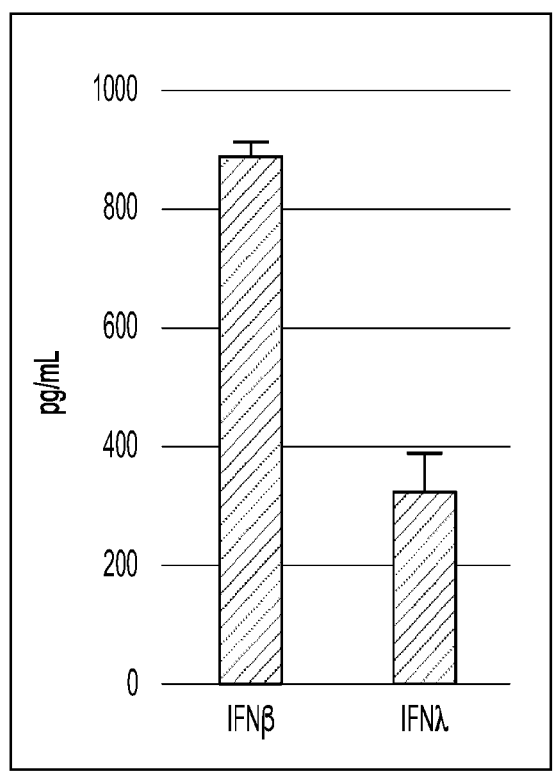
Figure 54C:
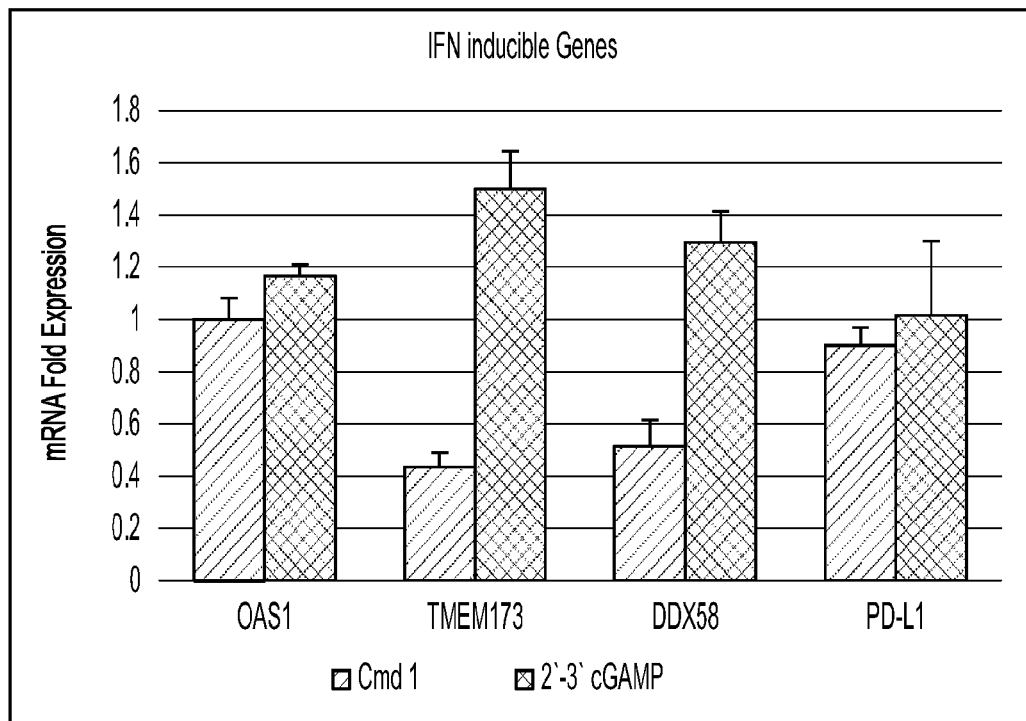
FIG. 54C-54D show the induction of apoptosis-related genes and ISGs by an exemplary compound (Cmd 1) compared with 2'3'-cGAMP in A20 mouse B cell lymphoma tumor cells.
Figure 54D:
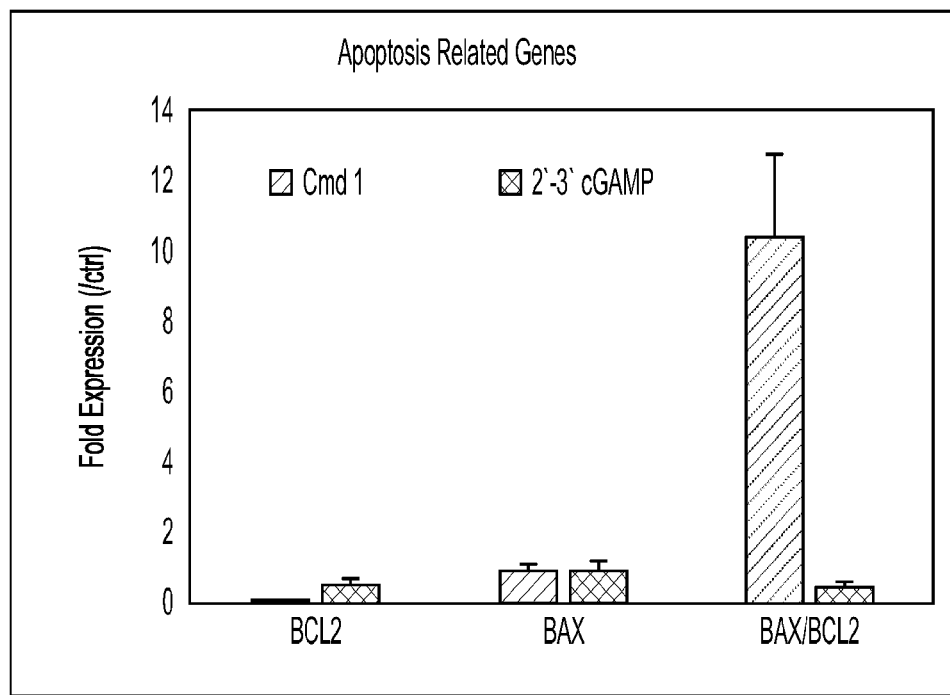
Figures 55A, 55B:
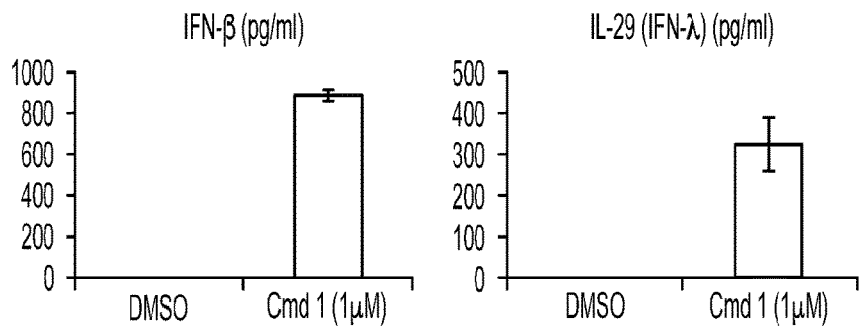
FIGS. 55A-55G are graphs showing the induction of various cytokines by Cmd 1 in wild type THP1 cells as determined by multiplex ELISA.
Figures 55C, 55D:
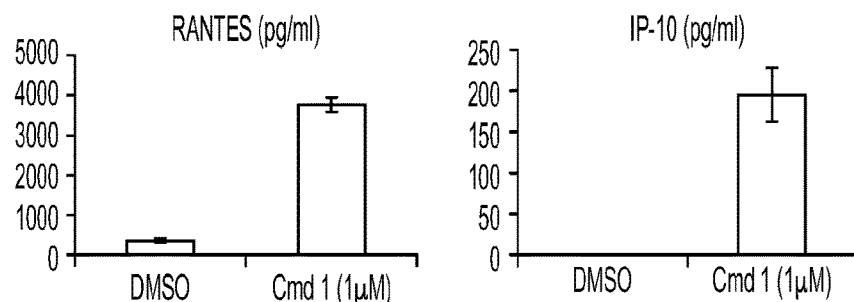
Figures 55E, 55F:
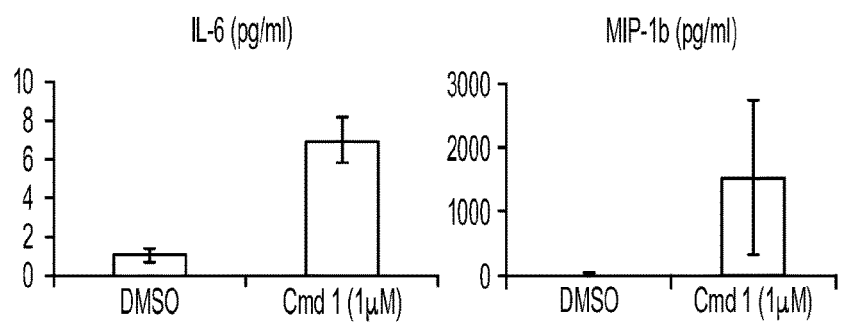
Figure 55G:
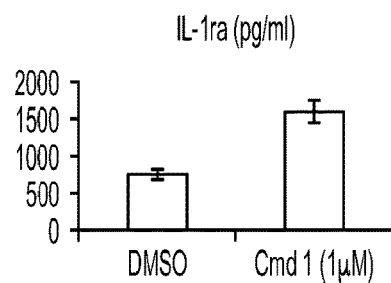
Figure 56A:
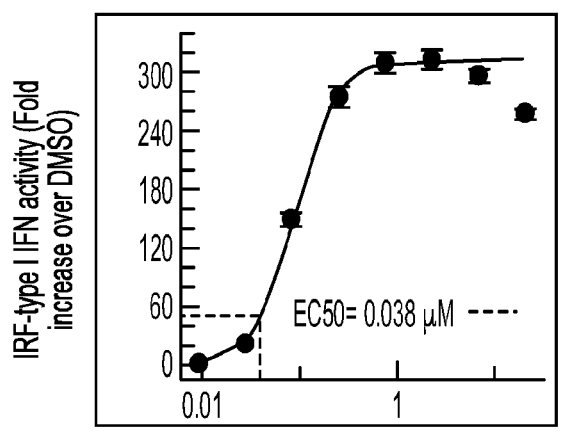
FIGS. 56A-56D are graphs showing that an exemplary compound (Cmd 1) strongly activates the IRF-type I and type III IFN response.
Figure 56B:
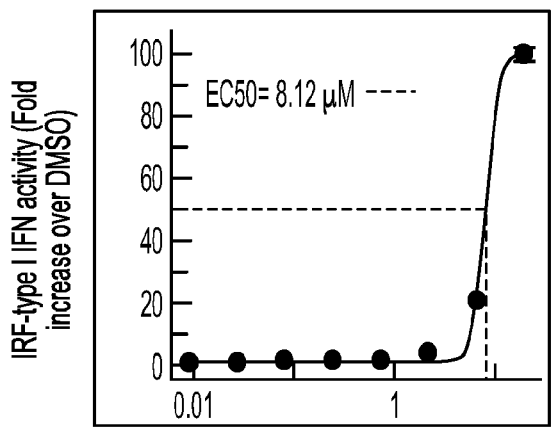
Figure 56C:
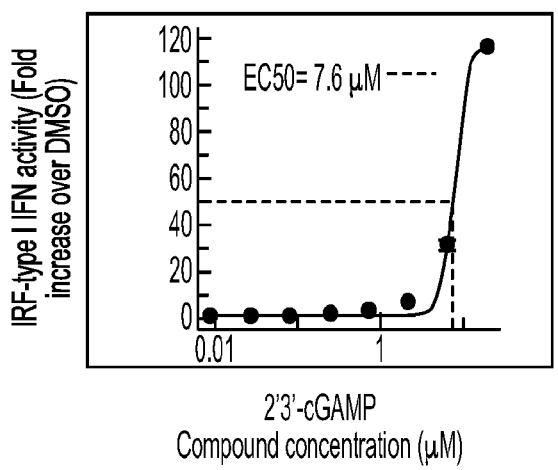
Figure 56D:
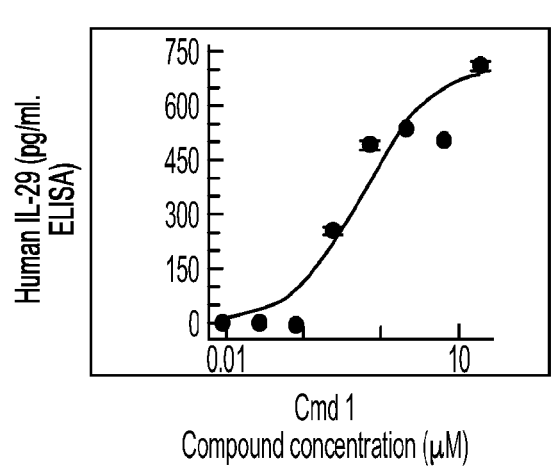
Figure 57:
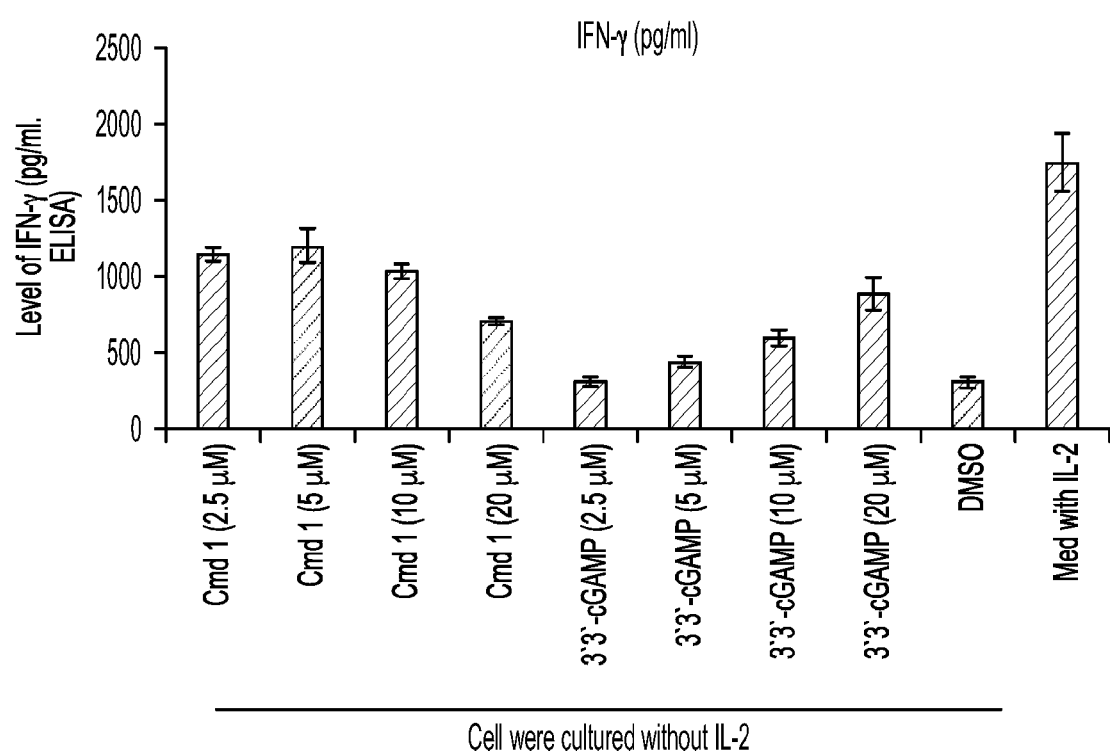
FIG. 57 is a chart showing that an exemplary compound (Cmd 1) activates human natural killer (NK) cells and induces IFN-γ production.
Figures 58A, 58B:
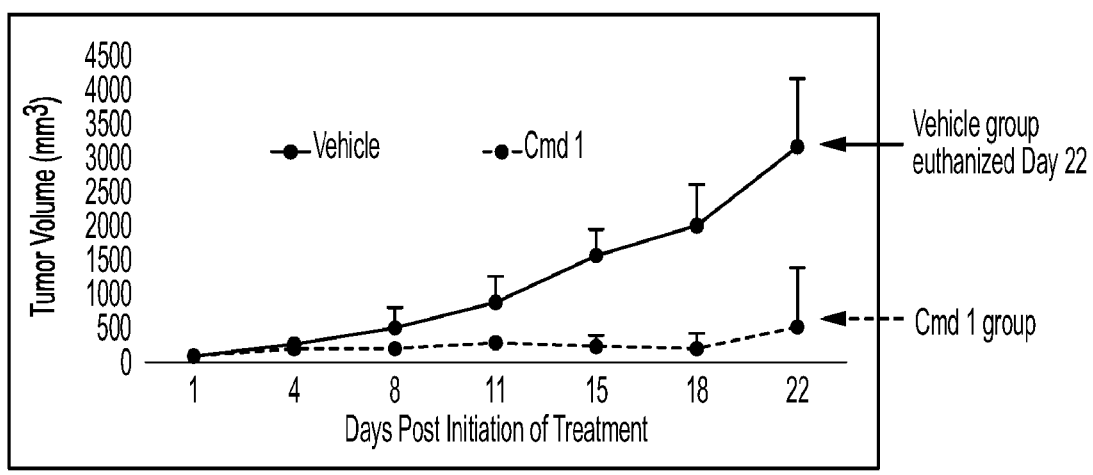
FIGS. 58A-58B show that an exemplary compound (Cmd 1) potently inhibits lymphoma tumor growth in the syngeneic A20 lymphoma model.
Figure 59A:
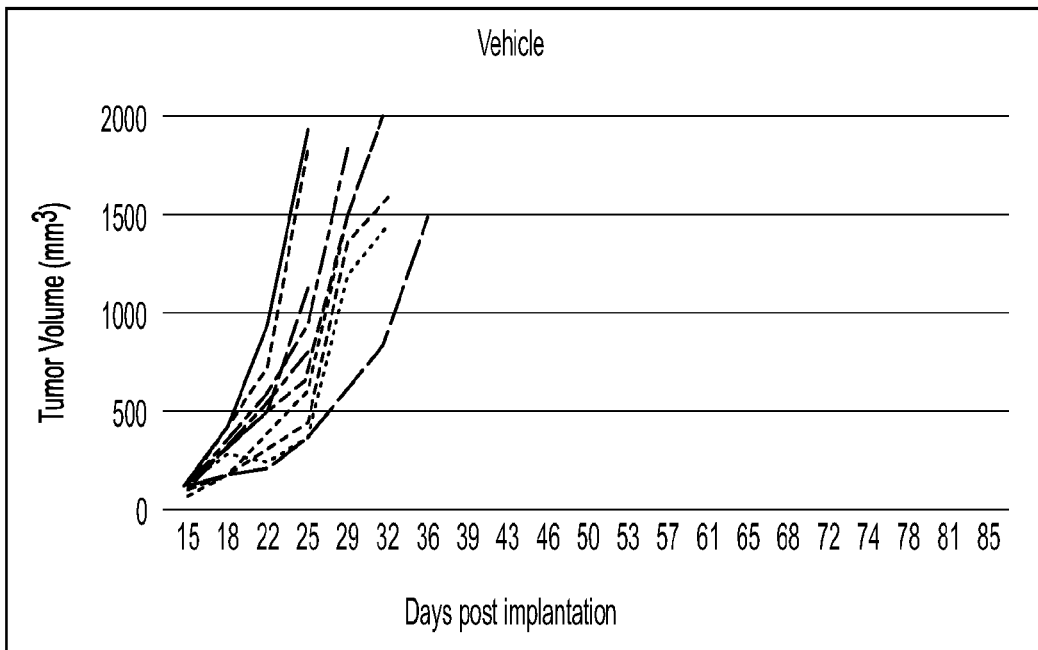
FIGS. 59A-59D are graphs showing that an exemplary compound (Cmd 1) administered in combination with cyclophosphamide results in tumor-free survival in a syngeneic A20 lymphoma mouse model.
Figure 59B:
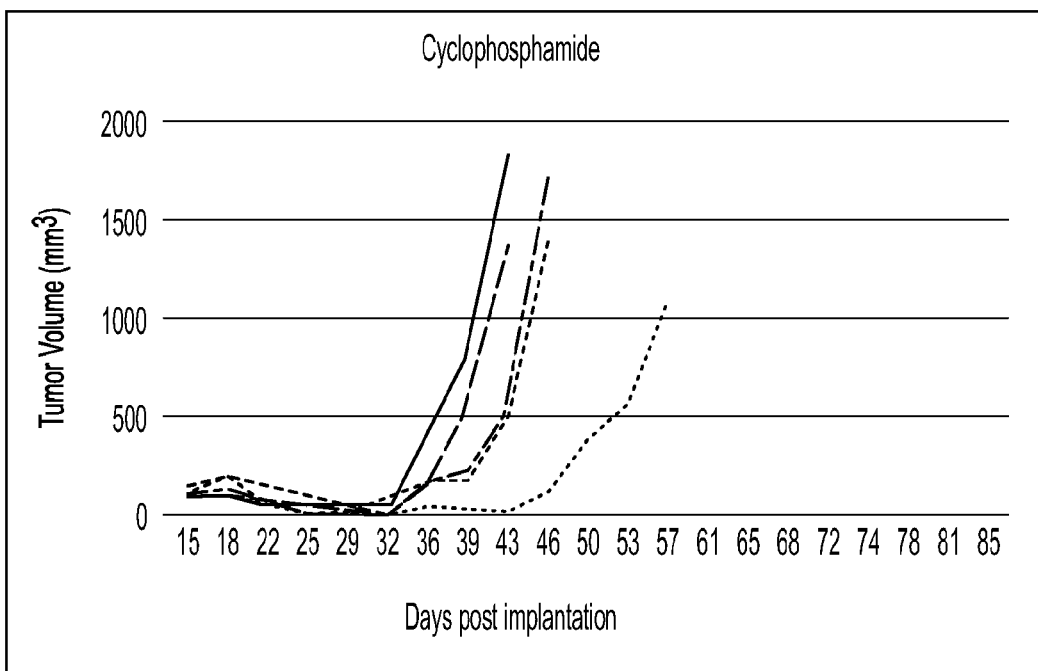
Figure 59C:
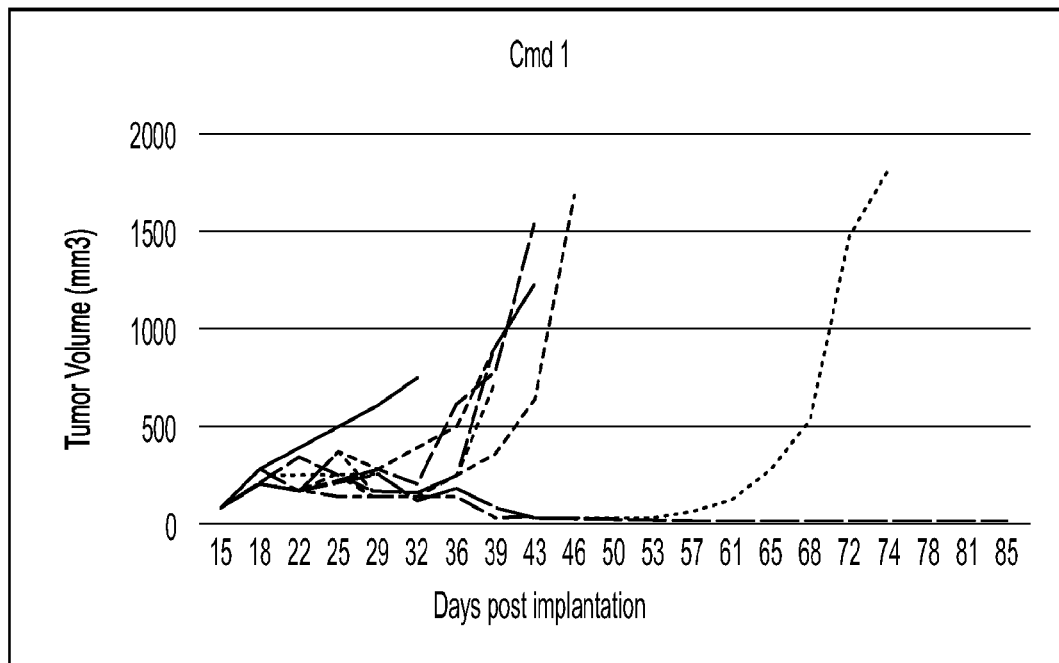
Figure 59D:
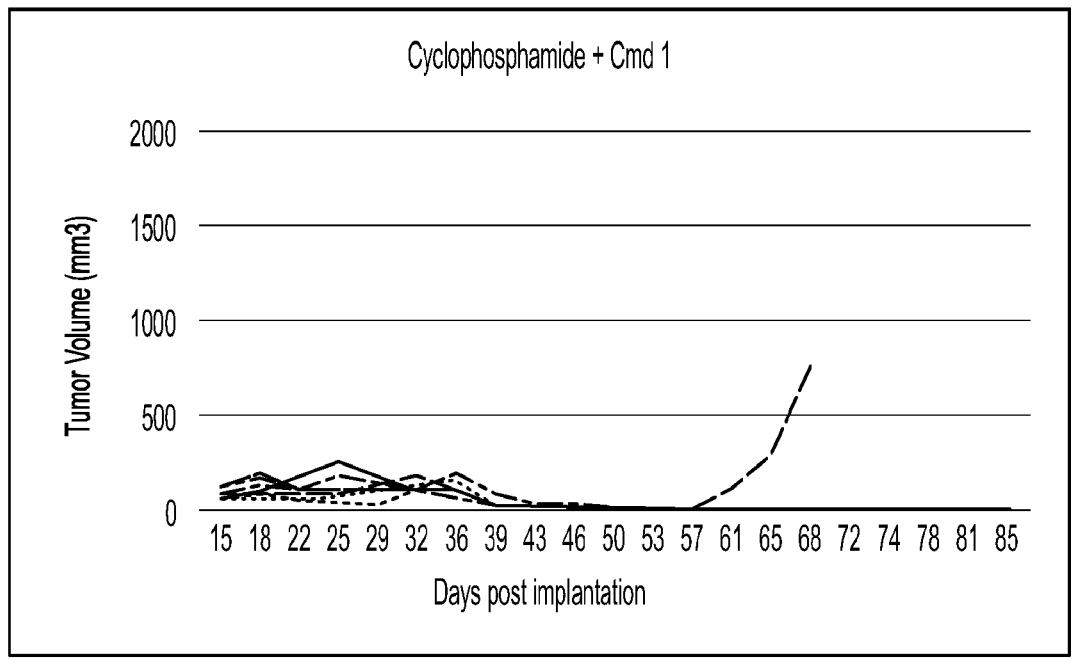
Figures 60A, 60B:
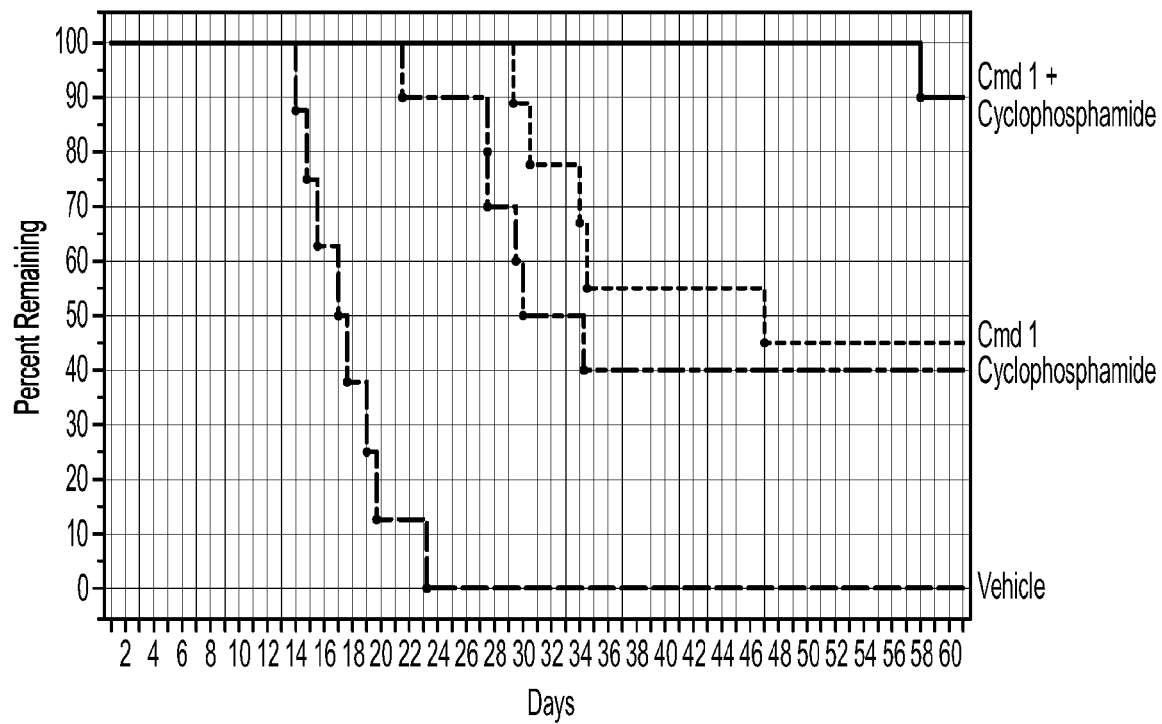
FIGS. 60A-60B show that monotherapy of Cmd 1 and combination therapy of Cmd 1 plus cyclophosphamide significantly improve the survival rate of mice in the syngeneic A20 lymphoma mouse model. Note that in FIG. 60B, VS 1 refers to Cmd 1.
Figures 62A, 62B:
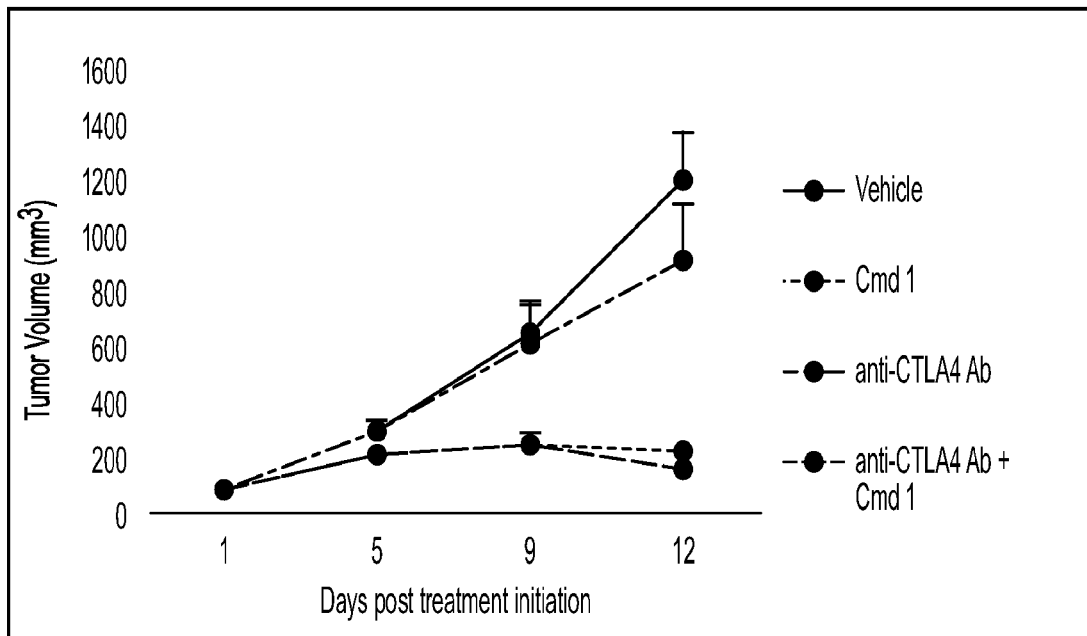
FIGS. 62A-62B show that an exemplary compound (Cmd 1) is highly effective in inhibiting tumor growth in the syngeneic CT26 colon cancer model.
Figures 63A, 63B:
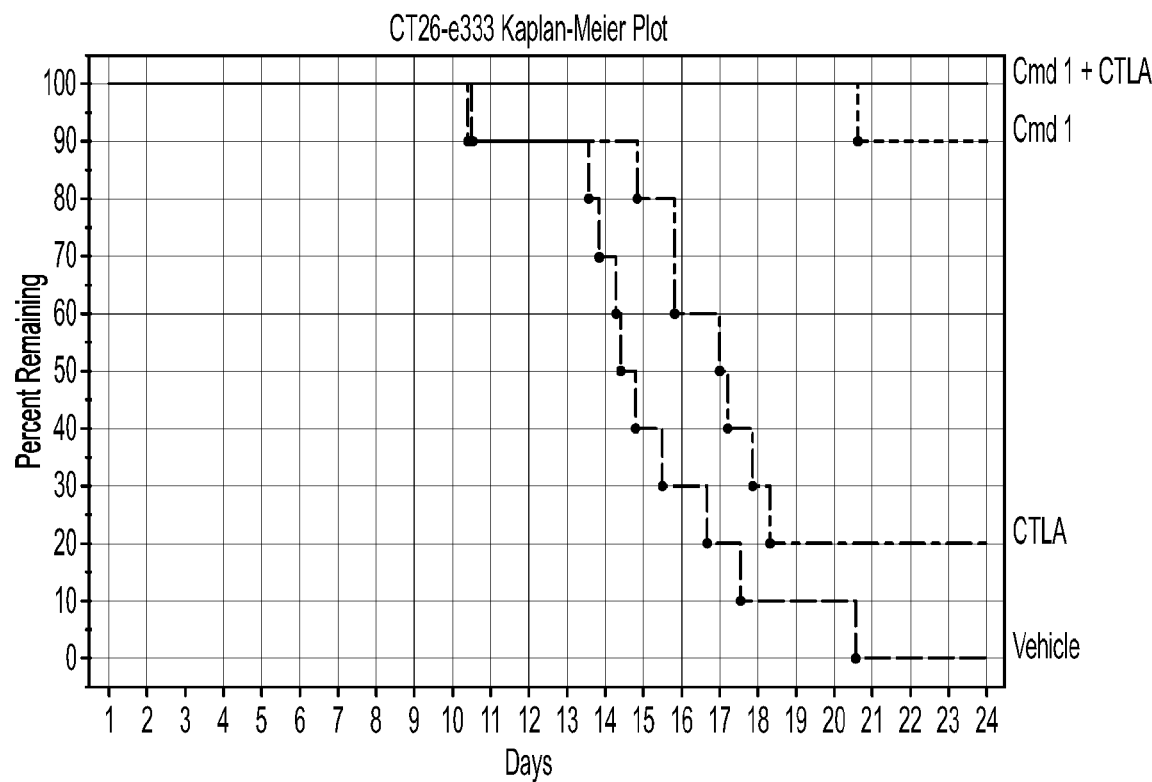
FIGS. 63A-63B show that monotherapy of Cmd 1 and combination therapy of Cmd 1 plus an anti-CTLA4 antibody significantly improve the survival rate of mice in the syngeneic CT26 colon cancer mouse model. Note that in FIG. 63B, VS 1 refers to Cmd 1.
Figure 64:
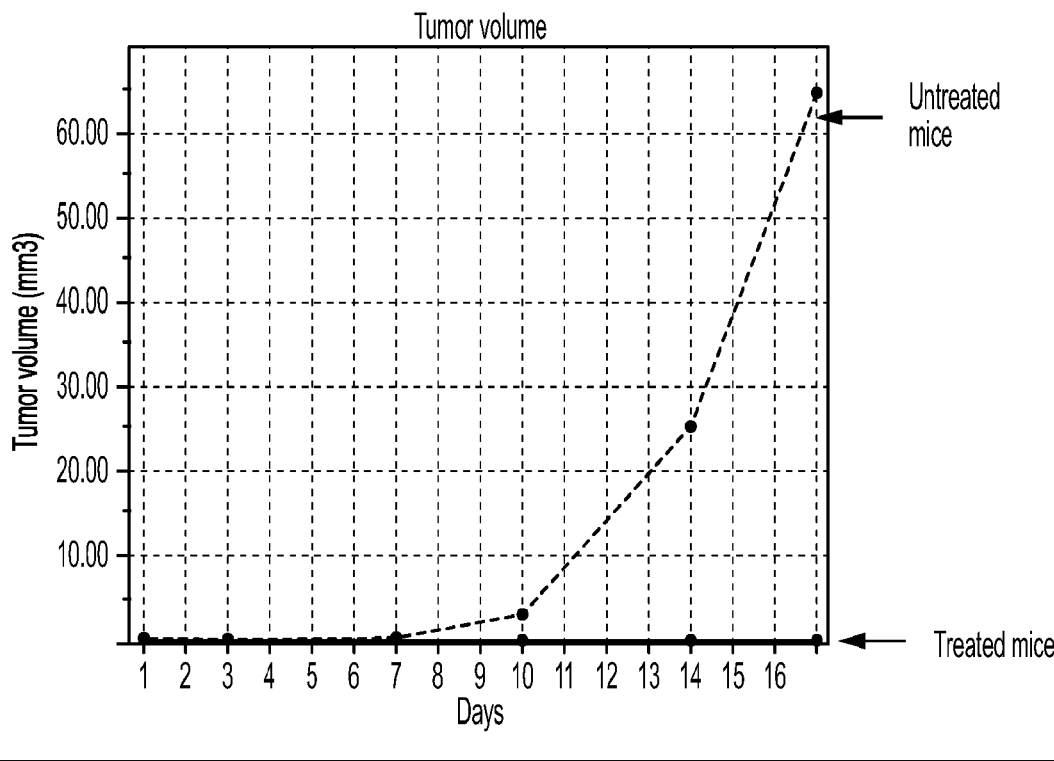
FIG. 64 shows that mice that are found to be tumor-free following treatment with either Cmd 1 or Cmd1+cyclocphosphamide experience no tumor growth compared with control upon re-challenging the mice with tumor cells (A20 lymphoma tumor challenge study).
Figure 65A:
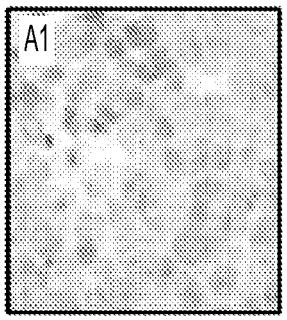
FIGS. 65A-65H are images showing immunohistochemistry data using an anti-CD38 antibody on tumor tissue collected from mice treated with vehicle (FIGS. 65A-65D) or Cmd 1 (FIGS. 65E-65H) in the syngeneic A20 lymphoma model. The images show that Cmd 1 induces migration of CD8 T into the tumor site.
Figure 65B:
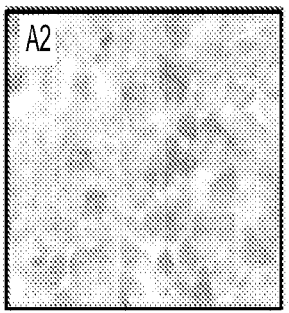
Figure 65C:
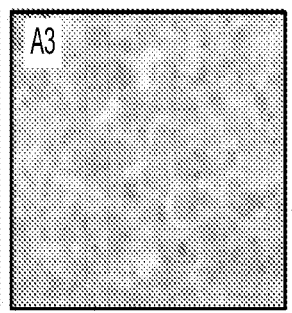
Figure 65D:
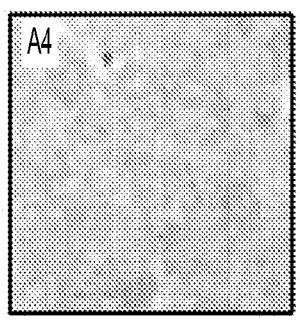
Figure 65E:
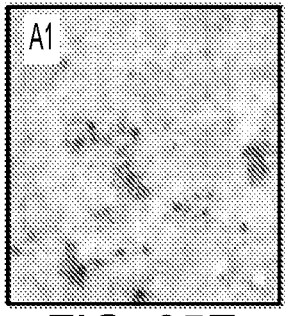
Figure 65F:
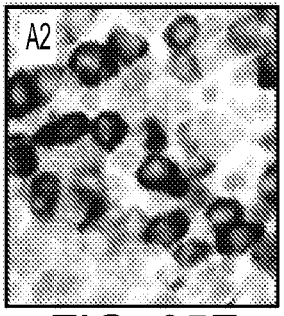
Figure 65G:
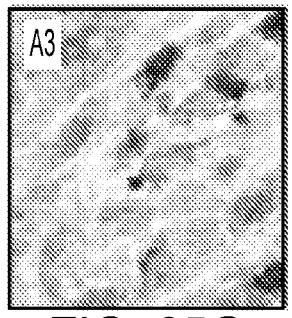
Figure 65H:
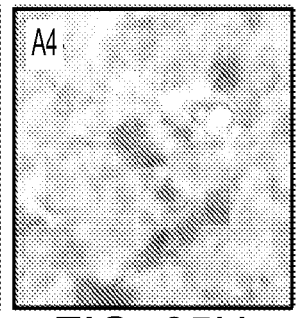
Figures 66A, 66B, 66C, 66D:
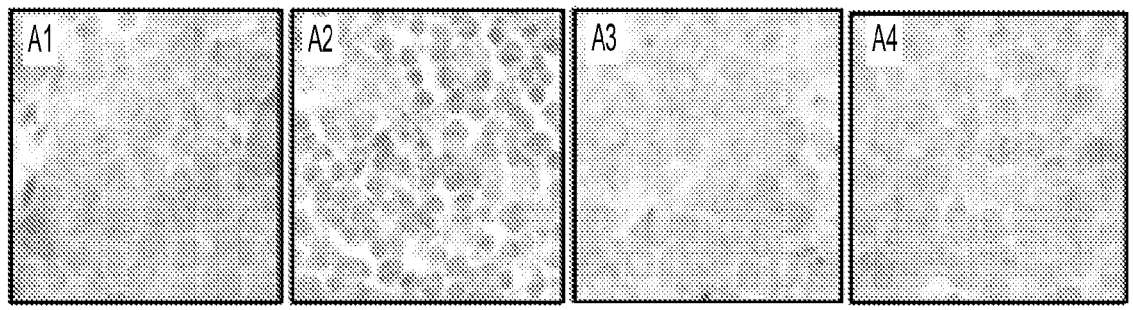
FIGS. 66A-66H are images showing immunohistochemistry data using an anti-granzyme B antibody on tumor tissue collected from mice treated with vehicle (FIGS. 66A-66D) or Cmd 1 (FIGS. 66E-66H) in the syngeneic A20 lymphoma model. The images show that Cmd 1 induces migration of NK cells into the tumor site.
Figures 66E, 66F, 66G, 66H:
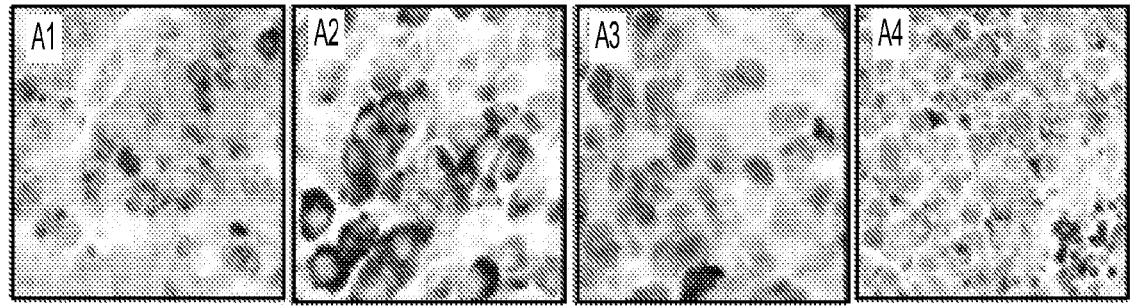
Figures 67A, 67B, 67C, 67D:
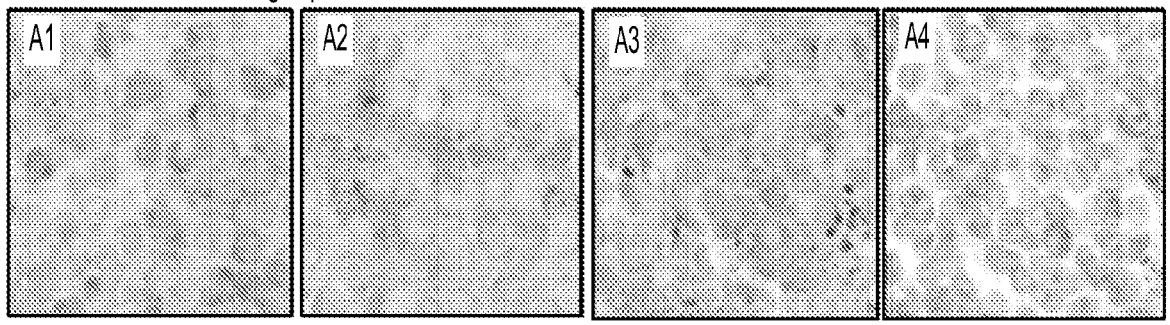
FIGS. 67A-67H are images showing immunohistochemistry data using an anti-F4/80 antibody on tumor tissue collected from mice treated with vehicle (FIGS. 67A-67D) or Cmd 1 (FIGS. 67E-67H) in the syngeneic A20 lymphoma model. The images show that Cmd 1 induces migration of macrophages into the tumor site.
Figures 67E, 67F, 67G, 67H:
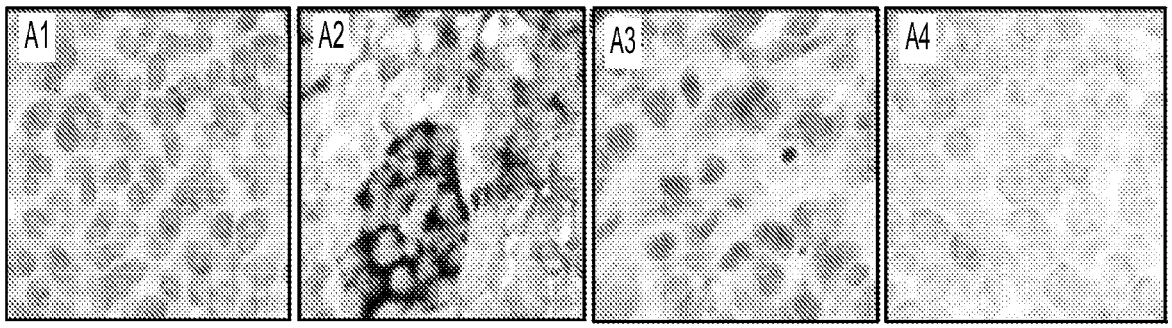
Figure 69A:
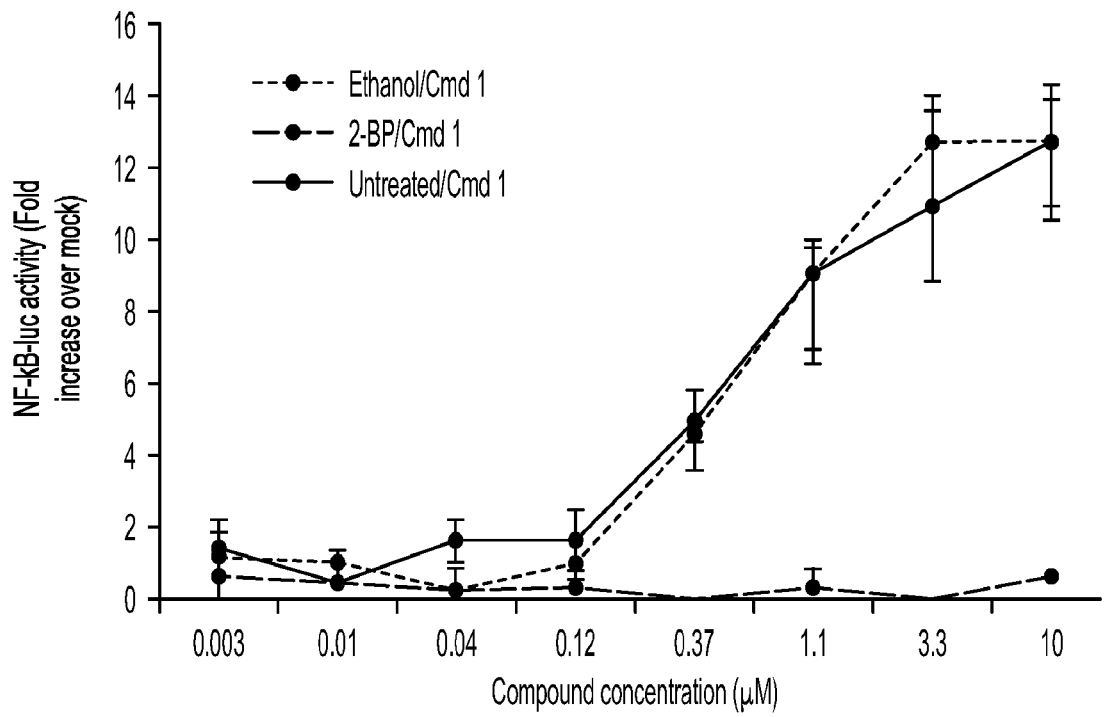
FIGS. 69A-69D show that palmitoylation of STING is involved in Cmd 1-induced activation of NF-κB (FIGS. 69A-69B) and the IRF-type I interferon response in THP1 cells (FIGS. 69C-69D).
Figure 69B:
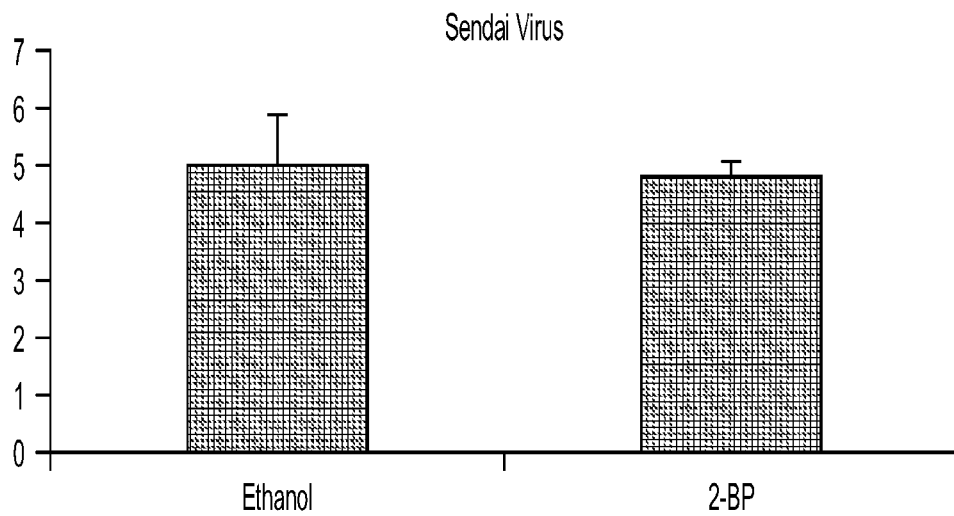
Figure 69C:
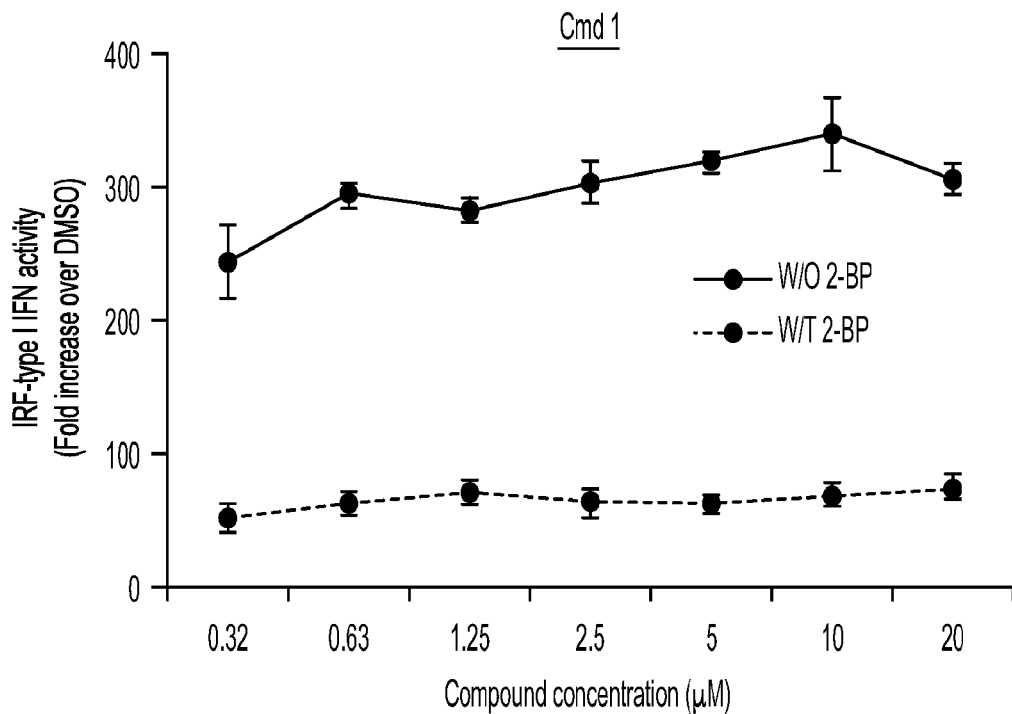
Figure 69D:
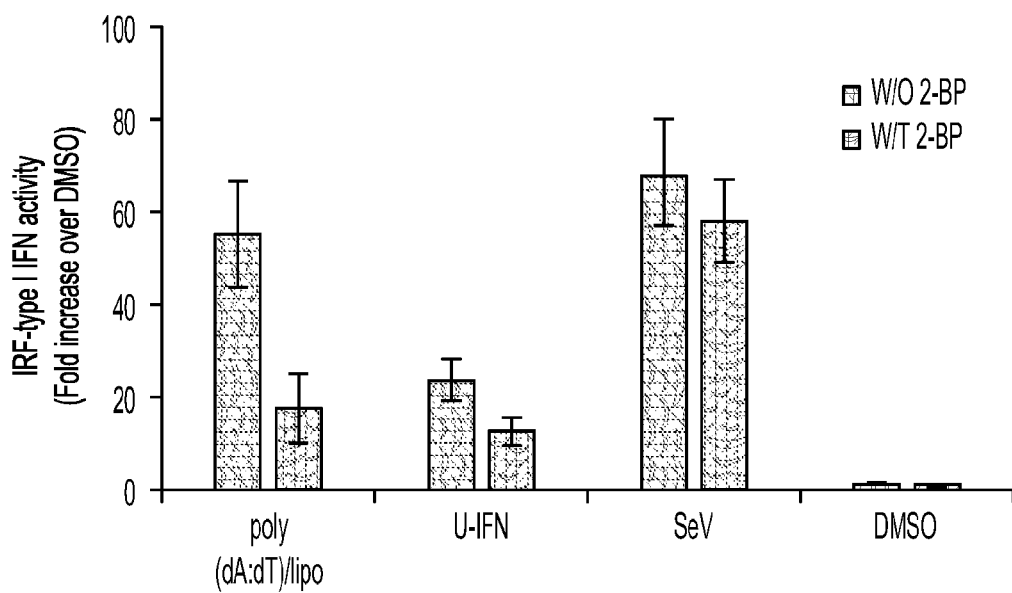

Example 10. FIG. 12 Shows that Cmd 1 Inhibits Tumor Cell Growth

Tumor cells in 96-well plate were treated once daily with Cmd 1 (no lipofectamine) or recombinant IFN (U-IFN) for 3 days. Cells were fixed with 1% paraformaldehyde and stained with DAPI. Cells were automatically imaged on ImageXpress and total number of survival cells were analyzed using MetaXpress software. Results are shown as total number of cells per group or % reduction calculated by normalizing to DMSO treated cells.

Example 11. FIG. 21 Shows that Cmd 4 has Enhanced Activity in Acute Monocytic Leukemia Cell Line (THP1) Compared to Primary Cells PBMCs Gene expression analysis in THP1 and PBMCs: THP1 cells and PBMCs grown in complete media were treated with 5 uM of either Cmd 4 or 2',3'-cGAMP or DMSO control with Lipofectamine LTX. After incubation for 20 h, RNA was extracted and gene expression of different Interferon Stimulated Genes (ISGs) and various Pattern Recognition Receptors (PRRs) was evaluated by real time PCR. Fold Induction was calculated by ΔΔct method.

Example 12. Efficacy of Exemplary Compounds Via Intraperitoneal Administration in a Breast Carcinoma Model The efficacy of intraperitoneal administration of Cmd 1 was investigated in the 4T1.luc2 orthotopic murine breast carcinoma model. Thirty female BALB/c mice between 7-10 weeks old were randomized into four treatment groups based on Day 1 body weight, and the treatment was carried out according to the regimen outlined in Table 4 below. Cmd 1 was dissolved in saline and administered at 10 mL/kg (0.200 mL/20 g mouse), with a cell injection volume of 0.05 mL/mouse.

TABLE 4

IP administration in breast carcinoma model: study regimen

| | | | Regimen 1 | | |
|---|---|---|---|---|---|
| Gr. | N | Agent | mg/kg | Route | Schedule |
| 1 | 10 | Vehicle | — | ip | days 5, 7, 9, 11, 14, 18 |
| 2 | 10 | Cmd 1 | 10 | ip | days 5, 7, 9, 11, 14, 18 |
| 3 | 5 | Vehicle | — | ip | days 5, 7, 9, 11, 14, 18 |
| 4 | 5 | Cmd 1 | 10 | ip | days 5, 7, 9, 11, 14, 18 |

Figure 70:
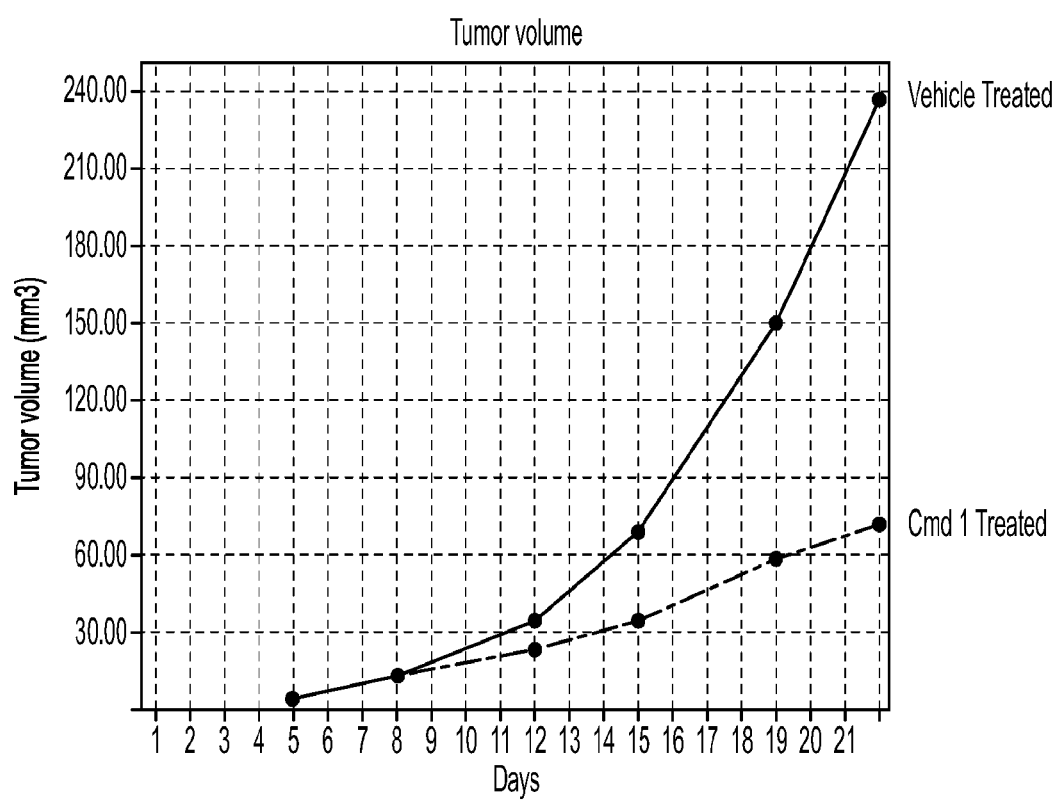
FIG. 70 is a graph showing that intraperitoneal administration of Cmd 1 causes significant decline in tumor volume in the syngeneic mouse metastatic breast cancer model as described in Example 12.
Figure 71:
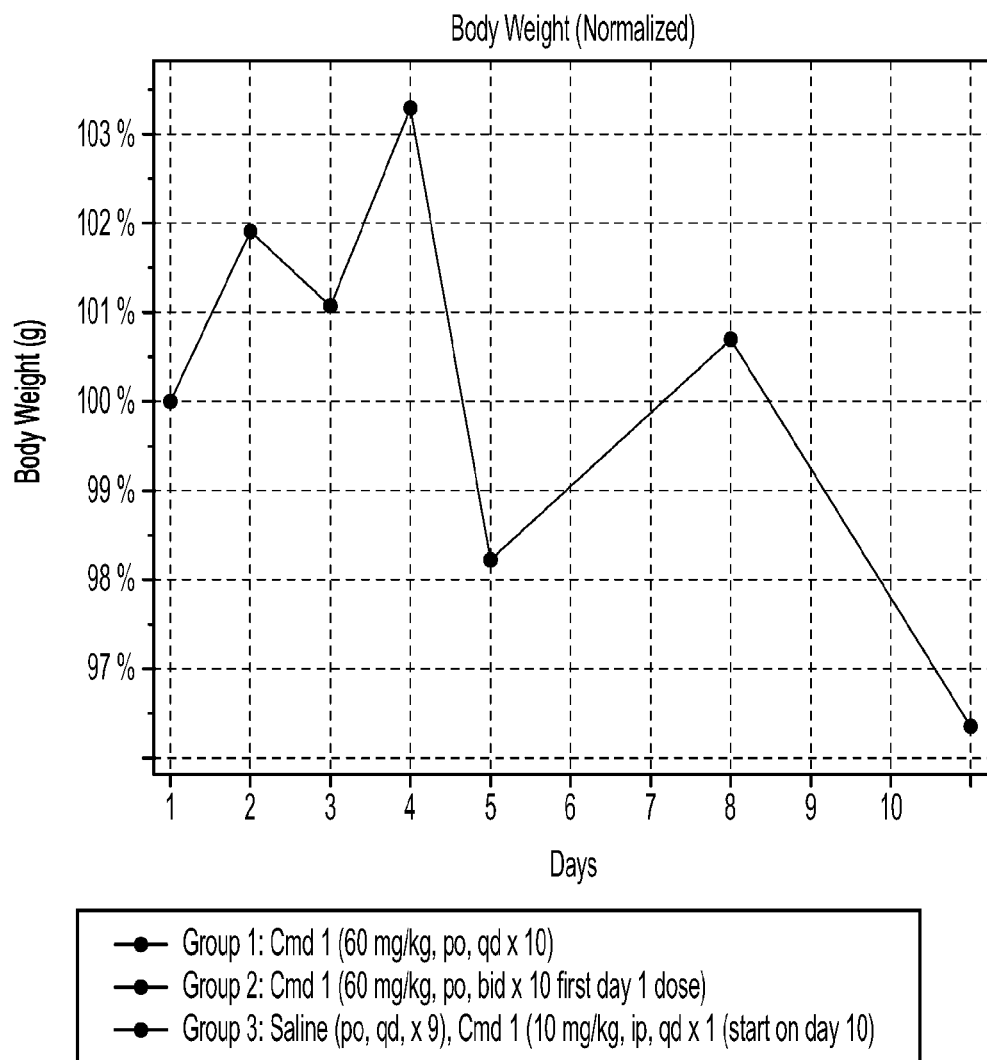
FIG. 71 is a graph showing the results of the oral dosage study, indicating that all participating subjects are within acceptable body weight ranges.
Figure 72:
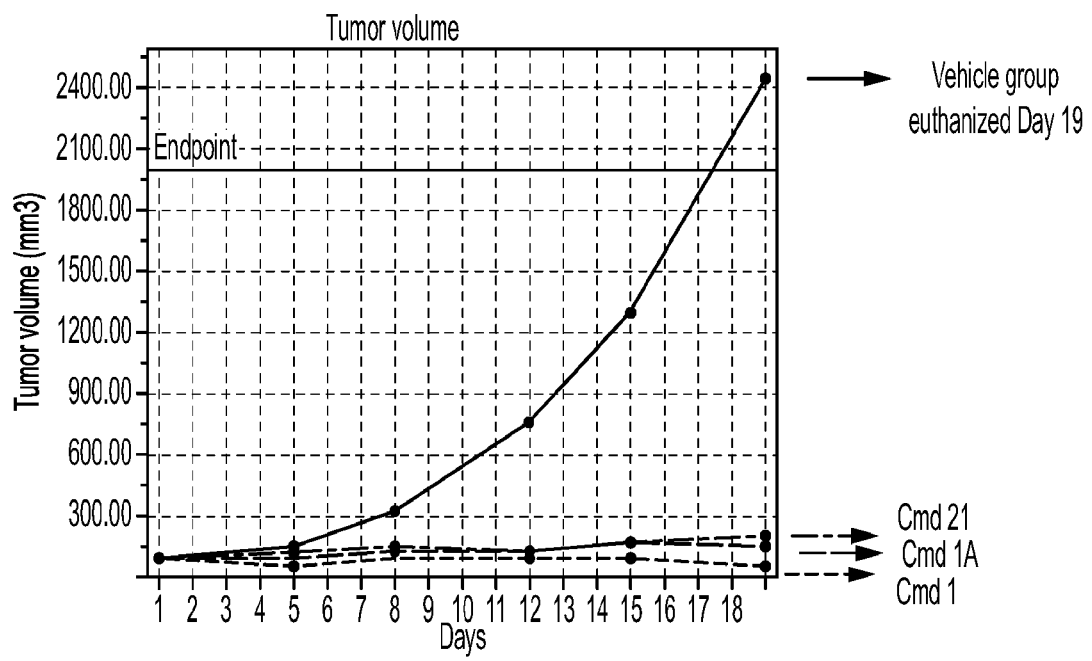
FIG. 72 is a graph showing the anti-tumor activity of Cmd 1, Cmd X, and Cmd 21 in the syngeneic mouse A20 lymphoma model. All compounds showed considerable tumor growth inhibition compared with the vehicle.
Figure 73A:
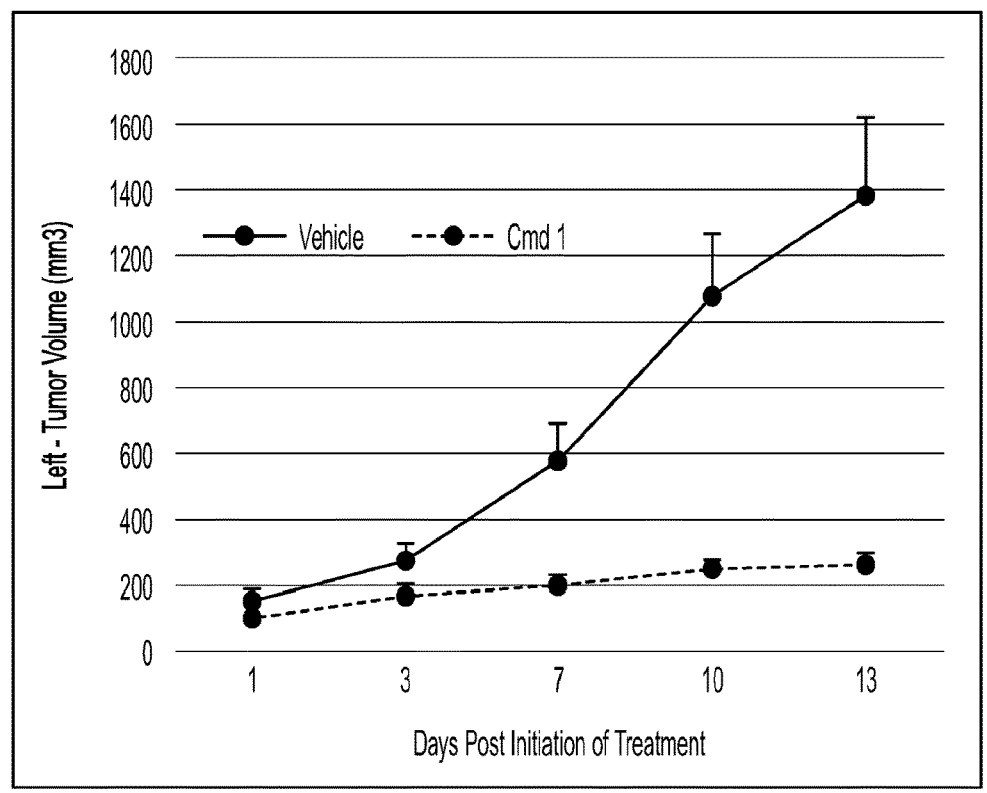
FIGS. 73A-73B are graphs showing the abscopal antitumoral activity of Cmd 1 when administered intratumorally in CT26 colon cancer model.
Figure 73B:
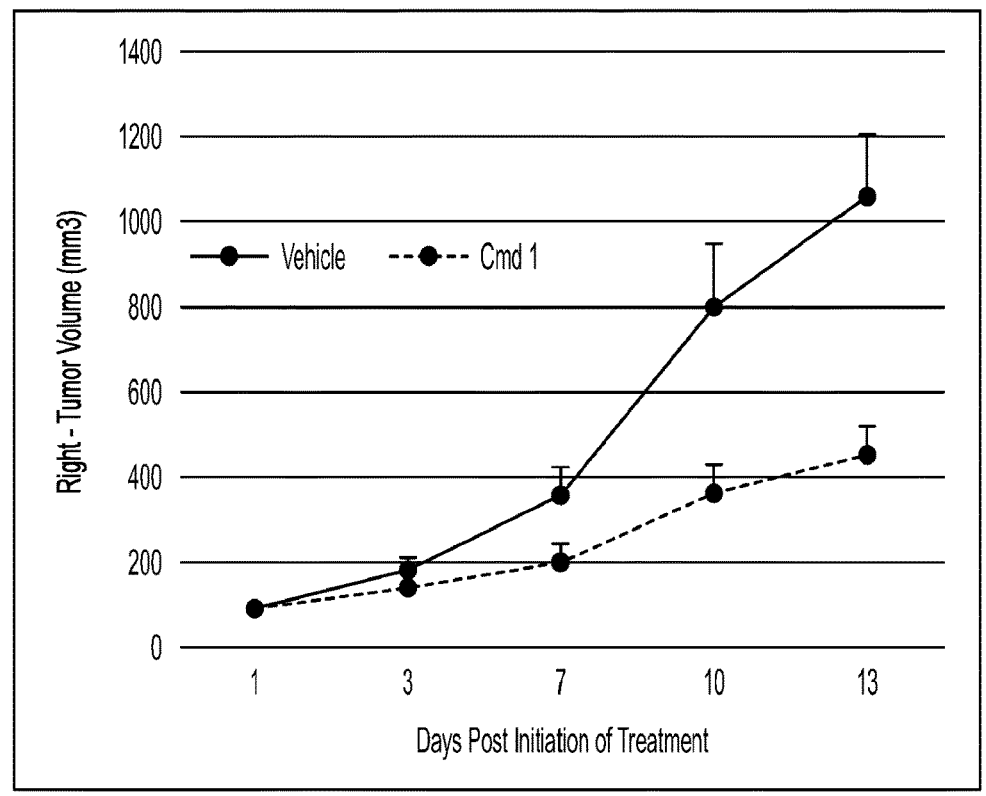
Figure 74:
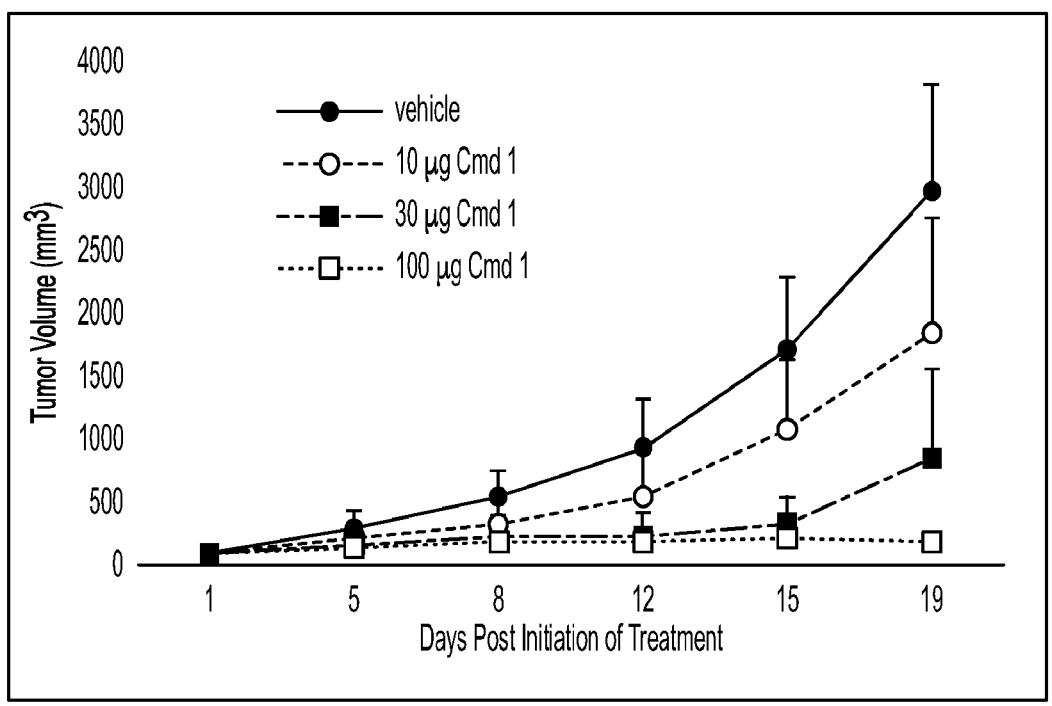
FIG. 74 is a graph showing effects on tumor growth at a dose of vehicle and 10 μg, 30 μg, and 100 μg of Cmd 1 in a CT26 colon cancer model. Cmd 1 showed considerable tumor growth inhibition at all three doses compared with the vehicle.
Figure 75:
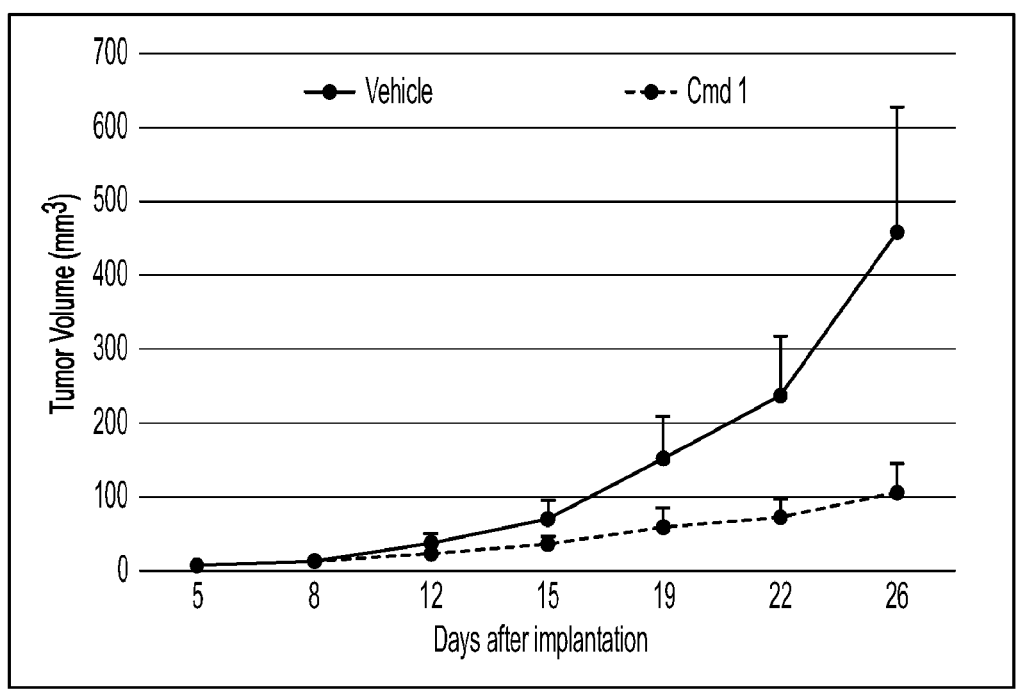
FIG. 75 is a graph showing effects on tumor growth of Cmd 1 and vehicle in a 4T1 breast cancer model. Cmd 1 showed considerable tumor growth inhibition compared with the vehicle.
Figure 76A:
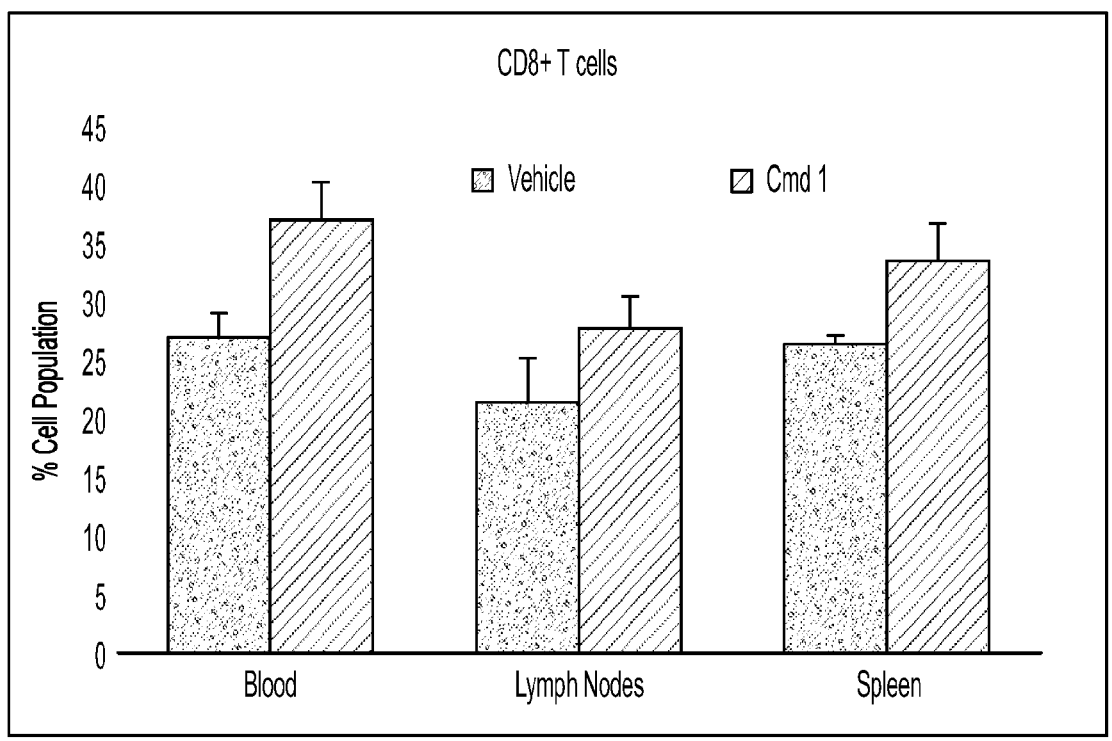
FIGS. 76A-76D are bar graphs percent induction of CD8+ T cells, CD4+ T cells, and MDSCs by Cmd 1 in spleen, lymph nodes and blood on day 19 measured by flow cytometry. Cmd 1 showed increase in CD8+ T cells, CD4+ T cells, and MDSCs when compared with the vehicle.
Figure 76B:
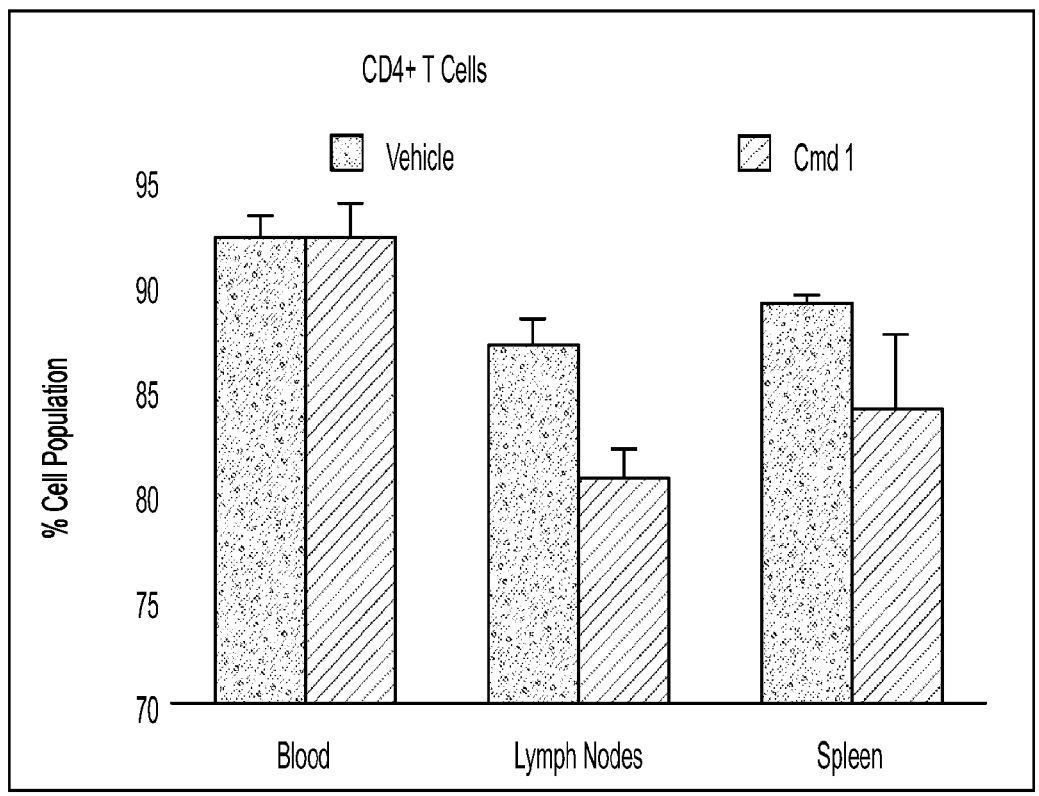
Figure 76C:
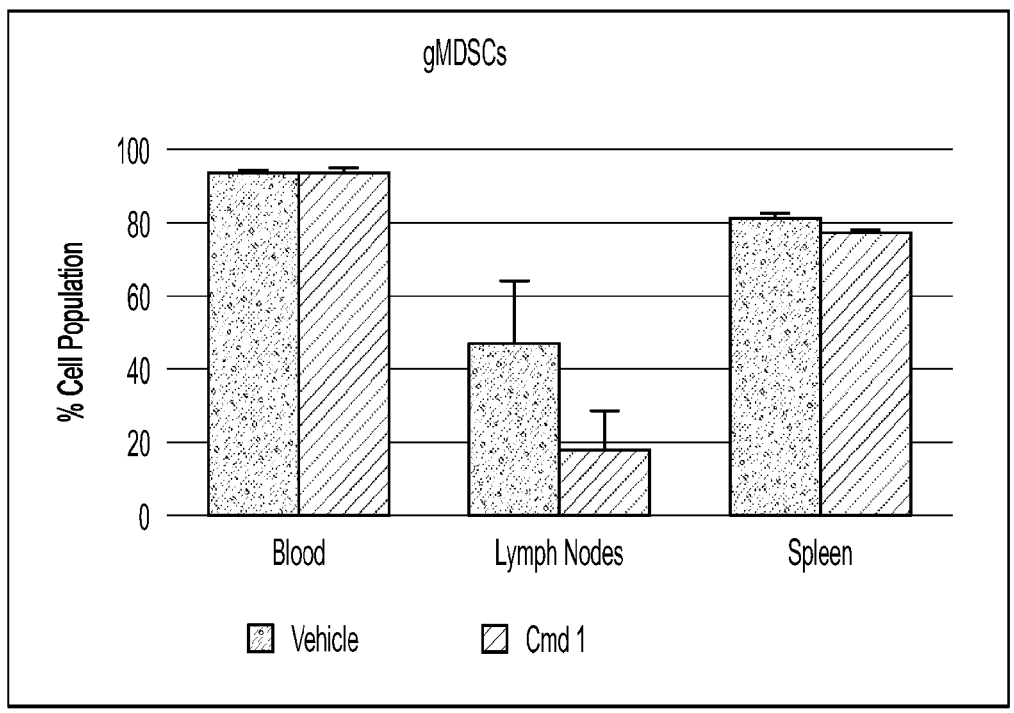
Figure 76D:
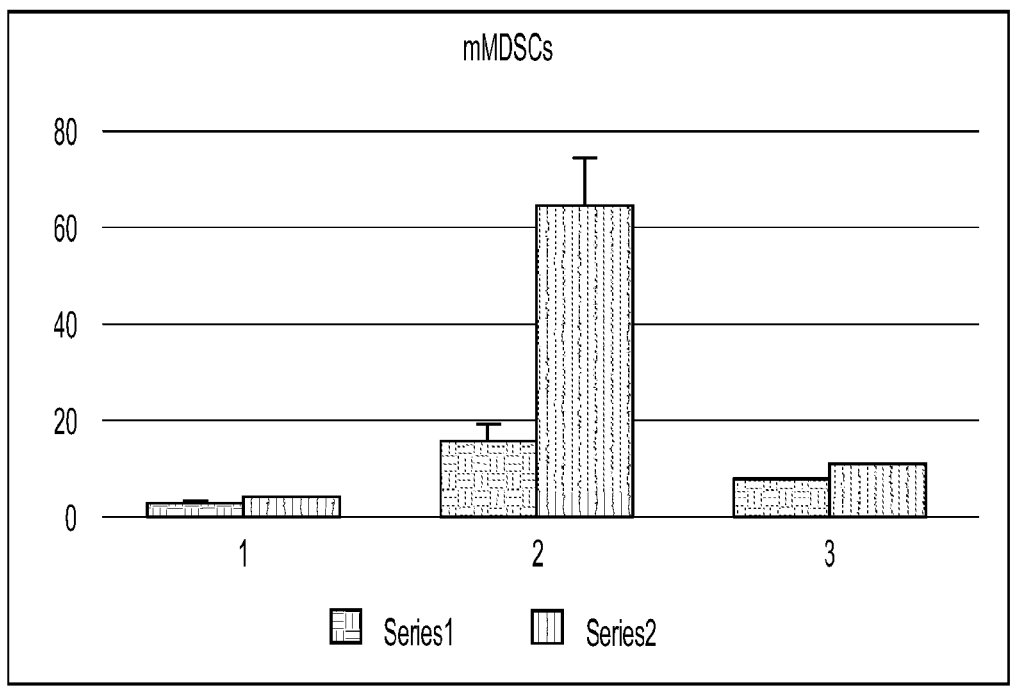
Figure 77:
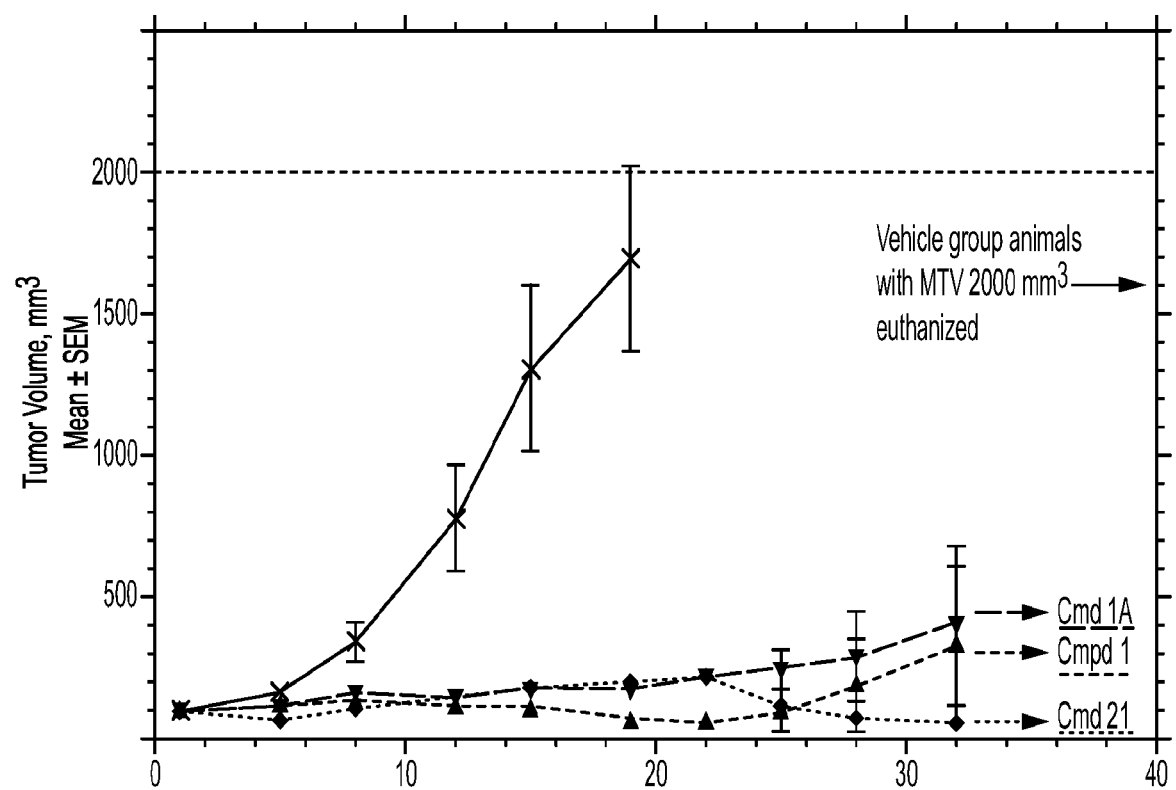
FIG. 77 is a graph showing anti-tumor activity of vehicle Cmd 1, Cmd 1A (isomer of Cmd 1), and Cmd 21. The graph shows that Cmd 1, Cmd 1A and Cmd 21 inhibit mouse A20 B cell lymphoma tumor cells.
Figure 78:
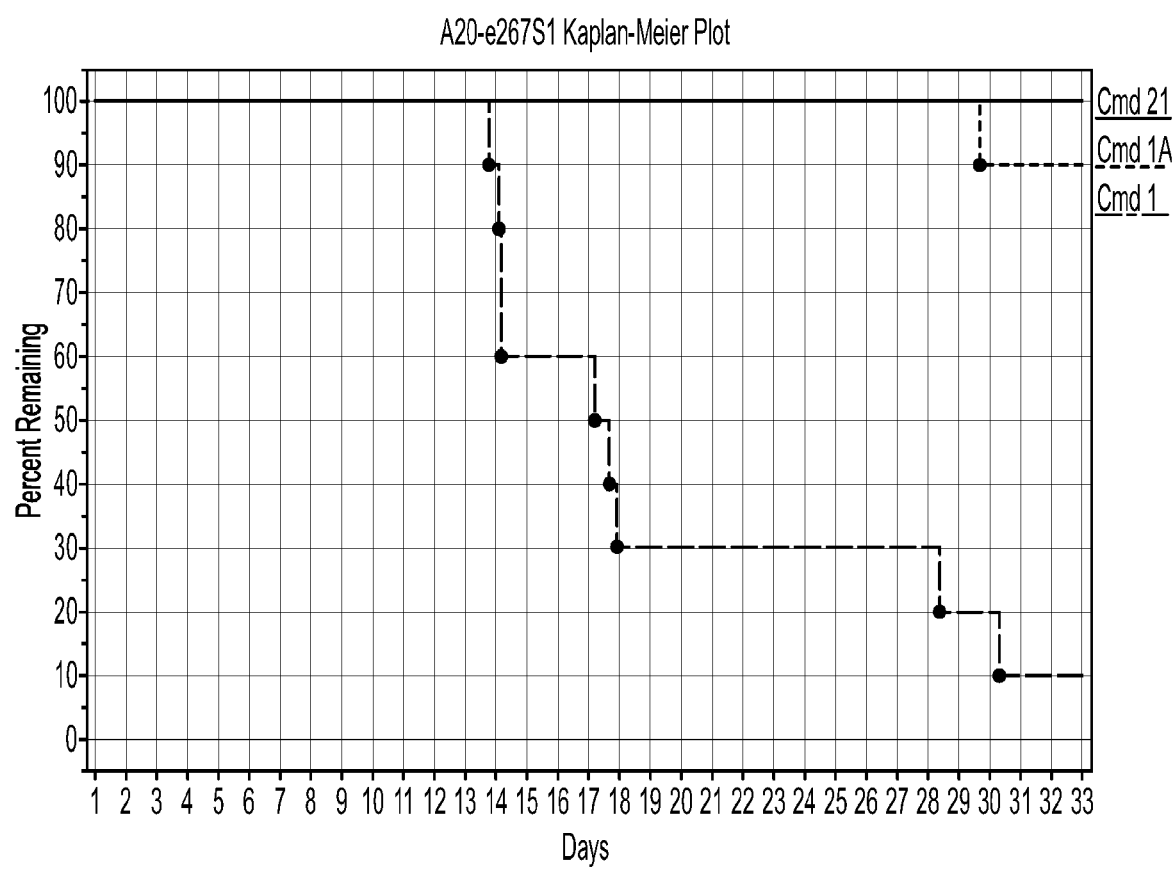
FIG. 78 is a Kaplan-Meier plot showing that Cmd 1, Cmd 1A, and Cmd 21 significantly improve the survival rate of mice in the A26 lymphoma model.
Figure 79:
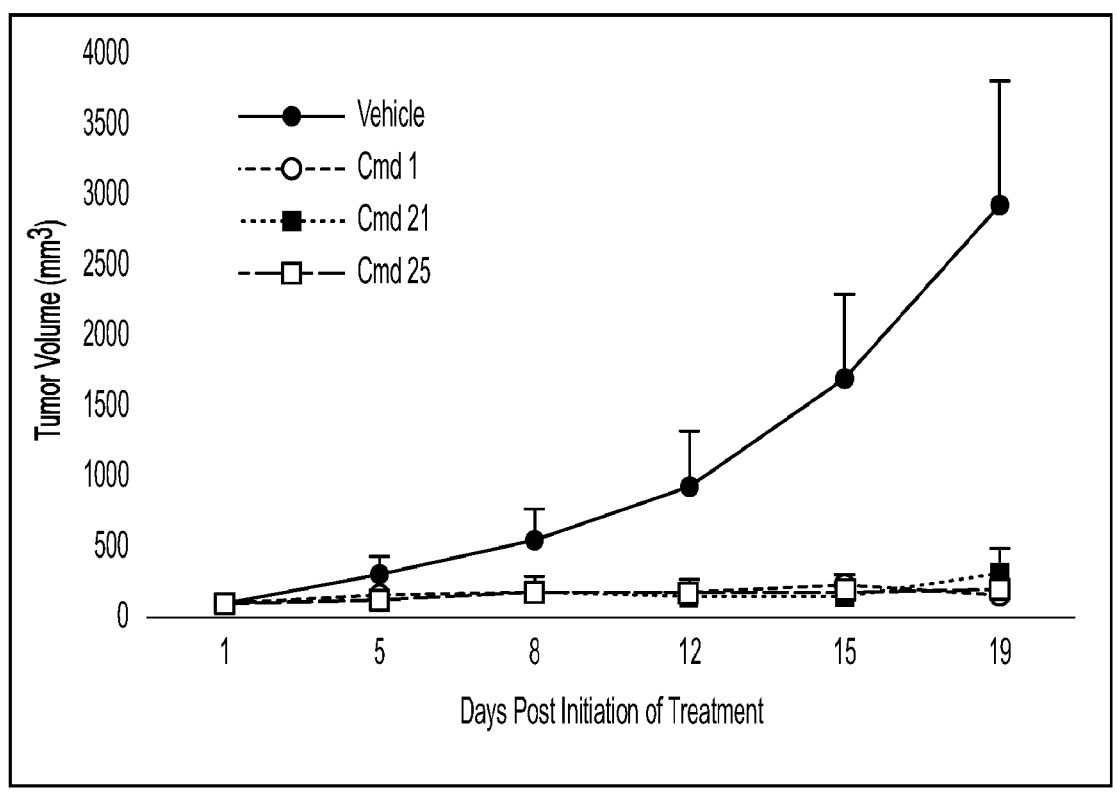
FIG. 79 is a graph showing effects on tumor growth of intratumoral administration of Cmd 1, Cmd 21, and Cmd 25 in a CT26 colorectal carcinoma model. Cmd 1, Cmd 21, and Cmd 25 showed considerable tumor growth inhibition compared with the vehicle.
Figure 80:
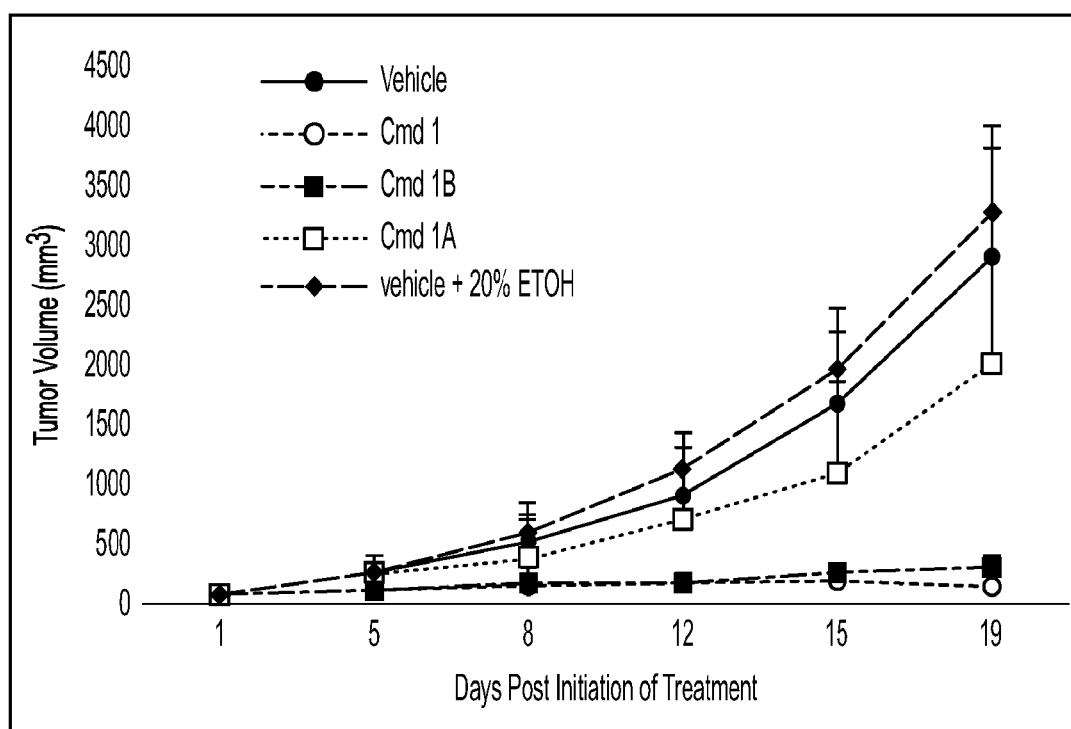
FIG. 80 is a graph showing effects on tumor growth of intratumoral administration of vehicle, vehicle and Ethanol. Cmd 1, Cmd 1A, and Cmd 1A in a CT26 colorectal carcinoma model. Cmd 1, Cmd 21, and Cmd 25 showed considerable tumor growth inhibition compared with the vehicle.
Figure 81A:
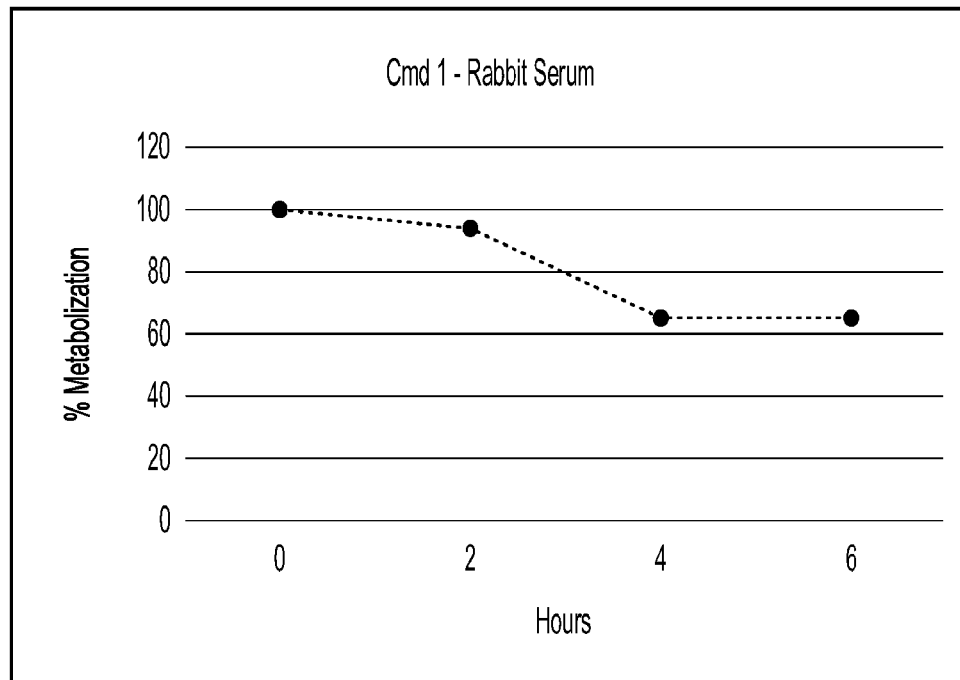
FIG. 81 is a graph showing the stability of Cmd 1 in Rabbit serum (FIG. 81A) and in Human microsomes (FIG. 81B).
Figure 81B:
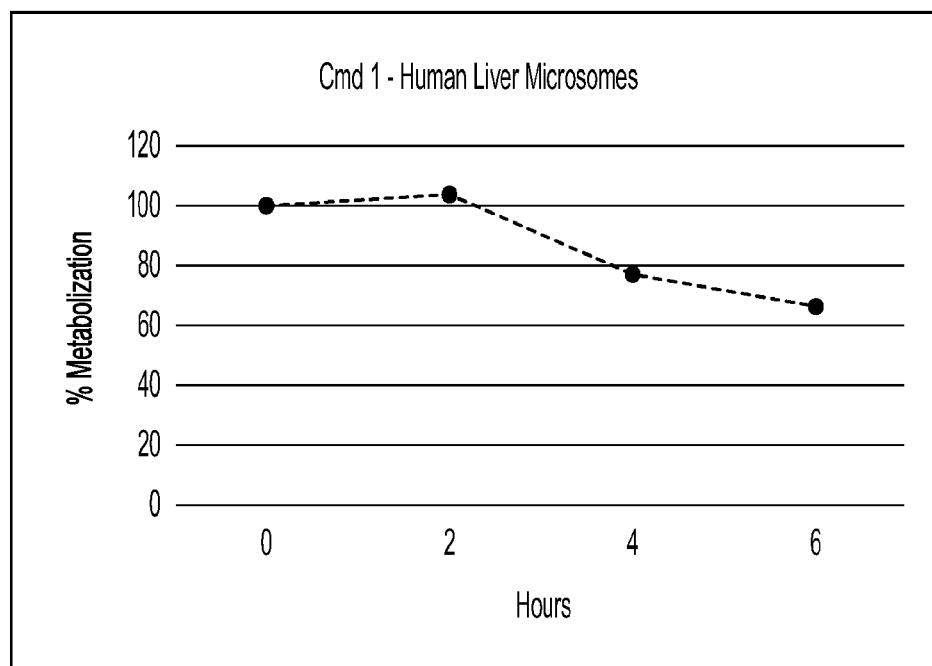
Figure 82:
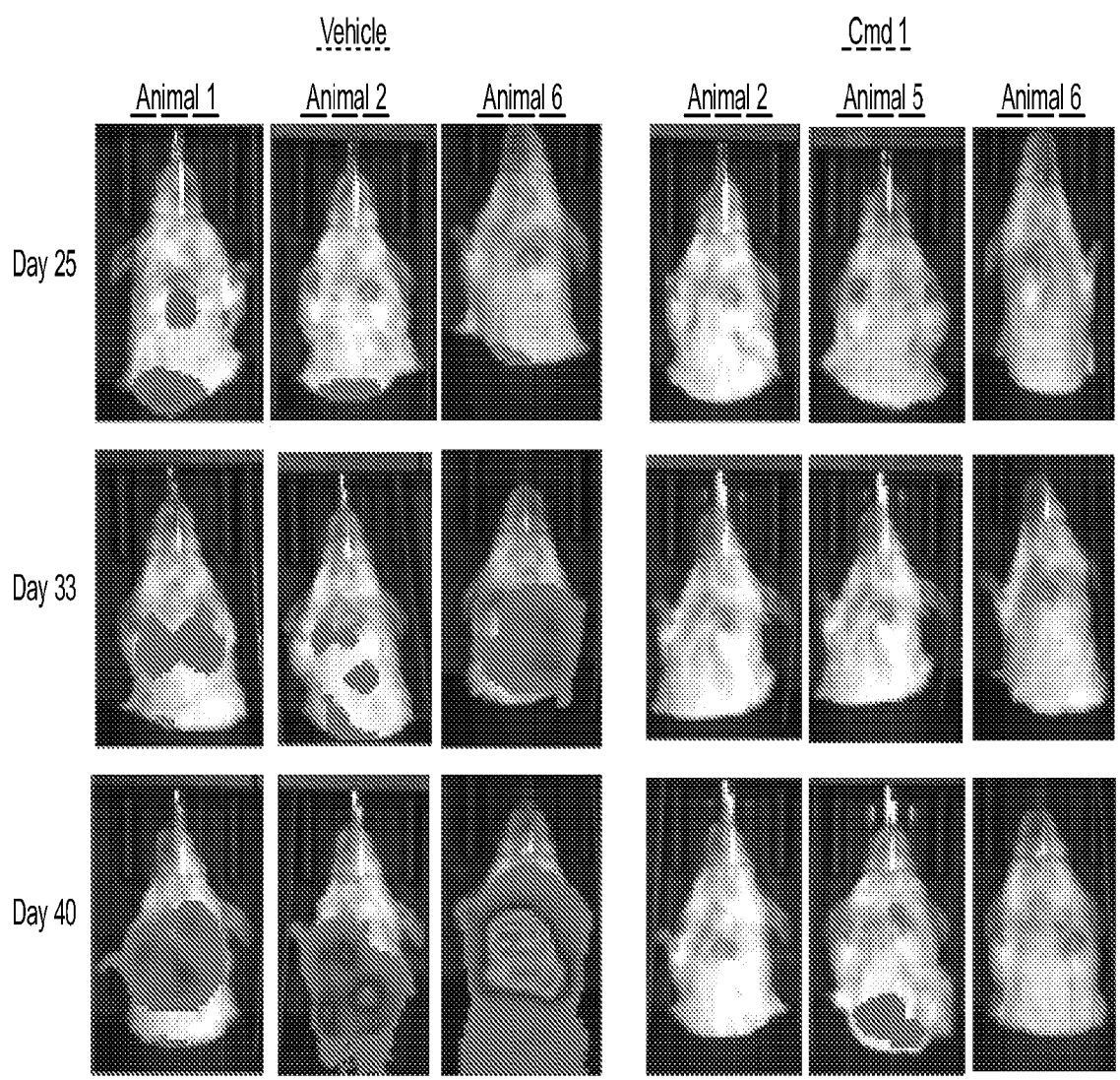
FIG. 82 are luminescence images showing effects on tumor growth of intraperitoneal administration of Cmd 1 in a 4T1 breast cancer syngeneic mouse model. Cmd 1 showed considerable tumor growth inhibition at all three doses compared with the vehicle.

Each animal was monitored individually. The endpoint of the experiment was a tumor volume of 2000 mm2 or 45 days. Animals in Groups 1 and 2 were subjected to whole body bioluminescent imaging starting on Day 5 and once a week thereafter (Days 12, 19, 26, 33, and 41). At the endpoint, blood and tissue (lung, lymph nodes, spleen, and tumor) was analyzed for presence of metastases and biomarker (CD45, CD3, CD4, CD8, CD11b, CD25, Ly-6G, Ly-6C, FoxP3) levels. As seen in FIG. 70, mice treated with Cmd 1 showed a significant decrease in tumor growth compared with control Example 13. Determination of Maximum Tolerated Dose of Orally Administered Exemplary Compounds In order to investigate the maximum tolerated dosage of orally administered compounds, 15 female BALB/c mice between 7-10 weeks old were split into three treatment groups. Each group was administered either Cmd 1 or vehicle orally, according to the schedule outlined in Table 5 below. Cmd 1 was provided at 10 mL/kg (0.200 mL/20 g mouse). Upon oral administration of Cmd 1, once daily or twice daily up to 60 mgkg/day, there were no adverse clinical signs and the compound was well tolerated as shown in Table 5.

TABLE 5

Oral MTD study regimen and results

| | | | Treatment Regimen 1 | | | | Treatment Regimen 2 | | | BW | | | | Mean Day |
|---|---|---|---|---|---|---|---|---|---|---|---|---|---|---|
| Group | n | Agent | Vehicle | mg/kg | Route | Schedule | Vehicle | Route | Schedule | Nadir | TR | NTR | NTRm | of Death |
| 1 | 5 | Cmd 1 | | 60 | po | qd x 10 | — | — | — | — | 0 | 0 | 0 | — |
| 2 | 5 | Cmd 1 | | 60 | po | bid x 10 first day 1 dose | — | — | — | -3.6% (11) | 0 | 0 | 0 | — |
| 3 | 5 | saline | | — | po | qd x 9 | | ip | qd x 1 (start on day 10) | — | 0 | 1 | 0 | — |

EQUIVALENTS

The disclosures of each and every patent, patent application, and publication cited herein are hereby incorporated by reference in their entirety. While this disclosure has been described with reference to specific aspects, it is apparent that other aspects and variations may be devised by others skilled in the art without departing from the true spirit and scope of the disclosure. The appended claims are intended to be construed to include all such aspects and equivalent variations. Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference.

While this disclosure has been particularly shown and described with references to preferred embodiments thereof, it will be understood by those skilled in the art that various changes in form and details may be made therein without departing from the scope of the disclosure encompassed by the appended claims.

What is claimed is:

1. A compound of Formula (I):

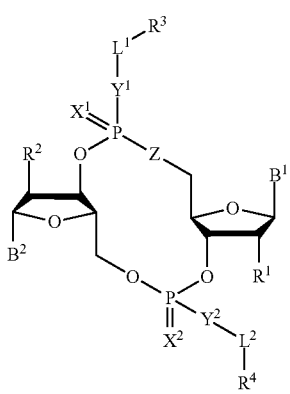

Formula (I)

or a pharmaceutically acceptable salt or stereoisomer thereof, wherein:

Z is either S or O;
$B^1$ is adeninyl;
$B^2$ is uracilyl;
each of $X^1$ and $X^2$ is independently O or S;
$Y^1$ is S or $NR^5$ and $Y^2$ is O, S, or $NR^5$; or $Y^2$ is S or $NR^5$ and $Y^1$ is O, S, or $NR^5$;
each of $L^1$ and $L^2$ is independently absent, $C_1$-$C_6$ alkyl or $C_1$-$C_6$ heteroalkyl, wherein each alkyl and heteroalkyl is optionally substituted with $R^6$;
each of $R^1$ and $R^2$ is independently hydrogen, halo, —CN, $C_1$-$C_{20}$ alkyl, or $OR^7$;
each of $R^3$ and $R^4$ is independently hydrogen, $C_1$-$C_{20}$ alkyl, $C_1$-$C_{20}$, $OC(O)OC_1$-$C_{20}$ alkyl, cycloalkyl, heterocyclyl, aryl, or heteroaryl, wherein each alkyl, heteroalkyl, cycloalkyl, heterocyclyl, aryl, and heteroaryl is optionally substituted with one or more $R^8$;
$R^5$ is hydrogen or $C_1$-$C_{20}$ alkyl;
$R^6$ is halo, —CN, $C_1$-$C_{20}$ alkyl, $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$;
$R^7$ is hydrogen, $C_1$-$C_{20}$ alkyl, cycloalkyl, heterocyclyl, aryl, or heteroaryl, wherein each alkyl, cycloalkyl, heterocyclyl, aryl, and heteroaryl is optionally substituted with one or more $R^9$;
each $R^8$ is independently $C_1$-$C_{20}$ alkyl, $C_1$-$C_{20}$ heteroalkyl, $C(O)$—$C_1$-$C_{20}$ alkyl, $OC(O)$—$C_1$-$C_{20}$ alkyl, $C(O)O$—$C_1$-$C_{20}$ alkyl, $OC(O)O$—$C_1$-$C_{20}$ alkyl, $C(O)N(R^5)$—$C_1$-$C_{20}$ alkyl, $N(R^5)C(O)$—$C_1$-$C_{20}$ alkyl, $OC(O)N(R^5)$—$C_1$-$C_{20}$ alkyl, O-aryl, O-heteroaryl, $C(O)$-aryl, $C(O)$-heteroaryl, $OC(O)$-aryl, $C(O)O$-aryl, $OC(O)$-heteroaryl, $C(O)O$-heteroaryl, $C(O)O$-aryl, $C(O)O$-heteroaryl, $C(O)N(R^5)$-aryl, $C(O)N(R^5)$-heteroaryl, $N(R^5)C(O)$-aryl, $N(R^5)_2C(O)$-aryl, or $N(R^5)C(O)$-heteroaryl, $S(O)_2N(R^5)$-aryl, wherein each alkyl, heteroalkyl, aryl, and heteroaryl is optionally substituted by one or more $R^9$;
and each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

2. The compound of claim 1, wherein the compound is a compound of Formulas (I-b), (I-c), (I-d), or (I-e):

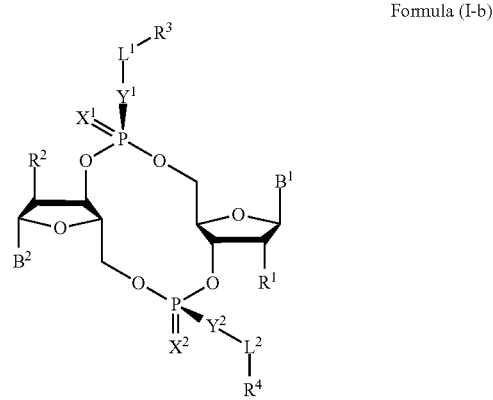

Formula (I-b)

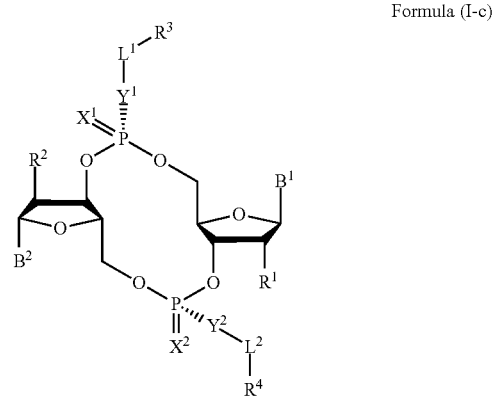

Formula (I-c)

Formula (I-d)

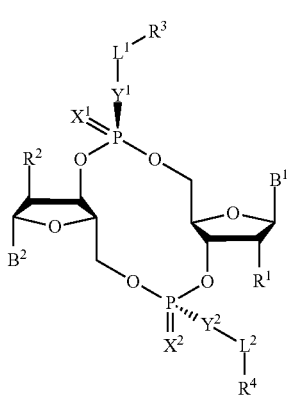

Formula (I-e)

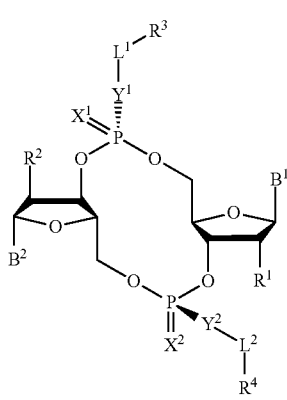

or a pharmaceutically acceptable salt thereof, wherein each of $B^1, B^2, X^1, X^2, Y^1, Y^2, L^1, L^2, R^1, R^2, R^3, R^4$, and subvariables thereof are defined as in claim 1.

3. The compound of claim 1, wherein each of $R^1$ and $R^2$ is independently hydrogen, halo, or $OR^7$.

4. The compound of claim 1, wherein each of $R^1$ and $R^2$ is independently halo.

5. The compound of claim 1, wherein each of $R^1$ and $R^2$ is not hydrogen or $OR^7$.

6. The compound of claim 1, wherein each of $X^1$ and $X^2$ is independently O.

7. The compound of claim 1, wherein each of $Y^1$ and $Y^2$ is independently O or S.

8. The compound of claim 1, wherein one of $Y^1$ or $Y^2$ is O and the other of $Y^1$ or $Y^2$ is S.

9. The compound of claim 1, wherein each of $Y^1$ or $Y^2$ is independently S.

10. The compound of claim 1, wherein each of $L^1$ and $L^2$ is independently $C_1$-$C_6$ alkyl.

11. The compound of claim 1, wherein each of $R^3$ and $R^4$ is independently hydrogen, aryl, or heteroaryl, wherein aryl and heteroaryl is optionally substituted with 1-5 $R^8$.

12. The compound of claim 1, wherein $R^3$ is aryl or heteroaryl, each of which is optionally substituted with 1-5 $R^8$, and $R^4$ is hydrogen.

13. The compound of claim 1, wherein $R^3$ is phenyl substituted with 1 $R^8$ and $R^4$ is hydrogen.

14. The compound of claim 1, wherein each of $R^3$ and $R^4$ is independently phenyl substituted with 1 $R^8$.

15. The compound of claim 1, wherein $Y^2$ is O and $R^4$ is hydrogen.

16. The compound of claim 1, wherein each of $Y^1$ and $Y^2$ is independently S and each of $R^3$ and $R^4$ is independently substituted with 1 $R^8$.

17. The compound of claim 1, wherein $Y^1$ is S and $R^3$ is substituted with 1 $R^8$.

18. The compound of claim 1, wherein $R^8$ is OC(O)-aryl optionally substituted by 1-5 $R^9$.

19. The compound of claim 1, wherein $R^9$ is O—$C_1$-$C_{12}$ alkyl.

20. The compound of claim 1, wherein the compound is selected from:

| Structure |
|---|
| 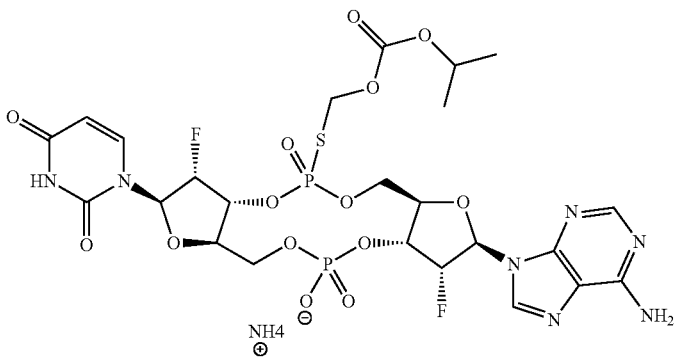 [SMILES: CC(C)OC(=O)OCSP1(=O)OC[C@H]2O[C@@H](n3cnc4c(N)ncnc43)[C@H](F)[C@@H]2OP(=O)([O-])OC[C@H]2O[C@@H](n3ccc(=O)[nH]c3=O)[C@H](F)[C@@H]2O1 ; [NH4+]] |

| Structure |
|---|
| 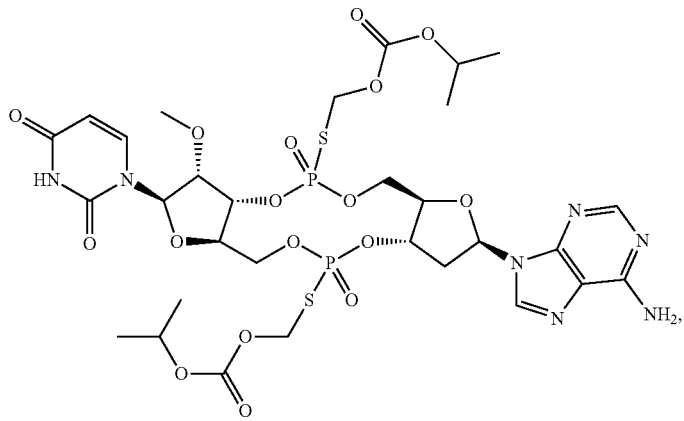 [SMILES: CO[C@@H]1[C@@H]2OP(=O)(SCOC(=O)OC(C)C)OC[C@H]3O[C@@H](n4cnc5c(N)ncnc54)C[C@@H]3OP(=O)(SCOC(=O)OC(C)C)OC[C@H]2O[C@H]1n1ccc(=O)[nH]c1=O] |
| 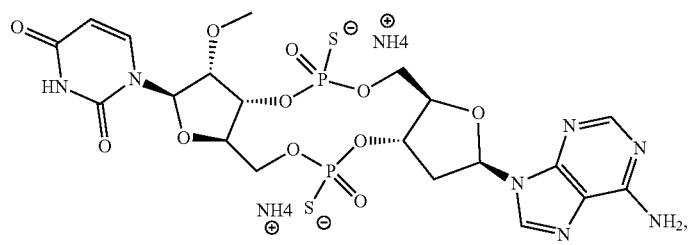 [SMILES: CO[C@@H]1[C@@H]2OP(=O)([S-])OC[C@H]3O[C@@H](n4cnc5c(N)ncnc54)C[C@@H]3OP(=O)([S-])OC[C@H]2O[C@H]1n1ccc(=O)[nH]c1=O ; [NH4+] ; [NH4+]] |
| 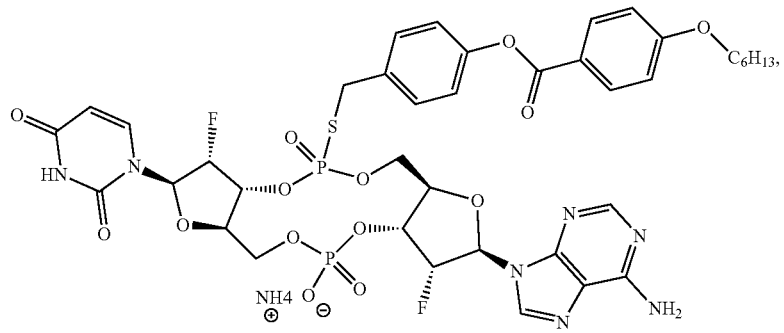 |
| 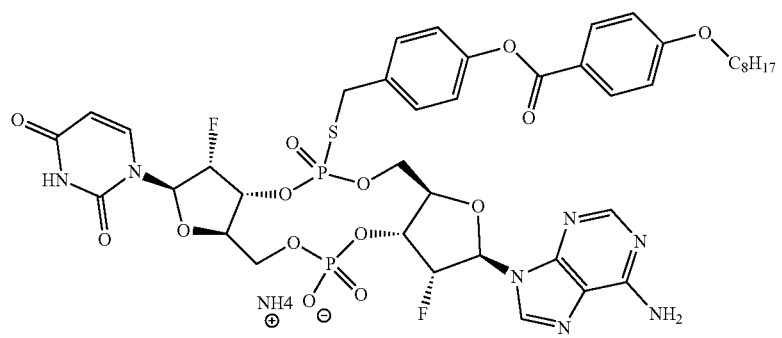 |

107 -continued
Structure
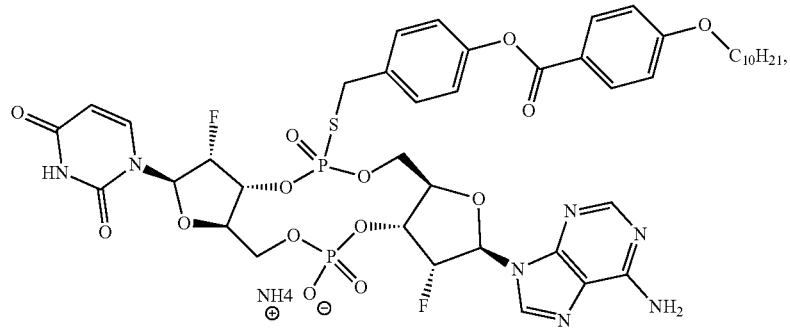
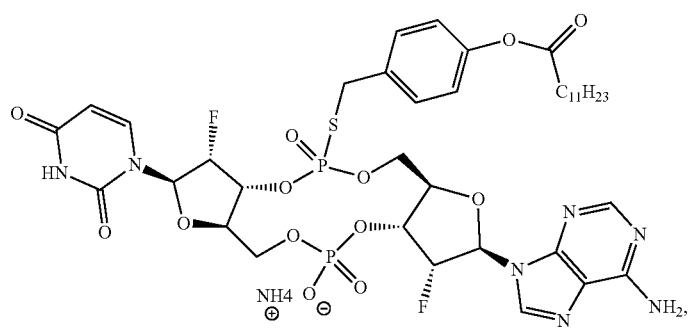
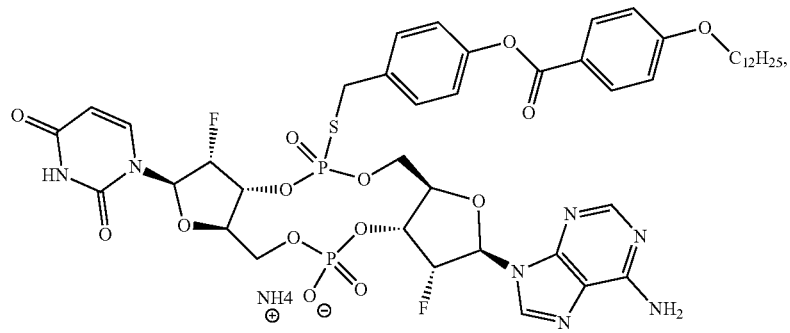
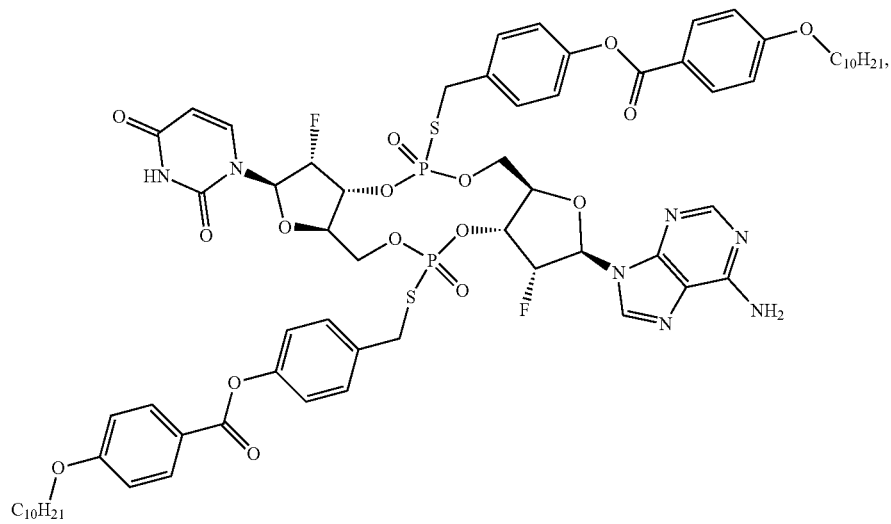

| Structure |
|---|
| 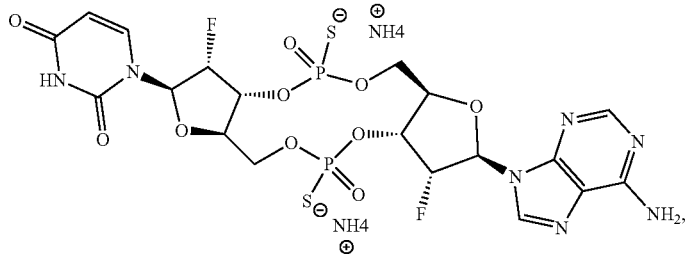 [SMILES: Nc1ncnc2c1ncn2[C@@H]1O[C@@H]2COP(=O)([S-])O[C@H]3[C@@H](F)[C@H](n4ccc(=O)[nH]c4=O)O[C@@H]3COP(=O)([S-])O[C@H]2[C@H]1F ; [NH4+] ; [NH4+]] |
| 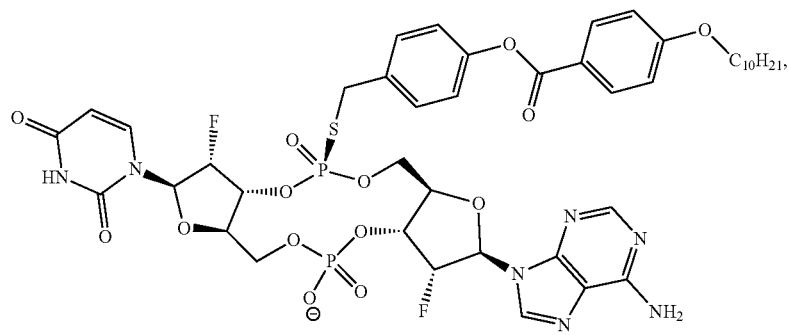 |
| 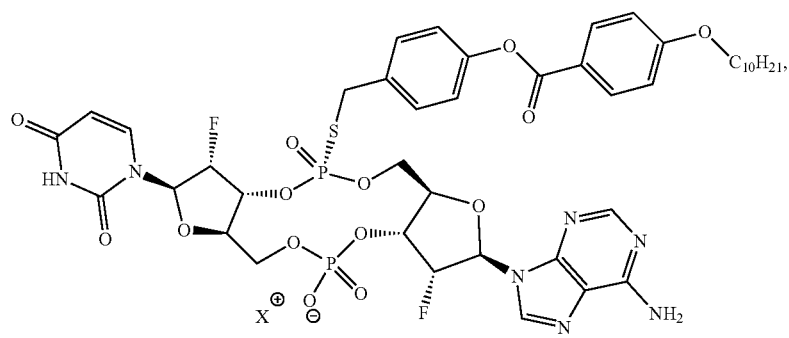 |
| 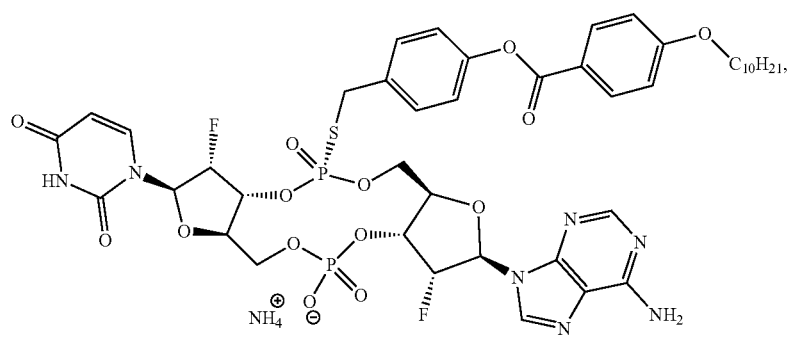 |

-continued
Structure
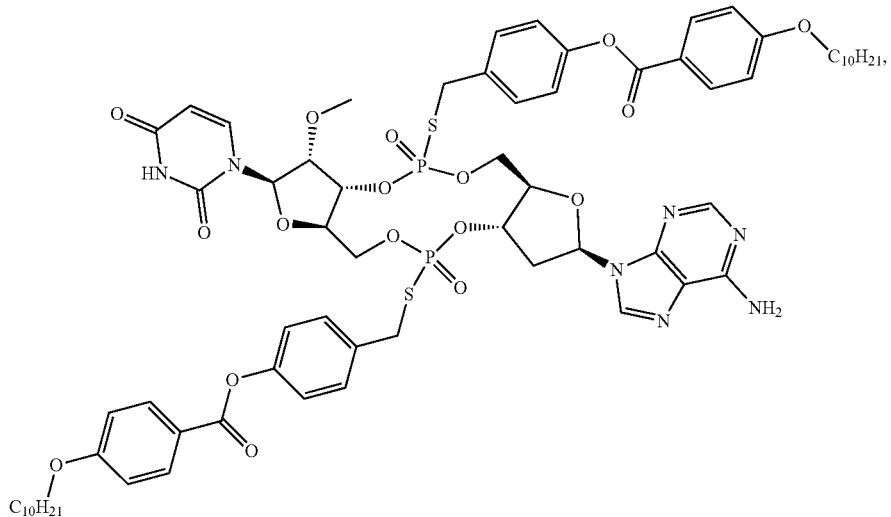
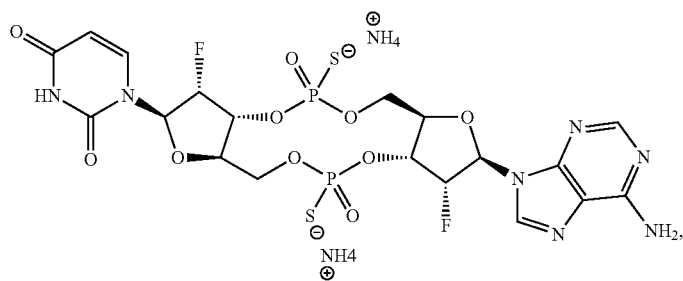 [SMILES: Nc1ncnc2c1ncn2[C@@H]1O[C@@H]2COP(=O)([S-])O[C@H]3[C@@H](F)[C@H](n4ccc(=O)[nH]c4=O)O[C@@H]3COP(=O)([S-])O[C@H]2[C@H]1F ; [NH4+] ; [NH4+]]
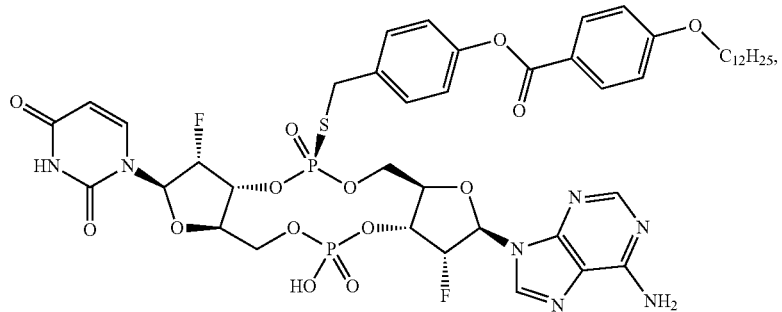
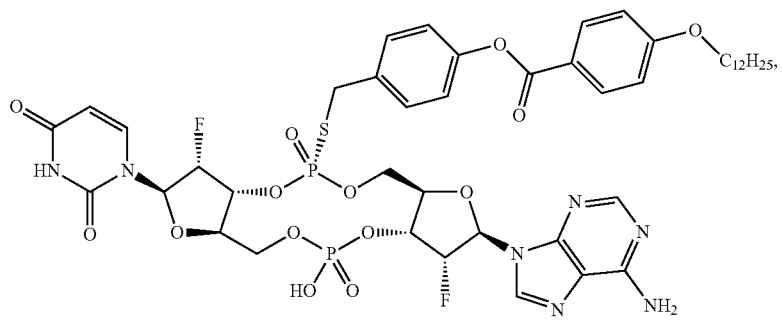

| Structure |
|---|
| 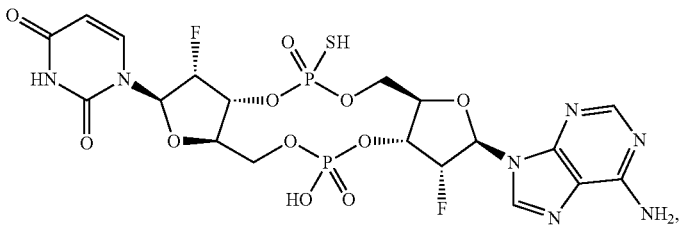 [SMILES: Nc1ncnc2c1ncn2[C@@H]1O[C@@H]2COP(=O)(S)O[C@H]3[C@@H](F)[C@H](n4ccc(=O)[nH]c4=O)O[C@@H]3COP(=O)(O)O[C@H]2[C@H]1F] |
| 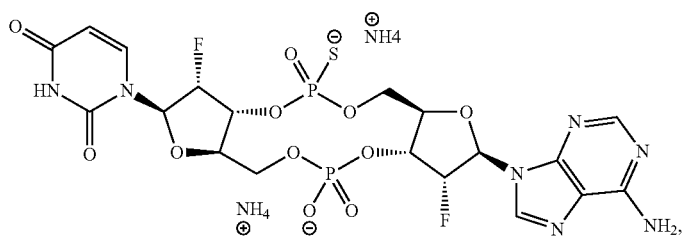 [SMILES: Nc1ncnc2c1ncn2[C@@H]1O[C@@H]2COP(=O)([S-])O[C@H]3[C@@H](F)[C@H](n4ccc(=O)[nH]c4=O)O[C@@H]3COP(=O)([O-])O[C@H]2[C@H]1F ; [NH4+] ; [NH4+]] |
| 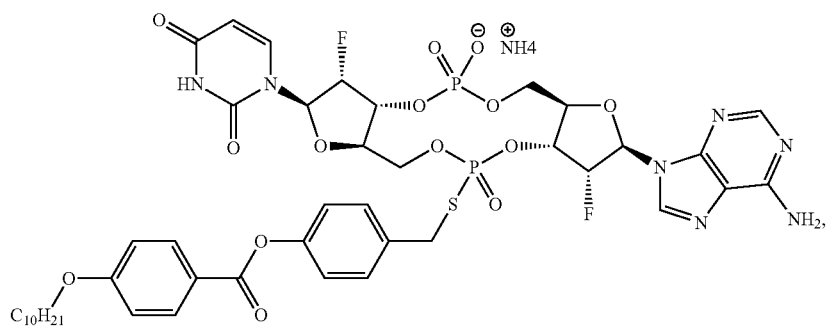 |
| 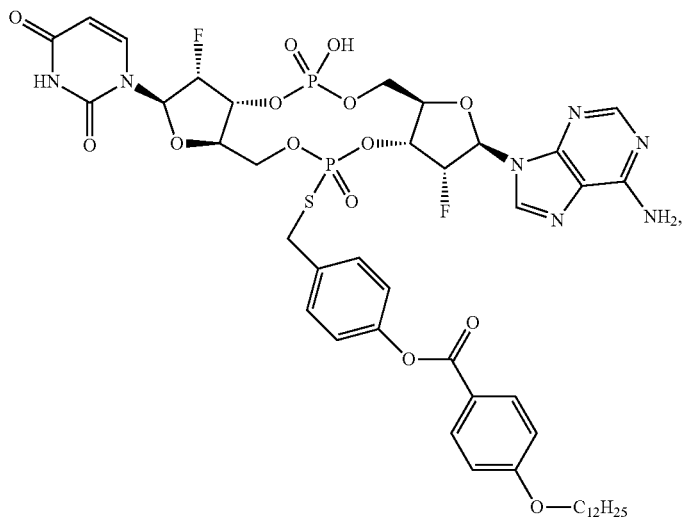 |

| Structure |
|---|
| 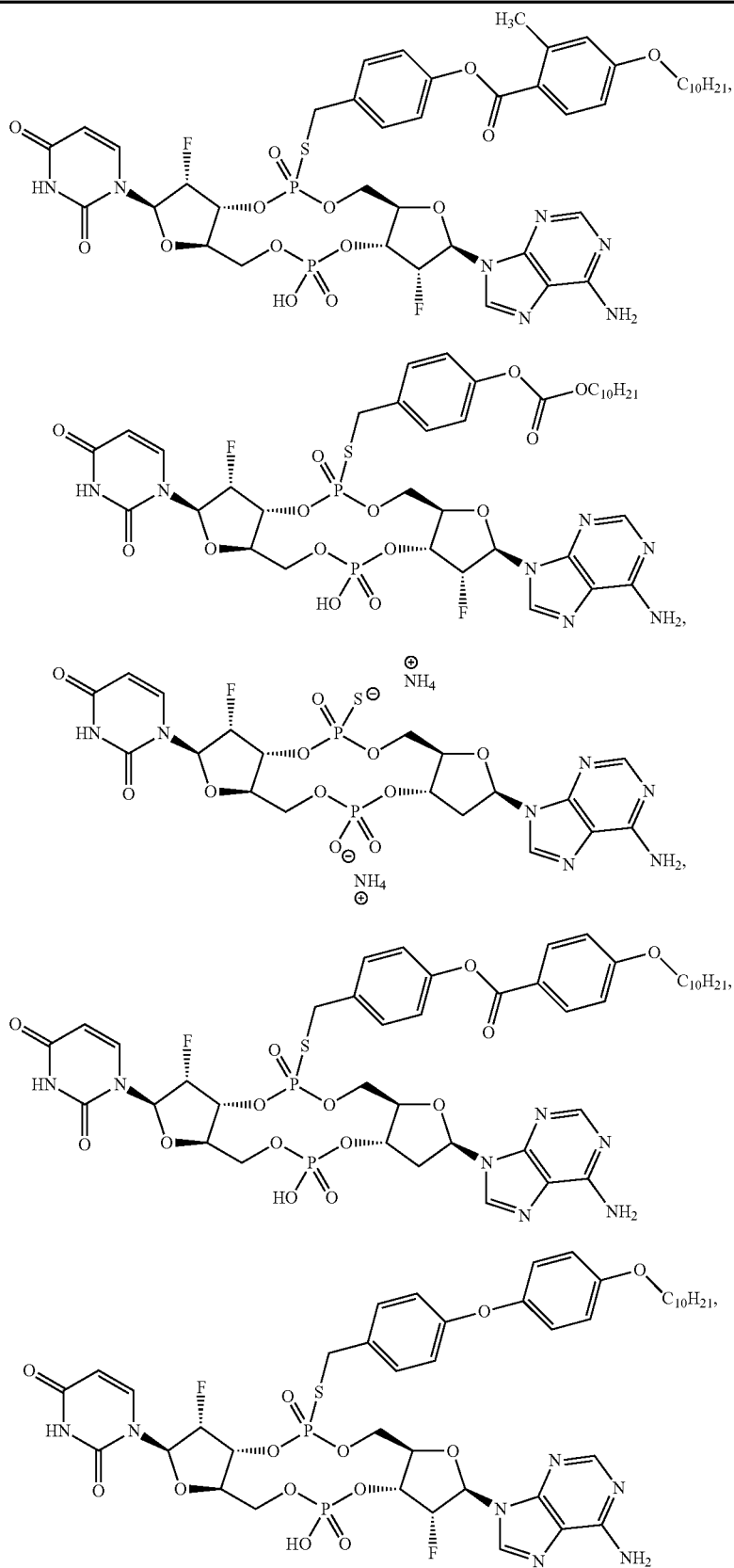 |

| Structure |
|---|
| 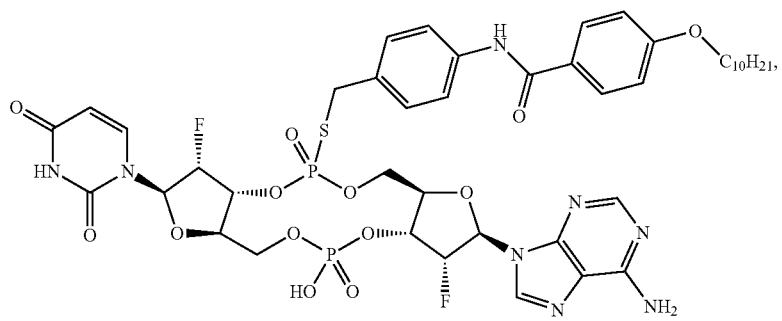 |
| 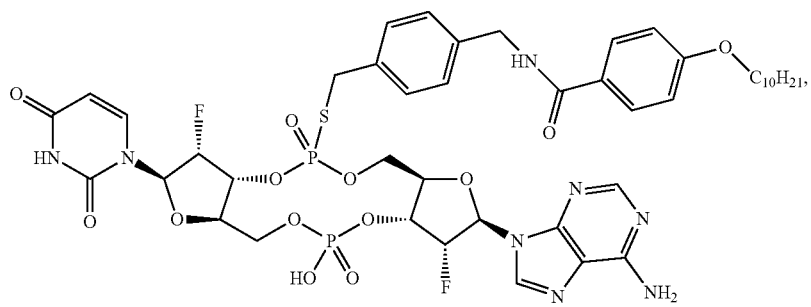 |
| 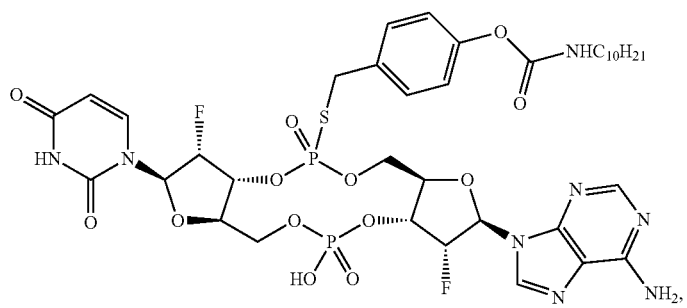 |
| 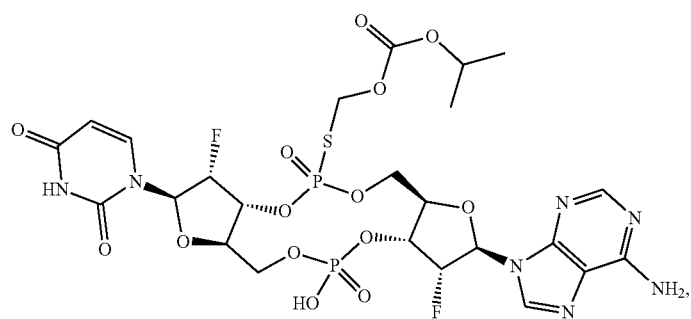 [SMILES: CC(C)OC(=O)OCSP1(=O)OC[C@H]2O[C@@H](n3cnc4c(N)ncnc43)[C@H](F)[C@@H]2OP(=O)(O)OC[C@H]2O[C@@H](n3ccc(=O)[nH]c3=O)[C@H](F)[C@@H]2O1] |
| 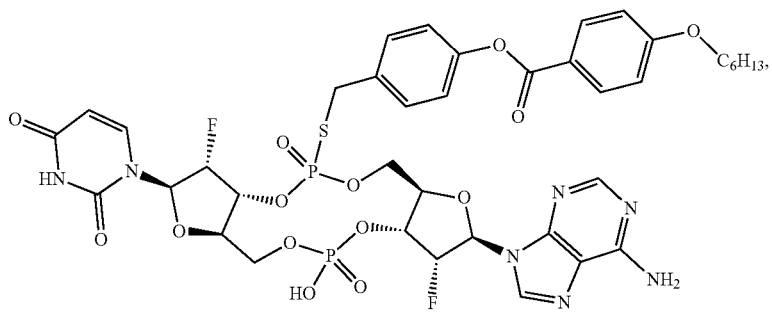 |

| Structure |
|---|
| 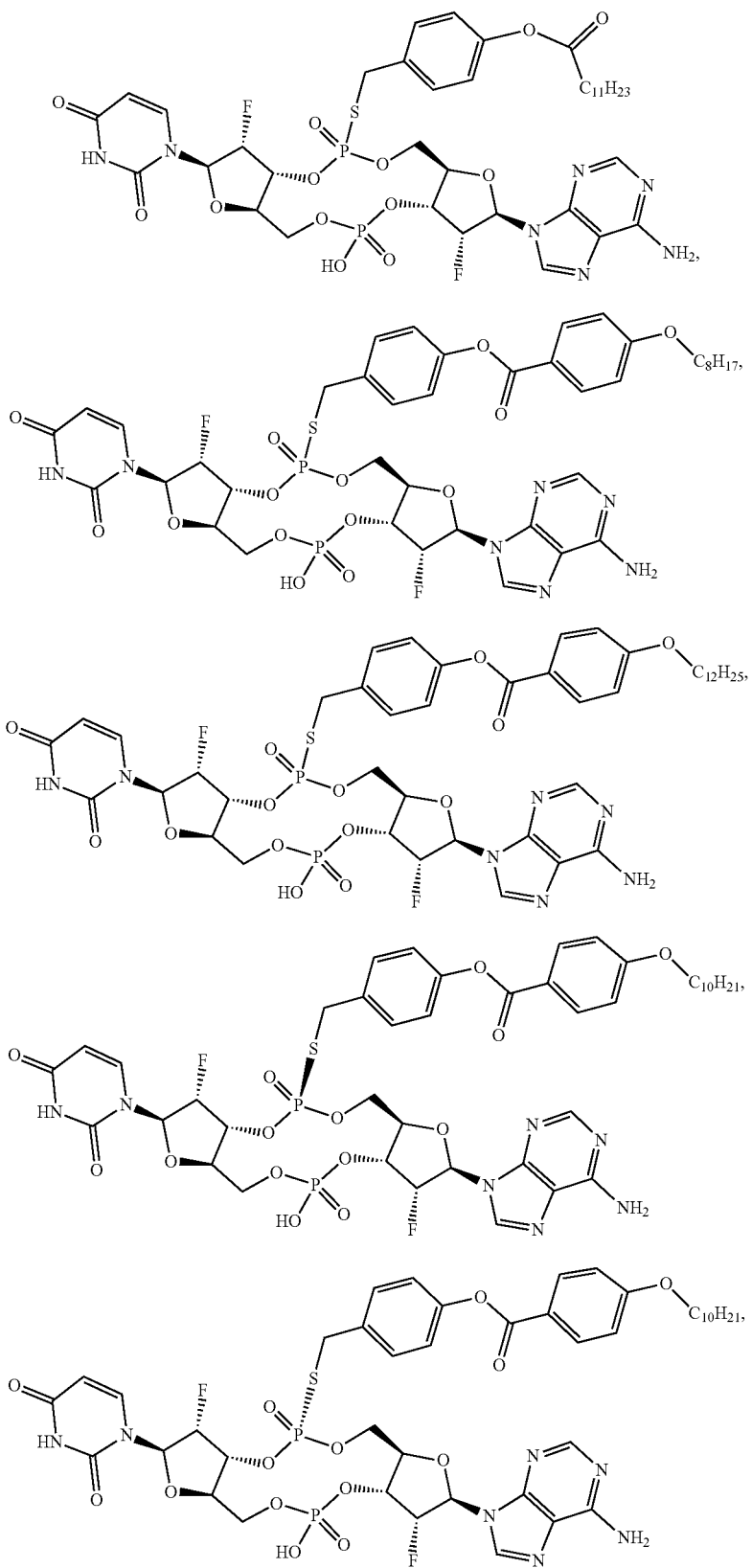 |

-continued
Structure
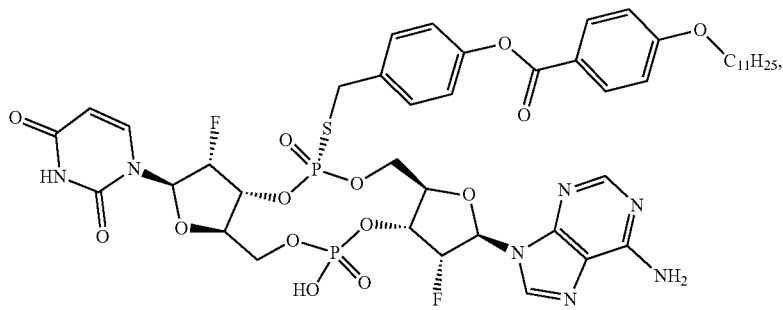
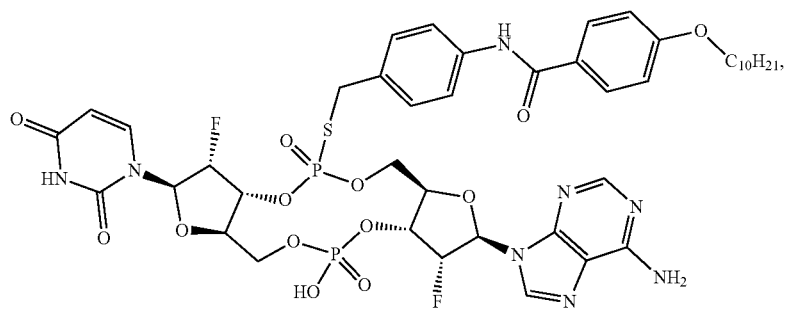
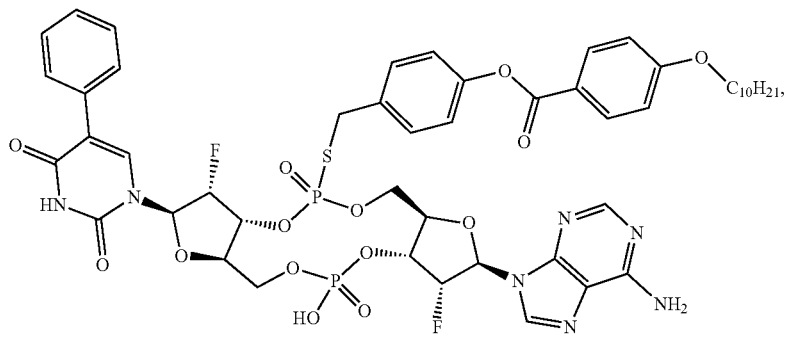
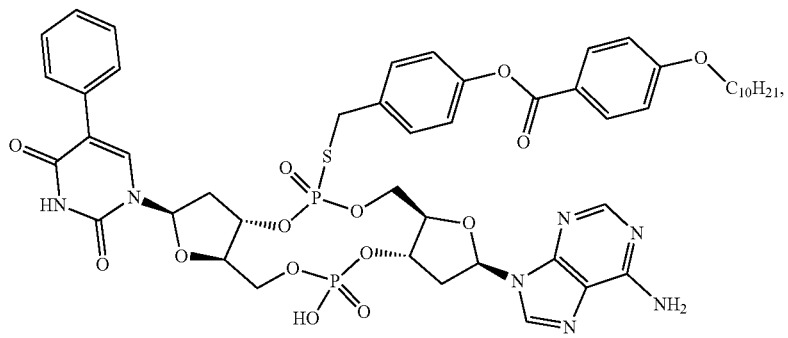

| Structure |
|---|
| 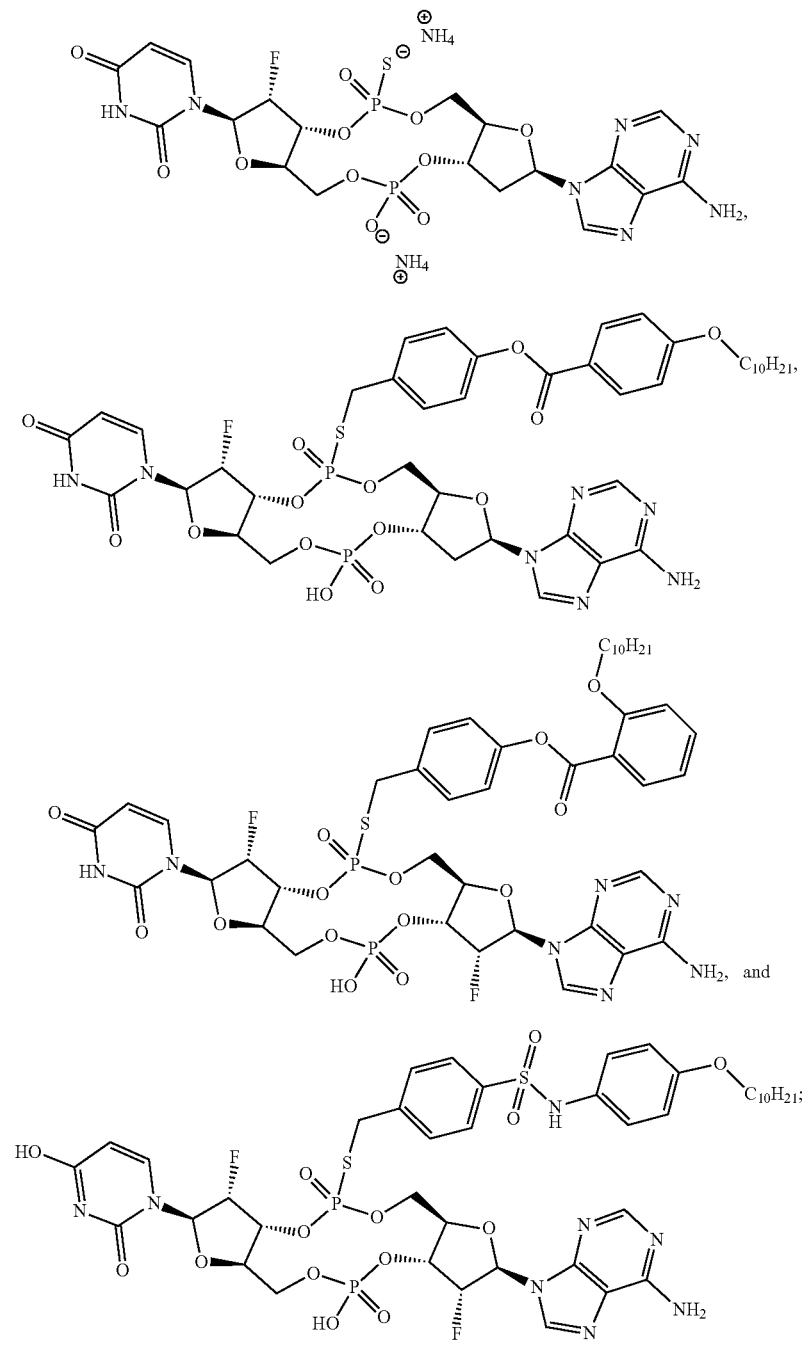 | or a pharmaceutically acceptable salt thereof; wherein X is a pharmaceutically acceptable cation.

21. A method of treating acute monocytic leukemia, lymphoma, melanoma, colon cancer, or breast cancer in a subject, the method comprising administering to the subject a therapeutically effective amount of a compound of claim 1.

22. The method of claim 21, wherein the method comprises intratumoral administration of the compound, a pharmaceutically acceptable salt thereof, or a pharmaceutical composition thereof.

23. The method of claim 21, wherein the method comprises oral administration of the compound, a pharmaceutically acceptable salt thereof, or a pharmaceutical composition thereof.

24. The method of claim 21, wherein the method comprises parenteral administration of the compound, a pharmaceutically acceptable salt thereof, or a pharmaceutical composition thereof.

25. The method of claim 24, wherein the parenteral administration comprises intraperitoneal administration.

26. The method of claim 21, further comprising administration of an additional agent.

27. The method of claim 26, wherein the additional agent comprises methotrexate, 5-fluorouracil, doxorubicin, vincristine, bleomycin, vinblastine, dacarbazine, toposide, cisplatin, epirubicin, or sorafenib tosylate.

28. A method of inducing the expression of a pattern recognition receptors (PRRs) for immune-modulation in a subject, the method comprising administering to the subject a therapeutically effective amount of a compound of claim 1.

29. A method of inducing the expression of a pattern recognition receptors for immunomodulation and inducing a therapeutic response in a subject having cancer, the method comprising administering to the subject a therapeutically effective amount of a compound of claim 1.

30. A method of inducing an immune response in a subject, the method comprising administering to the subject a therapeutically effective amount of a compound of claim 1.

31. The method of claim 30, wherein the immune response comprises antitumoral immunity.

32. The method of claim 30, wherein the immune response comprises induction of a PRR.

* * * * *